US012297283B2

(12) United States Patent
Tuna et al.

(10) Patent No.: US 12,297,283 B2
(45) Date of Patent: *May 13, 2025

(54) FC BINDING FRAGMENTS COMPRISING AN OX40 ANTIGEN-BINDING SITE

(71) Applicant: INVOX PHARMA LIMITED, London (GB)

(72) Inventors: Mihriban Tuna, London (GB); Miguel Gaspar, Cambridge (GB); Sandra Uhlenbroich, Cambridge (GB); Katy Everett, Cambridge (GB); Delphine Buffet, Cambridge (GB)

(73) Assignee: INVOX PHARMA LIMITED, London (GB)

( * ) Notice: Subject to any disclaimer, the term of this patent is extended or adjusted under 35 U.S.C. 154(b) by 315 days.

This patent is subject to a terminal disclaimer.

(21) Appl. No.: 17/259,714

(22) PCT Filed: Jul. 12, 2019

(86) PCT No.: PCT/EP2019/068808

§ 371 (c)(1),
(2) Date: Jan. 12, 2021

(87) PCT Pub. No.: WO2020/011974

PCT Pub. Date: Jan. 16, 2020

(65) Prior Publication Data

US 2021/0355228 A1 Nov. 18, 2021

(30) Foreign Application Priority Data

Jul. 12, 2018 (GB) ..................................... 1811410

(51) Int. Cl.
*C07K 16/28* (2006.01)
*A61K 39/00* (2006.01)
*A61P 35/00* (2006.01)

(52) U.S. Cl.
CPC .......... *C07K 16/2878* (2013.01); *A61P 35/00* (2018.01); *A61K 2039/505* (2013.01); *C07K 2317/526* (2013.01); *C07K 2317/565* (2013.01); *C07K 2317/71* (2013.01)

(58) Field of Classification Search
CPC .......... C07K 16/2878; C07K 2317/526; C07K 2317/565; C07K 2317/71; A61P 35/00; A61K 2039/505
See application file for complete search history.

(56) References Cited

U.S. PATENT DOCUMENTS 3,909,459 A 9/1975 Friese et al.
3,967,230 A 6/1976 Kamigaito et al.
4,004,183 A 1/1977 Oki et al.
5,595,756 A * 1/1997 Bally .................. A61K 9/1272 264/4.1
6,380,664 B1 4/2002 Pollner
7,288,638 B2 10/2007 Jure-Kunkel et al.
7,592,426 B2 9/2009 Ebel et al.
8,217,149 B2 7/2012 Irving et al.
8,383,796 B2 2/2013 Korman et al.
8,911,732 B2 12/2014 Dennis et al.
9,567,399 B1 2/2017 Campbell et al.
9,617,338 B1 4/2017 Campbell et al.
10,090,646 B2 10/2018 Takaoka et al.
10,205,305 B2 2/2019 Uegaki et al.
10,233,258 B2 3/2019 Akamatsu et al.
10,604,576 B2 3/2020 Campbell et al.
11,214,618 B2 1/2022 Tuna et al.
11,214,620 B2 1/2022 Campbell et al.
11,548,948 B2 1/2023 Tuna et al.
11,629,193 B2 4/2023 Tuna et al.
2003/0030355 A1 2/2003 Honda
2007/0071675 A1 3/2007 Wu et al.
2009/0055944 A1 2/2009 Korman et al.
2012/0237498 A1 9/2012 Ahrens et al.
2012/0276104 A1 11/2012 Woisetschlager
2013/0034559 A1 2/2013 Queva et al.
2014/0004121 A1 1/2014 Fanslow, III et al.
2014/0341917 A1 11/2014 Nastri et al.
2015/0214697 A1 7/2015 Yoshida et al.
2015/0259420 A1 9/2015 Triebel et al.
2016/0043531 A1 2/2016 Firstenberg et al.
2016/0137740 A1 5/2016 Hammond et al.
2016/0244528 A1 8/2016 Gray et al.
(Continued)

FOREIGN PATENT DOCUMENTS

CN 101802006 A 8/2010
CN 104968364 A 10/2015
(Continued)

OTHER PUBLICATIONS

Heppner and Miller (Tumor heterogeneity: biological implications and therapeutic consequences, 1983, Cancer Metastasis Reviews, vol. 2, pp. 5-23 (Year: 1983).*
Cooper, The Development and Causes of Cancer, 2000, The Cell: A Molecular Approach, 2nd edition (Year: 2000).*
Turaj et al., Augmentation of CD134 (OX40)- dependent NK anti-tumour activity is dependent on antibody crosslinking, 2018, Scientific Reports, vol. 8, Issue 2278, pp. 1-11 (Year: 2018).*
(Continued)

*Primary Examiner* — Jeffrey Stucker
*Assistant Examiner* — Brittney E Donoghue
(74) *Attorney, Agent, or Firm* — Wolf, Greenfield & Sacks, P.C.

(57) ABSTRACT

The application relates to specific binding members that bind OX40. The specific binding members comprise an OX40 antigen-binding site located in a constant domain of the specific binding member and find application in the treatment of cancer and infectious diseases, for example.

15 Claims, 18 Drawing Sheets

Specification includes a Sequence Listing.

(56) References Cited

U.S. PATENT DOCUMENTS

| | | | |
|---|---|---|---|
| 2017/0198050 | A1 | 7/2017 | Eckelman et al. |
| 2017/0355756 | A1 | 12/2017 | Julien et al. |
| 2017/0362321 | A1 | 12/2017 | Campbell et al. |
| 2018/0118841 | A1 | 5/2018 | Ellmark et al. |
| 2018/0175592 | A1 | 6/2018 | Uegaki et al. |
| 2018/0194862 | A1 | 7/2018 | Akamatsu et al. |
| 2018/0339031 | A1 | 11/2018 | Masternak et al. |
| 2019/0106494 | A1 | 4/2019 | Wang et al. |
| 2019/0202920 | A1 | 7/2019 | Tuna et al. |
| 2019/0256602 | A1 | 8/2019 | Campbell et al. |
| 2019/0330344 | A1 | 10/2019 | Tuna et al. |
| 2019/0330351 | A1 | 10/2019 | Campbell et al. |
| 2019/0338032 | A1 | 11/2019 | Campbell et al. |
| 2019/0338049 | A1 | 11/2019 | Tuna et al. |
| 2020/0407446 | A1 | 12/2020 | McCourt et al. |
| 2021/0139590 | A1 | 5/2021 | Tuna et al. |
| 2021/0237498 | A1 | 8/2021 | Yoda et al. |
| 2021/0238299 | A1 | 8/2021 | Pechouckova et al. |
| 2021/0277134 | A1 | 9/2021 | Lakins et al. |
| 2021/0301022 | A1 | 9/2021 | Wollerton et al. |
| 2021/0309753 | A1 | 10/2021 | Tuna et al. |
| 2022/0048996 | A1 | 2/2022 | Tuna et al. |
| 2022/0049007 | A1 | 2/2022 | Lakins et al. |
| 2022/0185890 | A1 | 6/2022 | Tuna et al. |
| 2022/0185894 | A1 | 6/2022 | Campbell et al. |
| 2022/0267421 | A1 | 8/2022 | Munoz-Olaya et al. |
| 2022/0275092 | A1 | 9/2022 | Morrow et al. |
| 2023/0357413 | A1 | 11/2023 | Tuna et al. |
| 2023/0406935 | A1 | 12/2023 | Tuna et al. |

FOREIGN PATENT DOCUMENTS

| | | | |
|---|---|---|---|
| CN | 104955845 | A | 9/2016 |
| CN | 107523546 | A | 12/2017 |
| EP | 1025230 | B1 | 2/2006 |
| EP | 1180123 | B1 | 7/2008 |
| EP | 2407487 | A1 | 1/2012 |
| EP | 2546268 | A1 | 1/2013 |
| EP | 2242771 | B1 | 7/2013 |
| EP | 2905030 | A1 | 8/2015 |
| EP | 2215121 | B1 | 2/2016 |
| EP | 3354661 | A1 | 8/2018 |
| EP | 3470426 | A1 | 4/2019 |
| JP | S51-046628 | A | 4/1976 |
| JP | 2003-022886 | A | 1/2003 |
| JP | 2011-521905 | A | 7/2011 |
| JP | 2012-500006 | A | 1/2012 |
| JP | 2016-513467 | A | 5/2016 |
| JP | 2016-533395 | A | 10/2016 |
| JP | 2017-010741 | A | 1/2017 |
| JP | 2018-508475 | A | 3/2018 |
| RU | 2017112379 | A | 10/2018 |
| TW | 201642897 | A | 12/2016 |
| WO | WO 2001/077342 | A | 10/2001 |
| WO | WO 2005/035584 | A1 | 4/2005 |
| WO | WO 2006/072620 | A1 | 7/2006 |
| WO | WO 2006/088447 | A1 | 8/2006 |
| WO | WO 2006/099141 | A2 | 9/2006 |
| WO | WO 2008/003103 | A2 | 1/2008 |
| WO | WO 2008/068048 | A2 | 6/2008 |
| WO | WO 2009/000006 | A1 | 12/2008 |
| WO | WO 2009/068204 | A1 | 6/2009 |
| WO | WO 2009/126944 | A1 | 10/2009 |
| WO | WO 2009/132876 | A1 | 11/2009 |
| WO | WO 2010/019570 | A2 | 2/2010 |
| WO | WO 2010/057047 | A1 | 5/2010 |
| WO | WO 2010/111282 | A1 | 9/2010 |
| WO | WO 2010/124797 | A1 | 11/2010 |
| WO | WO 2012/130831 | A1 | 10/2012 |
| WO | WO 2013/181634 | A2 | 12/2013 |
| WO | WO 2014/004549 | A2 | 1/2014 |
| WO | WO 2014/008218 | A1 | 1/2014 |
| WO | WO 2014/052064 | A1 | 4/2014 |
| WO | WO 2014/089113 | A1 | 6/2014 |
| WO | WO 2014/140180 | A1 | 9/2014 |
| WO | WO 2014/151910 | A1 | 9/2014 |
| WO | WO 2015/048312 | A1 | 4/2015 |
| WO | WO 2015/049537 | A1 | 4/2015 |
| WO | WO 2015/119923 | A1 | 8/2015 |
| WO | WO 2015/138920 | A1 | 9/2015 |
| WO | WO 2015/198312 | A1 | 12/2015 |
| WO | WO 2015/200119 | A1 | 12/2015 |
| WO | WO 2016/028672 | A1 | 2/2016 |
| WO | WO 2016/040880 | A1 | 3/2016 |
| WO | WO 2016/111645 | A1 | 7/2016 |
| WO | WO 2016/162505 | A1 | 10/2016 |
| WO | WO 2016/177802 | A1 | 11/2016 |
| WO | WO 2016/185016 | A1 | 11/2016 |
| WO | WO 2016/200782 | A1 | 12/2016 |
| WO | WO 2017/009456 | A1 | 1/2017 |
| WO | WO 2017/015560 | A2 | 1/2017 |
| WO | WO 2017/019846 | A8 | 2/2017 |
| WO | WO 2017/025498 | A1 | 2/2017 |
| WO | WO 2017/049452 | A1 | 3/2017 |
| WO | WO 2017/052241 | A1 | 3/2017 |
| WO | WO 2017/055398 | A2 | 4/2017 |
| WO | WO 2017/062888 | A1 | 4/2017 |
| WO | WO 2017/077085 | A2 | 5/2017 |
| WO | WO 2017/087589 | A2 | 5/2017 |
| WO | WO 2017/087901 | A2 | 5/2017 |
| WO | WO 2017/123650 | A2 | 7/2017 |
| WO | WO 2017/182672 | A1 | 10/2017 |
| WO | WO 2017/193032 | A2 | 11/2017 |
| WO | WO 2017/205738 | A1 | 11/2017 |
| WO | WO 2017/220555 | A1 | 12/2017 |
| WO | WO 2017/220569 | A1 | 12/2017 |
| WO | WO 2018/017673 | A1 | 1/2018 |
| WO | WO 2017/220990 | A9 | 3/2018 |
| WO | WO 2018/056821 | A1 | 3/2018 |
| WO | WO 2018/060480 | A1 | 4/2018 |
| WO | WO 2018/091740 | A2 | 5/2018 |
| WO | WO 2018/115859 | A1 | 6/2018 |
| WO | WO 2018/127610 | A1 | 7/2018 |
| WO | WO 2018/222711 | A2 | 12/2018 |
| WO | WO 2019/025545 | A1 | 2/2019 |

OTHER PUBLICATIONS

Gough et al., OX40 Agonist Therapy Enhances CD8 Infiltration and Decreases Immune Suppression in the Tumor, 2008, Cancer Research, vol. 68, Issue 13, pp. 5206-5215 (Year: 2008).*

[No Author Listed] Abstract for CHI Immuno-Oncology Summit Europe. Mar. 18-22, 2019. 1 page. PDR303.

[No Author Listed] F-Star Modular Bispecific Antibodies. Summary for ATLAS deck. Presented at JP Morgan. Jan. 2017. 1 page. PDR159.

[No Author Listed] First-in-Class bispecific antibodies for cancer immunotherapy. Presentation at Takeda. Dec. 13, 2016. 24 pages. PDR160.

[No Author Listed], FS118 First in Human Study in Patients With Advanced Malignancies. Sponsored by F-star Therapeutics Limited. Clinical Trial. Retreived from https://clinicaltrials.gov/ct2/show/NCT03440437. Feb. 22, 2018. 7 pages.

[No Author Listed], Pipeline Overview: F-star is developing a pipeline of bispecific antibodies focused on oncology and immuno-oncology. F-Start website update. Sep. 2016. 2 pages. PDR126.

Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 20, 2017;35(15):9520-9520. Abstract only. doi: 10.1200/JCO.2017.35.15_suppl.9520. EPub May 30, 2017.

Asgarov et al., A new anti-mesothelin antibody targets selectively the membrane-associated form. MAbs. Apr. 2017;9(3):Supplementary Data. doi: 10.1080/19420862.2017.1288770. 6 pages.

Awuah et al., Reduced Shedding of Surface Mesothelin Improves Efficacy of Mesothelin-Targeting Recombinant Immunotoxins. Mol Cancer Ther. Jul. 2016;15(7):1648-55. doi: 10.1158/1535-7163.MCT-15-0863. Epub May 18, 2016.

(56) References Cited

OTHER PUBLICATIONS

Berg et al., Biochemistry. 5th ed. New York. 2002. Accessible at https://www.ncbi.nlm.nih.gov/books/NBK22358/section5.5. Accessed Jun. 9, 2021. 4 pages.
Bernett et al., Abstract P122: Multiple bispecific checkpoint combinations enhance T cell activity. J Immunother Cancer. 2016;4(Suppl 1):P122. 2 pages.
Bernett et al., Multiple bispecific checkpoint combinations enhance T cell activity. Xencor Poster Presentation. 2016. 1 page.
Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115.010592. Epub Aug. 25, 2015.
Borlak et al., Immune-mediated liver injury of the cancer therapeutic antibody catumaxomab targeting EpCAM, CD3 and Fc? receptors. Oncotarget. May 10, 2016;7(19):28059-74. doi: 10.18632/oncotarget.8574.
Brewis, Development of an anti-PD-L1 Fcab. Presentation. Human Antibodies and Hybrodomas Conference. Oct. 2018. 22. PDR 312.
Brewis, Identification of a PD-L1 binding Fcab: a potent inhibitor of immunosuppressive signals. Abstract. Huamn Antibodies and Hybridomas 2018. Jun. 1, 20181. 1 page. PDR282.
Brewis, The use of bispecific antibodies to modulate anti-tumour immune responses. Oral Presentation at ELRIG- Research and Innovation. Mar. 29, 2017. 33 pages. PDR177.
Brewis, The use of bispecific antibodies to modulate anti-tumour immune responses. Oral Presentation at PEPtalk. Jan. 12, 2017. 26 pages. PDR163.
Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.
Burova et al., Abstract P195: A novel anti-human LAG-3 antibody in combination with anti-human PD-1 (REGN2810) shows enhanced anti-tumor activity in PD-1 x LAG-3 dual-humanized mice and favorable pharmacokinetic and safety profiles in cynomolgus monkey. J Immunother Cancer. 2016;4(Suppl 1):P195. 2 pages.
Callahan et al., Targeting T Cell Co-receptors for Cancer Therapy. Immunity. May 17, 2016;44(5):1069-78. doi: 10.1016/j.immuni.2016.04.023.
Camisaschi et al., LAG-3 expression defines a subset of CD4(+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.
Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.
Chatterjee et al., Noninvasive Imaging of Immune Checkpoint Ligand PD-L1 in Tumors and Metastases for Guiding Immunotherapy. Mol Imaging. Jan.-Dec. 16, 2017:1536012117718459. doi: 10.1177/1536012117718459. 5 pages.
Chen et al., Molecular mechanisms of T cell co-stimulation and co-inhibition. Nat Rev Immunol. Apr. 2013;13(4):227-42. doi: 10.1038/nri3405. Epub Mar. 8, 2013. Erratum in: Nat Rev Immunol. Jul. 2013;13(7):542.
Chiu et al., Antibody Structure and Function: The Basis for Engineering Therapeutics. Antibodies (Basel). Dec. 3, 2019;8(4):55. doi: 10.3390/antib8040055.
Chu et al., An Update on Anti-CD137 Antibodies in Immunotherapies for Cancer. Int J Mol Sci. Apr. 12, 2019;20(8):1822. doi: 10.3390/ijms20081822. 17 pages.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.
Dahlín et al., Bispecific antibodies in cancer immunotherapy. Ther Adv Vaccines Immunother. Feb. 2018;6(1):3-17. doi: 10.1177/2515135518763280. Epub Mar. 28, 2018.
Davies, Analytical challenges for next generation biologics. Oral Presentation at Waters Biopharma Mini-Seminar. May 24, 2017. 20 pages. PDR191.
Davies, Bispecific Antibodies: New Opportunities for Novel Therapies. Oral Presentation at Bioprocess UK 2016. Nov. 26, 2016. 14 pages. PDR 135.
Davies, Overcoming the Manufacturing Challenges for Bisepcific mAbs. Oral Presentation at 5th Annual Cell Culture and Bioprocessing Congress. Nov. 6, 2016. 16 pages. PDR142.
Davies, Overcoming the Manufacturing Challenges for Bisepcific mAbs. Oral Presentation at Biopronet 3rd Annual Scientific Symposium. Oct. 20, 2016. 16 pages. PDR136.
Daxini et al., Vasculitis associated with immune checkpoint inhibitors-a systematic review. Clin Rheumatol. Sep. 2018;37(9):2579-2584. doi: 10.1007/s10067-018-4177-0. Epub Jun. 19, 2018.
Del Bano et al., A Bispecific Antibody-Based Approach for Targeting Mesothelin in Triple Negative Breast Cancer. Front Immunol. Jul. 10, 2019;10:1593. doi: 10.3389/fimmu.2019.01593.
Demeure et al., T Lymphocytes infiltrating various tumour types express the MHC class II ligand lymphocyte activation gene-3 (LAG-3): role of LAG-3/MHC class II interactions in cell-cell contacts. Eur J Cancer. Sep. 2001;37(13):1709-18. doi: 10.1016/s0959-8049(01)00184-8.
Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.
Doody et al., Abstract B091: a LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26-6066.IMM2016-B091. Published Nov. 2016. 8 pages.
Doody, In vivo Efficacy of bispecific antibodies targeting two immmune-modulatory receptors. Oral Presentation at PEGS Europe. Nov. 4, 2016. 16 pages. PDR144.
El-Khoueiry et al., The relationship of pharmacodynamics (PD) and pharmacokinetics (PK) to clinical outcomes in a phase I study of OX40 agonistic monoclonal antibody (mAb) PF-04518600 (PF-8600). J Clin Oncol. May 20, 2017. 35(15_suppl):3027-3027. Meeting Abstract. 2017 ASCO Annual Meeting I. doi: 10.1200/JCO.2017.35.15_suppl.3027. 4 pages.
Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.
Everett et al., Abstract PR06: a LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. DOI: 10.1158/2326-6074.TUMIMM16-PR06. Published Mar. 2017. 8 pages.
Everett, A LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.
F-STAR, First-in-Class Bispecific Antibodies for Cance Immunotherapy. Jul. 2016. Presentation. 14 pages. PDR119.
F-STAR, Next-Generation Bispecifics for Cancer Immunotherapy. Feb. 2020. Presented on Mar. 11, 2020 at Immuno-Oncology Summit Europe 2020. London. 46 pages.
F-STAR, Redirecting T Cells. Overcoming Cancer. Improving Lives. Oct. 2019 Presentation in Investor Meeting. 36 pages.
F-STAR, Redirecting T Cells. Overcoming Cancer. Improving Lives. Apr. 2020 Presentation in Investor Meeting. 43 pages.
F-STAR, Redirecting T Cells. Overcoming Cancer. Improving Lives. Jan. 2020 Presentation in Investor Meeting. 41 pages.
Faroudi et al., Abstract 2399: LAG-3/PD-L1 mAb2 can overcome PD-L1-mediated compensatory upregulation of LAG-3 induced by single-agent checkpoint blockade. Proceedings: AACR Annual Meet-

(56) References Cited

OTHER PUBLICATIONS ing 2019; Mar. 29-Apr. 3, 2019. Atlanta, GA. DOI: 10.1158/1538-7445.AM2019-2399. Published Jul. 2019. 4 pages.
Faroudi et al., Abstract B009: FS118, a LAG-3/PD-L1 bispecific antibody, capable of driving potent anti-tumour immune responses and overcome PD-(L)1-mediated compensatory. Sep. 25-28, 2019. Fifth CRI-CIMT-EATI-AACR International Cancer Immunotherapy Conference (2019): Translating Science into Survival. Paris. 1 page.
Faroudi et al., FS118, a LAG-3/PD-L1 bispecific antibody, capable of driving potent anti-tumour immune responses and overcome PD-(L)1-mediated compensatory. Sep. 25-28, 2019. Poster. Fifth CRI-CIMT-EATI-AACR International Cancer Immunotherapy Conference (2019): Translating Science into Survival. Paris. 1 page.
Fiehler, Development of an anti-PD-L1 Fcab. Presentation. European Antibody Congress. Oct. 29, 2018. 26 pages. PDR312.
Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 24, 2016;11(2):e0150084. doi: 10.1371/journal.pone.0150084.
Frenzel et al., Phage display-derived human antibodies in clinical development and therapy. MAbs. Oct. 2016;8(7):1177-1194. doi: 10.1080/19420862.2016.1212149. Epub Jul. 14, 2016.
Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.
Gaspar et al., FS120 mAb2, a dual agonist bispecific antibody targeting OX40 and CD137, activates T cells in vitro and induces FcyR-independent anti-tumour activity. SITC 2018. Nov. 7, 2018. Poster. 10 pages.
Gaspar, FS120 mAb2, a dual agonist bispecific antibody targeting OX40 and CD137. SITC 2018. Nov. 11, 2018. Presentation. 12 pages.
Geuijen et al., Abstract 541: An unbiased screen identifies a CD137xPD-L1 bispecific IgG1 antibody with unique T cell activation and binding properties. Cancer Res. 2019;79(13_Supplement):541. Poster Presentation AACR Conference 2019. Jul. 1, 2019. doi: 10.1158/1538-7445.AM2019-541. 4 pages.
Gliddon, Pushing all the buttons: innovating in immuno-oncology with mAb. Oral Presentation at Phacilitate Immunotherapy World 2017. Jan. 1, 20178. 11 pages. PDR165.
Glisson et al., Phase 1 study of MEDI0562, a humanized OX40 agonist monoclonal antibody (mAb), in adult patients (pts) with advanced solid tumors. Annals Onocol. Oct. 1, 2016;27(6):vi361. doi: 10.1093/annonc/mdw378.07.
Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.
Gunde et al., Abstract 1532: A novel, monovalent tri-specific antibody-based molecule that simultaneously modulates PD-L1 and 4-1BB exhibits potent anti-tumoral activity in vivo. Cancer Res. 2019;79(13_Supplement): 1532. AACR Conference 2019. Jul. 1, 2019. doi: 10.1158/1538-7445.AM2019-1532. 4 pages.
Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.
Hassan et al., Mesothelin Immunotherapy for Cancer: Ready for Prime Time? J Clin Oncol. Dec. 2016;34(34):4171-4179. doi: 10.1200/JCO.2016.68.3672. Epub Oct. 31, 2016.
Hassan et al., Phase II clinical trial of amatuximab, a chimeric antimesothelin antibody with pemetrexed and cisplatin in advanced unresectable pleural mesothelioma. Clin Cancer Res. Dec. 1, 2014;20(23):5927-36. doi: 10.1158/1078-0432.CCR-14-0804. Epub Sep. 17, 2014.
Hebb et al., Administration of low-dose combination anti-CTLA4, anti-CD137, and anti-OX40 into murine tumor or proximal to the tumor draining lymph node induces systemic tumor regression. Cancer Immunol Immunother. Jan. 2018;67(1):47-60. doi: 10.1007/s00262-017-2059-y. Epub Sep. 13, 2017. Author Manuscript. 20 pages.
Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.
Hid Cadena et al., Checks and Balances in Autoimmune Vasculitis. Front Immunol. Feb. 22, 2018;9:315. doi: 10.3389/fimmu.2018.00315.
Ho et al., A novel high-affinity human monoclonal antibody to mesothelin. Int J Cancer. May 1, 2011;128(9):2020-30. doi: 10.1002/ijc.25557.
Horn et al., CD3xPDL1 bi-specific T cell engager (BiTE) simultaneously activates T cells and NKT cells, kills PDL1$^+$ tumor cells, and extends the survival of tumor-bearing humanized mice. Oncotarget. Aug. 3, 2017;8(35):57964-57980. doi: 10.18632/oncotarget.19865.
Huang et al., Abstract PR03: Combinatorial blockade of PD-1, CTLA-4, and LAG-3 pathways inhibits murine ovarian tumor growth. Abstracts: AACR Special Conference: Advances in Ovarian Cancer Research: Exploiting Vulnerabilities. Oct. 17-20, 2015. Orlando, FL. doi: 10.1158/1557-3265.OVCA15-PR03. Published Jan. 2016. 8 pages.
Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.
Jochems et al., Analyses of functions of an anti-PD-L1/TGFβR2 bispecific fusion protein (M7824). Oncotarget. Sep. 8, 2017;8(43):75217-75231. doi: 10.18632/oncotarget.20680.
Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.
Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.
Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018.1466016.
Kraman et al., A LAG-3/PD-L1 bispecific antibody inhibits tmour growth in two syngeneic colon carcinoma models. Poster Presentation. BSI/NVVI Congress. Dec. 6, 2016. 1 page. PDR153.
Kraman et al., A LAG-3/PD-L1 bispecific antibody inhibits tumour growth in two syngeneic colon carcinoma models. Abstract B091. Poster Presentation. CRI-CIMT-EATI-AACR Cancer Immunotherapy Conference. Sep. 26, 2016. 1 page. PDR129.
Kraman et al., A LAG-3/PD-L1 bispecific antibody inhibits tumour growth in two syngeneic colon carcinoma models. Poster 003. Poster Presentation. 2nd Annual Advances in Immuno-Oncology Congress. May 15, 2017. 1 page. PDR185.
Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.
Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.
Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.
Kraman et al., A Lag-3/PD-L1 bispecific antibody inhibits tumour growth in two syngeneic colon carcinoma models. Poster Presentation. International Conference on Human & Translational Immunology. Sep. 16, 2016. 1 page. PDR123.

(56) References Cited

OTHER PUBLICATIONS

Kraman et al., A LAG-3/PD-L1 bispecific antibody inhibits tumour growth in two syngeneic colon carcinoma models. Poster 3005. Poster Presentation. Keystome Symposium—Biobetters and Next-Generation Biologics. Jan. 22-26, 2017. 1 page. PDR164.
Kraman et al., Abstract 5651:A LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.
Kraman et al., Dual blockade of PD-L1 and LAG-3 with FS118, a unique bispecific antibody, induces CD8+ T-cell activation and modulates the tumour microenvironment to promote anti-tumour immune responses. Apr. 14-18, 2018. Poster 2719. Proceedings of the American Association for Cancer Research Annual Meeting 2018. Chicago, IL. 2 pages.
Kraman et al., Dual blockade of PD-L1 and LAG-3 with FS118, a unique bispecific antibody, induces T-cell activation with the potential to drive potent anti-tumour immune responses. Nov. 7, 2017;5 Suppl 2 (87): Abstract P348. 32nd Annual Meeting and Pre-Conference Programs of the Society for Immunotherapy of Cancer (SITC). Part II. Nov. 8-12, 2017. National Harbor, MD. 2 pages.
Kraman et al., Dual blockade of PD-L1 and LAG-3 with FS118, a unique bispecific antibody, induces T-cell activation with the potential to drive potent anti-tumour immune responses. Apr. 14-18, 2018;78(13 Suppl);Abstract 2719. Proceedings of the American Association for Cancer Research Annual Meeting 2018. Chicago, IL. 5 pages.
Kraman et al., Dual blockade of PD-L1 and LAG-3 with FS118, a unique bispecific antibody, induces T-cell activation with the potential to drive potent anti-tumour immune responses. Poster P348. 32nd Annual Meeting and Pre-Conference Programs of the Society for Immunotherapy of Cancer (SITC). Part II. Nov. 8-12, 2017. National Harbor, MD. 1 page.
Kraman et al., FS118, a Bispecific Antibody Targeting LAG-3 and PD-L1, Enhances T-Cell Activation Resulting in Potent Antitumor Activity. Clin Cancer Res. Jul. 1, 2020;26(13):3333-3344. doi: 10.1158/1078-0432.CCR-19-3548. Epub Apr. 16, 2020.
Kunik et al., Structural consensus among antibodies defines the antigen binding site. PLoS Comput Biol. 2012;8(2):e1002388. doi: 10.1371/journal.pcbi.1002388. Epub Feb. 23, 2012. 12 pages.
Kvarnhammar et al., The CTLA-4 x OX40 bispecific antibody ATOR-1015 induces anti-tumor effects through tumor-directed immune activation. J Immunother Cancer. Apr. 11, 2019;7(1):103. doi: 10.1186/s40425-019-0570-8.
La Motte-Mohs et al., Abstract 3217: MGD013, a bispecific PD-1 x LAG-3 Dual-Affinity Re-Targeting (DART®) protein with T-cell immunomodulatory activity for cancer treatment. AACR 107th Annual Meeting. Apr. 16-20, 2016. New Orleans, LA. Doi: 10.1158/1538-7445.AM2016-3217. 8 pages.
La Motte-Mohs et al., MGD013, a bispecific PD-1 x LAG-3 Dual-Affinity Re-Targeting (DART®) protein with T-cell immunomodulatory activity for cancer treatment. Poster Presentation. 2016. http://ir.macrogenics.com/events.cfm. 1 page.
Lakins et al., FS222 mAb2, a bispecific conditional agonist antibody targeting CD137 and PD-L1, induces potent lymphocyte activation and has a favourable safety profile. F-star, Cambridge, UK. Poster Presentation. AACR Annual Meeting Mar. 29-Apr. 3, 2019. Atlanta, GA. Poster No. 1540. 1 page.
Lakins et al., Optimising TNFRSF agonism and checkpoint blockade with a novel CD137/PD-L1 bispecific antibody. Abstracts Therapeutic Development. Dec. 1, 2018;29(Supplement 10):X30. doi: 10.1093/annonc/mdy487.014. 1 page.
Larkin et al., Combined Nivolumab and Ipilimumab or Monotherapy in Untreated Melanoma. N Engl J Med. Jul. 2, 2015;373(1):23-34. doi: 10.1056/NEJMoa1504030. Epub May 31, 2015. Erratum in: N Engl J Med. Nov. 29, 2018;379(22):2185.
Levitan, Amgen Halts Rilotumumab Development Due to Increased Death Signal. Cancer Network. Nov. 26, 2014. Retrieved from www.cancernetwork.com/view/amgen-halts-rilotumumab-development-due-increased-death-signal. 3 pages.
Li et al., Discovery and preclinical characterization of the antagonist anti-PD-L1 monoclonal antibody LY3300054. J Immunother Cancer. Apr. 30, 2018;6(1):31. doi: 10.1186/s40425-018-0329-7. Erratum in: J Immunother Cancer. Jun. 4, 2018;6(1):45.
Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.
Ma et al., Recognition of mesothelin by the therapeutic antibody MORAb-009: structural and mechanistic insights. J Biol Chem. Sep. 28, 2012;287(40):33123-31. doi: 10.1074/jbc.M112.381756. Epub Jul. 11, 2012.
Mayes et al., Abstract 539: A bispecific Fc-silenced IgG1 antibody (MCLA-145) requires PD-L1 binding to activate CD137. Cancer Res. 2019;79(13_Supplement):539. AACR Presentation 2019. Jul. 1, 2019. doi: 10.1158/1538-7445.AM2019-539. 4 pages.
McCourt et al., KY1055; a novel ICOS/PD-L1 bispecific antibody, enhance T cell activation and delivers potent monotherapy anti-tumour response in vivo. Abstract. CIMT 2018. Feb. 28, 2018. 1 page. PDR245.
McCourt et al., KY1055; a novel ICOS/PD-L1 bispecific antibody, enhance T cell activation and delivers potent monotherapy anti-tumour response in vivo. Poster Presentation. CIMT Conference. May 9, 2018. 1 page. PDR 264.
McCourt et al., KY1055; a novel ICOS/PD-L1 bispecific antibody, enhance T cell activation and delivers potent monotherapy anti-tumour response in vivo. Presentation. CIMT Conference. May 9, 2018. 13 pages. PDR265.
McCourt, Development of an ICOS/PD-L1 Bispecific, Mar. 18-22, 2019. Abstract. Cambridge Healthtech Institute's 4th Annual Immuno-Oncology Summit Europe 2019 (London).
Melero et al., Clinical development of immunostimulatory monoclonal antibodies and opportunities for combination. Clin Cancer Res. Mar. 1, 2013;19(5):997-1008. doi: 10.1158/1078-0432.CCR-12-2214.
Michaelson et al., Anti-tumor activity of stability-engineered IgG-like bispecific antibodies targeting TRAIL-R2 and LTbetaR. MAbs. Mar.-Apr. 2009;1(2):128-41. doi: 10.4161/mabs.1.2.7631. Epub Mar. 11, 2009.
Munoz-Olaya, Development of an anti-PD-L1Fcab. Presentation. PEGS Lisbon. Nov. 16, 2018. 24 pages. PDR321.
Nalivaiko et al., A Recombinant Bispecific CD20xCD95 Antibody With Superior Activity Against Normal and Malignant B-cells. Mol Ther. Feb. 2016;24(2):298-305. doi: 10.1038/mt.2015.209. Epub Nov. 19, 2015.
Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.
Perez-Ruiz et al., Anti-CD137 and PD-1/PD-L1 Antibodies En Route toward Clinical Synergy. Clin Cancer Res. Sep. 15, 2017;23(18):5326-5328. doi: 10.1158/1078-0432.CCR-17-1799. Epub Aug. 8, 2017.
Poon et al., Dual agonist bispecific antibody targeting OX40 and DC137 mediates anti-tumour immunity and synergises with PD-1/PD-L1 blockade to improve survival in a syngeneic mouse model. AACR 2019. Mar. 29, 2019. Poster. 9 pages.
Powles et al., MPDL3280A (anti-PD-L1) treatment leads to clinical activity in metastatic bladder cancer. Nature. Nov. 27, 2014;515(7528):558-62. doi: 10.1038/nature13904.
Ryan et al., A novel biologic platform elicits profound T cell costimulatory activity and antitumor immunity in mice. Cancer Immunol Immunother. Apr. 2018;67(4):605-613. doi: 10.1007/s00262-018-2116-1. Epub Jan. 11, 2018.
Sainson et al., KY1055, a novel ICOS/PD-L1 bispecific antibody, efficiently enhances T cell activation and delivers a potent anti-tumour response in vivo. Abstract. AACR. Jan. 22, 2018. 1 page. PDR236.
Sainson et al., KY1055, a novel ICOS/PD-L1 bispecific antibody, efficiently enhances T cell activation and delivers a potent anti-tumour response in vivo. Poster Presentation. AACR 2018. Apr. 4, 2018. 1 page. PDR254.
Schroeder, Chapter 13: Immunoglobulins and Their Genes. From Arthritis and Allied Conditions: A Textbook of Rheumatology. 15th

(56) References Cited

OTHER PUBLICATIONS

Ed. vol 1. Eds Koopman et al. Lippincot Williams & Wilkins. pp. 289-304. Supplied by the British Library Jul. 31, 2023.

Strauss et al., Phase I Trial of M7824 (MSB0011359C), a Bifunctional Fusion Protein Targeting PD-L1 and TGF?, in Advanced Solid Tumors. Clin Cancer Res. Mar. 15, 2018;24(6):1287-1295. doi: 10.1158/1078-0432.CCR-17-2653. Epub Jan. 3, 2018.

Tang et al., A human single-domain antibody elicits potent antitumor activity by targeting an epitope in mesothelin close to the cancer cell surface. Mol Cancer Ther. Apr. 2013;12(4):416-26. doi: 10.1158/1535-7163.MCT-12-0731. Epub Jan. 31, 2013.

Tuna, Delivering the next immuno-oncology breakthrough. PEGS Europe 2018. Nov. 11, 2018. Presentation. 24 pages.

Tuna, Identification of a PD-L1 binding FCAB: a potent inhibitor of immunosuppressive signals. Abstract. European Antibody Congress. May 3, 2018. 1 page. PDR270.

Tuna, The use of bispecific antibodies to modulate anti-tumour immune responses. Oral Presentation at 10th Annual Proteins and Antibodies Congress. 2017 Ap 24. 26 pages. PDR183.

Vanamee et al., Structural principles of tumor necrosis factor superfamily signaling. Sci Signal. Jan. 2, 2018;11(511):eaao4910. doi: 10.1126/scisignal.aao4910. 12 pages.

Weismann, a LAG-3/PD-L1 Bispecific Antibody Inhibits Tumour Growth In Two Syngeneic Colon Carcinoma Models. International Conference on Human and Translational Immunology. Rhodes, Greece. 2016 Spe 16-21. Presentation. 6 pages. PDR128.

Wherry, T cell exhaustion. Nat Immunol. Jun. 2011;12(6):492-9. doi: 10.1038/ni.2035.

Wilton, KY1055, a bispecific mAb2 targeting ICOS and PD-L1. Presentation. Feb. 21, 2018. 17 pages. PDR238.

Wolchok et al., Nivolumab plus ipilimumab in advanced melanoma. N Engl J Med. Jul. 11, 2013;369(2):122-33. doi: 10.1056/NEJMoa1302369. Epub Jun. 2, 2013. Erratum in: N Engl J Med. Nov. 29, 2018;379(22):2185. Author Manuscript.

Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.

Workman et al., Negative regulation of T cell homeostasis by lymphocyte activation gene-3 (CD223). J Immunol. Jan. 15, 2005;174(2):688-95. doi: 10.4049/jimmunol.174.2.688.

Workman et al., The CD4-related molecule, LAG-3 (CD223), regulates the expansion of activated T cells. Eur J Immunol. Apr. 2003;33(4):970-9. doi: 10.1002/eji.200323382.

Wydro, Bispecific antibodies: new opportunities for novel therapies. Oral Presentation at 7th Annual Biologics Symposium. Mar. 1, 2017. 24 pages. PDR172.

Wykes et al., Immune checkpoint blockade in infectious diseases. Nat Rev Immunol. Feb. 2018;18(2):91-104. doi: 10.1038/nri.2017.112. Epub Oct. 9, 2017.

Yap et al., A first-in-human phase I study of FS118, an anti-LAG-3/PD-L1 bispecific antibody in patients with solid tumors that have progressed on prior PD-1/PD-L1 therapy. Journal of Clinical Oncology. Jun. 1, 2019. Poster TPS2652. 2019 ASCO Annual Meeting Proceedings. 20 pages.

Yap et al., A first-in-human phase I study of FS118, an anti-LAG-3/PD-L1 bispecific antibody in patients with solid tumors that have progressed on prior PD-1/PD-L1 therapy. Journal of Clinical Oncology. May 26, 2019;37(15_suppl). 4 pages.

Yap et al., Abstract TPS2652: A first-in-human phase I study of FS118, an anti-LAG-3/PD-L1 bispecific antibody in patients with solid tumors that have progressed on prior PD-1/PD-L1 therapy. Journal of Clinical Oncology. May 15, 2019;37(15_suppl). 2019 ASCO Annual Meeting Proceedings. 4 pages.

Yonezawa et al., Boosting Cancer Immunotherapy with Anti-CD137 Antibody Therapy. Clin Cancer Res. Jul. 15, 2015;21(14):3113-20. doi: 10.1158/1078-0432.CCR-15-0263. Epub Apr. 23, 2015.

Zhang et al., Structural basis of a novel PD-L1 nanobody for immune checkpoint blockade. Cell Discov. Mar. 7, 2017;3:17004. doi: 10.1038/celldisc.2017.4.

Zhao et al., Novel Antibody Therapeutics Targeting Mesothelin In Solid Tumors. Clin Cancer Drugs. Oct. 2016;3(2):76-86. doi: 10.2174/2212697X03666160218215744.

International Search Report and Written Opinion for Application No. PCT/EP2019/068808, mailed Oct. 15, 2019.

International Preliminary Report on Patentability for Application No. PCT/EP2019/068808, mailed Jan. 21, 2021.

[No Author Listed] F-star Alpha: A new asset centric company. Retrieved from http://www.onenucleus.com/media/Events/LSLS/11%20feb%202014/Jane%20Dancer.pdf on Jan. 8, 2015. 15 pages.

Asgarov et al., A new anti-mesothelin antibody targets selectively the membrane-associated form. MAbs. Apr. 2017;9(3):567-577. doi: 10.1080/19420862.2017.1288770.

Bacac et al., Abstract 1494: CEA TCB: A novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.

Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.

Chester et al., Dual antibody therapy to harness the innate anti-tumor immune response to enhance antibody targeting of tumors. Curr Opin Immunol. Apr. 2015;33:1-8. doi: 10.1016/j.coi.2014.12.010. Epub Jan. 7, 2015.

Goding et al., Combination of adoptive cell transfer, anti-PD-L1 and anti-LAG-3 antibodies for the treatment of recurrent tumors: better with more. OncoImmunology. Oct. 22, 2013;2(8):e25050-1-e25050-3.

Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.

Hasenhindl et al., Stability assessment on a library scale: a rapid method for the evaluation of the commutability and insertion of residues in C-terminal loops of the CH3 domains of IgG1-Fc. Protein Eng Des Sel. 2013;26(10):675-682.

Jing et al., Combined immune checkpoint protein blockade and low dose whole body irradiation as immunotherapy for myeloma. Journal of Immunotherapy of Cancer. doi: 10.1186/S40425-014-0043-Z. Jan. 20, 2015. 15 pages.

Kraman et al., A LAG-3/PD-L1 bispecific antibody inhibits tumor growth in two syngeneic colon carcinoma models. Journal of ImmunoTherapy of Cancer. 2016;4(Suppl 1):82(abstract P124).

Kraman et al., A LAG-3/PD-L1 bispecific antibody inhibits tumor growth in two syngeneic colon carcinoma models. Retrieved from http://www.f-star.com/media/73722/A-LAG-3-PD-L1-bispecific-antibody-inhibits-tumour-growth-in-two-syngeneic-colon-carcinoma-models.pdf. Nov. 9-13, 2016. 1 page.

Lakins et al., A Novel CD137/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.

Lee et al., 4-1BB and OX40 dual costimulation synergistically stimulate primary specific CD8 T cells for robust effector function. J Immunol. Sep. 1, 2004;173(5):3002-12. doi: 10.4049/jimmunol.173.5.3002.

Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.

Lobner et al., Engineered IgG1-Fc—one fragment to bind them all. Immunol Rev. Mar. 2016;270(1):113-31. doi: 10.1111/imr.12385.

Lobner et al., Two-faced Fcab prevents polymerization with VEGF and reveals thermodynamics and the 2.15 A crystal structure of the complex. MAbs. Oct. 2017;9(7):1088-1104. doi: 10.1080/19420862.2017.1364825. Epub Aug. 17, 2017.

Lundqvist et al., 31st Annual Meeting and Associated Programs of the Society for Immunotherapy of Cancer (SITC 2016): Part One. Journal for Immunotherapy of Cancer. Nov. 16, 2016;4(1):74(abstract P124).

(56) References Cited

OTHER PUBLICATIONS

Qui et al., CD134 plus CD137 dual costimulation induces Eomesodermin in CD4 T cells to program cytotoxic Th1 differentiation. J Immunol. Oct. 1, 2011;187(7):3555-64. doi: 10.4049/jimmunol.1101244. Epub Aug. 31, 2011.
Ramelet et al., Beneficial outcome of combination therapy with 4-1BB targeting antibody. Eur J Cancer. Nov. 29, 2016;69(Suppl 1):S96-S97.
Sallin et al., The anti-lymphoma activities of anti-CD137 monoclonal antibodies are enhanced in Fc?RIII(-/-) mice. Cancer Immunol Immunother. Sep. 2014;63(9):947-58. doi: 10.1007/s00262-014-1567-2. Epub Jun. 14, 2014.
Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.
Shindo et al., Combination immunotherapy with 4-1BB activation and PD-1 blockade enhances antitumor efficacy in a mouse model of subcutaneous tumor. Anticancer Res. Jan. 2015;35(1):129-36.
Vilgelm et al., Combinatorial approach to cancer immunotherapy: strength in Nos. Journal of Leukocyte Biology. 2016;100(2):275-90. Epub Jun. 2, 2016.
Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.
Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.
Xu et al., In vitro characterization of five humanized OKT3 effector function variant antibodies. Cell Immunol. Feb. 25, 2000;200(1):16-26.
Golfier et al., Anetumab ravtansine: a novel mesothelin-targeting antibody-drug conjugate cures tumors with heterogeneous target expression favored by bystander effect. Mol Cancer Ther. Jun. 2014;13(6):1537-48. doi: 10.1158/1535-7163.MCT-13-0926. Epub Apr. 8, 2014.
Han et al., Bispecific anti-CD3 x anti-HER2 antibody mediates T cell cytolytic activity to HER2-positive colorectal cancer in vitro and in vivo. Int J Oncol. Dec. 2014;45(6):2446-54. doi: 10.3892/ijo.2014.2663. Epub Sep. 18, 2014.
Lamberts et al., ImmunoPET with Anti-Mesothelin Antibody in Patients with Pancreatic and Ovarian Cancer before Anti-Mesothelin Antibody-Drug Conjugate Treatment. Clin Cancer Res. Apr. 1, 2016;22(7):1642-52. doi: 10.1158/1078-0432.CCR-15-1272. Epub Nov. 20, 2015.
Lin et al., Fc-dependent expression of CD137 on human NK cells: insights into "agonistic" effects of anti-CD137 monoclonal antibodies. Blood. Aug. 1, 2008;112(3):699-707. doi: 10.1182/blood-2007-11-122465. Epub Jun. 2, 2008.
Link et al., Abstract 3752: Preclinical pharmacology of MP0310: a 4-1BB/FAP bispecific DARPin drug candidate promoting tumor-restricted T-cell costimulation. Cancer Res. Jul. 1, 2018;78(13_Supplement):3752.
Liu et al., Abstract 3642: Tumor-antigen expression-dependent activation of the CD137 costimulatory pathway by bispecific DART® proteins. Cancer Res. Jul. 1, 2017;77(13_Supplement):3642.
Reichen et al., Abstract 3029: FAP-mediated tumor accumulation of a T-cell agonistic FAP/4-1BB DARPin drug candidate analyzed by SPECT/CT and quantitative biodistribution. Cancer Res. Jul. 1, 2018;78(13_Supplement):3029.
Segal et al., Results from an Integrated Safety Analysis of Urelumab, an Agonist Anti-CD137 Monoclonal Antibody. Clin Cancer Res. Apr. 15, 2017;23(8):1929-1936. doi: 10.1158/1078-0432.CCR-16-1272. Epub Oct. 18, 2016.
Wang et al., Retargeting T cells for HER2-positive tumor killing by a bispecific Fv-Fc antibody. PLoS One. Sep. 23, 2013;8(9):e75589. doi: 10.1371/journal.pone.0075589. eCollection 2013.
[No Author Listed], mesothelin isoform 1 preproprotein [*Homo sapiens*]. NCBI Reference Sequence: NP_001170826.1. May 2, 2024. Retrieved from https://www.ncbi.nlm.nih.gov/protein/NP_001170826.1/. 4 pages.
[No Author Listed], mesothelin isoform 1 preproprotein [Mus musculus]. NCBI Reference Sequence: NP_001343215.1. Jun. 18, 2024. Retrieved from https://www.ncbi.nlm.nih.gov/protein/NP_001343215.1. 3 pages.
[No Author Listed], Molecular biological basis of immunotherapy. New and Orphan Drugs for Leukemia Therapeutics. Sep. 30, 2016. 387-390. Retrieved on Dec. 18, 2023. 7 pages.
[No Author Listed], Predicted: mesothelin isoform X4 [Macaca fascicularis]. NCBI Reference Sequence: XP_005590874.2. Jan. 25, 2016. Retrieved from https://www.ncbi.nlm.nih.gov/protein/XP_005590874.2. 2 pages.
[No Author Listed], tumor necrosis factor receptor superfamily member 9 precursor [Homo sapiens]. NCBI Reference Sequence: NP_001552.2. Jun. 9, 2024. Retrieved from https://www.ncbi.nlm.nih.gov/protein/NP_001552.2. 4 pages.
Badri et al., Optimization of radiation dosing schedules for proneural glioblastoma. J Math Biol. Apr. 2016;72(5):1301-36. doi: 10.1007/s00285-015-0908-x.
Baylot et al., TCTP Has a Crucial Role in the Different Stages of Prostate Cancer Malignant Progression. Results Probl Cell Differ. 2017;64:255-261. doi: 10.1007/978-3-319-67591-6_13.
Brinkmann et al., The making of bispecific antibodies. MAbs. Feb./Mar. 2017;9(2):182-212. doi: 10.1080/19420862.2016.1268307.
Chen et al., Enhancement and destruction of antibody function by somatic mutation: unequal occurrence is controlled by V gene combinatorial associations. Embo J. Jun. 15, 1995;14(12):2784-94. doi: 10.1002/j.1460-2075.1995.tb07278.x.
Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.
Koenig et al., Mutational landscape of antibody variable domains reveals a switch modulating the interdomain conformational dynamics and antigen binding. Proc Natl Acad Sci U S A. Jan. 24, 2017;114(4):E486-E495. doi: 10.1073/pnas.1613231114. Epub Jan. 5, 2017.
Kussie et al., A single engineered amino acid substitution changes antibody fine specificity. J Immunol. Jan. 1, 1994;152(1):146-52.
Lo et al., Effector-attenuating Substitutions That Maintain Antibody Stability and Reduce Toxicity in Mice. J Biol Chem. Mar. 3, 2017;292(9):3900-3908. doi: 10.1074/jbc.M116.767749. Epub Jan. 11, 2017.
Muller et al., Spliceosomal peptide P140 for immunotherapy of systemic lupus erythematosus: results of an early phase II clinical trial. Arthritis Rheum. Dec. 2008;58(12):3873-83. doi: 10.1002/art.24027.
Seckinger et al., Development and characterization of NILK-2301, a novel CEACAM5xCD3 KA bispecific antibody for immunotherapy of CEACAM5-expressing cancers. J Hematol Oncol. Dec. 12, 2023;16(1):117. doi: 10.1186/s13045-023-01516-3.
Shen et al., Single variable domain-IgG fusion. A novel recombinant approach to Fc domain-containing bispecific antibodies. J Biol Chem. Apr. 21, 2006;281(16):10706-14. doi: 10.1074/jbc.M513415200. Epub Feb. 15, 2006.
Torres et al., The immunoglobulin constant region contributes to affinity and specificity. Trends Immunol. Feb. 2008;29(2):91-7. doi: 10.1016/j.it.2007.11.004. Epub Jan. 10, 2008.

* cited by examiner

| | | | | | | | | | | | | | | | AB | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IMGT | 1.4 | 1.3 | 1.2 | 1.1 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 35 | 36 | 37 | 38 | 39 | 40 | 41 | 42 |
| IMGT exon numbering | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
| EU numbering | 341 | 342 | 343 | 344 | 345 | 346 | 347 | 348 | 349 | 350 | 351 | 352 | 353 | 354 | 355 | 356 | 357 | 358 | 359 | 360 | 361 | 362 | 363 | 364 | 365 | 366 | 367 | 368 | 369 | 370 | 371 | 372 | 373 | 374 | 375 | 376 | 377 | 378 | 379 | 380 | 381 | 382 |
| Kabat numbering | 361 | 363 | 364 | 365 | 366 | 367 | 368 | 369 | 370 | 371 | 372 | 373 | 374 | 375 | 376 | 377 | 378 | 381 | 382 | 383 | 384 | 385 | 386 | 387 | 388 | 389 | 390 | 391 | 392 | 393 | 394 | 395 | 396 | 397 | 398 | 399 | 400 | 401 | 402 | 405 | 406 | 407 |
| **Wt Fcab** (SEQ ID NO: 4) | G | Q | P | R | E | P | Q | V | Y | T | L | P | P | S | R | D | E | L | T | K | N | Q | V | S | L | T | C | L | V | K | G | F | Y | P | S | D | I | A | V | E | W | E |
| FS20-11 (SEQ ID NOs: 10-11) | | | | | | | | | | | | | | | | | | T | S | E | E | N | | | | | | | | | | | | | | | | | | | | |
| FS20-11-127 (SEQ ID NO: 15) | | | | | | | | | | | | | | | | E | | D | D | N | D | ~ | | | | | | | | | | | | | | | | | | | | |
| FS20-11-131 (SEQ ID NO: 24) | | | | | | | | | | | | | | | | E | | D | D | N | D | ~ | | | | | | | | | | | | | | | | | | | | |
| FS20-11-134 (SEQ ID NO: 33) | | | | | | | | | | | | | | | | E | | D | D | N | D | ~ | | | | | | | | | | | | | | | | | | | | |
| FS20-22 (SEQ ID NOs: 41-42) | | | | | | | | | | | | | | | | | | Y | W | D | Q | E | | | | | | | | | | | | | | | | | | | | |
| FS20-22-38 (SEQ ID NO: 46) | | | | | | | | | | | | | | | | | | Y | W | D | Q | E | | | | | | | | | | | | | | | | | | | | |
| FS20-22-41 (SEQ ID NO: 55) | | | | | | | | | | | | | | | | | | Y | W | D | Q | E | | | | | | | | | | | | | | | | | | | | |
| FS20-22-47 (SEQ ID NO: 63) | | | | | | | | | | | | | | | | | | Y | W | D | Q | E | | | | | | | | | | | | | | | | | | | | |
| FS20-22-49 (SEQ ID NO: 72) | | | | | | | | | | | | | | | | | | Y | W | D | Q | E | | | | | | | | | | | | | | | | | | | | |
| FS20-22-85 (SEQ ID NO: 81) | | | | | | | | | | | | | | | | | | Y | W | D | Q | E | | | | | | | | | | | | | | | | | | | | |
| FS20-31 (SEQ ID NOs: 89-90) | | | | | | | | | | | | | | | | | | Y | Y | S | G | E | | | | | | | | | | | | | | | | | | | | |
| FS20-31-58 (SEQ ID NO: 94) | | | | | | | | | | | | | | | | | | Y | Y | S | G | E | | | | | | | | | | | | | | | | | | | | |
| FS20-31-66 (SEQ ID NO: 103) | | | | | | | | | | | | | | | | | | Y | Y | S | G | E | | | | | | | | | | | | | | | | | | | | |
| FS20-31-94 (SEQ ID NO: 114) | | | | | | | | | | | | | | | | | | W | E | H | G | E | | | | | | | | | | | | | | | | | | | | |
| FS20-31-102 (SEQ ID NO: 124) | | | | | | | | | | | | | | | | | | W | A | S | G | E | | | | | | | | | | | | | | | | | | | | |
| FS20-31-108 (SEQ ID NO: 134) | | | | | | | | | | | | | | | | | | W | A | S | G | E | | | | | | | | | | | | | | | | | | | | |
| FS20-31-115 (SEQ ID NO: 143) | | | | | | | | | | | | | | | | | | W | A | S | G | E | | | | | | | | | | | | | | | | | | | | |

Figure 1A

| | CD | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| IMGT | 43 | 44 | 45 | 45.1 | 45.2 | 45.3 | 45.4 | 77 | 78 | 79 | 80 | 81 | 82 | 83 | 84 | 84.1 | 84.2 | 84.3 | 84.4 | 85.4 | 85.3 | 85.2 | 85.1 | 85 | 86 | 87 | 88 | 89 | 90 | 91 |
| IMGT exon numbering | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 |
| EU numbering | 383 | 384 | 385 | 386 | 387 | 388 | 389 | 390 | 391 | 392 | 393 | 394 | 395 | 396 | 397 | 398 | 399 | 400 | 401 | 402 | 403 | 404 | 405 | 406 | 407 | 408 | 409 | 410 | 411 | 412 |
| Kabat numbering | 408 | 410 | 411 | 414 | 415 | 416 | 417 | 418 | 419 | 420 | 421 | 422 | 423 | 424 | 425 | 426 | 427 | 428 | 430 | 433 | 434 | 435 | 436 | 437 | 438 | 439 | 440 | 441 | 442 | 443 |
| **Wt Fcab** (SEQ ID NO: 4) | S | N | G | Q | P | E | N | N | Y | K | T | T | P | P | V | L | D | S | D | G | S | F | F | L | Y | S | K | L | T | V |
| FS20-11 (SEQ ID NOs: 10-11) | | | | | | | | | | | | | | | | | | | | | | | | | | | | | | |
| FS20-11-127 (SEQ ID NO: 15) | | | | I | | I | G | P | | | | | | | | | | | | | | | | | | | | | | |
| FS20-11-131 (SEQ ID NO: 24) | | | | I | | I | G | P | | | | | | | | | | | | | | | | | | | | | | |
| FS20-11-134 (SEQ ID NO: 33) | | | | I | | I | G | P | | | | | | | | | | | | | | | | | | | | | | |
| FS20-22 (SEQ ID NOs: 41-42) | | | | | | | | | | | | | | | | | | | | | | | | | | | | | | |
| FS20-22-38 (SEQ ID NO: 46) | | | | A | E | K | Y | Q | | | | | | | | | | | | | | | | | | | | | | |
| FS20-22-41 (SEQ ID NO: 55) | | | | D | E | Q | F | A | | | | | | | | | | | | | | | | | | | | | | |
| FS20-22-47 (SEQ ID NO: 63) | | | | D | E | Q | F | A | | | | | | | | | | | | | | | | | | | | | | |
| FS20-22-49 (SEQ ID NO: 72) | | | | D | E | Q | F | A | | | | | | | | | | | | | | | | | | | | | | |
| FS20-22-85 (SEQ ID NO: 81) | | | | D | E | Q | F | A | | | | | | | | | | | | | | | | | | | | | | L |
| FS20-31 (SEQ ID NOs: 89-90) | | | | | | | | D | | | | | | | | | | | | | | | | | | | | | | |
| FS20-31-58 (SEQ ID NO: 94) | | | | | | | | D | | | | | | | | | | | | | | | | | | | | | | |
| FS20-31-66 (SEQ ID NO: 103) | | | | | | | | D | | | | | | | | | | | | | | | | | | | | | | |
| FS20-31-94 (SEQ ID NO: 114) | | | | I | R | | H | D | | | | | | | | | | | | | | | | | | | | | | |
| FS20-31-102 (SEQ ID NO: 124) | | | | | | | V | D | | | | | | | | | | | | | | | | | | | | | | |
| FS20-31-108 (SEQ ID NO: 134) | | | | E | K | | I | D | | | | | | | | | | | | | | | | | | | | | | |
| FS20-31-115 (SEQ ID NO: 143) | | | | E | Q | | F | D | | | | | | | | | | | | | | | | | | | | | | |

Figure 1B

| | EF | | | | | | | | | | | | | |
|---|---|---|---|---|---|---|---|---|---|---|---|---|---|---|
| IMGT | 92 | 93 | 94 | 95 | 96 | 97 | 98 | 99 | 100 | 101 | 101.1 | 101.2 | 101.3 | 101.4 |
| IMGT exon numbering | 73 | 74 | 75 | 76 | 77 | 78 | 79 | 80 | 81 | 82 | | | | |
| EU numbering | 413 | 414 | 415 | 416 | 417 | 418 | 419 | 420 | 421 | 422 | | | | |
| Kabat numbering | 444 | 445 | 446 | 447 | 448 | 449 | 450 | 451 | 452 | 453 | | | | |
| **Wt Fcab** (SEQ ID NO: 4) | D | K | S | R | W | Q | Q | G | N | V | | | | |
| FS20-11 (SEQ ID NOs: 10-11) | | | | | | W | K | H | Y | | D | E | H | P |
| FS20-11-127 (SEQ ID NO: 15) | | | | | | W | R | H | Y | | E | E | H | P |
| FS20-11-131 (SEQ ID NO: 24) | | | N | | | W | K | H | Y | | D | E | H | P |
| FS20-11-134 (SEQ ID NO: 33) | | | | | | W | K | H | Y | | E | E | H | P |
| FS20-22 (SEQ ID NOs: 41-42) | | Q | Y | | | N | P | | G | Y | | | | |
| FS20-22-38 (SEQ ID NO: 46) | | Q | Y | | | N | P | | D | Y | | | | |
| FS20-22-41 (SEQ ID NO: 55) | | Q | Y | | | N | P | | D | Y | | | | |
| FS20-22-47 (SEQ ID NO: 63) | | Q | Y | | | S | P | | D | Y | | | | |
| FS20-22-49 (SEQ ID NO: 72) | | Q | Y | | | N | P | A | D | Y | | | | |
| FS20-22-85 (SEQ ID NO: 81) | | Q | Y | | | N | P | F | D | D | | | | |
| FS20-31 (SEQ ID NOs: 89-90) | P | Y | W | | | G | G | P | G | T | | | | |
| FS20-31-58 (SEQ ID NO: 94) | P | Y | W | | | G | S | P | R | T | | | | |
| FS20-31-66 (SEQ ID NO: 103) | P | Y | W | | | G | V | P | R | T | | | | |
| FS20-31-94 (SEQ ID NO: 114) | P | Y | W | | | G | G | P | G | T | | | | |
| FS20-31-102 (SEQ ID NO: 124) | P | Y | W | | | G | V | P | R | T | | | | |
| FS20-31-108 (SEQ ID NO: 134) | P | Y | W | | | G | A | K | R | T | | | | |
| FS20-31-115 (SEQ ID NO: 143) | P | Y | W | | | G | A | K | R | T | | | | |

| IMGT | 102 | 103 | 104 | 105 | 106 | 107 | 108 | 109 | 110 | 112 | 113 | 114 | 115 | 116 | 117 | 118 | 119 | 120 | 121 | 122 | 123 | 124 | 125 | 129 |
|---|---|---|---|---|---|---|---|---|---|---|---|---|---|---|---|---|---|---|---|---|---|---|---|---|
| IMGT exon numbering | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | CHS 106 |
| EU numbering | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 |
| Kabat numbering | 454 | 455 | 456 | 457 | 458 | 459 | 460 | 461 | 462 | 463 | 464 | 465 | 466 | 467 | 468 | 469 | 470 | 471 | 472 | 473 | 474 | 475 | 476 | 477 |
| **Wt Fcab** (SEQ ID NO: 4) | F | S | C | S | V | M | H | E | A | L | H | N | H | Y | T | Q | K | S | L | S | L | S | P | G |
| FS20-11 (SEQ ID NOs: 10-11) | | L | | | | | | | | | | | | | | | E | | | | | | | |
| FS20-11-127 (SEQ ID NO: 15) | | L | | | | | | | | | | | | | | | | | | | | | | |
| FS20-11-131 (SEQ ID NO: 24) | | L | | | | | | | | | | | | | | | | | | | | | | |
| FS20-11-134 (SEQ ID NO: 33) | | L | | | | | | | | | | | | | | | | | | | | | | |
| FS20-22 (SEQ ID NOs: 41-42) | | | | | | | | | | | | | | | | | | | | | | | | |
| FS20-22-38 (SEQ ID NO: 46) | | | | | | | | | | | | | | | | | | | | | | | | |
| FS20-22-41 (SEQ ID NO: 55) | | | | | | | | | | | | | | | | | | | | | | | | |
| FS20-22-47 (SEQ ID NO: 63) | | | | | | | | | | | | | | | | | | | | | | | | |
| FS20-22-49 (SEQ ID NO: 72) | | | | | | | | | | | | | | | | | | | | | | | | |
| FS20-22-85 (SEQ ID NO: 81) | | | | | | | | | | | | | | | | | | | | | | | | |
| FS20-31 (SEQ ID NOs: 89-90) | | | | | | | | | | | | | | | | | | | | | | | | |
| FS20-31-58 (SEQ ID NO: 94) | | | | | | | | | | | | | | | | | | | | | | | | |
| FS20-31-66 (SEQ ID NO: 103) | | | | | | | | | | | | | | | | | | | | | | | | |
| FS20-31-94 (SEQ ID NO: 114) | | | | | | | | | | | | | | | | | | | | | | | | |
| FS20-31-102 (SEQ ID NO: 124) | | | | | | | | | | | | | | | | | | | | | | | | |
| FS20-31-108 (SEQ ID NO: 134) | | | | | | | | | | | | | | | | | | | | | | | | |
| FS20-31-115 (SEQ ID NO: 143) | | | | | | | | | | | | | | | | | | | | | | | | |

Figure 1C

A
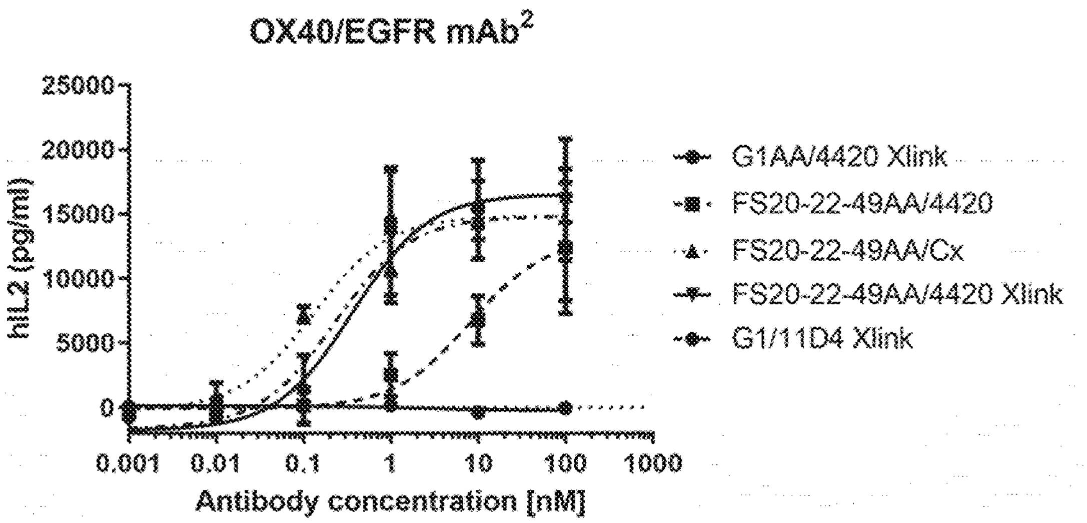
B
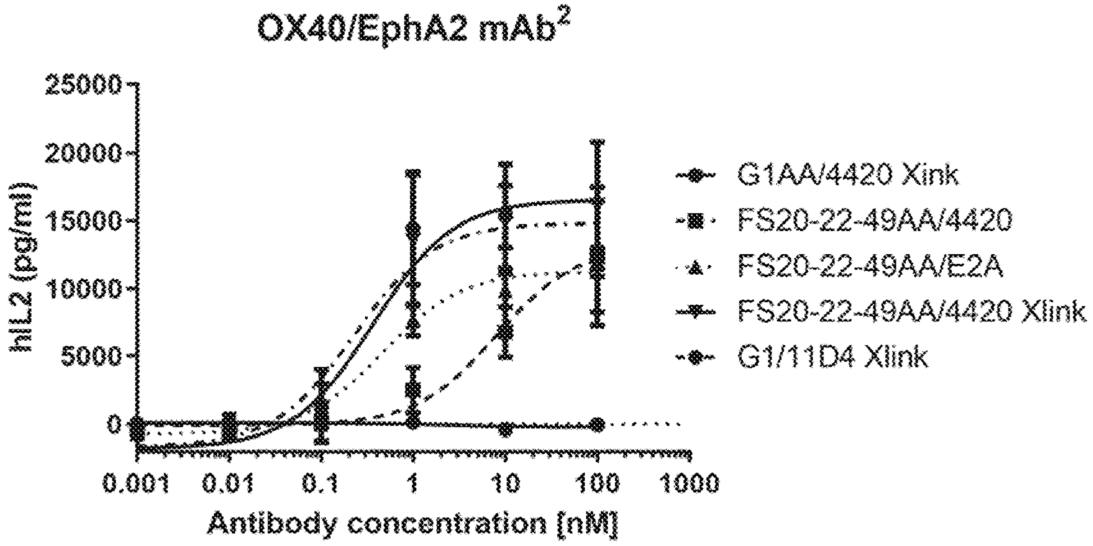
Figure 4

C
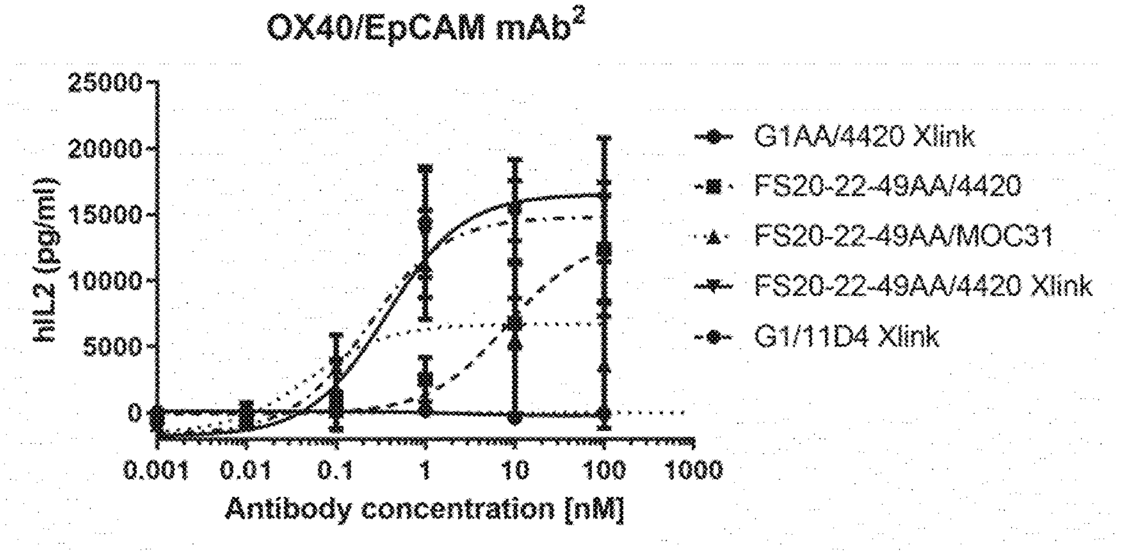
D
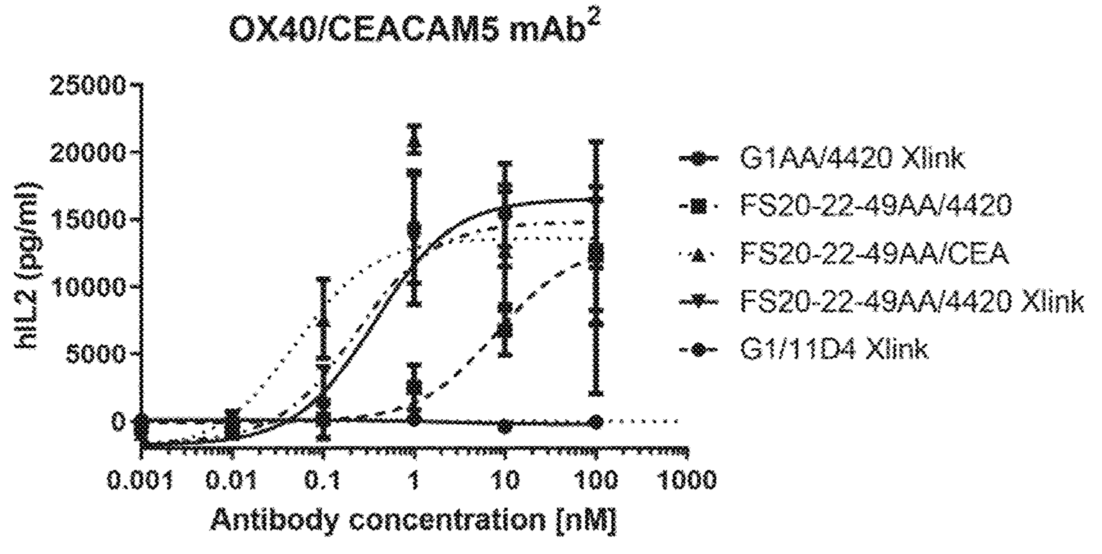
Figure 4 continued

A
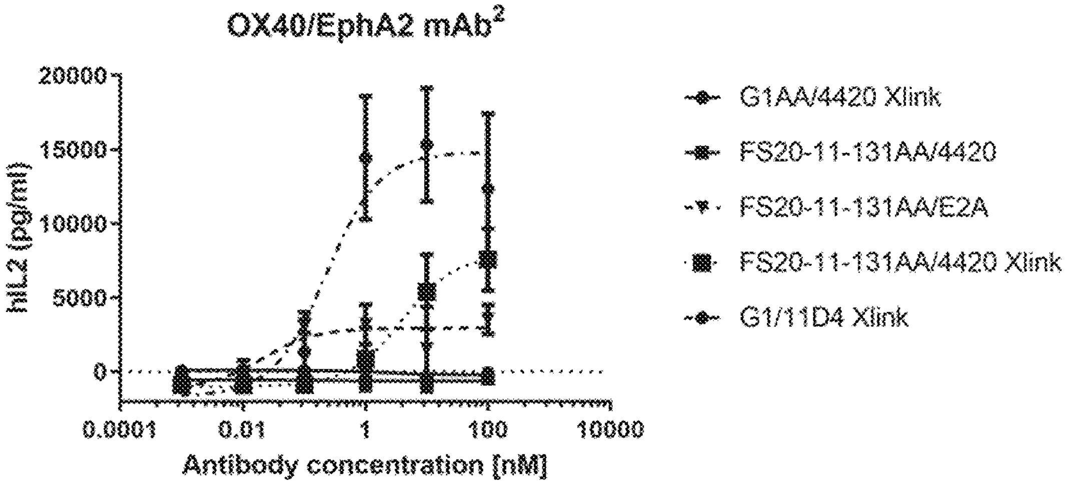
B
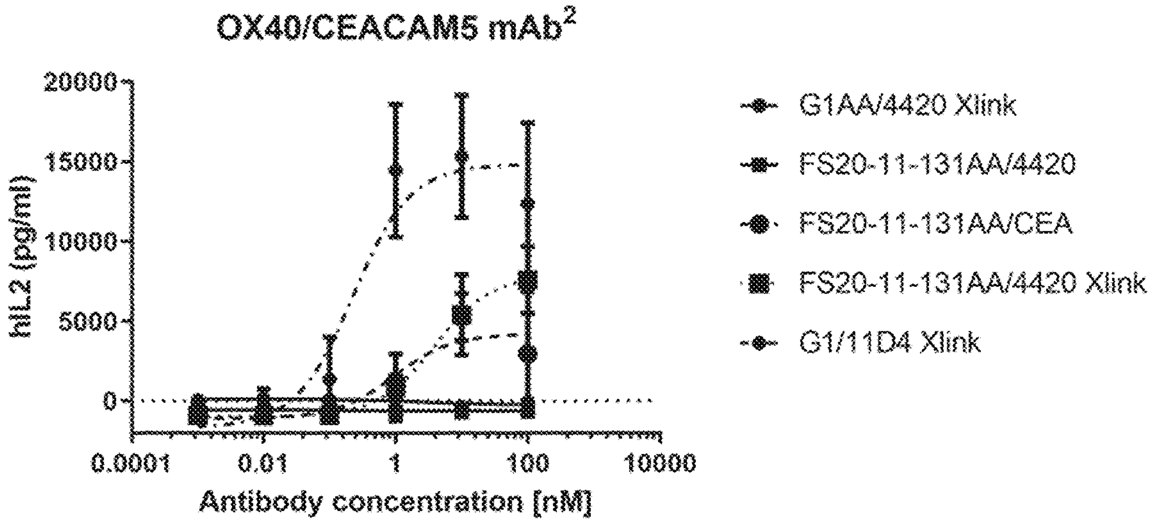
Figure 5

SEQUENCE LISTING

```
<160> NUMBER OF SEQ ID NOS: 193

<210> SEQ ID NO 1
<211> LENGTH: 8
<212> TYPE: PRT
<213> ORGANISM: Artificial Sequence
<220> FEATURE:
<223> OTHER INFORMATION: CH3 WT Fcab AB loop

<400> SEQUENCE: 1

Arg Asp Glu Leu Thr Lys Asn Gln
1               5


<210> SEQ ID NO 2
<211> LENGTH: 9
<212> TYPE: PRT
<213> ORGANISM: Artificial Sequence
<220> FEATURE:
<223> OTHER INFORMATION: CH3 WT Fcab CD loop

<400> SEQUENCE: 2

Ser Asn Gly Gln Pro Glu Asn Asn Tyr
1               5


<210> SEQ ID NO 3
<211> LENGTH: 10
<212> TYPE: PRT
<213> ORGANISM: Artificial Sequence
<220> FEATURE:
```

<223> OTHER INFORMATION: CH3 WT Fcab EF loop

<400> SEQUENCE: 3

```
Asp Lys Ser Arg Trp Gln Gln Gly Asn Val
1               5                   10
```

<210> SEQ ID NO 4
<211> LENGTH: 106
<212> TYPE: PRT
<213> ORGANISM: Artificial Sequence
<220> FEATURE:
<223> OTHER INFORMATION: WT Fcab CH3 domain

<400> SEQUENCE: 4

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 5
<211> LENGTH: 110
<212> TYPE: PRT
<213> ORGANISM: Artificial Sequence
<220> FEATURE:
<223> OTHER INFORMATION: Fcab CH2 domain

<400> SEQUENCE: 5

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 6
<211> LENGTH: 110
<212> TYPE: PRT
<213> ORGANISM: Artificial Sequence
<220> FEATURE:
<223> OTHER INFORMATION: Fcab CH2 domain with LALA mutation

<400> SEQUENCE: 6

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 7
<211> LENGTH: 110
<212> TYPE: PRT
<213> ORGANISM: Artificial Sequence
<220> FEATURE:
<223> OTHER INFORMATION: Fcab CH2 domain with LALA-PA mutation

<400> SEQUENCE: 7

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Ala Ala Pro Ile Glu Lys Thr Ile Ser Lys Ala Lys
            100                 105                 110


<210> SEQ ID NO 8
<211> LENGTH: 223
<212> TYPE: PRT
<213> ORGANISM: Artificial Sequence
<220> FEATURE:
<223> OTHER INFORMATION: WT Fcab with LALA mutation

<400> SEQUENCE: 8

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95
```

```
Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220


<210> SEQ ID NO 9
<211> LENGTH: 222
<212> TYPE: PRT
<213> ORGANISM: Artificial Sequence
<220> FEATURE:
<223> OTHER INFORMATION: WT Fcab without LALA mutation

<400> SEQUENCE: 9

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 10
```

-continued

<211> LENGTH: 226
<212> TYPE: PRT
<213> ORGANISM: Artificial Sequence
<220> FEATURE:
<223> OTHER INFORMATION: Fcab FS20-11 with LALA mutation

<400> SEQUENCE: 10

```
Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Thr Ser Glu Glu Asn Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Trp Lys His Tyr Val Asp Glu His Pro Phe Leu Cys Ser Val Met
        195                 200                 205

His Glu Ala Leu His Asn His Tyr Thr Gln Glu Ser Leu Ser Leu Ser
    210                 215                 220

Pro Gly
225
```

<210> SEQ ID NO 11
<211> LENGTH: 226
<212> TYPE: PRT
<213> ORGANISM: Artificial Sequence
<220> FEATURE:
<223> OTHER INFORMATION: Fcab FS20-11 without LALA mutation

<400> SEQUENCE: 11

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
```

```
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Thr Ser Glu Glu Asn Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Trp Lys His Tyr Val Asp Glu His Pro Phe Leu Cys Ser Val Met
        195                 200                 205

His Glu Ala Leu His Asn His Tyr Thr Gln Glu Ser Leu Ser Leu Ser
    210                 215                 220

Pro Gly
225


<210> SEQ ID NO 12
<211> LENGTH: 4
<212> TYPE: PRT
<213> ORGANISM: Artificial Sequence
<220> FEATURE:
<223> OTHER INFORMATION: Fcab FS20-11-127 CH3 domain structural loop
      sequences

<400> SEQUENCE: 12

Asp Asp Asn Asp
1


<210> SEQ ID NO 13
<211> LENGTH: 5
<212> TYPE: PRT
<213> ORGANISM: Artificial Sequence
<220> FEATURE:
<223> OTHER INFORMATION: Fcab FS20-11-127 CH3 domain structural loop
      sequences

<400> SEQUENCE: 13

Ile Pro Ile Gly Pro
1               5


<210> SEQ ID NO 14
<211> LENGTH: 9
<212> TYPE: PRT
<213> ORGANISM: Artificial Sequence
<220> FEATURE:
<223> OTHER INFORMATION: Fcab FS20-11-127 CH3 domain structural loop
      sequences

<400> SEQUENCE: 14

Trp Arg His Tyr Val Glu Glu His Pro
1               5


<210> SEQ ID NO 15
<211> LENGTH: 109
<212> TYPE: PRT
<213> ORGANISM: Artificial Sequence
<220> FEATURE:
<223> OTHER INFORMATION: Fcab FS20-11-127 CH3 domain
```

<400> SEQUENCE: 15

Gly Gln Pro Arg Glu Pro Gln Val Tyr Thr Leu Pro Pro Ser Arg Glu
1               5                   10                  15

Glu Asp Asp Asn Asp Val Ser Leu Thr Cys Leu Val Lys Gly Phe Tyr
            20                  25                  30

Pro Ser Asp Ile Ala Val Glu Trp Glu Ser Asn Gly Ile Pro Ile Gly
        35                  40                  45

Pro Tyr Lys Thr Thr Pro Pro Val Leu Asp Ser Asp Gly Ser Phe Phe
    50                  55                  60

Leu Tyr Ser Lys Leu Thr Val Asp Lys Ser Arg Trp Trp Arg His Tyr
65                  70                  75                  80

Val Glu Glu His Pro Phe Leu Cys Ser Val Met His Glu Ala Leu His
                85                  90                  95

Asn His Tyr Thr Gln Lys Ser Leu Ser Leu Ser Pro Gly
            100                 105

<210> SEQ ID NO 16
<211> LENGTH: 327
<212> TYPE: DNA
<213> ORGANISM: Artificial Sequence
<220> FEATURE:
<223> OTHER INFORMATION: Fcab FS20-11-127 CH3 domain

<400> SEQUENCE: 16
ggacagcctc gagaaccaca ggtgtacacc ctgcccccat cccgggagga agatgataac 60
gatgtcagcc tgacctgcct ggtcaaaggc ttctatccca gcgacatcgc cgtggagtgg 120
gagagcaatg ggatcccaat cggtccatac aagaccacgc ctcccgtgct ggactccgac 180
ggctccttct tcctctacag caagctcacc gtggacaaga gcagatggtg gaggcattat 240
gttgaggagc atccgttctt gtgctccgtg atgcatgagg ctctgcacaa ccactacact 300
cagaagagct tgtccctgtc gcccgga 327

<210> SEQ ID NO 17
<211> LENGTH: 225
<212> TYPE: PRT
<213> ORGANISM: Artificial Sequence
<220> FEATURE:
<223> OTHER INFORMATION: Fcab FS20-11-127 with LALA mutation

<400> SEQUENCE: 17

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

```
Pro Ser Arg Glu Glu Asp Asp Asn Asp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Ile Pro Ile Gly Pro Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Trp Arg His Tyr Val Glu Glu His Pro Phe Leu Cys Ser Val Met His
        195                 200                 205

Glu Ala Leu His Asn His Tyr Thr Gln Lys Ser Leu Ser Leu Ser Pro
    210                 215                 220

Gly
225
```

<210> SEQ ID NO 18
<211> LENGTH: 675
<212> TYPE: DNA
<213> ORGANISM: Artificial Sequence
<220> FEATURE:
<223> OTHER INFORMATION: Fcab FS20-11-127 with LALA mutation

<400> SEQUENCE: 18

```
acttgcccgc cttgcccagc cccggaagct gccggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg acagcctcga    360

gaaccacagg tgtacaccct gcccccatcc cgggaggaag atgataacga tgtcagcctg    420

acctgcctgg tcaaaggctt ctatcccagc gacatcgccg tggagtggga gagcaatggg    480

atcccaatcg gtccatacaa gaccacgcct cccgtgctgg actccgacgg ctccttcttc    540

ctctacagca agctcaccgt ggacaagagc agatggtgga ggcattatgt tgaggagcat    600

ccgttcttgt gctccgtgat gcatgaggct ctgcacaacc actacactca gaagagcttg    660

tccctgtcgc ccgga                                                     675
```

<210> SEQ ID NO 19
<211> LENGTH: 225
<212> TYPE: PRT
<213> ORGANISM: Artificial Sequence
<220> FEATURE:
<223> OTHER INFORMATION: Fcab FS20-11-127 without LALA mutation

<400> SEQUENCE: 19

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80
```

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Glu Glu Asp Asp Asn Asp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Ile Pro Ile Gly Pro Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Trp Arg His Tyr Val Glu Glu His Pro Phe Leu Cys Ser Val Met His
        195                 200                 205

Glu Ala Leu His Asn His Tyr Thr Gln Lys Ser Leu Ser Leu Ser Pro
    210                 215                 220

Gly
225

<210> SEQ ID NO 20
<211> LENGTH: 675
<212> TYPE: DNA
<213> ORGANISM: Artificial Sequence
<220> FEATURE:
<223> OTHER INFORMATION: Fcab FS20-11-127 without LALA mutation

<400> SEQUENCE: 20
acttgcccgc cttgcccagc cccggaactg ctgggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg acagcctcga 360
gaaccacagg tgtacaccct gcccccatcc cgggaggaag atgataacga tgtcagcctg 420
acctgcctgg tcaaaggctt ctatcccagc gacatcgccg tggagtggga gagcaatggg 480
atcccaatcg gtccatacaa gaccacgcct cccgtgctgg actccgacgg ctccttcttc 540
ctctacagca agctcaccgt ggacaagagc agatggtgga ggcattatgt tgaggagcat 600
ccgttcttgt gctccgtgat gcatgaggct ctgcacaacc actacactca gaagagcttg 660
tccctgtcgc ccgga 675

<210> SEQ ID NO 21
<211> LENGTH: 450
<212> TYPE: PRT
<213> ORGANISM: Artificial Sequence
<220> FEATURE:
<223> OTHER INFORMATION: Heavy chain of FS20-11-127/4420 mock mAb? with
      LALA mutation

<400> SEQUENCE: 21

Glu Val Lys Leu Asp Glu Thr Gly Gly Gly Leu Val Gln Pro Gly Arg
1               5                   10                  15

-continued

```
Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Asp Asp Asn Asp Val Ser Leu Thr Cys Leu
        355                 360                 365

Val Lys Gly Phe Tyr Pro Ser Asp Ile Ala Val Glu Trp Glu Ser Asn
    370                 375                 380

Gly Ile Pro Ile Gly Pro Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Trp Arg His Tyr Val Glu Glu His Pro Phe Leu Cys Ser Val Met
            420                 425                 430

His Glu Ala Leu His Asn His Tyr Thr Gln Lys Ser Leu Ser Leu Ser
```

```
        435                 440                 445

Pro Gly
    450


<210> SEQ ID NO 22
<211> LENGTH: 450
<212> TYPE: PRT
<213> ORGANISM: Artificial Sequence
<220> FEATURE:
<223> OTHER INFORMATION: Heavy chain of FS20-11-127/4420 mock mAb?
      without LALA mutation

<400> SEQUENCE: 22

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Glu Glu Asp Asp Asn Asp Val Ser Leu Thr Cys Leu
        355                 360                 365

Val Lys Gly Phe Tyr Pro Ser Asp Ile Ala Val Glu Trp Glu Ser Asn
    370                 375                 380

Gly Ile Pro Ile Gly Pro Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Trp Arg His Tyr Val Glu Glu His Pro Phe Leu Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 23
<211> LENGTH: 9
<212> TYPE: PRT
<213> ORGANISM: Artificial Sequence
<220> FEATURE:
<223> OTHER INFORMATION: Fcab FS20-11-131 CH3 domain structural loop
      sequence

<400> SEQUENCE: 23

Trp Lys His Tyr Val Asp Glu His Pro
1               5


<210> SEQ ID NO 24
<211> LENGTH: 109
<212> TYPE: PRT
<213> ORGANISM: Artificial Sequence
<220> FEATURE:
<223> OTHER INFORMATION: Fcab FS20-11-131 CH3 domain

<400> SEQUENCE: 24

Gly Gln Pro Arg Glu Pro Gln Val Tyr Thr Leu Pro Pro Ser Arg Glu
1               5                   10                  15

Glu Asp Asp Asn Asp Val Ser Leu Thr Cys Leu Val Lys Gly Phe Tyr
            20                  25                  30

Pro Ser Asp Ile Ala Val Glu Trp Glu Ser Asn Gly Ile Pro Ile Gly
        35                  40                  45

Pro Tyr Lys Thr Thr Pro Pro Val Leu Asp Ser Asp Gly Ser Phe Phe
    50                  55                  60

Leu Tyr Ser Lys Leu Thr Val Asp Lys Asn Arg Trp Trp Lys His Tyr
65                  70                  75                  80

Val Asp Glu His Pro Phe Leu Cys Ser Val Met His Glu Ala Leu His
                85                  90                  95

Asn His Tyr Thr Gln Lys Ser Leu Ser Leu Ser Pro Gly
            100                 105


<210> SEQ ID NO 25
<211> LENGTH: 327
<212> TYPE: DNA
<213> ORGANISM: Artificial Sequence
<220> FEATURE:
<223> OTHER INFORMATION: Fcab FS20-11-131 CH3 domain

<400> SEQUENCE: 25
```

-continued

```
ggacagcctc gagaaccaca ggtgtacacc ctgcccccat cccgggagga agatgataac      60

gatgtcagcc tgacctgcct ggtcaaaggc ttctatccca gcgacatcgc cgtggagtgg     120

gagagcaatg ggatcccaat cggtccatac aagaccacgc ctcccgtgct ggactccgac     180

ggctccttct tcctctacag caagctcacc gtggacaaga acagatggtg gaagcattat     240

gttgatgagc atccgttctt gtgctccgtg atgcatgagg ctctgcacaa ccactacact     300

cagaagagct tgtccctgtc gcccgga                                         327


<210> SEQ ID NO 26
<211> LENGTH: 225
<212> TYPE: PRT
<213> ORGANISM: Artificial Sequence
<220> FEATURE:
<223> OTHER INFORMATION: Fcab FS20-11-131 with LALA mutation

<400> SEQUENCE: 26

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Glu Glu Asp Asp Asn Asp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Ile Pro Ile Gly Pro Tyr Lys Thr Thr Pro Pro Val Leu Asp Ser Asp
                165                 170                 175

Gly Ser Phe Phe Leu Tyr Ser Lys Leu Thr Val Asp Lys Asn Arg Trp
            180                 185                 190

Trp Lys His Tyr Val Asp Glu His Pro Phe Leu Cys Ser Val Met His
        195                 200                 205

Glu Ala Leu His Asn His Tyr Thr Gln Lys Ser Leu Ser Leu Ser Pro
    210                 215                 220

Gly
225


<210> SEQ ID NO 27
<211> LENGTH: 675
<212> TYPE: DNA
<213> ORGANISM: Artificial Sequence
<220> FEATURE:
<223> OTHER INFORMATION: Fcab FS20-11-131 with LALA mutation

<400> SEQUENCE: 27

acttgcccgc cttgcccagc cccggaagct gccggtggtc cttcggtgtt cctcttcccg      60
```

-continued

```
cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg acagcctcga    360

gaaccacagg tgtacaccct gcccccatcc cgggaggaag atgataacga tgtcagcctg    420

acctgcctgg tcaaaggctt ctatcccagc gacatcgccg tggagtggga gagcaatggg    480

atcccaatcg gtccatacaa gaccacgcct cccgtgctgg actccgacgg ctccttcttc    540

ctctacagca agctcaccgt ggacaagaac agatggtgga agcattatgt tgatgagcat    600

ccgttcttgt gctccgtgat gcatgaggct ctgcacaacc actacactca gaagagcttg    660

tccctgtcgc ccgga                                                      675


<210> SEQ ID NO 28
<211> LENGTH: 225
<212> TYPE: PRT
<213> ORGANISM: Artificial Sequence
<220> FEATURE:
<223> OTHER INFORMATION: Fcab FS20-11-131 without LALA mutation

<400> SEQUENCE: 28

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Glu Glu Asp Asp Asn Asp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Ile Pro Ile Gly Pro Tyr Lys Thr Thr Pro Pro Val Leu Asp Ser Asp
                165                 170                 175

Gly Ser Phe Phe Leu Tyr Ser Lys Leu Thr Val Asp Lys Asn Arg Trp
            180                 185                 190

Trp Lys His Tyr Val Asp Glu His Pro Phe Leu Cys Ser Val Met His
        195                 200                 205

Glu Ala Leu His Asn His Tyr Thr Gln Lys Ser Leu Ser Leu Ser Pro
    210                 215                 220

Gly
225


<210> SEQ ID NO 29
```

<211> LENGTH: 675
<212> TYPE: DNA
<213> ORGANISM: Artificial Sequence
<220> FEATURE:
<223> OTHER INFORMATION: Fcab FS20-11-131 without LALA mutation

<400> SEQUENCE: 29

```
acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg acagcctcga    360

gaaccacagg tgtacaccct gcccccatcc cgggaggaag atgataacga tgtcagcctg    420

acctgcctgg tcaaaggctt ctatcccagc gacatcgccg tggagtggga gagcaatggg    480

atcccaatcg gtccatacaa gaccacgcct cccgtgctgg actccgacgg ctccttcttc    540

ctctacagca agctcaccgt ggacaagaac agatggtgga agcattatgt tgatgagcat    600

ccgttcttgt gctccgtgat gcatgaggct ctgcacaacc actacactca gaagagcttg    660

tccctgtcgc ccgga                                                     675
```

<210> SEQ ID NO 30
<211> LENGTH: 450
<212> TYPE: PRT
<213> ORGANISM: Artificial Sequence
<220> FEATURE:
<223> OTHER INFORMATION: Heavy chain of FS20-11-131/4420 mock mAb? with LALA mutation

<400> SEQUENCE: 30

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Asp Asp Asn Asp Val Ser Leu Thr Cys Leu
355 360 365

Val Lys Gly Phe Tyr Pro Ser Asp Ile Ala Val Glu Trp Glu Ser Asn
370 375 380

Gly Ile Pro Ile Gly Pro Tyr Lys Thr Thr Pro Pro Val Leu Asp Ser
385 390 395 400

Asp Gly Ser Phe Phe Leu Tyr Ser Lys Leu Thr Val Asp Lys Asn Arg
405 410 415

Trp Trp Lys His Tyr Val Asp Glu His Pro Phe Leu Cys Ser Val Met
420 425 430

His Glu Ala Leu His Asn His Tyr Thr Gln Lys Ser Leu Ser Leu Ser
435 440 445

Pro Gly
450

<210> SEQ ID NO 31
<211> LENGTH: 450
<212> TYPE: PRT
<213> ORGANISM: Artificial Sequence
<220> FEATURE:
<223> OTHER INFORMATION: Heavy chain of FS20-11-131/4420 mock mAb? without LALA mutation

<400> SEQUENCE: 31

Glu Val Lys Leu Asp Glu Thr Gly Gly Gly Leu Val Gln Pro Gly Arg
1 5 10 15

Pro Met Lys Leu Ser Cys Val Ala Ser Gly Phe Thr Phe Ser Asp Tyr
20 25 30

Trp Met Asn Trp Val Arg Gln Ser Pro Glu Lys Gly Leu Glu Trp Val
35 40 45

Ala Gln Ile Arg Asn Lys Pro Tyr Asn Tyr Glu Thr Tyr Tyr Ser Asp
50 55 60

Ser Val Lys Gly Arg Phe Thr Ile Ser Arg Asp Asp Ser Lys Ser Ser
65 70 75 80

Val Tyr Leu Gln Met Asn Asn Leu Arg Val Glu Asp Met Gly Ile Tyr
85 90 95

```
Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Asp Asp Asn Asp Val Ser Leu Thr Cys Leu
        355                 360                 365

Val Lys Gly Phe Tyr Pro Ser Asp Ile Ala Val Glu Trp Glu Ser Asn
    370                 375                 380

Gly Ile Pro Ile Gly Pro Tyr Lys Thr Thr Pro Pro Val Leu Asp Ser
385                 390                 395                 400

Asp Gly Ser Phe Phe Leu Tyr Ser Lys Leu Thr Val Asp Lys Asn Arg
                405                 410                 415

Trp Trp Lys His Tyr Val Asp Glu His Pro Phe Leu Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 32
<211> LENGTH: 9
<212> TYPE: PRT
<213> ORGANISM: Artificial Sequence
<220> FEATURE:
<223> OTHER INFORMATION: Fcab FS20-11-134 CH3 domain structural loop sequence

<400> SEQUENCE: 32

Trp Lys His Tyr Val Glu Glu His Pro
1               5

<210> SEQ ID NO 33
<211> LENGTH: 109
<212> TYPE: PRT
<213> ORGANISM: Artificial Sequence
<220> FEATURE:
<223> OTHER INFORMATION: Fcab FS20-11-134 CH3 domain

<400> SEQUENCE: 33

Gly Gln Pro Arg Glu Pro Gln Val Tyr Thr Leu Pro Pro Ser Arg Glu
1               5                   10                  15

Glu Asp Asp Asn Asp Val Ser Leu Thr Cys Leu Val Lys Gly Phe Tyr
            20                  25                  30

Pro Ser Asp Ile Ala Val Glu Trp Glu Ser Asn Gly Ile Pro Ile Gly
        35                  40                  45

Pro Tyr Lys Thr Thr Pro Pro Val Leu Asp Ser Asp Gly Ser Phe Phe
    50                  55                  60

Leu Tyr Ser Lys Leu Thr Val Asp Lys Ser Arg Trp Trp Lys His Tyr
65                  70                  75                  80

Val Glu Glu His Pro Phe Leu Cys Ser Val Met His Glu Ala Leu His
                85                  90                  95

Asn His Tyr Thr Gln Lys Ser Leu Ser Leu Ser Pro Gly
            100                 105

<210> SEQ ID NO 34
<211> LENGTH: 327
<212> TYPE: DNA
<213> ORGANISM: Artificial Sequence
<220> FEATURE:
<223> OTHER INFORMATION: Fcab FS20-11-134 CH3 domain

<400> SEQUENCE: 34
ggacagcctc gagaaccaca ggtgtacacc ctgcccccat cccgggagga agatgataac     60
gatgtcagcc tgacctgcct ggtcaaaggc ttctatccca gcgacatcgc cgtggagtgg    120
gagagcaatg ggatcccaat cggtccatac aagaccacgc ctcccgtgct ggactccgac    180
ggctccttct tcctctacag caagctcacc gtggacaaga gcagatggtg gaagcattat    240
gttgaggagc atccgttctt gtgctccgtg atgcatgagg ctctgcacaa ccactacact    300
cagaagagct tgtccctgtc gcccgga                                        327

<210> SEQ ID NO 35
<211> LENGTH: 225
<212> TYPE: PRT
<213> ORGANISM: Artificial Sequence
<220> FEATURE:
<223> OTHER INFORMATION: Fcab FS20-11-134 with LALA mutation

<400> SEQUENCE: 35

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

```
Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Glu Glu Asp Asp Asn Asp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Ile Pro Ile Gly Pro Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Trp Lys His Tyr Val Glu Glu His Pro Phe Leu Cys Ser Val Met His
        195                 200                 205

Glu Ala Leu His Asn His Tyr Thr Gln Lys Ser Leu Ser Leu Ser Pro
    210                 215                 220

Gly
225


<210> SEQ ID NO 36
<211> LENGTH: 675
<212> TYPE: DNA
<213> ORGANISM: Artificial Sequence
<220> FEATURE:
<223> OTHER INFORMATION: Fcab FS20-11-134 with LALA mutation

<400> SEQUENCE: 36

acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg acagcctcga     360

gaaccacagg tgtacaccct gcccccatcc cgggaggaag atgataacga tgtcagcctg     420

acctgcctgg tcaaaggctt ctatcccagc gacatcgccg tggagtggga gagcaatggg     480

atcccaatcg gtccatacaa gaccacgcct cccgtgctgg actccgacgg ctccttcttc     540

ctctacagca agctcaccgt ggacaagagc agatggtgga agcattatgt tgaggagcat     600

ccgttcttgt gctccgtgat gcatgaggct ctgcacaacc actacactca gaagagcttg     660

tccctgtcgc ccgga                                                      675


<210> SEQ ID NO 37
<211> LENGTH: 225
<212> TYPE: PRT
<213> ORGANISM: Artificial Sequence
<220> FEATURE:
<223> OTHER INFORMATION: Fcab FS20-11-134 without LALA mutation

<400> SEQUENCE: 37

Thr Cys Pro Pro Cys Pro Ala Pro Glu Leu Leu Gly Gly Pro Ser Val
```

```
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Glu Glu Asp Asp Asn Asp Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Ile Pro Ile Gly Pro Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Trp Lys His Tyr Val Glu Glu His Pro Phe Leu Cys Ser Val Met His
        195                 200                 205

Glu Ala Leu His Asn His Tyr Thr Gln Lys Ser Leu Ser Leu Ser Pro
    210                 215                 220

Gly
225
```

<210> SEQ ID NO 38
<211> LENGTH: 675
<212> TYPE: DNA
<213> ORGANISM: Artificial Sequence
<220> FEATURE:
<223> OTHER INFORMATION: Fcab FS20-11-134 without LALA mutation

<400> SEQUENCE: 38

```
acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg acagcctcga    360

gaaccacagg tgtacaccct gcccccatcc cgggaggaag atgataacga tgtcagcctg    420

acctgcctgg tcaaaggctt ctatcccagc gacatcgccg tggagtggga gagcaatggg    480

atcccaatcg gtccatacaa gaccacgcct cccgtgctgg actccgacgg ctccttcttc    540

ctctacagca agctcaccgt ggacaagagc agatggtgga agcattatgt tgaggagcat    600

ccgttcttgt gctccgtgat gcatgaggct ctgcacaacc actacactca gaagagcttg    660

tccctgtcgc ccgga                                                     675
```

```
<210> SEQ ID NO 39
<211> LENGTH: 450
<212> TYPE: PRT
<213> ORGANISM: Artificial Sequence
<220> FEATURE:
<223> OTHER INFORMATION: Heavy chain of FS20-11-134/4420 mock mAb? with
      LALA mutation

<400> SEQUENCE: 39

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Asp Asp Asn Asp Val Ser Leu Thr Cys Leu
        355                 360                 365
```

```
Val Lys Gly Phe Tyr Pro Ser Asp Ile Ala Val Glu Trp Glu Ser Asn
    370                 375                 380

Gly Ile Pro Ile Gly Pro Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Trp Lys His Tyr Val Glu Glu His Pro Phe Leu Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 40
<211> LENGTH: 450
<212> TYPE: PRT
<213> ORGANISM: Artificial Sequence
<220> FEATURE:
<223> OTHER INFORMATION: Heavy chain of FS20-11-134/4420 mock mAb?
      without LALA mutation

<400> SEQUENCE: 40

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Asp Asp Asn Asp Val Ser Leu Thr Cys Leu
355 360 365

Val Lys Gly Phe Tyr Pro Ser Asp Ile Ala Val Glu Trp Glu Ser Asn
370 375 380

Gly Ile Pro Ile Gly Pro Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Trp Lys His Tyr Val Glu Glu His Pro Phe Leu Cys Ser Val Met
420 425 430

His Glu Ala Leu His Asn His Tyr Thr Gln Lys Ser Leu Ser Leu Ser
435 440 445

Pro Gly
450

<210> SEQ ID NO 41
<211> LENGTH: 222
<212> TYPE: PRT
<213> ORGANISM: Artificial Sequence
<220> FEATURE:
<223> OTHER INFORMATION: Fcab FS20-22 with LALA mutation

<400> SEQUENCE: 41

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Tyr Trp Asp Gln Glu Val Ser Leu Thr Cys Leu
130 135 140

Val Lys Gly Phe Tyr Pro Ser Asp Ile Ala Val Glu Trp Glu Ser Asn
145 150 155 160

Gly Gln Pro Glu Asn Asn Tyr Lys Thr Thr Pro Pro Val Leu Asp Ser
165 170 175

Asp Gly Ser Phe Phe Leu Tyr Ser Lys Leu Thr Val Asp Gln Tyr Arg
180 185 190

Trp Asn Pro Gly Gly Tyr Phe Ser Cys Ser Val Met His Glu Ala Leu
195 200 205

His Asn His Tyr Thr Gln Lys Ser Leu Ser Leu Ser Pro Gly
210 215 220

<210> SEQ ID NO 42
<211> LENGTH: 222
<212> TYPE: PRT
<213> ORGANISM: Artificial Sequence
<220> FEATURE:
<223> OTHER INFORMATION: Fcab FS20-22 without LALA mutation

<400> SEQUENCE: 42

Thr Cys Pro Pro Cys Pro Ala Pro Glu Leu Leu Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Tyr Trp Asp Gln Glu Val Ser Leu Thr Cys Leu
130 135 140

Val Lys Gly Phe Tyr Pro Ser Asp Ile Ala Val Glu Trp Glu Ser Asn
145 150 155 160

Gly Gln Pro Glu Asn Asn Tyr Lys Thr Thr Pro Pro Val Leu Asp Ser
165 170 175

Asp Gly Ser Phe Phe Leu Tyr Ser Lys Leu Thr Val Asp Gln Tyr Arg
180 185 190

Trp Asn Pro Gly Gly Tyr Phe Ser Cys Ser Val Met His Glu Ala Leu
195 200 205

His Asn His Tyr Thr Gln Lys Ser Leu Ser Leu Ser Pro Gly
210 215 220

<210> SEQ ID NO 43
<211> LENGTH: 5
<212> TYPE: PRT
<213> ORGANISM: Artificial Sequence
<220> FEATURE:
<223> OTHER INFORMATION: Fcab FS20-22-38 CH3 domain structural loop sequence

<400> SEQUENCE: 43

Tyr Trp Asp Gln Glu
1 5

<210> SEQ ID NO 44
<211> LENGTH: 5

<212> TYPE: PRT
<213> ORGANISM: Artificial Sequence
<220> FEATURE:
<223> OTHER INFORMATION: Fcab FS20-22-38 CH3 domain structural loop sequence

<400> SEQUENCE: 44

Ala Glu Lys Tyr Gln
1 5

<210> SEQ ID NO 45
<211> LENGTH: 9
<212> TYPE: PRT
<213> ORGANISM: Artificial Sequence
<220> FEATURE:
<223> OTHER INFORMATION: Fcab FS20-22-38 CH3 domain structural loop sequence

<400> SEQUENCE: 45

Gln Tyr Arg Trp Asn Pro Gly Asp Tyr
1 5

<210> SEQ ID NO 46
<211> LENGTH: 106
<212> TYPE: PRT
<213> ORGANISM: Artificial Sequence
<220> FEATURE:
<223> OTHER INFORMATION: Fcab FS20-22-38 CH3 domain

<400> SEQUENCE: 46

Gly Gln Pro Arg Glu Pro Gln Val Tyr Thr Leu Pro Pro Ser Arg Asp
1 5 10 15

Glu Tyr Trp Asp Gln Glu Val Ser Leu Thr Cys Leu Val Lys Gly Phe
20 25 30

Tyr Pro Ser Asp Ile Ala Val Glu Trp Glu Ser Asn Gly Ala Glu Lys
35 40 45

Tyr Gln Tyr Lys Thr Thr Pro Pro Val Leu Asp Ser Asp Gly Ser Phe
50 55 60

Phe Leu Tyr Ser Lys Leu Thr Val Asp Gln Tyr Arg Trp Asn Pro Gly
65 70 75 80

Asp Tyr Phe Ser Cys Ser Val Met His Glu Ala Leu His Asn His Tyr
85 90 95

Thr Gln Lys Ser Leu Ser Leu Ser Pro Gly
100 105

<210> SEQ ID NO 47
<211> LENGTH: 318
<212> TYPE: DNA
<213> ORGANISM: Artificial Sequence
<220> FEATURE:
<223> OTHER INFORMATION: Fcab FS20-22-38 CH3 domain

<400> SEQUENCE: 47
ggacagcctc gagaaccaca ggtgtacacc ctgcccccat cccgggatga gtactgggac 60
caggaagtca gcctgacctg cctggtcaaa ggcttctatc ccagcgacat cgccgtggag 120
tgggagagca atggggcaga aaaataccag tacaagacca cgcctcccgt gctggactcc 180
gacggctcct tcttcctcta cagcaagctc accgtggatc agtataggtg gaacccaggc 240
gactatttct catgctccgt gatgcatgag gctctgcaca accactacac acagaagagc 300
ctctccctgt ctccgggt 318

<210> SEQ ID NO 48
<211> LENGTH: 222
<212> TYPE: PRT
<213> ORGANISM: Artificial Sequence
<220> FEATURE:
<223> OTHER INFORMATION: Fcab FS20-22-38 with LALA mutation

<400> SEQUENCE: 48

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Trp Asp Gln Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Ala Glu Lys Tyr Gln Tyr Lys Thr Thr Pro Pro Val Leu Asp Ser
                165                 170                 175

Asp Gly Ser Phe Phe Leu Tyr Ser Lys Leu Thr Val Asp Gln Tyr Arg
            180                 185                 190

Trp Asn Pro Gly Asp Tyr Phe Ser Cys Ser Val Met His Glu Ala Leu
        195                 200                 205

His Asn His Tyr Thr Gln Lys Ser Leu Ser Leu Ser Pro Gly
    210                 215                 220

<210> SEQ ID NO 49
<211> LENGTH: 666
<212> TYPE: DNA
<213> ORGANISM: Artificial Sequence
<220> FEATURE:
<223> OTHER INFORMATION: Fcab FS20-22-38 with LALA mutation

<400> SEQUENCE: 49
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg acagcctcga 360
gaaccacagg tgtacaccct gcccccatcc cgggatgagt actgggacca ggaagtcagc 420
ctgacctgcc tggtcaaagg cttctatccc agcgacatcg ccgtggagtg ggagagcaat 480
ggggcagaaa aataccagta caagaccacg cctcccgtgc tggactccga cggctccttc 540

-continued

```
ttcctctaca gcaagctcac cgtggatcag tataggtgga acccaggcga ctatttctca    600

tgctccgtga tgcatgaggc tctgcacaac cactacacac agaagagcct ctccctgtct    660

ccgggt                                                               666


<210> SEQ ID NO 50
<211> LENGTH: 222
<212> TYPE: PRT
<213> ORGANISM: Artificial Sequence
<220> FEATURE:
<223> OTHER INFORMATION: Fcab FS20-22-38 without LALA mutation

<400> SEQUENCE: 50

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Trp Asp Gln Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Ala Glu Lys Tyr Gln Tyr Lys Thr Thr Pro Pro Val Leu Asp Ser
                165                 170                 175

Asp Gly Ser Phe Phe Leu Tyr Ser Lys Leu Thr Val Asp Gln Tyr Arg
            180                 185                 190

Trp Asn Pro Gly Asp Tyr Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 51
<211> LENGTH: 666
<212> TYPE: DNA
<213> ORGANISM: Artificial Sequence
<220> FEATURE:
<223> OTHER INFORMATION: Fcab FS20-22-38 without LALA mutation

<400> SEQUENCE: 51

acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg acagcctcga    360
```

```
gaaccacagg tgtacaccct gcccccatcc cgggatgagt actgggacca ggaagtcagc    420

ctgacctgcc tggtcaaagg cttctatccc agcgacatcg ccgtggagtg ggagagcaat    480

ggggcagaaa aataccagta caagaccacg cctcccgtgc tggactccga cggctccttc    540

ttcctctaca gcaagctcac cgtggatcag tataggtgga acccaggcga ctatttctca    600

tgctccgtga tgcatgaggc tctgcacaac cactacacac agaagagcct ctccctgtct    660

ccgggt                                                               666


<210> SEQ ID NO 52
<211> LENGTH: 447
<212> TYPE: PRT
<213> ORGANISM: Artificial Sequence
<220> FEATURE:
<223> OTHER INFORMATION: Heavy chain of FS20-22-38/4420 mock mAb? with
      LALA mutation

<400> SEQUENCE: 52

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
```

```
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Ala Glu Lys Tyr Gln Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Asn Pro Gly Asp Tyr Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 53
<211> LENGTH: 447
<212> TYPE: PRT
<213> ORGANISM: Artificial Sequence
<220> FEATURE:
<223> OTHER INFORMATION: Heavy chain of FS20-22-38/4420 mock mAb?
      without LALA mutation

<400> SEQUENCE: 53

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

-continued

```
Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Ala Glu Lys Tyr Gln Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Asn Pro Gly Asp Tyr Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 54
<211> LENGTH: 5
<212> TYPE: PRT
<213> ORGANISM: Artificial Sequence
<220> FEATURE:
<223> OTHER INFORMATION: Fcab FS20-22-41 CH3 domain structural loop
      sequence

<400> SEQUENCE: 54

Asp Glu Gln Phe Ala
1               5


<210> SEQ ID NO 55
<211> LENGTH: 106
<212> TYPE: PRT
<213> ORGANISM: Artificial Sequence
<220> FEATURE:
<223> OTHER INFORMATION: Fcab FS20-22-41 CH3 domain

<400> SEQUENCE: 55

Gly Gln Pro Arg Glu Pro Gln Val Tyr Thr Leu Pro Pro Ser Arg Asp
1               5                   10                  15

Glu Tyr Trp Asp Gln Glu Val Ser Leu Thr Cys Leu Val Lys Gly Phe
            20                  25                  30

Tyr Pro Ser Asp Ile Ala Val Glu Trp Glu Ser Asn Gly Asp Glu Gln
        35                  40                  45

Phe Ala Tyr Lys Thr Thr Pro Pro Val Leu Asp Ser Asp Gly Ser Phe
```

-continued

```
    50                  55                  60

Phe Leu Tyr Ser Lys Leu Thr Val Asp Gln Tyr Arg Trp Asn Pro Gly
65                  70                  75                  80

Asp Tyr Phe Ser Cys Ser Val Met His Glu Ala Leu His Asn His Tyr
                85                  90                  95

Thr Gln Lys Ser Leu Ser Leu Ser Pro Gly
            100                 105


<210> SEQ ID NO 56
<211> LENGTH: 318
<212> TYPE: DNA
<213> ORGANISM: Artificial Sequence
<220> FEATURE:
<223> OTHER INFORMATION: Fcab FS20-22-41 CH3 domain

<400> SEQUENCE: 56

ggacagcctc gagaaccaca ggtgtacacc ctgcccccat cccgggatga gtactgggac      60

caggaagtca gcctgacctg cctggtcaaa ggcttctatc ccagcgacat cgccgtggag     120

tgggagagca atggggatga acagttcgca tacaagacca cgcctcccgt gctggactcc     180

gacggctcct tcttcctcta cagcaagctc accgtggatc agtataggtg gaacccaggc     240

gactatttct catgctccgt gatgcatgag gctctgcaca accactacac acagaagagc     300

ctctccctgt ctccggga                                                   318


<210> SEQ ID NO 57
<211> LENGTH: 222
<212> TYPE: PRT
<213> ORGANISM: Artificial Sequence
<220> FEATURE:
<223> OTHER INFORMATION: Fcab FS20-22-41 with LALA mutation

<400> SEQUENCE: 57

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Trp Asp Gln Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Asp Glu Gln Phe Ala Tyr Lys Thr Thr Pro Pro Val Leu Asp Ser
                165                 170                 175

Asp Gly Ser Phe Phe Leu Tyr Ser Lys Leu Thr Val Asp Gln Tyr Arg
            180                 185                 190
```

```
Trp Asn Pro Gly Asp Tyr Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 58
<211> LENGTH: 666
<212> TYPE: DNA
<213> ORGANISM: Artificial Sequence
<220> FEATURE:
<223> OTHER INFORMATION: Fcab FS20-22-41 with LALA mutation

<400> SEQUENCE: 58

acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg acagcctcga     360

gaaccacagg tgtacaccct gcccccatcc cgggatgagt actgggacca ggaagtcagc     420

ctgacctgcc tggtcaaagg cttctatccc agcgacatcg ccgtggagtg ggagagcaat     480

ggggatgaac agttcgcata caagaccacg cctcccgtgc tggactccga cggctccttc     540

ttcctctaca gcaagctcac cgtggatcag tataggtgga acccaggcga ctatttctca     600

tgctccgtga tgcatgaggc tctgcacaac cactacacac agaagagcct ctccctgtct     660

ccggga                                                                666


<210> SEQ ID NO 59
<211> LENGTH: 222
<212> TYPE: PRT
<213> ORGANISM: Artificial Sequence
<220> FEATURE:
<223> OTHER INFORMATION: Fcab FS20-22-41 without LALA mutation

<400> SEQUENCE: 59

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Trp Asp Gln Glu Val Ser Leu Thr Cys Leu
    130                 135                 140

Val Lys Gly Phe Tyr Pro Ser Asp Ile Ala Val Glu Trp Glu Ser Asn
145                 150                 155                 160
```

Gly Asp Glu Gln Phe Ala Tyr Lys Thr Thr Pro Pro Val Leu Asp Ser
165 170 175

Asp Gly Ser Phe Phe Leu Tyr Ser Lys Leu Thr Val Asp Gln Tyr Arg
180 185 190

Trp Asn Pro Gly Asp Tyr Phe Ser Cys Ser Val Met His Glu Ala Leu
195 200 205

His Asn His Tyr Thr Gln Lys Ser Leu Ser Leu Ser Pro Gly
210 215 220

<210> SEQ ID NO 60
<211> LENGTH: 666
<212> TYPE: DNA
<213> ORGANISM: Artificial Sequence
<220> FEATURE:
<223> OTHER INFORMATION: Fcab FS20-22-41 without LALA mutation

<400> SEQUENCE: 60
acttgcccgc cttgcccagc cccggaactg ctgggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg acagcctcga 360
gaaccacagg tgtacaccct gcccccatcc cgggatgagt actgggacca ggaagtcagc 420
ctgacctgcc tggtcaaagg cttctatccc agcgacatcg ccgtggagtg ggagagcaat 480
ggggatgaac agttcgcata caagaccacg cctcccgtgc tggactccga cggctccttc 540
ttcctctaca gcaagctcac cgtggatcag tataggtgga acccaggcga ctatttctca 600
tgctccgtga tgcatgaggc tctgcacaac cactacacac agaagagcct ctccctgtct 660
ccggga 666

<210> SEQ ID NO 61
<211> LENGTH: 447
<212> TYPE: PRT
<213> ORGANISM: Artificial Sequence
<220> FEATURE:
<223> OTHER INFORMATION: Heavy chain of FS20-22-41/4420 mock mAb? with LALA mutation

<400> SEQUENCE: 61

Glu Val Lys Leu Asp Glu Thr Gly Gly Gly Leu Val Gln Pro Gly Arg
1 5 10 15

Pro Met Lys Leu Ser Cys Val Ala Ser Gly Phe Thr Phe Ser Asp Tyr
20 25 30

Trp Met Asn Trp Val Arg Gln Ser Pro Glu Lys Gly Leu Glu Trp Val
35 40 45

Ala Gln Ile Arg Asn Lys Pro Tyr Asn Tyr Glu Thr Tyr Tyr Ser Asp
50 55 60

Ser Val Lys Gly Arg Phe Thr Ile Ser Arg Asp Asp Ser Lys Ser Ser
65 70 75 80

Val Tyr Leu Gln Met Asn Asn Leu Arg Val Glu Asp Met Gly Ile Tyr
85 90 95

Tyr Cys Thr Gly Ser Tyr Tyr Gly Met Asp Tyr Trp Gly Gln Gly Thr
100 105 110

Ser Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Tyr Trp Asp Gln Glu Val Ser Leu Thr Cys
355 360 365

Leu Val Lys Gly Phe Tyr Pro Ser Asp Ile Ala Val Glu Trp Glu Ser
370 375 380

Asn Gly Asp Glu Gln Phe Ala Tyr Lys Thr Thr Pro Pro Val Leu Asp
385 390 395 400

Ser Asp Gly Ser Phe Phe Leu Tyr Ser Lys Leu Thr Val Asp Gln Tyr
405 410 415

Arg Trp Asn Pro Gly Asp Tyr Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 62
<211> LENGTH: 9
<212> TYPE: PRT
<213> ORGANISM: Artificial Sequence
<220> FEATURE:
<223> OTHER INFORMATION: Fcab FS20-22-47 CH3 domain structural loop sequence

<400> SEQUENCE: 62

Gln Tyr Arg Trp Ser Pro Gly Asp Tyr
1 5

<210> SEQ ID NO 63

<211> LENGTH: 106
<212> TYPE: PRT
<213> ORGANISM: Artificial Sequence
<220> FEATURE:
<223> OTHER INFORMATION: Fcab FS20-22-47 CH3 domain

<400> SEQUENCE: 63

```
Gly Gln Pro Arg Glu Pro Gln Val Tyr Thr Leu Pro Pro Ser Arg Asp
1               5                   10                  15

Glu Tyr Trp Asp Gln Glu Val Ser Leu Thr Cys Leu Val Lys Gly Phe
            20                  25                  30

Tyr Pro Ser Asp Ile Ala Val Glu Trp Glu Ser Asn Gly Asp Glu Gln
        35                  40                  45

Phe Ala Tyr Lys Thr Thr Pro Pro Val Leu Asp Ser Asp Gly Ser Phe
    50                  55                  60

Phe Leu Tyr Ser Lys Leu Thr Val Asp Gln Tyr Arg Trp Ser Pro Gly
65                  70                  75                  80

Asp Tyr Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 64
<211> LENGTH: 318
<212> TYPE: DNA
<213> ORGANISM: Artificial Sequence
<220> FEATURE:
<223> OTHER INFORMATION: Fcab FS20-22-47 CH3 domain

<400> SEQUENCE: 64

```
ggacagcctc gagaaccaca ggtgtacacc ctgcccccat cccgggatga gtactgggac      60

caggaagtca gcctgacctg cctggtcaaa ggcttctatc ccagcgacat cgccgtggag     120

tgggagagca atggggatga acagttcgca tacaagacca cgcctcccgt gctggactcc     180

gacggctcct tcttcctcta cagcaagctc accgtggatc agtataggtg gagtccgggt     240

gattatttct catgctccgt gatgcatgag gctctgcaca accactacac tcagaagagc     300

ttgtccctgt cgcccgga                                                   318
```

<210> SEQ ID NO 65
<211> LENGTH: 222
<212> TYPE: PRT
<213> ORGANISM: Artificial Sequence
<220> FEATURE:
<223> OTHER INFORMATION: Fcab FS20-22-47 with LALA mutation

<400> SEQUENCE: 65

```
Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95
```

```
Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Trp Asp Gln Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Asp Glu Gln Phe Ala Tyr Lys Thr Thr Pro Pro Val Leu Asp Ser
                165                 170                 175

Asp Gly Ser Phe Phe Leu Tyr Ser Lys Leu Thr Val Asp Gln Tyr Arg
            180                 185                 190

Trp Ser Pro Gly Asp Tyr Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 66
<211> LENGTH: 666
<212> TYPE: DNA
<213> ORGANISM: Artificial Sequence
<220> FEATURE:
<223> OTHER INFORMATION: Fcab FS20-22-47 with LALA mutation

<400> SEQUENCE: 66

acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg acagcctcga     360

gaaccacagg tgtacaccct gcccccatcc cgggatgagt actgggacca ggaagtcagc     420

ctgacctgcc tggtcaaagg cttctatccc agcgacatcg ccgtggagtg ggagagcaat     480

ggggatgaac agttcgcata caagaccacg cctcccgtgc tggactccga cggctccttc     540

ttcctctaca gcaagctcac cgtggatcag tataggtgga gtccgggtga ttatttctca     600

tgctccgtga tgcatgaggc tctgcacaac cactacactc agaagagctt gtccctgtcg     660

cccgga                                                                666


<210> SEQ ID NO 67
<211> LENGTH: 222
<212> TYPE: PRT
<213> ORGANISM: Artificial Sequence
<220> FEATURE:
<223> OTHER INFORMATION: Fcab FS20-22-47 without LALA mutation

<400> SEQUENCE: 67

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60
```

```
Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Trp Asp Gln Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Asp Glu Gln Phe Ala Tyr Lys Thr Thr Pro Pro Val Leu Asp Ser
                165                 170                 175

Asp Gly Ser Phe Phe Leu Tyr Ser Lys Leu Thr Val Asp Gln Tyr Arg
            180                 185                 190

Trp Ser Pro Gly Asp Tyr Phe Ser Cys Ser Val Met His Glu Ala Leu
        195                 200                 205

His Asn His Tyr Thr Gln Lys Ser Leu Ser Leu Ser Pro Gly
    210                 215                 220
```

```
<210> SEQ ID NO 68
<211> LENGTH: 666
<212> TYPE: DNA
<213> ORGANISM: Artificial Sequence
<220> FEATURE:
<223> OTHER INFORMATION: Fcab FS20-22-47 without LALA mutation

<400> SEQUENCE: 68

acttgcccgc cttgcccagc cccggaactg ctgggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg acagcctcga     360

gaaccacagg tgtacaccct gcccccatcc cgggatgagt actgggacca ggaagtcagc     420

ctgacctgcc tggtcaaagg cttctatccc agcgacatcg ccgtggagtg ggagagcaat     480

ggggatgaac agttcgcata caagaccacg cctcccgtgc tggactccga cggctccttc     540

ttcctctaca gcaagctcac cgtggatcag tataggtgga gtccgggtga ttatttctca     600

tgctccgtga tgcatgaggc tctgcacaac cactacactc agaagagctt gtccctgtcg     660

cccgga                                                                666

<210> SEQ ID NO 69
<211> LENGTH: 447
<212> TYPE: PRT
<213> ORGANISM: Artificial Sequence
<220> FEATURE:
<223> OTHER INFORMATION: Heavy chain of FS20-22-47/4420 mock mAb? with
      LALA mutation

<400> SEQUENCE: 69

Glu Val Lys Leu Asp Glu Thr Gly Gly Gly Leu Val Gln Pro Gly Arg
1               5                   10                  15
```

```
Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Ser Pro Gly Asp Tyr Phe Ser Cys Ser Val Met His Glu Ala
            420                 425                 430

Leu His Asn His Tyr Thr Gln Lys Ser Leu Ser Leu Ser Pro Gly
```

-continued

```
        435                 440                 445


<210> SEQ ID NO 70
<211> LENGTH: 447
<212> TYPE: PRT
<213> ORGANISM: Artificial Sequence
<220> FEATURE:
<223> OTHER INFORMATION: Heavy chain of FS20-22-47/4420 mock mAb?
      without LALA mutation

<400> SEQUENCE: 70

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Ser Pro Gly Asp Tyr Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 71
<211> LENGTH: 9
<212> TYPE: PRT
<213> ORGANISM: Artificial Sequence
<220> FEATURE:
<223> OTHER INFORMATION: Fcab FS20-22-49 CH3 domain structural loop
      sequence

<400> SEQUENCE: 71

Gln Tyr Arg Trp Asn Pro Ala Asp Tyr
1               5


<210> SEQ ID NO 72
<211> LENGTH: 106
<212> TYPE: PRT
<213> ORGANISM: Artificial Sequence
<220> FEATURE:
<223> OTHER INFORMATION: Fcab FS20-22-49 CH3 domain

<400> SEQUENCE: 72

Gly Gln Pro Arg Glu Pro Gln Val Tyr Thr Leu Pro Pro Ser Arg Asp
1               5                   10                  15

Glu Tyr Trp Asp Gln Glu Val Ser Leu Thr Cys Leu Val Lys Gly Phe
            20                  25                  30

Tyr Pro Ser Asp Ile Ala Val Glu Trp Glu Ser Asn Gly Asp Glu Gln
        35                  40                  45

Phe Ala Tyr Lys Thr Thr Pro Pro Val Leu Asp Ser Asp Gly Ser Phe
    50                  55                  60

Phe Leu Tyr Ser Lys Leu Thr Val Asp Gln Tyr Arg Trp Asn Pro Ala
65                  70                  75                  80

Asp Tyr Phe Ser Cys Ser Val Met His Glu Ala Leu His Asn His Tyr
                85                  90                  95

Thr Gln Lys Ser Leu Ser Leu Ser Pro Gly
            100                 105


<210> SEQ ID NO 73
<211> LENGTH: 318
<212> TYPE: DNA
<213> ORGANISM: Artificial Sequence
<220> FEATURE:
<223> OTHER INFORMATION: Fcab FS20-22-49 CH3 domain

<400> SEQUENCE: 73

ggacagcctc gagaaccaca ggtgtacacc ctgcccccat cccgggatga gtactgggac      60

caggaagtca gcctgacctg cctggtcaaa ggcttctatc ccagcgacat cgccgtggag     120

tgggagagca atggggatga acagttcgca tacaagacca cgcctcccgt gctggactcc     180
```

gacggctcct tcttcctcta cagcaagctc accgtggatc agtataggtg gaatcctgct 240
gattatttct catgctccgt gatgcatgag gctctgcaca accactacac tcagaagagc 300
ttgtccctgt cgcccgga 318

<210> SEQ ID NO 74
<211> LENGTH: 222
<212> TYPE: PRT
<213> ORGANISM: Artificial Sequence
<220> FEATURE:
<223> OTHER INFORMATION: Fcab FS20-22-49 with LALA mutation

<400> SEQUENCE: 74

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Tyr Trp Asp Gln Glu Val Ser Leu Thr Cys Leu
130 135 140

Val Lys Gly Phe Tyr Pro Ser Asp Ile Ala Val Glu Trp Glu Ser Asn
145 150 155 160

Gly Asp Glu Gln Phe Ala Tyr Lys Thr Thr Pro Pro Val Leu Asp Ser
165 170 175

Asp Gly Ser Phe Phe Leu Tyr Ser Lys Leu Thr Val Asp Gln Tyr Arg
180 185 190

Trp Asn Pro Ala Asp Tyr Phe Ser Cys Ser Val Met His Glu Ala Leu
195 200 205

His Asn His Tyr Thr Gln Lys Ser Leu Ser Leu Ser Pro Gly
210 215 220

<210> SEQ ID NO 75
<211> LENGTH: 666
<212> TYPE: DNA
<213> ORGANISM: Artificial Sequence
<220> FEATURE:
<223> OTHER INFORMATION: Fcab FS20-22-49 with LALA mutation

<400> SEQUENCE: 75
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg acagcctcga 360
gaaccacagg tgtacaccct gcccccatcc cgggatgagt actgggacca ggaagtcagc 420
ctgacctgcc tggtcaaagg cttctatccc agcgacatcg ccgtggagtg ggagagcaat 480
ggggatgaac agttcgcata caagaccacg cctcccgtgc tggactccga cggctccttc 540
ttcctctaca gcaagctcac cgtggatcag tataggtgga atcctgctga ttatttctca 600
tgctccgtga tgcatgaggc tctgcacaac cactacactc agaagagctt gtccctgtcg 660
cccgga 666

<210> SEQ ID NO 76
<211> LENGTH: 222
<212> TYPE: PRT
<213> ORGANISM: Artificial Sequence
<220> FEATURE:
<223> OTHER INFORMATION: Fcab FS20-22-49 without LALA mutation

<400> SEQUENCE: 76

Thr Cys Pro Pro Cys Pro Ala Pro Glu Leu Leu Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Tyr Trp Asp Gln Glu Val Ser Leu Thr Cys Leu
130 135 140

Val Lys Gly Phe Tyr Pro Ser Asp Ile Ala Val Glu Trp Glu Ser Asn
145 150 155 160

Gly Asp Glu Gln Phe Ala Tyr Lys Thr Thr Pro Pro Val Leu Asp Ser
165 170 175

Asp Gly Ser Phe Phe Leu Tyr Ser Lys Leu Thr Val Asp Gln Tyr Arg
180 185 190

Trp Asn Pro Ala Asp Tyr Phe Ser Cys Ser Val Met His Glu Ala Leu
195 200 205

His Asn His Tyr Thr Gln Lys Ser Leu Ser Leu Ser Pro Gly
210 215 220

<210> SEQ ID NO 77
<211> LENGTH: 666
<212> TYPE: DNA
<213> ORGANISM: Artificial Sequence
<220> FEATURE:
<223> OTHER INFORMATION: Fcab FS20-22-49 without LALA mutation

<400> SEQUENCE: 77
acttgcccgc cttgcccagc cccggaactg ctgggtggtc cttcggtgtt cctcttcccg 60
cccaagccga aggataccct gatgatctca cggacccccg aagtgacctg tgtggtggtg 120

```
gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg acagcctcga    360

gaaccacagg tgtacaccct gcccccatcc cgggatgagt actgggacca ggaagtcagc    420

ctgacctgcc tggtcaaagg cttctatccc agcgacatcg ccgtggagtg ggagagcaat    480

ggggatgaac agttcgcata caagaccacg cctcccgtgc tggactccga cggctccttc    540

ttcctctaca gcaagctcac cgtggatcag tataggtgga atcctgctga ttatttctca    600

tgctccgtga tgcatgaggc tctgcacaac cactacactc agaagagctt gtccctgtcg    660

cccgga                                                               666
```

<210> SEQ ID NO 78
<211> LENGTH: 447
<212> TYPE: PRT
<213> ORGANISM: Artificial Sequence
<220> FEATURE:
<223> OTHER INFORMATION: Heavy chain of FS20-22-49/4420 mock mAb? with LALA mutation

<400> SEQUENCE: 78

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Asn Pro Ala Asp Tyr Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 79
<211> LENGTH: 447
<212> TYPE: PRT
<213> ORGANISM: Artificial Sequence
<220> FEATURE:
<223> OTHER INFORMATION: Heavy chain of FS20-22-49/4420 mock mAb?
      without LALA mutation

<400> SEQUENCE: 79

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Asn Pro Ala Asp Tyr Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 80
<211> LENGTH: 9
<212> TYPE: PRT
<213> ORGANISM: Artificial Sequence
<220> FEATURE:
<223> OTHER INFORMATION: Fcab FS20-22-85 CH3 domain structural loop sequence

<400> SEQUENCE: 80

```
Gln Tyr Arg Trp Asn Pro Phe Asp Asp
1               5
```

<210> SEQ ID NO 81
<211> LENGTH: 106
<212> TYPE: PRT
<213> ORGANISM: Artificial Sequence
<220> FEATURE:
<223> OTHER INFORMATION: Fcab FS20-22-85 CH3 domain

<400> SEQUENCE: 81

```
Gly Gln Pro Arg Glu Pro Gln Val Tyr Thr Leu Pro Pro Ser Arg Asp
1               5                   10                  15
```

-continued

```
Glu Tyr Trp Asp Gln Glu Val Ser Leu Thr Cys Leu Val Lys Gly Phe
            20                  25                  30

Tyr Pro Ser Asp Ile Ala Val Glu Trp Glu Ser Asn Gly Asp Glu Gln
        35                  40                  45

Phe Ala Tyr Lys Thr Thr Pro Pro Val Leu Asp Ser Asp Gly Ser Phe
    50                  55                  60

Phe Leu Tyr Ser Lys Leu Thr Leu Asp Gln Tyr Arg Trp Asn Pro Phe
65                  70                  75                  80

Asp Asp Phe Ser Cys Ser Val Met His Glu Ala Leu His Asn His Tyr
                85                  90                  95

Thr Gln Lys Ser Leu Ser Leu Ser Pro Gly
            100                 105


<210> SEQ ID NO 82
<211> LENGTH: 318
<212> TYPE: DNA
<213> ORGANISM: Artificial Sequence
<220> FEATURE:
<223> OTHER INFORMATION: Fcab FS20-22-85 CH3 domain

<400> SEQUENCE: 82

ggacagcctc gagaaccaca ggtgtacacc ctgcccccat cccgggatga gtactgggac      60

caggaagtca gcctgacctg cctggtcaaa ggcttctatc ccagcgacat cgccgtggag     120

tgggagagca atggggatga acagttcgca tacaagacca cgcctcccgt gctggactcc     180

gacggctcct tcttcctcta cagcaagctc accttggatc agtataggtg gaatccgttt     240

gatgatttct catgctccgt gatgcatgag gctctgcaca accactacac tcagaagagc     300

ttgtccctgt cgcccgga                                                   318


<210> SEQ ID NO 83
<211> LENGTH: 222
<212> TYPE: PRT
<213> ORGANISM: Artificial Sequence
<220> FEATURE:
<223> OTHER INFORMATION: Fcab FS20-22-85 with LALA mutation

<400> SEQUENCE: 83

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Trp Asp Gln Glu Val Ser Leu Thr Cys Leu
    130                 135                 140

Val Lys Gly Phe Tyr Pro Ser Asp Ile Ala Val Glu Trp Glu Ser Asn
145                 150                 155                 160
```

```
Gly Asp Glu Gln Phe Ala Tyr Lys Thr Thr Pro Pro Val Leu Asp Ser
                165                 170                 175

Asp Gly Ser Phe Phe Leu Tyr Ser Lys Leu Thr Leu Asp Gln Tyr Arg
            180                 185                 190

Trp Asn Pro Phe Asp Asp Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 84
<211> LENGTH: 666
<212> TYPE: DNA
<213> ORGANISM: Artificial Sequence
<220> FEATURE:
<223> OTHER INFORMATION: Fcab FS20-22-85 with LALA mutation

<400> SEQUENCE: 84

acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg acagcctcga     360

gaaccacagg tgtacaccct gcccccatcc cgggatgagt actgggacca ggaagtcagc     420

ctgacctgcc tggtcaaagg cttctatccc agcgacatcg ccgtggagtg ggagagcaat     480

ggggatgaac agttcgcata caagaccacg cctcccgtgc tggactccga cggctccttc     540

ttcctctaca gcaagctcac cttggatcag tataggtgga atccgtttga tgatttctca     600

tgctccgtga tgcatgaggc tctgcacaac cactacactc agaagagctt gtccctgtcg     660

cccgga                                                                666


<210> SEQ ID NO 85
<211> LENGTH: 222
<212> TYPE: PRT
<213> ORGANISM: Artificial Sequence
<220> FEATURE:
<223> OTHER INFORMATION: Fcab FS20-22-85 without LALA mutation

<400> SEQUENCE: 85

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
```

```
        115                 120                 125

Pro Ser Arg Asp Glu Tyr Trp Asp Gln Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Asp Glu Gln Phe Ala Tyr Lys Thr Thr Pro Pro Val Leu Asp Ser
                165                 170                 175

Asp Gly Ser Phe Phe Leu Tyr Ser Lys Leu Thr Leu Asp Gln Tyr Arg
            180                 185                 190

Trp Asn Pro Phe Asp Asp Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 86
<211> LENGTH: 666
<212> TYPE: DNA
<213> ORGANISM: Artificial Sequence
<220> FEATURE:
<223> OTHER INFORMATION: Fcab FS20-22-85 without LALA mutation

<400> SEQUENCE: 86

acttgcccgc cttgcccagc cccggaagct gccggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg acagcctcga    360

gaaccacagg tgtacaccct gcccccatcc cgggatgagt actgggacca ggaagtcagc    420

ctgacctgcc tggtcaaagg cttctatccc agcgacatcg ccgtggagtg ggagagcaat    480

ggggatgaac agttcgcata caagaccacg cctcccgtgc tggactccga cggctccttc    540

ttcctctaca gcaagctcac cttggatcag tataggtgga atccgtttga tgatttctca    600

tgctccgtga tgcatgaggc tctgcacaac cactacactc agaagagctt gtccctgtcg    660

cccgga                                                               666


<210> SEQ ID NO 87
<211> LENGTH: 447
<212> TYPE: PRT
<213> ORGANISM: Artificial Sequence
<220> FEATURE:
<223> OTHER INFORMATION: Heavy chain of FS20-22-85/4420 mock mAb? with
      LALA mutation

<400> SEQUENCE: 87

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80
```

```
Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Leu Asp Gln Tyr
                405                 410                 415

Arg Trp Asn Pro Phe Asp Asp Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 88
<211> LENGTH: 447
<212> TYPE: PRT
<213> ORGANISM: Artificial Sequence
<220> FEATURE:
<223> OTHER INFORMATION: Heavy chain of FS20-22-85/4420 mock mAb?
      without LALA mutation

<400> SEQUENCE: 88

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Leu Asp Gln Tyr
                405                 410                 415

Arg Trp Asn Pro Phe Asp Asp Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 89
<211> LENGTH: 222
<212> TYPE: PRT
<213> ORGANISM: Artificial Sequence
<220> FEATURE:
<223> OTHER INFORMATION: Fcab FS20-31 with LALA mutation

<400> SEQUENCE: 89

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Tyr Tyr Ser Gly Glu Val Ser Leu Thr Cys Leu
130 135 140

Val Lys Gly Phe Tyr Pro Ser Asp Ile Ala Val Glu Trp Glu Ser Asn
145 150 155 160

Gly Gln Pro Glu Asn Asp Tyr Lys Thr Thr Pro Pro Val Leu Asp Ser
165 170 175

Asp Gly Ser Phe Phe Leu Tyr Ser Lys Leu Thr Val Pro Tyr Trp Arg
180 185 190

Trp Gly Gly Pro Gly Thr Phe Ser Cys Ser Val Met His Glu Ala Leu
195 200 205

His Asn His Tyr Thr Gln Lys Ser Leu Ser Leu Ser Pro Gly
210 215 220

<210> SEQ ID NO 90
<211> LENGTH: 222
<212> TYPE: PRT
<213> ORGANISM: Artificial Sequence
<220> FEATURE:
<223> OTHER INFORMATION: Fcab FS20-31 without LALA mutation

<400> SEQUENCE: 90

Thr Cys Pro Pro Cys Pro Ala Pro Glu Leu Leu Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys

```
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Tyr Ser Gly Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asp Tyr Lys Thr Thr Pro Pro Val Leu Asp Ser
                165                 170                 175

Asp Gly Ser Phe Phe Leu Tyr Ser Lys Leu Thr Val Pro Tyr Trp Arg
            180                 185                 190

Trp Gly Gly Pro Gly Thr Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 91
<211> LENGTH: 5
<212> TYPE: PRT
<213> ORGANISM: Artificial Sequence
<220> FEATURE:
<223> OTHER INFORMATION: Fcab FS20-31-58 CH3 domain structural loop
      sequence

<400> SEQUENCE: 91

Tyr Tyr Ser Gly Glu
1               5


<210> SEQ ID NO 92
<211> LENGTH: 5
<212> TYPE: PRT
<213> ORGANISM: Artificial Sequence
<220> FEATURE:
<223> OTHER INFORMATION: Fcab FS20-31-58 CH3 domain structural loop
      sequence

<400> SEQUENCE: 92

Gln Pro Glu Asn Asp
1               5


<210> SEQ ID NO 93
<211> LENGTH: 10
<212> TYPE: PRT
<213> ORGANISM: Artificial Sequence
<220> FEATURE:
<223> OTHER INFORMATION: Fcab FS20-31-58 CH3 domain structural loop
      sequence

<400> SEQUENCE: 93

Pro Tyr Trp Arg Trp Gly Ser Pro Arg Thr
1               5                   10


<210> SEQ ID NO 94
<211> LENGTH: 106
<212> TYPE: PRT
<213> ORGANISM: Artificial Sequence
```

<220> FEATURE:
<223> OTHER INFORMATION: Fcab FS20-31-58 CH3 domain

<400> SEQUENCE: 94

Gly Gln Pro Arg Glu Pro Gln Val Tyr Thr Leu Pro Pro Ser Arg Asp
1 5 10 15

Glu Tyr Tyr Ser Gly Glu Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asp Tyr Lys Thr Thr Pro Pro Val Leu Asp Ser Asp Gly Ser Phe
50 55 60

Phe Leu Tyr Ser Lys Leu Thr Val Pro Tyr Trp Arg Trp Gly Ser Pro
65 70 75 80

Arg Thr Phe Ser Cys Ser Val Met His Glu Ala Leu His Asn His Tyr
85 90 95

Thr Gln Lys Ser Leu Ser Leu Ser Pro Gly
100 105

<210> SEQ ID NO 95
<211> LENGTH: 318
<212> TYPE: DNA
<213> ORGANISM: Artificial Sequence
<220> FEATURE:
<223> OTHER INFORMATION: Fcab FS20-31-58 CH3 domain

<400> SEQUENCE: 95
ggacagcctc gagaaccaca ggtgtacacc ctgcccccat cccgggatga gtactactct 60
ggtgaagtca gcctgacctg cctggtcaaa ggcttctatc ccagcgacat cgccgtggag 120
tgggagagca atgggcagcc ggagaacgac tacaagacca cgcctcccgt gctggactcc 180
gacggctcct tcttcctcta cagcaagctc accgtgcctt attggaggtg gggtagtccg 240
cgtactttct catgctccgt gatgcatgag gctctgcaca accactacac acagaagagc 300
ctctccctgt ctccgggt 318

<210> SEQ ID NO 96
<211> LENGTH: 220
<212> TYPE: PRT
<213> ORGANISM: Artificial Sequence
<220> FEATURE:
<223> OTHER INFORMATION: Fcab FS20-31-58 with LALA mutation

<400> SEQUENCE: 96

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Pro Arg Glu Pro Gln Val Tyr Thr Leu Pro Pro Ser
115 120 125

Arg Asp Glu Tyr Tyr Ser Gly Glu Val Ser Leu Thr Cys Leu Val Lys
130 135 140

Gly Phe Tyr Pro Ser Asp Ile Ala Val Glu Trp Glu Ser Asn Gly Gln
145 150 155 160

Pro Glu Asn Asp Tyr Lys Thr Thr Pro Pro Val Leu Asp Ser Asp Gly
165 170 175

Ser Phe Phe Leu Tyr Ser Lys Leu Thr Val Pro Tyr Trp Arg Trp Gly
180 185 190

Ser Pro Arg Thr Phe Ser Cys Ser Val Met His Glu Ala Leu His Asn
195 200 205

His Tyr Thr Gln Lys Ser Leu Ser Leu Ser Pro Gly
210 215 220

<210> SEQ ID NO 97
<211> LENGTH: 666
<212> TYPE: DNA
<213> ORGANISM: Artificial Sequence
<220> FEATURE:
<223> OTHER INFORMATION: Fcab FS20-31-58 with LALA mutation

<400> SEQUENCE: 97
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg acagcctcga 360
gaaccacagg tgtacaccct gcccccatcc cgggatgagt actactctgg tgaagtcagc 420
ctgacctgcc tggtcaaagg cttctatccc agcgacatcg ccgtggagtg ggagagcaat 480
gggcagccgg agaacgacta caagaccacg cctcccgtgc tggactccga cggctccttc 540
ttcctctaca gcaagctcac cgtgccttat tggaggtggg gtagtccgcg tactttctca 600
tgctccgtga tgcatgaggc tctgcacaac cactacacac agaagagcct ctccctgtct 660
ccgggt 666

<210> SEQ ID NO 98
<211> LENGTH: 222
<212> TYPE: PRT
<213> ORGANISM: Artificial Sequence
<220> FEATURE:
<223> OTHER INFORMATION: Fcab FS20-31-58 without LALA mutation

<400> SEQUENCE: 98

Thr Cys Pro Pro Cys Pro Ala Pro Glu Leu Leu Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

```
Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Tyr Ser Gly Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asp Tyr Lys Thr Thr Pro Pro Val Leu Asp Ser
                165                 170                 175

Asp Gly Ser Phe Phe Leu Tyr Ser Lys Leu Thr Val Pro Tyr Trp Arg
            180                 185                 190

Trp Gly Ser Pro Arg Thr Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 99
<211> LENGTH: 666
<212> TYPE: DNA
<213> ORGANISM: Artificial Sequence
<220> FEATURE:
<223> OTHER INFORMATION: Fcab FS20-31-58 without LALA mutation

<400> SEQUENCE: 99

acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg acagcctcga    360

gaaccacagg tgtacaccct gcccccatcc cgggatgagt actactctgg tgaagtcagc    420

ctgacctgcc tggtcaaagg cttctatccc agcgacatcg ccgtggagtg ggagagcaat    480

gggcagccgg agaacgacta caagaccacg cctcccgtgc tggactccga cggctccttc    540

ttcctctaca gcaagctcac cgtgccttat tggaggtggg gtagtccgcg tactttctca    600

tgctccgtga tgcatgaggc tctgcacaac cactacacac agaagagcct ctccctgtct    660

ccgggt                                                               666


<210> SEQ ID NO 100
<211> LENGTH: 445
<212> TYPE: PRT
<213> ORGANISM: Artificial Sequence
<220> FEATURE:
<223> OTHER INFORMATION: Heavy chain of FS20-31-58/4420 mock mAb? with
      LALA mutation

<400> SEQUENCE: 100

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30
```

-continued

```
Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Tyr Tyr Ser Gly Glu Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asp Tyr Lys Thr Thr Pro Pro Val Leu Asp Ser Asp
385                 390                 395                 400

Gly Ser Phe Phe Leu Tyr Ser Lys Leu Thr Val Pro Tyr Trp Arg Trp
                405                 410                 415

Gly Ser Pro Arg Thr Phe Ser Cys Ser Val Met His Glu Ala Leu His
            420                 425                 430

Asn His Tyr Thr Gln Lys Ser Leu Ser Leu Ser Pro Gly
        435                 440                 445
```

<210> SEQ ID NO 101
<211> LENGTH: 445
<212> TYPE: PRT
<213> ORGANISM: Artificial Sequence
<220> FEATURE:
<223> OTHER INFORMATION: Heavy chain of FS20-31-58/4420 mock mAb? without LALA mutation

<400> SEQUENCE: 101

Gln Val Gln Leu Gln Glu Ser Gly Pro Gly Leu Val Arg Pro Ser Gln
1 5 10 15

Thr Leu Ser Leu Thr Cys Thr Val Ser Gly Ser Thr Phe Ser Gly Tyr
20 25 30

Gly Val Asn Trp Val Arg Gln Pro Pro Gly Arg Gly Leu Glu Trp Ile
35 40 45

Gly Met Ile Trp Gly Asp Gly Asn Thr Asp Tyr Asn Ser Ala Leu Lys
50 55 60

Ser Arg Val Thr Met Leu Val Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Glu Arg Asp Tyr Arg Leu Asp Tyr Trp Gly Gln Gly Ser Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Tyr Tyr Ser Gly Glu Val Ser Leu Thr Cys Leu Val
355 360 365

```
Lys Gly Phe Tyr Pro Ser Asp Ile Ala Val Glu Trp Glu Ser Asn Gly
    370                 375                 380

Gln Pro Glu Asn Asp Tyr Lys Thr Thr Pro Pro Val Leu Asp Ser Asp
385                 390                 395                 400

Gly Ser Phe Phe Leu Tyr Ser Lys Leu Thr Val Pro Tyr Trp Arg Trp
                405                 410                 415

Gly Ser Pro Arg Thr Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 102
<211> LENGTH: 10
<212> TYPE: PRT
<213> ORGANISM: Artificial Sequence
<220> FEATURE:
<223> OTHER INFORMATION: Fcab FS20-31-66 CH3 domain structural loop
      sequence

<400> SEQUENCE: 102

Pro Tyr Trp Arg Trp Gly Val Pro Arg Thr
1               5                   10


<210> SEQ ID NO 103
<211> LENGTH: 106
<212> TYPE: PRT
<213> ORGANISM: Artificial Sequence
<220> FEATURE:
<223> OTHER INFORMATION: Fcab FS20-31-66 CH3 domain

<400> SEQUENCE: 103

Gly Gln Pro Arg Glu Pro Gln Val Tyr Thr Leu Pro Pro Ser Arg Asp
1               5                   10                  15

Glu Tyr Tyr Ser Gly Glu Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asp Tyr Lys Thr Thr Pro Pro Val Leu Asp Ser Asp Gly Ser Phe
    50                  55                  60

Phe Leu Tyr Ser Lys Leu Thr Val Pro Tyr Trp Arg Trp Gly Val Pro
65                  70                  75                  80

Arg Thr Phe Ser Cys Ser Val Met His Glu Ala Leu His Asn His Tyr
                85                  90                  95

Thr Gln Lys Ser Leu Ser Leu Ser Pro Gly
            100                 105


<210> SEQ ID NO 104
<211> LENGTH: 318
<212> TYPE: DNA
<213> ORGANISM: Artificial Sequence
<220> FEATURE:
<223> OTHER INFORMATION: Fcab FS20-31-66 CH3 domain

<400> SEQUENCE: 104

ggacagcctc gagaaccaca ggtgtacacc ctgcccccat cccgggatga gtactactct     60

ggtgaagtca gcctgacctg cctggtcaaa ggcttctatc ccagcgacat cgccgtggag    120

tgggagagca atgggcagcc ggagaacgac tacaagacca cgcctcccgt gctggactcc    180

gacggctcct tcttcctcta cagcaagctc accgtgccgt attggaggtg gggtgttccg    240

cgtactttct catgctccgt gatgcatgag gctctgcaca accactacac acagaagagc    300
```

ctctccctgt ctccgggt 318

<210> SEQ ID NO 105
<211> LENGTH: 222
<212> TYPE: PRT
<213> ORGANISM: Artificial Sequence
<220> FEATURE:
<223> OTHER INFORMATION: Fcab FS20-31-66 with LALA mutation

<400> SEQUENCE: 105

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Tyr Tyr Ser Gly Glu Val Ser Leu Thr Cys Leu
130 135 140

Val Lys Gly Phe Tyr Pro Ser Asp Ile Ala Val Glu Trp Glu Ser Asn
145 150 155 160

Gly Gln Pro Glu Asn Asp Tyr Lys Thr Thr Pro Pro Val Leu Asp Ser
165 170 175

Asp Gly Ser Phe Phe Leu Tyr Ser Lys Leu Thr Val Pro Tyr Trp Arg
180 185 190

Trp Gly Val Pro Arg Thr Phe Ser Cys Ser Val Met His Glu Ala Leu
195 200 205

His Asn His Tyr Thr Gln Lys Ser Leu Ser Leu Ser Pro Gly
210 215 220

<210> SEQ ID NO 106
<211> LENGTH: 666
<212> TYPE: DNA
<213> ORGANISM: Artificial Sequence
<220> FEATURE:
<223> OTHER INFORMATION: Fcab FS20-31-66 with LALA mutation

<400> SEQUENCE: 106
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg acagcctcga 360
gaaccacagg tgtacaccct gcccccatcc cgggatgagt actactctgg tgaagtcagc 420

```
ctgacctgcc tggtcaaagg cttctatccc agcgacatcg ccgtggagtg ggagagcaat    480

gggcagccgg agaacgacta caagaccacg cctcccgtgc tggactccga cggctccttc    540

ttcctctaca gcaagctcac cgtgccgtat tggaggtggg gtgttccgcg tactttctca    600

tgctccgtga tgcatgaggc tctgcacaac cactacacac agaagagcct ctccctgtct    660

ccgggt                                                               666


<210> SEQ ID NO 107
<211> LENGTH: 222
<212> TYPE: PRT
<213> ORGANISM: Artificial Sequence
<220> FEATURE:
<223> OTHER INFORMATION: Fcab FS20-31-66 without LALA mutation

<400> SEQUENCE: 107

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Tyr Ser Gly Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asp Tyr Lys Thr Thr Pro Pro Val Leu Asp Ser
                165                 170                 175

Asp Gly Ser Phe Phe Leu Tyr Ser Lys Leu Thr Val Pro Tyr Trp Arg
            180                 185                 190

Trp Gly Val Pro Arg Thr Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 108
<211> LENGTH: 666
<212> TYPE: DNA
<213> ORGANISM: Artificial Sequence
<220> FEATURE:
<223> OTHER INFORMATION: Fcab FS20-31-66 without LALA mutation

<400> SEQUENCE: 108

acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240
```

gtgctcactg tgctgcacca agactggctg aacgggaagg agtacaagtg caaagtgtcc 300
aacaaggcgc tgcctgcccc aattgagaaa actatctcga aagccaaggg acagcctcga 360
gaaccacagg tgtacaccct gcccccatcc cgggatgagt actactctgg tgaagtcagc 420
ctgacctgcc tggtcaaagg cttctatccc agcgacatcg ccgtggagtg ggagagcaat 480
gggcagccgg agaacgacta caagaccacg cctcccgtgc tggactccga cggctccttc 540
ttcctctaca gcaagctcac cgtgccgtat tggaggtggg gtgttccgcg tactttctca 600
tgctccgtga tgcatgaggc tctgcacaac cactacacac agaagagcct ctccctgtct 660
ccgggt 666

<210> SEQ ID NO 109
<211> LENGTH: 445
<212> TYPE: PRT
<213> ORGANISM: Artificial Sequence
<220> FEATURE:
<223> OTHER INFORMATION: Heavy chain of FS20-31-66/4420 mock mAb? with LALA mutation

<400> SEQUENCE: 109

Gln Val Gln Leu Gln Glu Ser Gly Pro Gly Leu Val Arg Pro Ser Gln
1 5 10 15

Thr Leu Ser Leu Thr Cys Thr Val Ser Gly Ser Thr Phe Ser Gly Tyr
20 25 30

Gly Val Asn Trp Val Arg Gln Pro Pro Gly Arg Gly Leu Glu Trp Ile
35 40 45

Gly Met Ile Trp Gly Asp Gly Asn Thr Asp Tyr Asn Ser Ala Leu Lys
50 55 60

Ser Arg Val Thr Met Leu Val Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Glu Arg Asp Tyr Arg Leu Asp Tyr Trp Gly Gln Gly Ser Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Ala Ala Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Tyr Tyr Ser Gly Glu Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asp Tyr Lys Thr Thr Pro Pro Val Leu Asp Ser Asp
385 390 395 400

Gly Ser Phe Phe Leu Tyr Ser Lys Leu Thr Val Pro Tyr Trp Arg Trp
405 410 415

Gly Val Pro Arg Thr Phe Ser Cys Ser Val Met His Glu Ala Leu His
420 425 430

Asn His Tyr Thr Gln Lys Ser Leu Ser Leu Ser Pro Gly
435 440 445

<210> SEQ ID NO 110
<211> LENGTH: 445
<212> TYPE: PRT
<213> ORGANISM: Artificial Sequence
<220> FEATURE:
<223> OTHER INFORMATION: Heavy chain of FS20-31-66/4420 mock mAb? without LALA mutation

<400> SEQUENCE: 110

Gln Val Gln Leu Gln Glu Ser Gly Pro Gly Leu Val Arg Pro Ser Gln
1 5 10 15

Thr Leu Ser Leu Thr Cys Thr Val Ser Gly Ser Thr Phe Ser Gly Tyr
20 25 30

Gly Val Asn Trp Val Arg Gln Pro Pro Gly Arg Gly Leu Glu Trp Ile
35 40 45

Gly Met Ile Trp Gly Asp Gly Asn Thr Asp Tyr Asn Ser Ala Leu Lys
50 55 60

Ser Arg Val Thr Met Leu Val Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Glu Arg Asp Tyr Arg Leu Asp Tyr Trp Gly Gln Gly Ser Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

```
Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Tyr Tyr Ser Gly Glu Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asp Tyr Lys Thr Thr Pro Pro Val Leu Asp Ser Asp
385                 390                 395                 400

Gly Ser Phe Phe Leu Tyr Ser Lys Leu Thr Val Pro Tyr Trp Arg Trp
                405                 410                 415

Gly Val Pro Arg Thr Phe Ser Cys Ser Val Met His Glu Ala Leu His
            420                 425                 430

Asn His Tyr Thr Gln Lys Ser Leu Ser Leu Ser Pro Gly
        435                 440                 445
```

<210> SEQ ID NO 111
<211> LENGTH: 5
<212> TYPE: PRT
<213> ORGANISM: Artificial Sequence
<220> FEATURE:
<223> OTHER INFORMATION: Fcab FS20-31-94 Fcab CH3 domain structural loop sequence

<400> SEQUENCE: 111

```
Trp Glu His Gly Glu
1               5
```

<210> SEQ ID NO 112
<211> LENGTH: 5
<212> TYPE: PRT
<213> ORGANISM: Artificial Sequence
<220> FEATURE:
<223> OTHER INFORMATION: Fcab FS20-31-94 Fcab CH3 domain structural loop sequence

<400> SEQUENCE: 112

```
Ile Arg Glu His Asp
1               5
```

<210> SEQ ID NO 113

<211> LENGTH: 10
<212> TYPE: PRT
<213> ORGANISM: Artificial Sequence
<220> FEATURE:
<223> OTHER INFORMATION: Fcab FS20-31-94 Fcab CH3 domain structural loop sequence

<400> SEQUENCE: 113

Pro Tyr Trp Arg Trp Gly Gly Pro Gly Thr
1 5 10

<210> SEQ ID NO 114
<211> LENGTH: 106
<212> TYPE: PRT
<213> ORGANISM: Artificial Sequence
<220> FEATURE:
<223> OTHER INFORMATION: Fcab FS20-31-94 Fcab CH3 domain

<400> SEQUENCE: 114

Gly Gln Pro Arg Glu Pro Gln Val Tyr Thr Leu Pro Pro Ser Arg Asp
1 5 10 15

Glu Trp Glu His Gly Glu Val Ser Leu Thr Cys Leu Val Lys Gly Phe
20 25 30

Tyr Pro Ser Asp Ile Ala Val Glu Trp Glu Ser Asn Gly Ile Arg Glu
35 40 45

His Asp Tyr Lys Thr Thr Pro Pro Val Leu Asp Ser Asp Gly Ser Phe
50 55 60

Phe Leu Tyr Ser Lys Leu Thr Val Pro Tyr Trp Arg Trp Gly Gly Pro
65 70 75 80

Gly Thr Phe Ser Cys Ser Val Met His Glu Ala Leu His Asn His Tyr
85 90 95

Thr Gln Lys Ser Leu Ser Leu Ser Pro Gly
100 105

<210> SEQ ID NO 115
<211> LENGTH: 318
<212> TYPE: DNA
<213> ORGANISM: Artificial Sequence
<220> FEATURE:
<223> OTHER INFORMATION: Fcab FS20-31-94 Fcab CH3 domain

<400> SEQUENCE: 115
ggacagcctc gagaaccaca ggtgtacacc ctgcccccat cccgggatga gtgggaacat 60
ggtgaagtca gcctgacctg cctggtcaaa ggcttctatc ccagcgacat cgccgtggag 120
tgggagagca atgggatcag agaacatgat tacaagacca cgcctcccgt gctggactcc 180
gacggctcct tcttcctcta cagcaagctc accgtgccat attggaggtg gggcggccca 240
ggcaccttct catgctccgt gatgcatgag gctctgcaca accactacac tcagaagagc 300
ttgtccctgt cgcccgga 318

<210> SEQ ID NO 116
<211> LENGTH: 222
<212> TYPE: PRT
<213> ORGANISM: Artificial Sequence
<220> FEATURE:
<223> OTHER INFORMATION: Fcab FS20-31-94 Fcab with LALA mutation

<400> SEQUENCE: 116

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr

-continued

```
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Trp Glu His Gly Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Ile Arg Glu His Asp Tyr Lys Thr Thr Pro Pro Val Leu Asp Ser
                165                 170                 175

Asp Gly Ser Phe Phe Leu Tyr Ser Lys Leu Thr Val Pro Tyr Trp Arg
            180                 185                 190

Trp Gly Gly Pro Gly Thr Phe Ser Cys Ser Val Met His Glu Ala Leu
        195                 200                 205

His Asn His Tyr Thr Gln Lys Ser Leu Ser Leu Ser Pro Gly
    210                 215                 220
```

<210> SEQ ID NO 117
<211> LENGTH: 666
<212> TYPE: DNA
<213> ORGANISM: Artificial Sequence
<220> FEATURE:
<223> OTHER INFORMATION: Fcab FS20-31-94 Fcab with LALA mutation

<400> SEQUENCE: 117

```
acttgcccgc cttgcccagc cccggaagct gccggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg acagcctcga    360

gaaccacagg tgtacaccct gcccccatcc cgggatgagt gggaacatgg tgaagtcagc    420

ctgacctgcc tggtcaaagg cttctatccc agcgacatcg ccgtggagtg ggagagcaat    480

gggatcagag aacatgatta caagaccacg cctcccgtgc tggactccga cggctccttc    540

ttcctctaca gcaagctcac cgtgccatat tggaggtggg gcggcccagg caccttctca    600

tgctccgtga tgcatgaggc tctgcacaac cactacactc agaagagctt gtccctgtcg    660

cccgga                                                               666
```

<210> SEQ ID NO 118
<211> LENGTH: 222
<212> TYPE: PRT
<213> ORGANISM: Artificial Sequence
<220> FEATURE:
<223> OTHER INFORMATION: Fcab FS20-31-94 Fcab without LALA mutation

<400> SEQUENCE: 118

Thr Cys Pro Pro Cys Pro Ala Pro Glu Leu Leu Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Trp Glu His Gly Glu Val Ser Leu Thr Cys Leu
130 135 140

Val Lys Gly Phe Tyr Pro Ser Asp Ile Ala Val Glu Trp Glu Ser Asn
145 150 155 160

Gly Ile Arg Glu His Asp Tyr Lys Thr Thr Pro Pro Val Leu Asp Ser
165 170 175

Asp Gly Ser Phe Phe Leu Tyr Ser Lys Leu Thr Val Pro Tyr Trp Arg
180 185 190

Trp Gly Gly Pro Gly Thr Phe Ser Cys Ser Val Met His Glu Ala Leu
195 200 205

His Asn His Tyr Thr Gln Lys Ser Leu Ser Leu Ser Pro Gly
210 215 220

<210> SEQ ID NO 119
<211> LENGTH: 666
<212> TYPE: DNA
<213> ORGANISM: Artificial Sequence
<220> FEATURE:
<223> OTHER INFORMATION: Fcab FS20-31-94 Fcab without LALA mutation

<400> SEQUENCE: 119
acttgcccgc cttgcccagc cccggaactg ctgggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg acagcctcga 360
gaaccacagg tgtacaccct gcccccatcc cgggatgagt gggaacatgg tgaagtcagc 420
ctgacctgcc tggtcaaagg cttctatccc agcgacatcg ccgtggagtg ggagagcaat 480
gggatcagag aacatgatta caagaccacg cctcccgtgc tggactccga cggctccttc 540
ttcctctaca gcaagctcac cgtgccatat tggaggtggg gcggcccagg caccttctca 600
tgctccgtga tgcatgaggc tctgcacaac cactacactc agaagagctt gtccctgtcg 660
cccgga 666

<210> SEQ ID NO 120
<211> LENGTH: 447
<212> TYPE: PRT
<213> ORGANISM: Artificial Sequence
<220> FEATURE:
<223> OTHER INFORMATION: Heavy chain of FS20-31-94/4420 mock mAb? with
LALA mutation

<400> SEQUENCE: 120

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Trp Glu His Gly Glu Val Ser Leu Thr Cys
        355                 360                 365
```

Leu Val Lys Gly Phe Tyr Pro Ser Asp Ile Ala Val Glu Trp Glu Ser
    370                 375                 380

Asn Gly Ile Arg Glu His Asp Tyr Lys Thr Thr Pro Pro Val Leu Asp
385                 390                 395                 400

Ser Asp Gly Ser Phe Phe Leu Tyr Ser Lys Leu Thr Val Pro Tyr Trp
                405                 410                 415

Arg Trp Gly Gly Pro Gly Thr Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 121
<211> LENGTH: 447
<212> TYPE: PRT
<213> ORGANISM: Artificial Sequence
<220> FEATURE:
<223> OTHER INFORMATION: Heavy chain of FS20-31-94/4420 mock mAb?
      without LALA mutation

<400> SEQUENCE: 121

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala

```
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Trp Glu His Gly Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Ile Arg Glu His Asp Tyr Lys Thr Thr Pro Pro Val Leu Asp
385                 390                 395                 400

Ser Asp Gly Ser Phe Phe Leu Tyr Ser Lys Leu Thr Val Pro Tyr Trp
                405                 410                 415

Arg Trp Gly Gly Pro Gly Thr Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 122
<211> LENGTH: 5
<212> TYPE: PRT
<213> ORGANISM: Artificial Sequence
<220> FEATURE:
<223> OTHER INFORMATION: Fcab FS20-31-102 CH3 domain structural loop
      sequence

<400> SEQUENCE: 122

Trp Ala Ser Gly Glu
1               5


<210> SEQ ID NO 123
<211> LENGTH: 5
<212> TYPE: PRT
<213> ORGANISM: Artificial Sequence
<220> FEATURE:
<223> OTHER INFORMATION: Fcab FS20-31-102 CH3 domain structural loop
      sequence

<400> SEQUENCE: 123

Gln Pro Glu Val Asp
1               5


<210> SEQ ID NO 124
<211> LENGTH: 106
<212> TYPE: PRT
<213> ORGANISM: Artificial Sequence
<220> FEATURE:
<223> OTHER INFORMATION: Fcab FS20-31-102 CH3 domain

<400> SEQUENCE: 124

Gly Gln Pro Arg Glu Pro Gln Val Tyr Thr Leu Pro Pro Ser Arg Asp
1               5                   10                  15

Glu Trp Ala Ser Gly Glu Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45
```

```
Val Asp Tyr Lys Thr Thr Pro Pro Val Leu Asp Ser Asp Gly Ser Phe
    50                  55                  60

Phe Leu Tyr Ser Lys Leu Thr Val Pro Tyr Trp Arg Trp Gly Val Pro
65                  70                  75                  80

Arg Thr Phe Ser Cys Ser Val Met His Glu Ala Leu His Asn His Tyr
                85                  90                  95

Thr Gln Lys Ser Leu Ser Leu Ser Pro Gly
            100                 105


<210> SEQ ID NO 125
<211> LENGTH: 318
<212> TYPE: DNA
<213> ORGANISM: Artificial Sequence
<220> FEATURE:
<223> OTHER INFORMATION: Fcab FS20-31-102 CH3 domain

<400> SEQUENCE: 125

ggccagcctc gagaaccaca ggtgtacacc ctgcccccat cccgggatga gtgggcatct      60

ggtgaagtca gcctgacctg cctggtcaaa ggcttctatc ccagcgacat cgccgtggag     120

tgggagagca atgggcagcc agaagttgat tacaagacca cgcctcccgt gctggactcc     180

gacggctcct tcttcctcta cagcaagctc accgtgccgt attggaggtg gggtgttccg     240

cgtactttct catgctccgt gatgcatgag gctctgcaca accactacac acagaagagc     300

ctctccctgt ctccgggt                                                   318


<210> SEQ ID NO 126
<211> LENGTH: 222
<212> TYPE: PRT
<213> ORGANISM: Artificial Sequence
<220> FEATURE:
<223> OTHER INFORMATION: Fcab FS20-31-102 with LALA mutation

<400> SEQUENCE: 126

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Trp Ala Ser Gly Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Val Asp Tyr Lys Thr Thr Pro Pro Val Leu Asp Ser
                165                 170                 175

Asp Gly Ser Phe Phe Leu Tyr Ser Lys Leu Thr Val Pro Tyr Trp Arg
            180                 185                 190
```

```
Trp Gly Val Pro Arg Thr Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 127
<211> LENGTH: 666
<212> TYPE: DNA
<213> ORGANISM: Artificial Sequence
<220> FEATURE:
<223> OTHER INFORMATION: Fcab FS20-31-102 with LALA mutation

<400> SEQUENCE: 127

acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg ccagcctcga     360

gaaccacagg tgtacaccct gcccccatcc cgggatgagt gggcatctgg tgaagtcagc     420

ctgacctgcc tggtcaaagg cttctatccc agcgacatcg ccgtggagtg ggagagcaat     480

gggcagccag aagttgatta caagaccacg cctcccgtgc tggactccga cggctccttc     540

ttcctctaca gcaagctcac cgtgccgtat tggaggtggg gtgttccgcg tactttctca     600

tgctccgtga tgcatgaggc tctgcacaac cactacacac agaagagcct ctccctgtct     660

ccgggt                                                                666


<210> SEQ ID NO 128
<211> LENGTH: 222
<212> TYPE: PRT
<213> ORGANISM: Artificial Sequence
<220> FEATURE:
<223> OTHER INFORMATION: Fcab FS20-31-102 without LALA mutation

<400> SEQUENCE: 128

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Trp Ala Ser Gly Glu Val Ser Leu Thr Cys Leu
    130                 135                 140

Val Lys Gly Phe Tyr Pro Ser Asp Ile Ala Val Glu Trp Glu Ser Asn
```

-continued

```
145                 150                 155                 160

Gly Gln Pro Glu Val Asp Tyr Lys Thr Thr Pro Pro Val Leu Asp Ser
                165                 170                 175

Asp Gly Ser Phe Phe Leu Tyr Ser Lys Leu Thr Val Pro Tyr Trp Arg
            180                 185                 190

Trp Gly Val Pro Arg Thr Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 129
<211> LENGTH: 666
<212> TYPE: DNA
<213> ORGANISM: Artificial Sequence
<220> FEATURE:
<223> OTHER INFORMATION: Fcab FS20-31-102 without LALA mutation

<400> SEQUENCE: 129

acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagt gggcatctgg tgaagtcagc    420

ctgacctgcc tggtcaaagg cttctatccc agcgacatcg ccgtggagtg ggagagcaat    480

gggcagccag aagttgatta caagaccacg cctcccgtgc tggactccga cggctccttc    540

ttcctctaca gcaagctcac cgtgccgtat tggaggtggg gtgttccgcg tactttctca    600

tgctccgtga tgcatgaggc tctgcacaac cactacacac agaagagcct ctccctgtct    660

ccgggt                                                               666


<210> SEQ ID NO 130
<211> LENGTH: 447
<212> TYPE: PRT
<213> ORGANISM: Artificial Sequence
<220> FEATURE:
<223> OTHER INFORMATION: Heavy chain of FS20-31-102/4420 mock mAb? with
      LALA mutation

<400> SEQUENCE: 130

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110
```

Ser Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Trp Ala Ser Gly Glu Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Val Asp Tyr Lys Thr Thr Pro Pro Val Leu Asp
385 390 395 400

Ser Asp Gly Ser Phe Phe Leu Tyr Ser Lys Leu Thr Val Pro Tyr Trp
405 410 415

Arg Trp Gly Val Pro Arg Thr Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 131
<211> LENGTH: 447
<212> TYPE: PRT
<213> ORGANISM: Artificial Sequence
<220> FEATURE:
<223> OTHER INFORMATION: Heavy chain of FS20-31-102/4420 mock mAb? without LALA mutation

<400> SEQUENCE: 131

Glu Val Lys Leu Asp Glu Thr Gly Gly Gly Leu Val Gln Pro Gly Arg
1 5 10 15

Pro Met Lys Leu Ser Cys Val Ala Ser Gly Phe Thr Phe Ser Asp Tyr

```
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Trp Ala Ser Gly Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Val Asp Tyr Lys Thr Thr Pro Pro Val Leu Asp
385                 390                 395                 400

Ser Asp Gly Ser Phe Phe Leu Tyr Ser Lys Leu Thr Val Pro Tyr Trp
                405                 410                 415

Arg Trp Gly Val Pro Arg Thr Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 132
<211> LENGTH: 5
<212> TYPE: PRT
<213> ORGANISM: Artificial Sequence
<220> FEATURE:
<223> OTHER INFORMATION: Fcab FS20-31-108 CH3 domain structural loop sequence

<400> SEQUENCE: 132

Glu Lys Glu Ile Asp
1               5

<210> SEQ ID NO 133
<211> LENGTH: 10
<212> TYPE: PRT
<213> ORGANISM: Artificial Sequence
<220> FEATURE:
<223> OTHER INFORMATION: Fcab FS20-31-108 CH3 domain structural loop sequence

<400> SEQUENCE: 133

Pro Tyr Trp Arg Trp Gly Ala Lys Arg Thr
1               5                   10

<210> SEQ ID NO 134
<211> LENGTH: 106
<212> TYPE: PRT
<213> ORGANISM: Artificial Sequence
<220> FEATURE:
<223> OTHER INFORMATION: Fcab FS20-31-108 CH3 domain

<400> SEQUENCE: 134

Gly Gln Pro Arg Glu Pro Gln Val Tyr Thr Leu Pro Pro Ser Arg Asp
1               5                   10                  15

Glu Trp Ala Ser Gly Glu Val Ser Leu Thr Cys Leu Val Lys Gly Phe
            20                  25                  30

Tyr Pro Ser Asp Ile Ala Val Glu Trp Glu Ser Asn Gly Glu Lys Glu
        35                  40                  45

Ile Asp Tyr Lys Thr Thr Pro Pro Val Leu Asp Ser Asp Gly Ser Phe
    50                  55                  60

Phe Leu Tyr Ser Lys Leu Thr Val Pro Tyr Trp Arg Trp Gly Ala Lys
65                  70                  75                  80

Arg Thr Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 135
<211> LENGTH: 318
<212> TYPE: DNA
<213> ORGANISM: Artificial Sequence
<220> FEATURE:
<223> OTHER INFORMATION: Fcab FS20-31-108 CH3 domain

<400> SEQUENCE: 135
ggccagcctc gagaaccaca ggtgtacacc ctgcccccat cccgggatga gtgggcatct 60
ggtgaagtca gcctgacctg cctggtcaaa ggcttctatc ccagcgacat cgccgtggag 120
tgggagagca atggggaaaa agaaatcgat tacaagacca cgcctcccgt gctggactcc 180
gacggctcct tcttcctcta cagcaagctc accgtgccgt attggaggtg gggtgctaag 240
cgtactttct catgctccgt gatgcatgag gctctgcaca accactacac acagaagagc 300
ctctccctgt ctccgggt 318

<210> SEQ ID NO 136
<211> LENGTH: 222
<212> TYPE: PRT
<213> ORGANISM: Artificial Sequence
<220> FEATURE:
<223> OTHER INFORMATION: Fcab FS20-31-108 with LALA mutation

<400> SEQUENCE: 136

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Trp Ala Ser Gly Glu Val Ser Leu Thr Cys Leu
130 135 140

Val Lys Gly Phe Tyr Pro Ser Asp Ile Ala Val Glu Trp Glu Ser Asn
145 150 155 160

Gly Glu Lys Glu Ile Asp Tyr Lys Thr Thr Pro Pro Val Leu Asp Ser
165 170 175

Asp Gly Ser Phe Phe Leu Tyr Ser Lys Leu Thr Val Pro Tyr Trp Arg
180 185 190

Trp Gly Ala Lys Arg Thr Phe Ser Cys Ser Val Met His Glu Ala Leu
195 200 205

His Asn His Tyr Thr Gln Lys Ser Leu Ser Leu Ser Pro Gly
210 215 220

<210> SEQ ID NO 137
<211> LENGTH: 666
<212> TYPE: DNA
<213> ORGANISM: Artificial Sequence
<220> FEATURE:
<223> OTHER INFORMATION: Fcab FS20-31-108 with LALA mutation

<400> SEQUENCE: 137
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagt gggcatctgg tgaagtcagc 420

```
ctgacctgcc tggtcaaagg cttctatccc agcgacatcg ccgtggagtg ggagagcaat    480

ggggaaaaag aaatcgatta caagaccacg cctcccgtgc tggactccga cggctccttc    540

ttcctctaca gcaagctcac cgtgccgtat tggaggtggg gtgctaagcg tactttctca    600

tgctccgtga tgcatgaggc tctgcacaac cactacacac agaagagcct ctccctgtct    660

ccgggt                                                               666
```

<210> SEQ ID NO 138
<211> LENGTH: 222
<212> TYPE: PRT
<213> ORGANISM: Artificial Sequence
<220> FEATURE:
<223> OTHER INFORMATION: Fcab FS20-31-108 without LALA mutation

<400> SEQUENCE: 138

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Trp Ala Ser Gly Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Glu Lys Glu Ile Asp Tyr Lys Thr Thr Pro Pro Val Leu Asp Ser
                165                 170                 175

Asp Gly Ser Phe Phe Leu Tyr Ser Lys Leu Thr Val Pro Tyr Trp Arg
            180                 185                 190

Trp Gly Ala Lys Arg Thr Phe Ser Cys Ser Val Met His Glu Ala Leu
        195                 200                 205

His Asn His Tyr Thr Gln Lys Ser Leu Ser Leu Ser Pro Gly
    210                 215                 220
```

<210> SEQ ID NO 139
<211> LENGTH: 666
<212> TYPE: DNA
<213> ORGANISM: Artificial Sequence
<220> FEATURE:
<223> OTHER INFORMATION: Fcab FS20-31-108 without LALA mutation

<400> SEQUENCE: 139

```
acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240
```

```
gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagt gggcatctgg tgaagtcagc    420

ctgacctgcc tggtcaaagg cttctatccc agcgacatcg ccgtggagtg ggagagcaat    480

ggggaaaaag aaatcgatta caagaccacg cctcccgtgc tggactccga cggctccttc    540

ttcctctaca gcaagctcac cgtgccgtat tggaggtggg gtgctaagcg tactttctca    600

tgctccgtga tgcatgaggc tctgcacaac cactacacac agaagagcct ctccctgtct    660

ccgggt                                                               666
```

```
<210> SEQ ID NO 140
<211> LENGTH: 447
<212> TYPE: PRT
<213> ORGANISM: Artificial Sequence
<220> FEATURE:
<223> OTHER INFORMATION: Heavy chain of FS20-31-108/4420 mock mAb? with
      LALA mutation

<400> SEQUENCE: 140

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Trp Ala Ser Gly Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Glu Lys Glu Ile Asp Tyr Lys Thr Thr Pro Pro Val Leu Asp
385                 390                 395                 400

Ser Asp Gly Ser Phe Phe Leu Tyr Ser Lys Leu Thr Val Pro Tyr Trp
                405                 410                 415

Arg Trp Gly Ala Lys Arg Thr Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 141
<211> LENGTH: 447
<212> TYPE: PRT
<213> ORGANISM: Artificial Sequence
<220> FEATURE:
<223> OTHER INFORMATION: Heavy chain of FS20-31-108/4420 mock mAb?
      without LALA mutation

<400> SEQUENCE: 141

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Trp Ala Ser Gly Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Glu Lys Glu Ile Asp Tyr Lys Thr Thr Pro Pro Val Leu Asp
385                 390                 395                 400

Ser Asp Gly Ser Phe Phe Leu Tyr Ser Lys Leu Thr Val Pro Tyr Trp
                405                 410                 415

Arg Trp Gly Ala Lys Arg Thr Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 142
<211> LENGTH: 5
<212> TYPE: PRT
<213> ORGANISM: Artificial Sequence
<220> FEATURE:
<223> OTHER INFORMATION: Fcab FS20-31-115 CH3 domain structural loop
      sequence

<400> SEQUENCE: 142

Glu Gln Glu Phe Asp
1               5


<210> SEQ ID NO 143
<211> LENGTH: 106
<212> TYPE: PRT
<213> ORGANISM: Artificial Sequence
<220> FEATURE:
<223> OTHER INFORMATION: Fcab FS20-31-115 CH3 domain

<400> SEQUENCE: 143

Gly Gln Pro Arg Glu Pro Gln Val Tyr Thr Leu Pro Pro Ser Arg Asp
1               5                   10                  15

Glu Trp Ala Ser Gly Glu Val Ser Leu Thr Cys Leu Val Lys Gly Phe
            20                  25                  30
```

```
Tyr Pro Ser Asp Ile Ala Val Glu Trp Glu Ser Asn Gly Glu Gln Glu
        35                  40                  45

Phe Asp Tyr Lys Thr Thr Pro Pro Val Leu Asp Ser Asp Gly Ser Phe
    50                  55                  60

Phe Leu Tyr Ser Lys Leu Thr Val Pro Tyr Trp Arg Trp Gly Ala Lys
65                  70                  75                  80

Arg Thr Phe Ser Cys Ser Val Met His Glu Ala Leu His Asn His Tyr
                85                  90                  95

Thr Gln Lys Ser Leu Ser Leu Ser Pro Gly
            100                 105


<210> SEQ ID NO 144
<211> LENGTH: 318
<212> TYPE: DNA
<213> ORGANISM: Artificial Sequence
<220> FEATURE:
<223> OTHER INFORMATION: Fcab FS20-31-115 CH3 domain

<400> SEQUENCE: 144

ggacagcctc gagaaccaca ggtgtacacc ctgcccccat cccgggatga gtgggcatct      60

ggtgaagtca gcctgacctg cctggtcaaa ggcttctatc ccagcgacat cgccgtggag     120

tgggagagca atggggaaca ggaattcgat tacaagacca cgcctcccgt gctggactcc     180

gacggctcct tcttcctcta cagcaagctc accgtgccgt attggaggtg ggtgctaag      240

cgtactttct catgctccgt gatgcatgag gctctgcaca accactacac tcagaagagc     300

ttgtccctgt cgcccgga                                                  318


<210> SEQ ID NO 145
<211> LENGTH: 222
<212> TYPE: PRT
<213> ORGANISM: Artificial Sequence
<220> FEATURE:
<223> OTHER INFORMATION: Fcab FS20-31-115 with LALA mutation

<400> SEQUENCE: 145

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Trp Ala Ser Gly Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Glu Gln Glu Phe Asp Tyr Lys Thr Thr Pro Pro Val Leu Asp Ser
                165                 170                 175
```

```
Asp Gly Ser Phe Phe Leu Tyr Ser Lys Leu Thr Val Pro Tyr Trp Arg
            180                 185                 190

Trp Gly Ala Lys Arg Thr Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 146
<211> LENGTH: 666
<212> TYPE: DNA
<213> ORGANISM: Artificial Sequence
<220> FEATURE:
<223> OTHER INFORMATION: Fcab FS20-31-115 with LALA mutation

<400> SEQUENCE: 146

acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg acagcctcga     360

gaaccacagg tgtacaccct gcccccatcc cgggatgagt gggcatctgg tgaagtcagc     420

ctgacctgcc tggtcaaagg cttctatccc agcgacatcg ccgtggagtg ggagagcaat     480

ggggaacagg aattcgatta caagaccacg cctcccgtgc tggactccga cggctccttc     540

ttcctctaca gcaagctcac cgtgccgtat tggaggtggg gtgctaagcg tactttctca     600

tgctccgtga tgcatgaggc tctgcacaac cactacactc agaagagctt gtccctgtcg     660

cccgga                                                                666


<210> SEQ ID NO 147
<211> LENGTH: 222
<212> TYPE: PRT
<213> ORGANISM: Artificial Sequence
<220> FEATURE:
<223> OTHER INFORMATION: Fcab FS20-31-115 without LALA mutation

<400> SEQUENCE: 147

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Trp Ala Ser Gly Glu Val Ser Leu Thr Cys Leu
```

```
    130                 135                 140

Val Lys Gly Phe Tyr Pro Ser Asp Ile Ala Val Glu Trp Glu Ser Asn
145                 150                 155                 160

Gly Glu Gln Glu Phe Asp Tyr Lys Thr Thr Pro Pro Val Leu Asp Ser
                165                 170                 175

Asp Gly Ser Phe Phe Leu Tyr Ser Lys Leu Thr Val Pro Tyr Trp Arg
            180                 185                 190

Trp Gly Ala Lys Arg Thr Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 148
<211> LENGTH: 666
<212> TYPE: DNA
<213> ORGANISM: Artificial Sequence
<220> FEATURE:
<223> OTHER INFORMATION: Fcab FS20-31-115 without LALA mutation

<400> SEQUENCE: 148

acttgcccgc cttgcccagc cccggaactg ctgggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg acagcctcga     360

gaaccacagg tgtacaccct gcccccatcc cgggatgagt gggcatctgg tgaagtcagc     420

ctgacctgcc tggtcaaagg cttctatccc agcgacatcg ccgtggagtg ggagagcaat     480

ggggaacagg aattcgatta caagaccacg cctcccgtgc tggactccga cggctccttc     540

ttcctctaca gcaagctcac cgtgccgtat tggaggtggg gtgctaagcg tactttctca     600

tgctccgtga tgcatgaggc tctgcacaac cactacactc agaagagctt gtccctgtcg     660

cccgga                                                                666


<210> SEQ ID NO 149
<211> LENGTH: 447
<212> TYPE: PRT
<213> ORGANISM: Artificial Sequence
<220> FEATURE:
<223> OTHER INFORMATION: Heavy chain of FS20-31-115/4420 mock mAb? with
      LALA mutation

<400> SEQUENCE: 149

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95
```

```
Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Trp Ala Ser Gly Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Glu Gln Glu Phe Asp Tyr Lys Thr Thr Pro Pro Val Leu Asp
385                 390                 395                 400

Ser Asp Gly Ser Phe Phe Leu Tyr Ser Lys Leu Thr Val Pro Tyr Trp
                405                 410                 415

Arg Trp Gly Ala Lys Arg Thr Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 150
<211> LENGTH: 447
<212> TYPE: PRT
<213> ORGANISM: Artificial Sequence
<220> FEATURE:
<223> OTHER INFORMATION: Heavy chain of FS20-31-115/4420 mock mAb? without LALA mutation

<400> SEQUENCE: 150

```
Glu Val Lys Leu Asp Glu Thr Gly Gly Gly Leu Val Gln Pro Gly Arg
```

-continued

```
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Trp Ala Ser Gly Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Glu Gln Glu Phe Asp Tyr Lys Thr Thr Pro Pro Val Leu Asp
385                 390                 395                 400

Ser Asp Gly Ser Phe Phe Leu Tyr Ser Lys Leu Thr Val Pro Tyr Trp
                405                 410                 415

Arg Trp Gly Ala Lys Arg Thr Phe Ser Cys Ser Val Met His Glu Ala
            420                 425                 430
```

```
Leu His Asn His Tyr Thr Gln Lys Ser Leu Ser Leu Ser Pro Gly
        435                 440                 445


<210> SEQ ID NO 151
<211> LENGTH: 112
<212> TYPE: PRT
<213> ORGANISM: Artificial Sequence
<220> FEATURE:
<223> OTHER INFORMATION: Fcab FS20m-232-91 CH3 domain

<400> SEQUENCE: 151

Gly Gln Pro Arg Glu Pro Gln Val Tyr Thr Leu Pro Pro Ser Arg Asp
1               5                   10                  15

Glu Leu Phe Asp Pro Met Tyr Tyr Tyr Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Glu Pro Leu Trp Asp Tyr Lys Thr Thr Pro Pro Val Leu Asp
    50                  55                  60

Ser Asp Gly Ser Phe Phe Leu Tyr Ser Lys Leu Thr Val Trp Arg Asp
65                  70                  75                  80

Arg Trp Glu Asp Gly Asn Val Phe Ser Cys Ser Val Met His Glu Ala
                85                  90                  95

Leu His Asn His Tyr Thr Gln Lys Ser Leu Ser Leu Ser Pro Gly Lys
            100                 105                 110


<210> SEQ ID NO 152
<211> LENGTH: 452
<212> TYPE: PRT
<213> ORGANISM: Artificial Sequence
<220> FEATURE:
<223> OTHER INFORMATION: Heavy chain of FS20m-232-91/4420 mock mAb? with
      LALA mutation

<400> SEQUENCE: 152

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Phe Asp Pro Met Tyr Tyr Tyr Asn Gln
355 360 365

Val Ser Leu Thr Cys Leu Val Lys Gly Phe Tyr Pro Ser Asp Ile Ala
370 375 380

Val Glu Trp Glu Ser Asn Gly Glu Pro Leu Trp Asp Tyr Lys Thr Thr
385 390 395 400

Pro Pro Val Leu Asp Ser Asp Gly Ser Phe Phe Leu Tyr Ser Lys Leu
405 410 415

Thr Val Trp Arg Asp Arg Trp Glu Asp Gly Asn Val Phe Ser Cys Ser
420 425 430

Val Met His Glu Ala Leu His Asn His Tyr Thr Gln Lys Ser Leu Ser
435 440 445

Leu Ser Pro Gly
450

<210> SEQ ID NO 153
<211> LENGTH: 452
<212> TYPE: PRT
<213> ORGANISM: Artificial Sequence
<220> FEATURE:
<223> OTHER INFORMATION: Heavy chain of FS20m-232-91/4420 mock mAb? without LALA mutation

<400> SEQUENCE: 153

Glu Val Lys Leu Asp Glu Thr Gly Gly Gly Leu Val Gln Pro Gly Arg
1 5 10 15

Pro Met Lys Leu Ser Cys Val Ala Ser Gly Phe Thr Phe Ser Asp Tyr
20 25 30

Trp Met Asn Trp Val Arg Gln Ser Pro Glu Lys Gly Leu Glu Trp Val
35 40 45

Ala Gln Ile Arg Asn Lys Pro Tyr Asn Tyr Glu Thr Tyr Tyr Ser Asp
50 55 60

Ser Val Lys Gly Arg Phe Thr Ile Ser Arg Asp Asp Ser Lys Ser Ser
65 70 75 80

```
Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Phe Asp Pro Met Tyr Tyr Tyr Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Glu Pro Leu Trp Asp Tyr Lys Thr Thr
385                 390                 395                 400

Pro Pro Val Leu Asp Ser Asp Gly Ser Phe Phe Leu Tyr Ser Lys Leu
                405                 410                 415

Thr Val Trp Arg Asp Arg Trp Glu Asp Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

<210> SEQ ID NO 154
<211> LENGTH: 450
<212> TYPE: PRT
<213> ORGANISM: Artificial Sequence
<220> FEATURE:

<223> OTHER INFORMATION: Heavy chain of FS20m-232-91/HelD1.3 mock mAb?
with LALA mutation

<400> SEQUENCE: 154

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Phe Asp Pro Met Tyr Tyr Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Glu Pro Leu Trp Asp Tyr Lys Thr Thr Pro Pro
385                 390                 395                 400
```

```
Val Leu Asp Ser Asp Gly Ser Phe Phe Leu Tyr Ser Lys Leu Thr Val
                405                 410                 415

Trp Arg Asp Arg Trp Glu Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 155
<211> LENGTH: 450
<212> TYPE: PRT
<213> ORGANISM: Artificial Sequence
<220> FEATURE:
<223> OTHER INFORMATION: Heavy chain of FS20m-232-91/HelD1.3 mock mAb?
      without LALA mutation

<400> SEQUENCE: 155

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
```

```
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Phe Asp Pro Met Tyr Tyr Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Glu Pro Leu Trp Asp Tyr Lys Thr Thr Pro Pro
385                 390                 395                 400

Val Leu Asp Ser Asp Gly Ser Phe Phe Leu Tyr Ser Lys Leu Thr Val
                405                 410                 415

Trp Arg Asp Arg Trp Glu Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 156
<211> LENGTH: 219
<212> TYPE: PRT
<213> ORGANISM: Artificial Sequence
<220> FEATURE:
<223> OTHER INFORMATION: Light chain of 4420 mAb

<400> SEQUENCE: 156

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

195 200 205

Pro Val Thr Lys Ser Phe Asn Arg Gly Glu Cys
210 215

<210> SEQ ID NO 157
<211> LENGTH: 214
<212> TYPE: PRT
<213> ORGANISM: Artificial Sequence
<220> FEATURE:
<223> OTHER INFORMATION: Light chain of HelD1.3 mock mAb2

<400> SEQUENCE: 157

Asp Ile Gln Met Thr Gln Ser Pro Ala Ser Leu Ser Ala Ser Val Gly
1 5 10 15

Glu Thr Val Thr Ile Thr Cys Arg Ala Ser Gly Asn Ile His Asn Tyr
20 25 30

Leu Ala Trp Tyr Gln Gln Lys Gln Gly Lys Ser Pro Gln Leu Leu Val
35 40 45

Tyr Asn Ala Lys Thr Leu Ala Asp Gly Val Pro Ser Arg Phe Ser Gly
50 55 60

Ser Gly Ser Gly Thr Gln Tyr Ser Leu Lys Ile Asn Ser Leu Gln Pro
65 70 75 80

Glu Asp Phe Gly Ser Tyr Tyr Cys Gln His Phe Trp Ser Thr Pro Arg
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 158
<211> LENGTH: 442
<212> TYPE: PRT
<213> ORGANISM: Homo sapiens

<400> SEQUENCE: 158

Met Tyr Arg Met Gln Leu Leu Ser Cys Ile Ala Leu Ser Leu Ala Leu
1 5 10 15

Val Thr Asn Ser Leu His Cys Val Gly Asp Thr Tyr Pro Ser Asn Asp
20 25 30

Arg Cys Cys His Glu Cys Arg Pro Gly Asn Gly Met Val Ser Arg Cys
35 40 45

Ser Arg Ser Gln Asn Thr Val Cys Arg Pro Cys Gly Pro Gly Phe Tyr
50 55 60

Asn Asp Val Val Ser Ser Lys Pro Cys Lys Pro Cys Thr Trp Cys Asn
65 70 75 80

```
Leu Arg Ser Gly Ser Glu Arg Lys Gln Leu Cys Thr Ala Thr Gln Asp
                85                  90                  95

Thr Val Cys Arg Cys Arg Ala Gly Thr Gln Pro Leu Asp Ser Tyr Lys
            100                 105                 110

Pro Gly Val Asp Cys Ala Pro Cys Pro Pro Gly His Phe Ser Pro Gly
        115                 120                 125

Asp Asn Gln Ala Cys Lys Pro Trp Thr Asn Cys Thr Leu Ala Gly Lys
    130                 135                 140

His Thr Leu Gln Pro Ala Ser Asn Ser Ser Asp Ala Ile Cys Glu Asp
145                 150                 155                 160

Arg Asp Pro Pro Ala Thr Gln Pro Gln Glu Thr Gln Gly Pro Pro Ala
                165                 170                 175

Arg Pro Ile Thr Val Gln Pro Thr Glu Ala Trp Pro Arg Thr Ser Gln
            180                 185                 190

Gly Pro Ser Thr Arg Pro Val Glu Val Pro Gly Gly Arg Ala Val Ala
        195                 200                 205

Gly Ser Pro Arg Gly Pro Thr Ile Lys Pro Cys Pro Pro Cys Lys Cys
    210                 215                 220

Pro Ala Pro Asn Leu Leu Gly Gly Pro Ser Val Phe Ile Phe Pro Pro
225                 230                 235                 240

Lys Ile Lys Asp Val Leu Met Ile Ser Leu Ser Pro Ile Val Thr Cys
                245                 250                 255

Val Val Val Asp Val Ser Glu Asp Asp Pro Asp Val Gln Ile Ser Trp
            260                 265                 270

Phe Val Asn Asn Val Glu Val His Thr Ala Gln Thr Gln Thr His Arg
        275                 280                 285

Glu Asp Tyr Asn Ser Thr Leu Arg Val Val Ser Ala Leu Pro Ile Gln
    290                 295                 300

His Gln Asp Trp Met Ser Gly Lys Glu Phe Lys Cys Lys Val Asn Asn
305                 310                 315                 320

Lys Asp Leu Pro Ala Pro Ile Glu Arg Thr Ile Ser Lys Pro Lys Gly
                325                 330                 335

Ser Val Arg Ala Pro Gln Val Tyr Val Leu Pro Pro Pro Glu Glu Glu
            340                 345                 350

Met Thr Lys Lys Gln Val Thr Leu Thr Cys Met Val Thr Asp Phe Met
        355                 360                 365

Pro Glu Asp Ile Tyr Val Glu Trp Thr Asn Asn Gly Lys Thr Glu Leu
    370                 375                 380

Asn Tyr Lys Asn Thr Glu Pro Val Leu Asp Ser Asp Gly Ser Tyr Phe
385                 390                 395                 400

Met Tyr Ser Lys Leu Arg Val Glu Lys Lys Asn Trp Val Glu Arg Asn
                405                 410                 415

Ser Tyr Ser Cys Ser Val Val His Glu Gly Leu His Asn His His Thr
            420                 425                 430

Thr Lys Ser Phe Ser Arg Thr Pro Gly Lys
        435                 440
```

<210> SEQ ID NO 159
<211> LENGTH: 447
<212> TYPE: PRT
<213> ORGANISM: Mus musculus

<400> SEQUENCE: 159

```
Met Tyr Arg Met Gln Leu Leu Ser Cys Ile Ala Leu Ser Leu Ala Leu
```

-continued

```
1               5                   10                  15

Val Thr Asn Ser Val Thr Ala Arg Arg Leu Asn Cys Val Lys His Thr
            20                  25                  30

Tyr Pro Ser Gly His Lys Cys Cys Arg Glu Cys Gln Pro Gly His Gly
        35                  40                  45

Met Val Ser Arg Cys Asp His Thr Arg Asp Thr Leu Cys His Pro Cys
    50                  55                  60

Glu Thr Gly Phe Tyr Asn Glu Ala Val Asn Tyr Asp Thr Cys Lys Gln
65                  70                  75                  80

Cys Thr Gln Cys Asn His Arg Ser Gly Ser Glu Leu Lys Gln Asn Cys
                85                  90                  95

Thr Pro Thr Gln Asp Thr Val Cys Arg Cys Arg Pro Gly Thr Gln Pro
            100                 105                 110

Arg Gln Asp Ser Gly Tyr Lys Leu Gly Val Asp Cys Val Pro Cys Pro
        115                 120                 125

Pro Gly His Phe Ser Pro Gly Asn Asn Gln Ala Cys Lys Pro Trp Thr
    130                 135                 140

Asn Cys Thr Leu Ser Gly Lys Gln Thr Arg His Pro Ala Ser Asp Ser
145                 150                 155                 160

Leu Asp Ala Val Cys Glu Asp Arg Ser Leu Leu Ala Thr Leu Leu Trp
                165                 170                 175

Glu Thr Gln Arg Pro Thr Phe Arg Pro Thr Thr Val Gln Ser Thr Thr
            180                 185                 190

Val Trp Pro Arg Thr Ser Glu Leu Pro Ser Pro Pro Thr Leu Val Thr
        195                 200                 205

Pro Glu Gly Pro Ala Gly Ser Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430
```

His Asn His His Thr Thr Lys Ser Phe Ser Arg Thr Pro Gly Lys
435 440 445

<210> SEQ ID NO 160
<211> LENGTH: 444
<212> TYPE: PRT
<213> ORGANISM: Macaca fascicularis

<400> SEQUENCE: 160

Met Tyr Arg Met Gln Leu Leu Ser Cys Ile Ala Leu Ser Leu Ala Leu
1 5 10 15

Val Thr Asn Ser Leu His Cys Val Gly Asp Thr Tyr Pro Ser Asn Asp
20 25 30

Arg Cys Cys Gln Glu Cys Arg Pro Gly Asn Gly Met Val Ser Arg Cys
35 40 45

Asn Arg Ser Gln Asn Thr Val Cys Arg Pro Cys Gly Pro Gly Phe Tyr
50 55 60

Asn Asp Val Val Ser Ala Lys Pro Cys Lys Ala Cys Thr Trp Cys Asn
65 70 75 80

Leu Arg Ser Gly Ser Glu Arg Lys Gln Pro Cys Thr Ala Thr Gln Asp
85 90 95

Thr Val Cys Arg Cys Arg Ala Gly Thr Gln Pro Leu Asp Ser Tyr Lys
100 105 110

Pro Gly Val Asp Cys Ala Pro Cys Pro Pro Gly His Phe Ser Pro Gly
115 120 125

Asp Asn Gln Ala Cys Lys Pro Trp Thr Asn Cys Thr Leu Ala Gly Lys
130 135 140

His Thr Leu Gln Pro Ala Ser Asn Ser Ser Asp Ala Ile Cys Glu Asp
145 150 155 160

Arg Asp Pro Pro Pro Thr Gln Pro Gln Glu Thr Gln Gly Pro Pro Ala
165 170 175

Arg Pro Thr Thr Val Gln Pro Thr Glu Ala Trp Pro Arg Thr Ser Gln
180 185 190

Arg Pro Ser Thr Arg Pro Val Glu Val Pro Arg Gly Pro Ala Val Ala
195 200 205

Ala Ile Gly Ser Pro Arg Gly Pro Thr Ile Lys Pro Cys Pro Pro Cys
210 215 220

Lys Cys Pro Ala Pro Asn Leu Leu Gly Gly Pro Ser Val Phe Ile Phe
225 230 235 240

Pro Pro Lys Ile Lys Asp Val Leu Met Ile Ser Leu Ser Pro Ile Val
245 250 255

Thr Cys Val Val Val Asp Val Ser Glu Asp Asp Pro Asp Val Gln Ile
260 265 270

Ser Trp Phe Val Asn Asn Val Glu Val His Thr Ala Gln Thr Gln Thr
275 280 285

His Arg Glu Asp Tyr Asn Ser Thr Leu Arg Val Val Ser Ala Leu Pro
290 295 300

Ile Gln His Gln Asp Trp Met Ser Gly Lys Glu Phe Lys Cys Lys Val
305 310 315 320

Asn Asn Lys Asp Leu Pro Ala Pro Ile Glu Arg Thr Ile Ser Lys Pro
325 330 335

Lys Gly Ser Val Arg Ala Pro Gln Val Tyr Val Leu Pro Pro Pro Glu
340 345 350

Glu Glu Met Thr Lys Lys Gln Val Thr Leu Thr Cys Met Val Thr Asp

```
        355                 360                 365

Phe Met Pro Glu Asp Ile Tyr Val Glu Trp Thr Asn Asn Gly Lys Thr
    370                 375                 380

Glu Leu Asn Tyr Lys Asn Thr Glu Pro Val Leu Asp Ser Asp Gly Ser
385                 390                 395                 400

Tyr Phe Met Tyr Ser Lys Leu Arg Val Glu Lys Lys Asn Trp Val Glu
                405                 410                 415

Arg Asn Ser Tyr Ser Cys Ser Val Val His Glu Gly Leu His Asn His
            420                 425                 430

His Thr Thr Lys Ser Phe Ser Arg Thr Pro Gly Lys
        435                 440


<210> SEQ ID NO 161
<211> LENGTH: 186
<212> TYPE: PRT
<213> ORGANISM: Homo sapiens

<400> SEQUENCE: 161

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
            180                 185


<210> SEQ ID NO 162
<211> LENGTH: 186
<212> TYPE: PRT
<213> ORGANISM: Macaca fascicularis

<400> SEQUENCE: 162

Leu His Cys Val Gly Asp Thr Tyr Pro Ser Asn Asp Arg Cys Cys Gln
1               5                   10                  15

Glu Cys Arg Pro Gly Asn Gly Met Val Ser Arg Cys Asn Arg Ser Gln
            20                  25                  30

Asn Thr Val Cys Arg Pro Cys Gly Pro Gly Phe Tyr Asn Asp Val Val
        35                  40                  45

Ser Ala Lys Pro Cys Lys Ala Cys Thr Trp Cys Asn Leu Arg Ser Gly
```

```
    50                  55                  60

Ser Glu Arg Lys Gln Pro Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Pro Thr Gln Pro Gln Glu Thr Gln Gly Pro Pro Ala Arg Pro Thr Thr
145                 150                 155                 160

Val Gln Pro Thr Glu Ala Trp Pro Arg Thr Ser Gln Arg Pro Ser Thr
                165                 170                 175

Arg Pro Val Glu Val Pro Arg Gly Pro Ala
            180                 185


<210> SEQ ID NO 163
<211> LENGTH: 192
<212> TYPE: PRT
<213> ORGANISM: Mus musculus

<400> SEQUENCE: 163

Val Thr Ala Arg Arg Leu Asn Cys Val Lys His Thr Tyr Pro Ser Gly
1               5                   10                  15

His Lys Cys Cys Arg Glu Cys Gln Pro Gly His Gly Met Val Ser Arg
            20                  25                  30

Cys Asp His Thr Arg Asp Thr Leu Cys His Pro Cys Glu Thr Gly Phe
        35                  40                  45

Tyr Asn Glu Ala Val Asn Tyr Asp Thr Cys Lys Gln Cys Thr Gln Cys
    50                  55                  60

Asn His Arg Ser Gly Ser Glu Leu Lys Gln Asn Cys Thr Pro Thr Gln
65                  70                  75                  80

Asp Thr Val Cys Arg Cys Arg Pro Gly Thr Gln Pro Arg Gln Asp Ser
                85                  90                  95

Gly Tyr Lys Leu Gly Val Asp Cys Val Pro Cys Pro Pro Gly His Phe
            100                 105                 110

Ser Pro Gly Asn Asn Gln Ala Cys Lys Pro Trp Thr Asn Cys Thr Leu
        115                 120                 125

Ser Gly Lys Gln Thr Arg His Pro Ala Ser Asp Ser Leu Asp Ala Val
    130                 135                 140

Cys Glu Asp Arg Ser Leu Leu Ala Thr Leu Leu Trp Glu Thr Gln Arg
145                 150                 155                 160

Pro Thr Phe Arg Pro Thr Thr Val Gln Ser Thr Thr Val Trp Pro Arg
                165                 170                 175

Thr Ser Glu Leu Pro Ser Pro Pro Thr Leu Val Thr Pro Glu Gly Pro
            180                 185                 190


<210> SEQ ID NO 164
<211> LENGTH: 249
<212> TYPE: PRT
<213> ORGANISM: Artificial Sequence
<220> FEATURE:
<223> OTHER INFORMATION: DO11.10-hOX40 and human OX40 receptor

<400> SEQUENCE: 164
```

```
Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245
```

<210> SEQ ID NO 165
<211> LENGTH: 253
<212> TYPE: PRT
<213> ORGANISM: Artificial Sequence
<220> FEATURE:
<223> OTHER INFORMATION: DO11.10-mOX40 and mouse OX40 receptor

<400> SEQUENCE: 165

```
Val Thr Ala Arg Arg Leu Asn Cys Val Lys His Thr Tyr Pro Ser Gly
1               5                   10                  15

His Lys Cys Cys Arg Glu Cys Gln Pro Gly His Gly Met Val Ser Arg
            20                  25                  30

Cys Asp His Thr Arg Asp Thr Leu Cys His Pro Cys Glu Thr Gly Phe
        35                  40                  45

Tyr Asn Glu Ala Val Asn Tyr Asp Thr Cys Lys Gln Cys Thr Gln Cys
    50                  55                  60

Asn His Arg Ser Gly Ser Glu Leu Lys Gln Asn Cys Thr Pro Thr Gln
65                  70                  75                  80

Asp Thr Val Cys Arg Cys Arg Pro Gly Thr Gln Pro Arg Gln Asp Ser
                85                  90                  95

Gly Tyr Lys Leu Gly Val Asp Cys Val Pro Cys Pro Pro Gly His Phe
            100                 105                 110
```

```
Ser Pro Gly Asn Asn Gln Ala Cys Lys Pro Trp Thr Asn Cys Thr Leu
        115                 120                 125

Ser Gly Lys Gln Thr Arg His Pro Ala Ser Asp Ser Leu Asp Ala Val
    130                 135                 140

Cys Glu Asp Arg Ser Leu Leu Ala Thr Leu Leu Trp Glu Thr Gln Arg
145                 150                 155                 160

Pro Thr Phe Arg Pro Thr Thr Val Gln Ser Thr Thr Val Trp Pro Arg
                165                 170                 175

Thr Ser Glu Leu Pro Ser Pro Pro Thr Leu Val Thr Pro Glu Gly Pro
            180                 185                 190

Ala Phe Ala Val Leu Leu Gly Leu Gly Leu Gly Leu Leu Ala Pro Leu
        195                 200                 205

Thr Val Leu Leu Ala Leu Tyr Leu Leu Arg Lys Ala Trp Arg Leu Pro
    210                 215                 220

Asn Thr Pro Lys Pro Cys Trp Gly Asn Ser Phe Arg Thr Pro Ile Gln
225                 230                 235                 240

Glu Glu His Thr Asp Ala His Phe Thr Leu Ala Lys Ile
                245                 250


<210> SEQ ID NO 166
<211> LENGTH: 250
<212> TYPE: PRT
<213> ORGANISM: Artificial Sequence
<220> FEATURE:
<223> OTHER INFORMATION: DO11.10-cOX40 and cynomolgus monkey OX40
      receptor

<400> SEQUENCE: 166

Lys Leu His Cys Val Gly Asp Thr Tyr Pro Ser Asn Asp Arg Cys Cys
1               5                   10                  15

Gln Glu Cys Arg Pro Gly Asn Gly Met Val Ser Arg Cys Asn Arg Ser
            20                  25                  30

Gln Asn Thr Val Cys Arg Pro Cys Gly Pro Gly Phe Tyr Asn Asp Val
        35                  40                  45

Val Ser Ala Lys Pro Cys Lys Ala Cys Thr Trp Cys Asn Leu Arg Ser
    50                  55                  60

Gly Ser Glu Arg Lys Gln Pro Cys Thr Ala Thr Gln Asp Thr Val Cys
65                  70                  75                  80

Arg Cys Arg Ala Gly Thr Gln Pro Leu Asp Ser Tyr Lys Pro Gly Val
                85                  90                  95

Asp Cys Ala Pro Cys Pro Pro Gly His Phe Ser Pro Gly Asp Asn Gln
            100                 105                 110

Ala Cys Lys Pro Trp Thr Asn Cys Thr Leu Ala Gly Lys His Thr Leu
        115                 120                 125

Gln Pro Ala Ser Asn Ser Ser Asp Ala Ile Cys Glu Asp Arg Asp Pro
    130                 135                 140

Pro Pro Thr Gln Pro Gln Glu Thr Gln Gly Pro Pro Ala Arg Pro Thr
145                 150                 155                 160

Thr Val Gln Pro Thr Glu Ala Trp Pro Arg Thr Ser Gln Arg Pro Ser
                165                 170                 175

Thr Arg Pro Val Glu Val Pro Arg Gly Pro Ala Val Ala Ala Ile Leu
            180                 185                 190

Gly Leu Gly Leu Ala Leu Gly Leu Leu Gly Pro Leu Ala Met Leu Leu
        195                 200                 205

Ala Leu Leu Leu Leu Arg Arg Asp Gln Arg Leu Pro Pro Asp Ala Pro
```

```
    210                 215                 220

Lys Ala Pro Gly Gly Gly Ser Phe Arg Thr Pro Ile Gln Glu Glu Gln
225                 230                 235                 240

Ala Asp Ala His Ser Ala Leu Ala Lys Ile
                245                 250


<210> SEQ ID NO 167
<211> LENGTH: 447
<212> TYPE: PRT
<213> ORGANISM: Artificial Sequence
<220> FEATURE:
<223> OTHER INFORMATION: Heavy chain of anti-FITC mAb G1AA/4420
      comprising LALA mutation

<400> SEQUENCE: 167

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 168
<211> LENGTH: 447
<212> TYPE: PRT
<213> ORGANISM: Artificial Sequence
<220> FEATURE:
<223> OTHER INFORMATION: Heavy chain of anti-FITC mAb G1/4420 without
      LALA mutation

<400> SEQUENCE: 168

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 169
<211> LENGTH: 446
<212> TYPE: PRT
<213> ORGANISM: Artificial Sequence
<220> FEATURE:
<223> OTHER INFORMATION: Heavy chain of the G1/HelD1.3 antibody with LALA mutation

<400> SEQUENCE: 169

Gln Val Gln Leu Gln Glu Ser Gly Pro Gly Leu Val Arg Pro Ser Gln
1 5 10 15

Thr Leu Ser Leu Thr Cys Thr Val Ser Gly Ser Thr Phe Ser Gly Tyr
20 25 30

Gly Val Asn Trp Val Arg Gln Pro Pro Gly Arg Gly Leu Glu Trp Ile
35 40 45

Gly Met Ile Trp Gly Asp Gly Asn Thr Asp Tyr Asn Ser Ala Leu Lys
50 55 60

Ser Arg Val Thr Met Leu Val Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Glu Arg Asp Tyr Arg Leu Asp Tyr Trp Gly Gln Gly Ser Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly

-continued

```
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 170
<211> LENGTH: 15
<212> TYPE: PRT
<213> ORGANISM: Artificial Sequence
<220> FEATURE:
<223> OTHER INFORMATION: Full-length IgG1 hinge region

<400> SEQUENCE: 170

Glu Pro Lys Ser Cys Asp Lys Thr His Thr Cys Pro Pro Cys Pro
1               5                   10                  15


<210> SEQ ID NO 171
<211> LENGTH: 6
<212> TYPE: PRT
<213> ORGANISM: Artificial Sequence
<220> FEATURE:
<223> OTHER INFORMATION: Truncated Fcab hinge region

<400> SEQUENCE: 171
```

Thr Cys Pro Pro Cys Pro
1 5

<210> SEQ ID NO 172
<211> LENGTH: 447
<212> TYPE: PRT
<213> ORGANISM: Artificial Sequence
<220> FEATURE:
<223> OTHER INFORMATION: Heavy chain sequence of FS20-22-49-AA/FS30-10-16

<400> SEQUENCE: 172

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Asp Met Ser Trp Val Arg Gln Ala Pro Gly Lys Gly Leu Glu Trp Val
35 40 45

Ser Asp Ile Asp Pro Thr Gly Ser Lys Thr Asp Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Leu Leu Val Tyr Gly Phe Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

```
Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Asn Pro Ala Asp Tyr Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 173
<211> LENGTH: 215
<212> TYPE: PRT
<213> ORGANISM: Artificial Sequence
<220> FEATURE:
<223> OTHER INFORMATION: Light chain sequence of FS20-22-49-AA/FS30-10-
      16

<400> SEQUENCE: 173

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Ser Tyr Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 174
<211> LENGTH: 447
<212> TYPE: PRT
<213> ORGANISM: Artificial Sequence
<220> FEATURE:
<223> OTHER INFORMATION: Heavy chain of FS20-22-41/4420 mock mAb?
```

without LALA mutation

<400> SEQUENCE: 174

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Asp Glu Gln Phe Ala Tyr Lys Thr Thr Pro Pro Val Leu Asp
385                 390                 395                 400
```

Ser Asp Gly Ser Phe Phe Leu Tyr Ser Lys Leu Thr Val Asp Gln Tyr
405 410 415

Arg Trp Asn Pro Gly Asp Tyr Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 175
<211> LENGTH: 446
<212> TYPE: PRT
<213> ORGANISM: Artificial Sequence
<220> FEATURE:
<223> OTHER INFORMATION: Heavy chain of G1/OX86 mAb comprising LALA mutation (G1AA/OX86)

<400> SEQUENCE: 175

Gln Val Gln Leu Lys Glu Ser Gly Pro Gly Leu Val Gln Pro Ser Gln
1 5 10 15

Thr Leu Ser Leu Thr Cys Thr Val Ser Gly Phe Ser Leu Thr Gly Tyr
20 25 30

Asn Leu His Trp Val Arg Gln Pro Pro Gly Lys Gly Leu Glu Trp Met
35 40 45

Gly Arg Met Arg Tyr Asp Gly Asp Thr Tyr Tyr Asn Ser Val Leu Lys
50 55 60

Ser Arg Leu Ser Ile Ser Arg Asp Thr Ser Lys Asn Gln Val Phe Leu
65 70 75 80

Lys Met Asn Ser Leu Gln Thr Asp Asp Thr Ala Ile Tyr Tyr Cys Thr
85 90 95

Arg Asp Gly Arg Gly Asp Ser Phe Asp Tyr Trp Gly Gln Gly Val Met
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Ala Ala Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 176
<211> LENGTH: 219
<212> TYPE: PRT
<213> ORGANISM: Artificial Sequence
<220> FEATURE:
<223> OTHER INFORMATION: Light chain of G1AA/OX86 mAb

<400> SEQUENCE: 176

Asp Ile Val Met Thr Gln Gly Ala Leu Pro Asn Pro Val Pro Ser Gly
1 5 10 15

Glu Ser Ala Ser Ile Thr Cys Arg Ser Ser Gln Ser Leu Val Tyr Lys
20 25 30

Asp Gly Gln Thr Tyr Leu Asn Trp Phe Leu Gln Arg Pro Gly Gln Ser
35 40 45

Pro Gln Leu Leu Thr Tyr Trp Met Ser Thr Arg Ala Ser Gly Val Ser
50 55 60

Asp Arg Phe Ser Gly Ser Gly Ser Gly Thr Tyr Phe Thr Leu Lys Ile
65 70 75 80

Ser Arg Val Arg Ala Glu Asp Ala Gly Val Tyr Tyr Cys Gln Gln Val
85 90 95

Arg Glu Tyr Pro Phe Thr Phe Gly Ser Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 177

<211> LENGTH: 8
<212> TYPE: PRT
<213> ORGANISM: Artificial Sequence
<220> FEATURE:
<223> OTHER INFORMATION: Heavy chain CDRs of FS30-10-16 mAb CDR1 (IMGT)

<400> SEQUENCE: 177

Gly Phe Thr Phe Ser Ser Tyr Asp
1 5

<210> SEQ ID NO 178
<211> LENGTH: 5
<212> TYPE: PRT
<213> ORGANISM: Artificial Sequence
<220> FEATURE:
<223> OTHER INFORMATION: Heavy chain CDRs of FS30-10-16 mAb CDR1 (Kabat)

<400> SEQUENCE: 178

Ser Tyr Asp Met Ser
1 5

<210> SEQ ID NO 179
<211> LENGTH: 8
<212> TYPE: PRT
<213> ORGANISM: Artificial Sequence
<220> FEATURE:
<223> OTHER INFORMATION: Heavy chain CDRs of FS30-10-16 mAb CDR2 (IMGT)

<400> SEQUENCE: 179

Ile Asp Pro Thr Gly Ser Lys Thr
1 5

<210> SEQ ID NO 180
<211> LENGTH: 17
<212> TYPE: PRT
<213> ORGANISM: Artificial Sequence
<220> FEATURE:
<223> OTHER INFORMATION: Heavy chain CDRs of FS30-10-16 mAb CDR2 (Kabat)

<400> SEQUENCE: 180

Asp Ile Asp Pro Thr Gly Ser Lys Thr Asp Tyr Ala Asp Ser Val Lys
1 5 10 15

Gly

<210> SEQ ID NO 181
<211> LENGTH: 11
<212> TYPE: PRT
<213> ORGANISM: Artificial Sequence
<220> FEATURE:
<223> OTHER INFORMATION: Heavy chain CDRs of FS30-10-16 mAb CDR3 (IMGT)

<400> SEQUENCE: 181

Ala Arg Asp Leu Leu Val Tyr Gly Phe Asp Tyr
1 5 10

<210> SEQ ID NO 182
<211> LENGTH: 9
<212> TYPE: PRT
<213> ORGANISM: Artificial Sequence
<220> FEATURE:
<223> OTHER INFORMATION: Heavy chain CDRs of FS30-10-16 mAb CDR3 (Kabat)

<400> SEQUENCE: 182

Asp Leu Leu Val Tyr Gly Phe Asp Tyr
1 5

<210> SEQ ID NO 183
<211> LENGTH: 118
<212> TYPE: PRT
<213> ORGANISM: Artificial Sequence
<220> FEATURE:
<223> OTHER INFORMATION: VH domain of FS30-10-16 mAb

<400> SEQUENCE: 183

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Tyr Gly Phe Asp Tyr Trp Gly Gln Gly Thr
            100                 105                 110

Leu Val Thr Val Ser Ser
        115
```

<210> SEQ ID NO 184
<211> LENGTH: 7
<212> TYPE: PRT
<213> ORGANISM: Artificial Sequence
<220> FEATURE:
<223> OTHER INFORMATION: Light chain CDRs of FS30-10-16 mAb CDR1 (IMGT)

<400> SEQUENCE: 184

```
Gln Ser Val Ser Ser Ser Tyr
1               5
```

<210> SEQ ID NO 185
<211> LENGTH: 12
<212> TYPE: PRT
<213> ORGANISM: Artificial Sequence
<220> FEATURE:
<223> OTHER INFORMATION: Light chain CDRs of FS30-10-16 mAb CDR1 (Kabat)

<400> SEQUENCE: 185

```
Arg Ala Ser Gln Ser Val Ser Ser Ser Tyr Leu Ala
1               5                   10
```

<210> SEQ ID NO 186
<211> LENGTH: 3
<212> TYPE: PRT
<213> ORGANISM: Artificial Sequence
<220> FEATURE:
<223> OTHER INFORMATION: Light chain CDRs of FS30-10-16 mAb CDR2 (IMGT)

<400> SEQUENCE: 186

```
Gly Ala Ser
1
```

<210> SEQ ID NO 187
<211> LENGTH: 7
<212> TYPE: PRT
<213> ORGANISM: Artificial Sequence
<220> FEATURE:
<223> OTHER INFORMATION: Light chain CDRs of FS30-10-16 mAb CDR2 (Kabat)

<400> SEQUENCE: 187

Gly Ala Ser Ser Arg Ala Thr
1 5

<210> SEQ ID NO 188
<211> LENGTH: 9
<212> TYPE: PRT
<213> ORGANISM: Artificial Sequence
<220> FEATURE:
<223> OTHER INFORMATION: Light chain CDRs of FS30-10-16 mAb CDR3 (IMGT)

<400> SEQUENCE: 188

Gln Gln Ser Tyr Ser Tyr Pro Val Thr
1 5

<210> SEQ ID NO 189
<211> LENGTH: 108
<212> TYPE: PRT
<213> ORGANISM: Artificial Sequence
<220> FEATURE:
<223> OTHER INFORMATION: VL domain of FS30-10-16 mAb

<400> SEQUENCE: 189

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Ser Tyr Ser Tyr Pro
85 90 95

Val Thr Phe Gly Gln Gly Thr Lys Val Glu Ile Lys
100 105

<210> SEQ ID NO 190
<211> LENGTH: 110
<212> TYPE: PRT
<213> ORGANISM: Artificial Sequence
<220> FEATURE:
<223> OTHER INFORMATION: Fcab FS20-11

<400> SEQUENCE: 190

Gly Gln Pro Arg Glu Pro Gln Val Tyr Thr Leu Pro Pro Ser Arg Asp
1 5 10 15

Glu Thr Ser Glu Glu Asn Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

Phe Leu Tyr Ser Lys Leu Thr Val Asp Lys Ser Arg Trp Trp Lys His
65 70 75 80

Tyr Val Asp Glu His Pro Phe Leu Cys Ser Val Met His Glu Ala Leu
85 90 95

His Asn His Tyr Thr Gln Glu Ser Leu Ser Leu Ser Pro Gly 100 105 110

<210> SEQ ID NO 191
<211> LENGTH: 106
<212> TYPE: PRT
<213> ORGANISM: Artificial Sequence
<220> FEATURE:
<223> OTHER INFORMATION: Fcab FS0-22

<400> SEQUENCE: 191

Gly Gln Pro Arg Glu Pro Gln Val Tyr Thr Leu Pro Pro Ser Arg Asp
1 5 10 15

Glu Tyr Trp Asp Gln Glu Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

Phe Leu Tyr Ser Lys Leu Thr Val Asp Gln Tyr Arg Trp Asn Pro Gly
65 70 75 80

Gly Tyr Phe Ser Cys Ser Val Met His Glu Ala Leu His Asn His Tyr
85 90 95

Thr Gln Lys Ser Leu Ser Leu Ser Pro Gly
100 105

<210> SEQ ID NO 192
<211> LENGTH: 106
<212> TYPE: PRT
<213> ORGANISM: Artificial Sequence
<220> FEATURE:
<223> OTHER INFORMATION: Fcab FS20-31

<400> SEQUENCE: 192

Gly Gln Pro Arg Glu Pro Gln Val Tyr Thr Leu Pro Pro Ser Arg Asp
1 5 10 15

Glu Tyr Tyr Ser Gly Glu Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asp Tyr Lys Thr Thr Pro Pro Val Leu Asp Ser Asp Gly Ser Phe
50 55 60

Phe Leu Tyr Ser Lys Leu Thr Val Pro Tyr Trp Arg Trp Gly Gly Pro
65 70 75 80

Gly Thr Phe Ser Cys Ser Val Met His Glu Ala Leu His Asn His Tyr
85 90 95

Thr Gln Lys Ser Leu Ser Leu Ser Pro Gly
100 105

<210> SEQ ID NO 193
<211> LENGTH: 9
<212> TYPE: PRT
<213> ORGANISM: Artificial Sequence
<220> FEATURE:
<223> OTHER INFORMATION: Light chain CDRs of FS30-10-16 mAb CDR3 (Kabat)

<400> SEQUENCE: 193

Gln Gln Ser Tyr Ser Tyr Pro Val Thr
1 5

FC BINDING FRAGMENTS COMPRISING AN OX40 ANTIGEN-BINDING SITE

RELATED APPLICATIONS

This Application is a national stage filing under 35 U.S.C. § 371 of International Patent Application Serial No. PCT/EP2019/068808, filed Jul. 12, 2019, the entire contents of which is incorporated herein by reference in its entirety.

FIELD OF THE INVENTION

The invention relates to specific binding members that bind OX40. The specific binding members comprise an OX40 antigen-binding site located in a constant domain of the specific binding member and find application in the treatment of cancer and infectious diseases, for example.

BACKGROUND TO THE INVENTION

Cell signalling is an essential part of the life of all organisms and normally involves cell surface receptors that interact with soluble or surface expressed ligands. This interaction results in changes to the receptor, the ligand or both. For example, ligand binding can induce conformational changes in the receptors causing them to cluster together into dimers or oligomers. This clustering effect then results in activation of intracellular signalling pathways. There are numerous receptors that are activated in this way, including members of the tumour necrosis factor receptor superfamily (TNFRSF), such as OX40.

OX40 (also known as CD134 and TNFRSF4) is predominantly expressed on activated T cells, including CD4+ T cells, CD8+ T cells, type 1 and type 2 T helper (Th1 and Th2) cells and regulatory T (Treg) cells, and is also expressed on activated natural killer (NK) cells.

Interaction of OX40 with its ligand, OX40L, expressed on antigen presenting cells (APCs), results in clustering of the OX40 receptor. OX40L is expressed at the cell surface as a trimer, like the majority of ligands of other tumour necrosis factor (TNF) receptors. The proposed model for OX40 activation is that interaction with surface expressed trimeric OX40L induces the clustering of OX40 receptors that exist either as monomers or pre-formed trimers at the cell surface. This clustering effect of OX40 receptors activates the NFkB signalling pathway (Croft, 2010). Activation of the NFkB signalling pathway in turn increases T cell activation, T cell clonal expansion, T cell differentiation and survival, and enhances the generation of memory T cells. A major role of the OX40/OX40L interaction is to regulate the number of effector (protective or pathogenic) T cells that accumulate late in primary immune responses, and thus to increase the number of memory T cells that are available to respond during a secondary immune response when the antigen is re-encountered at a later time (Croft, 2010). OX40 can mediate its effect on T cells either directly as described above or indirectly via the enhanced production of inflammatory cytokines, such as IL2 and IFNγ. OX40 signalling can also modulate the function of Treg cells to abrogate their immunosuppressive activity (Croft, 2010).

The therapeutic efficacy of OX40 agonists has been demonstrated in mouse tumour models. Specifically, OX40 agonists (OX40L-Ig and anti-OX40 mAb OX86) have been shown to be therapeutically effective in mouse tumour models of melanoma, glioma, breast and colon carcinoma, sarcoma, renal carcinoma and prostate cancer (Weinberg et al., 2000; Morris et al., 2001; Ali et al., 2004; Sadun et al., 2008; Redmond et al., 2009). The effectiveness of OX40 agonist monotherapy appears to correlate with tumour immunogenicity (Kjaergaard et al. 2000), suggesting that OX40 expression on tumour-specific T cells requires sufficient priming by tumour antigens, and that insufficient priming is provided by poorly immunogenic tumours.

The efficacy of anti-OX40 agonist antibodies is also being investigated in clinical trials, both as a monotherapy and in combination with other monoclonal antibodies (mAbs).

Clinical tests of anti-OX40 mAbs as a monotherapy include a phase I study of a mouse monoclonal anti-OX40 mAb in patients with advanced cancers which showed an acceptable toxicity profile and regression of at least one metastatic lesion in 12 out of 30 patients (Curti et al., 2013). Preliminary results from a phase I study of a humanised anti-OX40 mAb (MED10562; MedImmune) in patients with advanced solid tumours revealed no dose-limiting toxicities (DLTs) and one out of 32 patients showed an objective response (Glisson et al., 2016).

As mentioned above, anti-OX40 mAbs are also being investigated in cancer treatment in combination with other mAbs. For example, anti-OX40 mAbs are being tested in combination with either an anti-PD-L1 mAb (durvalumab) or anti-CTLA4 mAb (tremelimumab) (ClinicalTrials.gov Identifier: NCT02705482) in advanced solid tumours. These combinations have been tested in pre-clinical models and have shown improved tumour regression and survival (Guo et al., 2014; Redmond et al., 2014).

An anti-OX40 mAb (MOXR0916; Genentech) is being tested in the clinic both as a monotherapy (NCT02219724) and in combination with an anti-PD-L1 mAb (atezolizumab) (NCT03029832) in the treatment of locally advanced or metastatic solid tumours. A humanised anti-OX40 mAb (GSK3174998; GlaxoSmithKline) is being evaluated in combination with an anti-PD-1 mAb (pembrolizumab) in the treatment of selected advanced or recurrent solid tumours (NCT02528357). A human anti-OX40 mAb (PF-04518600; Pfizer) was tested in clinical trials in the treatment of locally advanced or metatstatic cancers and was shown to be well-tolerated and achieved either a partial response (2 patients) or stable disease (25 patients) in 27 of 48 patients (NCT02315066; El-Khoueiry et al., 2017). This mAb is also being tested in combination with an anti-4-1 BB agonist mAb (PF-05082566/utomilumab) (NCT02315066) and anti-PD-L1 mAb (avelumab) (NCT02554812) in the treatment of locally advanced or metastatic solid tumours. A human IgG1 anti-OX40 mAb (BMS-986178; Bristol-Myers Squibb) is being tested in clinical trials in combination with either an anti-PD-1 mAb (nivolumab) or an anti-CTLA-4 mAb (ipilimumab) or both in the treatment of solid cancers that are advanced or have spread (NCT02737475).

STATEMENTS OF INVENTION

The present inventors performed an extensive selection and affinity maturation program to isolate a panel of antibody Fc-region fragments (Fcabs™) comprising an OX40 antigen-binding site engineered into their CH3 domain.

The Fcab molecules consist of two identical polypeptide chains, each comprising a truncated hinge region, a CH2 domain and a CH3 domain. The two polypeptide chains are held together through multiple disulphide bonds in the hinge region and a hydrophobic region present in the CH3 domains. As explained above, initial ligation of an OX40 ligand to its receptor, OX40, initiates a chain of events that leads to OX40 receptor clustering, followed by activation of the NFkB intracellular signalling pathway and subsequent initiation of potent T cell activity. For a therapeutic agent to efficiently achieve activation, several OX40 monomers need to be bridged together in a way that mimics a surface expressed trimeric ligand. A subset of the anti-OX40 Fcabs isolated by the inventors on the basis of their ability to bind OX40 were shown to be able to drive clustering and activation of OX40 on a T cell surface. This was surprising given the rigid structure and small molecular distance between the constant domains, in particular the two CH3 domains, of the Fcab molecules in contrast to the known flexibility of an antibody molecule in the hinge region, which allows the Fab arms of an anti-OX40 antibody molecule to move and bind to their targets. In light of the tight geometry of the constant domain binding sites of the Fcab molecules, it was not expected that these binding sites would be able to induce clustering and agonism of OX40 molecules that may not initially be in close proximity on the T cell surface. However, contrary to expectations, the results obtained by the present inventors described herein clearly show that anti-OX40 Fcabs are able to induce clustering and activation of OX40 both in vitro and in vivo.

The Fcabs were selected to bind dimeric OX40 with high affinity, i.e. are expected to bind OX40 with high avidity. A high affinity for dimeric OX40 is thought to be beneficial for inducing OX40 clustering, and activation.

'Affinity' as referred to herein may refer to the strength of the binding interaction between an antibody molecule and its cognate antigen as measured by $K_D$. As would be readily apparent to the skilled person, where the antibody molecule is capable of forming multiple binding interactions with an antigen (e.g. where the antibody molecule is capable of binding the antigen bivalently and, optionally, the antigen is dimeric) the affinity, as measured by $K_D$, may also be influenced by avidity, whereby avidity refers to the overall strength of an antibody-antigen complex.

The Fcabs identified by the inventors as being able to induce OX40 clustering and activation, fell into two groups. The first group of Fcabs (the FS20-11 lineage) was dependent on crosslinking by e.g. an anti-CH2 domain antibody for OX40 clustering and activation, while the second group (the FS20-22 and FS20-31 lineages) showed a low level of OX40 clustering and activation even in the absence of crosslinking. OX40 agonist antibodies have not shown any DLTs in the clinic. OX40 agonist activity in the absence of crosslinking is therefore not expected to represent a problem for clinical treatment. To the contrary, depending on the condition to be treated, a low level of OX40 agonist activity by the Fcabs in the absence of crosslinking may be advantageous. Without wishing to be bound by theory, it is thought that anti-OX40 Fcabs with this property may be useful, for example, in the context of cancer treatment by inducing limited activation and expansion of tumour-reactive T cells in the absence of crosslinking, leading to a larger pool of tumour-reactive T cells which can then be further activated by crosslinked Fcab molecules in the tumour microenvironment.

Conventional antibodies specific for TNF receptors such as OX40 typically have no or only very moderate intrinsic agonistic activity and require secondary crosslinking of antibody-TNFRSF member complexes using external crosslinking agents, such as protein A or G or secondary antibodies, or binding of the antibody to plasma membrane localised Fcγ receptors, in order to induce higher levels of TNF receptor member clustering and activation (Wajant, 2015). The low levels or lack of agonist activity of TNF receptor-specific antibodies in the absence of crosslinking can be explained by the fact that a normal bivalent antibody can maximally crosslink two monomeric TNF receptors which is insufficient for TNF receptor activation. Therefore, for in vivo efficacy, a monospecific antibody targeting OX40 requires the presence of Fcγ receptor-expressing cells in close proximity to OX40-expressing T cells to achieve crosslinking of the OX40-specific antibodies and subsequent clustering and activation of the OX40 receptor. Fcγ receptor-mediated crosslinking, however, is thought to be inefficient. In addition, cells expressing Fcγ receptors are present throughout the body and thus antibody crosslinking and activation of T cells expressing OX40 is not restricted to a particular site such as the tumour microenvironment, for example. Furthermore, the isotype of such OX40 antibodies needs to be selected to mediate effective binding to Fcγ receptors for crosslinking. However, this can result in the antibodies eliciting effector functions mediated by Fcγ receptors, such as ADCC, thereby eliminating the T cells intended to be activated by the antibody.

The present inventors have performed mass spectrometry analysis of crosslinked Fcab-OX40 complexes (with the Fcab in $mAb^2$ format), which showed that 17% of the complexes comprised two OX40 moieties, demonstrating that the anti-OX40 Fcabs of the invention can bind OX40 bivalently.

The present inventors recognised that the anti-OX40 Fcabs of the invention can be used to prepare multispecific, e.g. bispecific, molecules which bind a second antigen in addition to OX40, such as a tumour antigen. Preferably the multispecific molecule also binds the second antigen bivalently, although it is expected that where the second antigen is a cell-bound tumour antigen, monovalent binding of the antigen will be sufficient to crosslink the specific binding member/antibody molecule and induce OX40 clustering and activation.

The present inventors have prepared antibody molecules comprising the anti-OX40 Fcabs of the invention which can bind a second antigen bivalently via their Fab region. The present inventors have shown that such bispecific antibody molecules are capable of activating OX40 conditionally in the presence of said second antigen without the need for e.g. Fcγ receptor crosslinking as require by conventional antibody molecules. The same effect was observed regardless of whether the second antigen was a cell-surface receptor or multimeric soluble factor. It is thought that binding of the antibody molecules to the second antigen causes crosslinking of the antibody molecules at the site of said antigen, which in turn leads to clustering and activation of OX40 on the T cell surface. The agonistic activity of the antibody molecules is therefore dependent on both the second antigen and OX40 being present, or is enhanced when both are present. In other words, the agonistic activity is conditional. In addition, crosslinking of the antibodies in the presence of the second antigen is thought to assist with clustering of OX40 bound via a constant domain antigen-binding site of the antibody molecule, as an increase in the agonistic activity of the antibody molecules was observed when both binding sites of the antibody molecule were bound to their respective targets but not when only one binding site was bound. Multispecific molecules comprising the anti-OX40 Fcabs of the invention are therefore expected to be effective in activating immune cells in a disease-dependent manner, for example in a tumour microenvironment.

The present inventors have shown that bispecific antibody molecules comprising an anti-OX40 Fcab of the invention are capable of suppressing tumour growth in vivo. Furthermore, more effective tumour growth suppression was observed with these bispecific antibody molecules as compared to a combination of two monospecific antibody molecules where one of the antibody molecules comprised the same constant domain and the other antibody molecule the same variable domain binding site as the bispecific molecule, demonstrating that enhanced clustering and signalling of OX40, and thus T cell activation and corresponding anti-tumour effects, are seen when the two binding sites are present in the same molecule.

As explained above, in contrast to conventional antibodies, antibody molecules comprising an anti-OX40 Fcab of the invention are not dependent on Fcγ receptor crosslinking in order to drive OX40 clustering and activation. Mutations for abrogating Fcγ receptor binding are known in the art and may be included in the molecules of the invention. However, in some contexts, such as cancer treatment, it may be beneficial to retain Fcγ receptor binding. For example, if the antibody molecule was bound to a tumour antigen via its Fab region and the OX40 antigen-binding site was not engaged, antibody-dependent cell-mediated cytotoxicity (ADCC) of the tumour cells would be induced. This ADCC effect would be in addition to T cell activation and subsequent T cell-mediated killing of tumour cells induced by the antibody molecule.

Antibody molecules comprising an anti-OX40 Fcab of the invention and a Fab region specific for a second antigen, preferably bind both OX40 and the second antigen bivalently. This is advantageous, as the bivalent binding of both targets is expected to make the bridging between the T cell expressing OX40 and the second antigen more stable and thereby extend the time during which the T cell is localised at a particular site, such as a tumour microenvironment, and can act on the disease, e.g. the tumour. This is different to the vast majority of conventional bispecific antibody formats which are heterodimeric and bind each target antigen monovalently via one Fab arm. Such a monovalent interaction is expected to be not only less stable but in many cases is insufficient to induce clustering of TNFRSF receptors such as OX40 in the first place.

A further feature of the antibody molecules comprising an anti-OX40 Fcab of the invention is that the two antigen binding sites for OX40 and the second antigen are both contained within the antibody structure itself. In particular, the antibody molecules do not require other proteins to be fused to the antibody molecule via linkers or other means to result in a molecule that binds bivalently to both of its targets. This has a number of advantages. Specifically, the antibody molecules can be produced using methods similar to those employed for the production of standard antibodies, as they do not comprise any additional fused portions. The structure is also expected to result in improved antibody stability, as linkers may degrade over time, resulting in a heterogeneous population of antibody molecules. Those antibodies in the population having only one protein fused will not be able to induce conditional agonism of TNFRSF receptors such as OX40 as efficiently as antibodies having two proteins fused. Cleavage or degradation of the linker could take place prior to administration or after administration of the therapeutic to the patient (e.g. through enzymatic cleavage or the in vivo pH of the patient), thereby resulting in a reduction of its effectiveness whilst circulating in the patient. As there are no linkers in the antibody molecules of the invention, the antibody molecules are expected to retain the same number of binding sites both before and after administration. Furthermore, the structure of the antibody molecules of the invention is also preferred from the perspective of immunogenicity of the molecules, as the introduction of fused proteins or linkers or both may induce immunogenicity when antibody molecules are administered to a patient, resulting in reduced effectiveness of the therapeutic.

Thus, the invention provides:

[1]A specific binding member that binds OX40 and comprises an OX40 antigen-binding site located in a CH3 domain of the specific binding member, wherein the OX40 antigen-binding site comprises a first, second, and/or third, preferably a first and third sequence, more preferably a first, second and third sequence of specific binding member FS20-22-49, FS20-22-41, FS20-22-47, FS20-22-85, or FS20-22-38, wherein the first, second and third sequence of specific binding member:

(i) FS20-22-49 are set forth in SEQ ID NOs 43, 54 and 71, respectively;
(ii) FS20-22-41 are set forth in SEQ ID NOs 43, 54 and 45, respectively;
(iii) FS20-22-47 are set forth in SEQ ID NOs 43, 54 and 62, respectively;
(iv) FS20-22-85 are set forth in SEQ ID NOs 43, 54 and 80, respectively; and
(v) FS20-22-38 are set forth in SEQ ID NOs 43, 44 and 45, respectively; and wherein the first, second, and third sequence are located in the AB, CD and EF structural loops of the CH3 domain of the specific binding member, respectively.

[2]A specific binding member that binds OX40 and comprises an OX40 antigen-binding site located in a CH3 domain of the specific binding member, wherein the OX40 antigen-binding site comprises a first, second, and/or third, preferably a first and third sequence, more preferably a first, second and third sequence of specific binding member FS20-31-115, FS20-31-108, FS20-31-58, FS20-31-94, FS20-31-102, or FS20-31-66, wherein the first, second and third sequence of specific binding member:

(i) FS20-31-115 are set forth in SEQ ID NOs 122, 142 and 133, respectively;
(ii) FS20-31-108 are set forth in SEQ ID NOs 122, 132 and 133, respectively;
(iii) FS20-31-58 are set forth in SEQ ID NOs 91, 92 and 93, respectively;
(iv) FS20-31-94 are set forth in SEQ ID NOs 111, 112 and 113, respectively;
(v) FS20-31-102 are set forth in SEQ ID NOs 122, 123 and 102, respectively; and
(vi) FS20-31-66 are set forth in SEQ ID NOs 91, 92 and 102, respectively; and wherein the first, second, and third sequence are located in the AB, CD and EF structural loops of the CH3 domain of the specific binding member, respectively.

[3]A specific binding member that binds OX40 and comprises an OX40 antigen-binding site located in a CH3 domain of the specific binding member, wherein the OX40 antigen-binding site comprises a first, second, and/or third, preferably a first and third sequence, more preferably a first, second and third sequence of specific binding member FS20-11-131, FS20-11-127, or FS20-11-134, wherein the first, second and third sequence of specific binding member:

(i) FS20-11-131 are set forth in SEQ ID NOs 12, 13 and 23, respectively;
(ii) FS20-11-127 are set forth in SEQ ID NOs 12, 13 and 14, respectively; and
(iii) FS20-11-134 are set forth in SEQ ID NOs 12, 13 and 32, respectively; and wherein the first, second, and third sequence are located in the AB, CD and EF structural loops of the CH3 domain of the specific binding member, respectively.

[4] The specific binding member according to [1], wherein the third sequence is located between positions 92 and 102 of the CH3 domain, wherein the amino acid residue numbering is according to the ImMunoGeneTics (IMGT) numbering scheme.

[5] The specific binding member according to [2], wherein the third sequence is located between positions 91 and 102 of the CH3 domain, wherein the amino acid residue numbering is according to the ImMunoGeneTics (IMGT) numbering scheme.

[6] The specific binding member according to [3], wherein the third sequence is located between positions 96 and 102 of the CH3 domain, wherein the amino acid residue numbering is according to the ImMunoGeneTics (IMGT) numbering scheme.

[7] The specific binding member according to [3] or [6], wherein the specific binding member comprises an amino acid deletion at position 14, 15, 16, 17, or 18 of the CH3 domain, wherein the amino acid residue numbering is according to the IMGT numbering scheme.

[8] The specific binding member according to any one of [1] to [7], wherein the first sequence is located between positions 13 and 19 of the CH3 domain, wherein the amino acid residue numbering is according to the ImMunoGeneTics (IMGT) numbering scheme.

[9] The specific binding member according to any one of [1] to [8], wherein the second sequence is located between positions 45 and 78 of the CH3 domain, wherein the amino acid residue numbering is according to the ImMunoGeneTics (IMGT) numbering scheme.

[10] The specific binding member according to any one of [1] to [9], wherein the CH3 domain is a human IgG1 CH3 domain.

[11] The specific binding member according to any one of [1], [4], and [8] to [10], wherein the specific binding member comprises the CH3 domain sequence of specific binding member FS20-22-49, FS20-22-41, FS20-22-47, FS20-22-85, or FS20-22-38 set forth in SEQ ID NOs 72, 55, 63, 81, and 46, respectively.

[12] The specific binding member according to [11], wherein the specific binding member comprises the CH3 domain sequence of specific binding member FS20-22-49 set forth in SEQ ID NO: 72.

[13] The specific binding member according to any one of [2], [5], and [8] to [10, wherein the specific binding member comprises the CH3 domain sequence of specific binding member FS20-31-115, FS20-31-108, FS20-31-58, FS20-31-94, FS20-31-102, or FS20-31-66 set forth in SEQ ID NOs 143, 134, 94, 114, 124, and 103, respectively.

[14] The specific binding member according to any one of [3], [6], [7] and [8] to [10], wherein the specific binding member comprises the CH3 domain sequence of specific binding member FS20-11-131, FS20-11-127, or FS20-11-134 set forth in SEQ ID NOs 24, 15, and 33, respectively.

[15] The specific binding member according to any one of [1] to [14], wherein the specific binding member further comprises a CH2 domain, preferably the CH2 domain of human IgG1.

[16] The specific binding member according to [15], wherein the CH2 domain has the sequence set forth in SEQ ID NO: 5, 6 or 7.

[17] The specific binding member according to any one of [15] to [16] further comprising an immunoglobulin hinge region, or part thereof, at the N-terminus of the CH2 domain.

[18] The specific binding member according to [1], wherein the hinge region, or part thereof, is a human IgG1 hinge region, or part thereof.

[19] The specific binding member according to [18], wherein the hinge region has the sequence set forth in SEQ ID NO: 170 or a fragment thereof.

[20] The specific binding member according to [18] or [19], wherein the hinge region has the sequence set forth in SEQ ID NO: 171.

[21] The specific binding member according to any one of [1], [4], [8] to [10], [11] to [12] and [15] to [20], wherein the specific binding member comprises the sequence of specific binding member:

(i) FS20-22-49, FS20-22-41, FS20-22-47, FS20-22-85, or FS20-22-38 set forth in SEQ ID NOs 74, 57, 65, 83, and 48, respectively; or (ii) FS20-22-49, FS20-22-41, FS20-22-47, FS20-22-85, or FS20-22-38 set forth in SEQ ID NOs 76, 59, 67, 85, and 50, respectively.

[22] The specific binding member according to [21], wherein the specific binding member comprises the sequence of specific binding member FS20-22-49 set forth in SEQ ID NO: 74 or SEQ ID NO: 76.

[23] The specific binding member according to any one of [2], [5], [8] to [10], [13], and [15] to [20], wherein the specific binding member comprises the sequence of specific binding member:

(i) FS20-31-115, FS20-31-108, FS20-31-58, FS20-31-94, FS20-31-102, or FS20-31-66 set forth in SEQ ID NOs 145, 136, 96, 116, 126, and 105, respectively; or (ii) FS20-31-115, FS20-31-108, FS20-31-58, FS20-31-94, FS20-31-102, or FS20-31-66set forth in SEQ ID NOs 147, 138, 98, 118, 128, and 107, respectively.

[24] The specific binding member according to any one of [3], [6], [7] to [10], and [14] to [20], wherein the specific binding member comprises the sequence of specific binding member:

(i) FS20-11-131, FS20-11-127, or FS20-11-134 set forth in SEQ ID NOs 26, 17, and 35, respectively; or (ii) FS20-11-131, FS20-11-127, or FS20-11-134 set forth in SEQ ID NOs 28, 19, and 37, respectively.

[25] The specific binding member according to any one of [1] to [24], wherein the specific binding member binds human OX40.

[26] The specific binding member according to [25], wherein the human OX40 has, comprises or consists of the sequence set forth in SEQ ID NO: 161.

[27] The specific binding member according to any one of [1], [2], [4], [5], [8] to [13], [15] to [23], and [25] to [26], wherein the specific binding member binds cynomolgus OX40.

[28] The specific binding member or antibody molecule according to [27], wherein the cynomolgus OX40 has, comprises or consists of the sequence set forth in SEQ ID NO: 166.

[29] The specific binding member according to any one of [1] to [28], wherein the specific binding member is a multispecific molecule.

[30] The specific binding member according to [29], wherein the specific binding member is a bispecific, trispecific, or tetraspecific molecule.

[31] The specific binding member according to [30], wherein the specific binding member is a bispecific molecule.

[32] The specific binding member according to any one of [1] to [31], wherein the specific binding member further comprises a second antigen-binding site.

[33] The specific binding member according to [32], wherein the second antigen-binding site is a CDR-based antigen-binding site.

[34] The specific binding member according to [33], wherein the second antigen-binding site comprises a heavy chain variable domain CDR1, CDR2, and CDR3, and a light chain variable domain CDR1, CDR2, and CDR3.

[35] The specific binding member according to [33] to [34], wherein the second antigen-binding site comprises a heavy chain variable and a light chain variable domain.

[36] The specific binding member according to any one of [32] to [35], wherein the specific binding member is an antibody molecule.

[37] An antibody molecule according to [36], wherein the antibody molecule is a human IgG1 molecule.

[38] The antibody molecule according to any one of [33] to [37], wherein the CDR-based antigen-binding site of the antibody molecule binds a second antigen selected from the group consisting of: an immune cell antigen, and a disease antigen.

[39] The antibody molecule according to [38], wherein the disease antigen is a tumour antigen or a pathogenic antigen.

[40] The antibody molecule according to [38], wherein the immune cell antigen is a member of the tumour necrosis factor receptor superfamily (TNFRSF).

[41] The antibody molecule according to [39], wherein the tumour antigen is a tumour-associated antigen (TAA).

[42] The antibody molecule according to [39], wherein the pathogenic antigen is a bacterial or viral antigen.

[43] The antibody molecule according to any one of [32] to [42] wherein the antibody molecule is capable of activating OX40 present on a T cell in the presence of the second antigen.

[44] The antibody molecule according to any one of [32] to [43] wherein binding of the antibody molecule to OX40 and the second antigen causes clustering of OX40 on immune cell.

[45] The antibody molecule according to [43] or [44], wherein the immune cell is a T cell.

[46] The antibody molecule according to any one of [38], [41], and [43] to [45], wherein the tumour antigen is a cell surface antigen on a cancer cell.

[47] The antibody molecule according to any one of [38], [41], and [43] to [45], wherein the tumour antigen is a soluble multimer.

[48] The antibody molecule according to [47], wherein soluble multimer is at least a dimer.

[49] The antibody molecule according to [48], wherein soluble multimer is at least a trimer.

[50] The specific binding member or antibody molecule according to any one of [1] to [49], wherein the specific binding member or antibody molecule has been modified to reduce or abrogate binding of the CH2 domain of the specific binding member or antibody molecule to one or more Fcγ receptors.

[51] The specific binding member or antibody molecule according to any one of [1] to [50], wherein the specific binding member or antibody molecule does not bind to Fcγ receptors.

[52] The specific binding member or antibody molecule according to [50] or [51], wherein the Fcγ receptors are selected from the group consisting of: FcγRI, FcγRIIa, FcγRIIb and FcγRll.

[53] The specific binding member or antibody molecule according to any one of [1] to [52], wherein the specific binding member or antibody molecule is conjugated to a bioactive molecule.

[54] The specific binding member or antibody molecule according to any one of [1] to [52], wherein the specific binding member or antibody molecule is conjugated to a detectable label.

[55]A nucleic acid molecule encoding the specific binding member or antibody molecule according to any one of [1] to [52].

[56] The nucleic acid molecule according to [55], wherein the nucleic acid molecule(s) comprise(s):

(i) the CH3 domain nucleic acid sequence of specific binding member FS20-22-49, FS20-22-41, FS20-22-47, FS20-22-85, or FS20-22-38 set forth in SEQ ID NO: 73, 56, 64, 82 and 47, respectively;

(ii) the CH3 domain nucleic acid sequence of specific binding member FS20-31-115, FS20-31-108, FS20-31-58, FS20-31-94, FS20-31-102, or FS20-31-66 set forth in SEQ ID NO: 144, 135, 95, 115, 125, and 104, respectively; or (iii) the CH3 domain nucleic acid sequence of specific binding member FS20-11-131, FS20-11-127, or FS20-11-134 set forth in SEQ ID NO: 25, 16, and 34, respectively.

[57] The nucleic acid molecule according to [55] or [56], wherein the nucleic acid molecule comprises the nucleic acid sequence of specific binding member: (i) FS20-22-49, FS20-22-41, FS20-22-47, FS20-22-85, or FS20-22-38set forth in SEQ ID NO: 75, 58, 66, a84 and 49, respectively;

(ii) FS20-31-115, FS20-31-108, FS20-31-58, FS20-31-94, FS20-31-102, or FS20-31-66 set forth in SEQ ID NO: 146, 137, 97, 117, 127, and 106, respectively; or (iii) FS20-11-131, FS20-11-127, or FS20-11-134 set forth in SEQ ID NO: 27, 18, and 36, respectively.

[58] The nucleic acid molecule according to [55] or [56], wherein the nucleic acid molecule comprises the nucleic acid sequence of specific binding member:

(i) FS20-22-49, FS20-22-41, FS20-22-47, FS20-22-85, or FS20-22-38 set forth in SEQ ID NO: 77, 60, 68, 86, and 51, respectively;

(ii) FS20-31-115, FS20-31-108, FS20-31-58, FS20-31-94, FS20-31-102, or FS20-31-66 set forth in SEQ ID NO: 148, 139, 99, 119, 129, and 108, respectively.

(ii) FS20-11-131, FS20-11-127, or FS20-11-134 set forth in SEQ ID NO: 29, 20, and 38, respectively.

[59]A vector comprising the nucleic acid according to any one of [55] to [58].

[60]A recombinant host cell comprising the nucleic acid according to any one of [55] to [58], or the vector of [59].

[61]A method of producing a specific binding member or antibody molecule according to any one of [1] to [52], comprising culturing the recombinant host cell of [60] under conditions for production of the specific binding member or antibody molecule.

[62] The method of [61] further comprising isolating and/or purifying the specific binding member or antibody molecule.

[63]A pharmaceutical composition comprising a specific binding member or antibody molecule according to any one of [1] to [54] and a pharmaceutically acceptable excipient.

[64] The specific binding member or antibody molecule according to any one of [1] to [54] for use in a method for treatment of the human or animal body by therapy.

[65]A method of treating a disease or disorder in an individual comprising administering to the individual a therapeutically effective amount of the specific binding member or antibody molecule according to any one of [1] to [54].

[66] The specific binding member or antibody molecule for use according to [64], or the method according to [65] wherein the treatment is the treatment of cancer or an infectious disease in an individual.

[67] The specific binding member or antibody molecule for use according to [64] or [66], or the method according to [65] or [66], wherein the method of treatment comprises administering the specific binding member or antibody molecule to the individual in combination with a second therapeutic.

BRIEF DESCRIPTION OF THE FIGURES

FIG. 1A-C shows an alignment of the sequences of the CH3 domains of Fcabs FS20-11, FS20-11-127, FS20-11-131, FS20-11-134, FS20-22, FS20-22-38, FS20-22-41, FS20-22-47, FS20-22-49, FS20-22-85, FS20-31, FS20-31-58, FS20-31-66, FS20-31-94, FS20-31-102, FS20-31-108, and FS20-31-115, as well as the wild-type (WT) Fcab. The positions of the AB, CD and EF structural loops, as well as any amino acid substitutions, deletions (denoted by a tilde "~") or insertions present in the CH3 domains of the Fcabs compared with the WT sequence are indicated. The numbers of the residues according to the IMGT, IMGT exon (consecutive numbering), EU and Kabat numbering systems are shown.

FIG. 4A to D show representative plots of IL-2 release in a T cell activation assay in the presence of HPAC cells. mAb/$mAb^2$ were used at increasing concentrations in this assay, labelled according to their Fcab/Fab clone name. The results show that there is a concentration dependent increase in the activation of T cells by OX40-targeting mAb/$mAb^2$ when crosslinked by either a crosslinking agent (anti-human CH2 antibody or FITC-dextran) or by TAA+ HPAC cells.

FIGS. 5A and B show representative plots of IL-2 release in a T cell activation assay in the presence of HPAC cells. mAb/$mAb^2$ were used at increasing concentrations in this assay, labelled according to their Fcab/Fab clone name. The results show that there is a concentration dependent increase in the activation of T cells by OX40-targeting mAb/$mAb^2$ when crosslinked by either a crosslinking agent (anti-human CH2 antibody or FITC-dextran) or by TAA+ HPAC cells.

DETAILED DESCRIPTION

Figure 2:
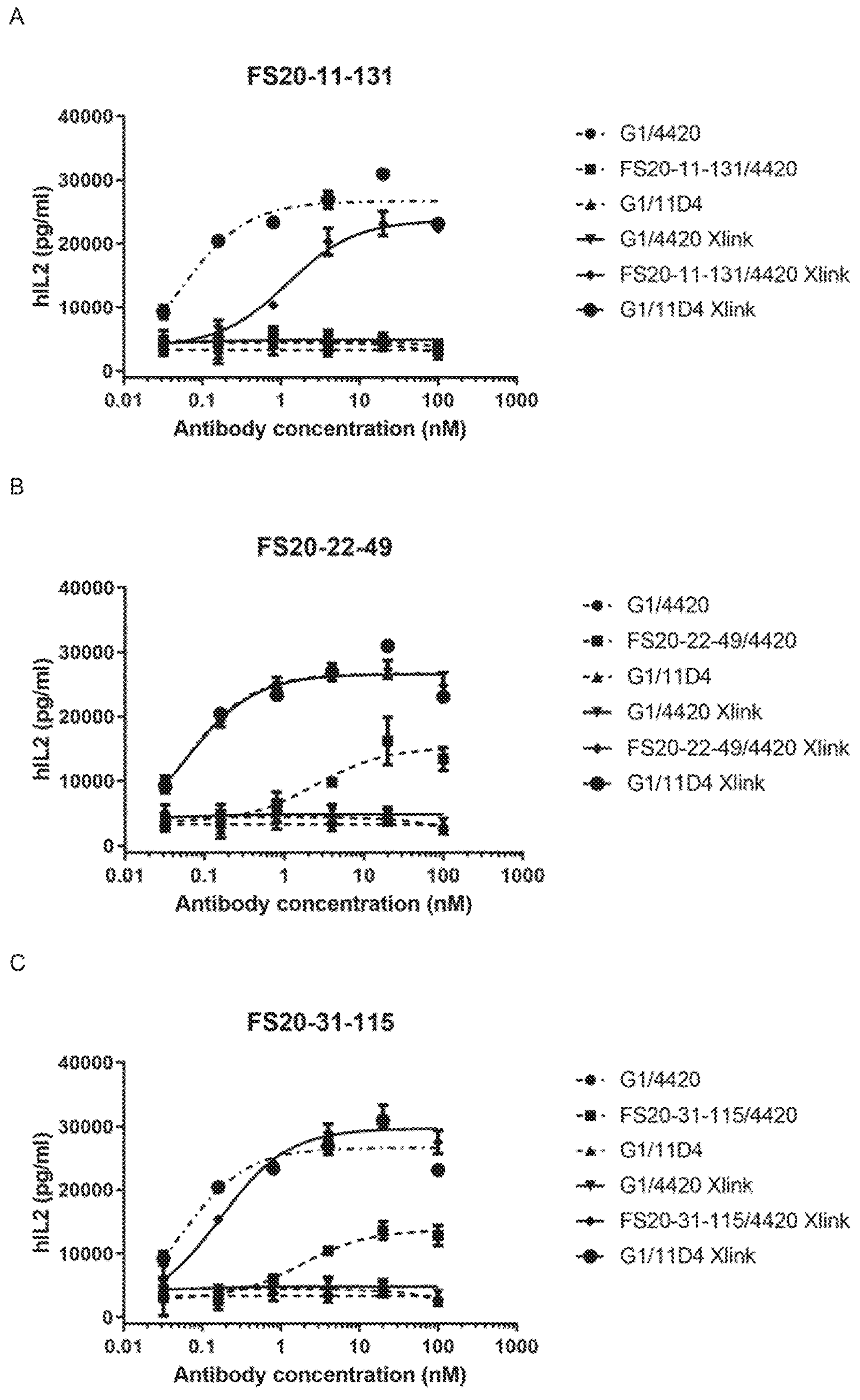
FIG. 2 shows IL-2 release in T cell activation assay in the presence of anti-human OX40 Fcabs. A representative plot for one anti-human OX40 Fcab in each lineage (FS20-11, FS20-22 and FS20-31) is shown in FIGS. 2A, 2B and 2C, respectively. The anti-human OX40 Fcab were tested in in mock (4420 LALA) $mAb^2$format. IL-2 release was tested in the presence and absence of cross-linking agents (Xlink). The anti-FITC antibody 4420 and anti-OX40 antibody 11 D4, each in a human IgG1 backbone (G1/4420 and G1/11 D4), were included as negative and positive controls, respectively. The effect of the anti-human OX40 Fcabs and control antibodies on IL-2 release was tested at increasing concentrations. A concentration dependent increase in the activation of T cells, as evidenced by an increase in IL-2 release, by the crosslinked positive control mAb (G1/11 D4) and anti-human OX40 Fcabs, but not by non-crosslinked positive control mAb or by the negative control mAb (G1/4420) was observed. The FS20-11-131 Fcab in mock (4420 LALA) $mAb^2$ format showed no activity in the absence of crosslinking. The FS20-22-49 and FS20-31-115 Fcabs in mock (4420 LALA) $mAb^2$ format showed some activity in the absence of crosslinking and this activity increased with crosslinking.

The invention relates to specific binding members that bind OX40. OX40 is also known as tumor necrosis factor receptor superfamily member 4 (TNFRSF4) or CD134. Specifically, the specific binding members comprise an OX40 antigen-binding site located in a constant domain of the specific binding member. The specific binding member is preferably capable of binding OX40 bivalently. The specific binding member preferably binds human OX40, more preferably human and cynomolgus OX40. The portion of OX40 bound by the specific binding member is preferably the OX40 extracellular domain. The extracellular domain of human and cynomolgus OX40 may comprise or consist of the sequence set forth in SEQ ID NOs 161 and 162, respectively. The specific binding member is preferably capable of binding to OX40 expressed on the surface of a cell, preferably a T cell, such as a CD4+ T cell, CD8+ T cell, type 1 T helper (Th1) cell, type 2 T helper (Th2) cell, or regulatory T (Treg) cell, or a tumour-infiltrating T cell, or a natural killer (NK) cell. Tumour-infiltrating T cells are a subset of tumour-infiltrating lymphocytes (TILs) found in many cancers.

The specific binding member preferably binds OX40 specifically. The term "specific" may refer to the situation in which the specific binding member will not show any significant binding to molecules other than its specific binding partner(s). The term "specific" is also applicable where the specific binding member is specific for particular epitopes, such as epitopes on OX40, that are carried by a number of antigens, in which case the specific binding member will be able to bind to the various antigens carrying the epitope. The specific binding member preferably does not bind, or does not show any significant binding, to CD40, TNFRI, TNFRII, NGFR and/or CD137.

The specific binding members of the invention were selected for their ability to bind dimeric OX40. The specific binding members may bind to dimeric OX40 with a higher affinity than to monomeric OX40. A high affinity for dimeric OX40 is thought to be beneficial in inducing OX40 clustering and consequently T cell activation. Antibodies which bind to the TNF receptor Fas with high affinity have been shown to have reduced agonist activity. Like OX40, Fas requires trimerisation for activation. It is thought that bivalent agonists such as IgG antibodies must be able to bind Fas and then partially dissociate in order to recruit further Fas monomers and form an active signalling complex. Antibodies which bind to Fas monomers with high affinity are thought to become locked in a non-signalling state (Chodorge et al., 2012).

The specific binding member preferably binds to dimeric human OX40 with an affinity ($K_D$) of 70 nM, 60 nM, 50 nM, 40 nM, 30 nM, 20 nM, 10 nM, 5 nM, 4 nM, 3 nM, 2 nM, or 1 nM or a higher affinity. Preferably, the specific binding member binds to human OX40, with an affinity ($K_D$) of 1 nM, or a higher affinity.

The specific binding members of the FS20-22 and FS20-31 lineages have also been shown to bind dimeric cynomolgus OX40. Binding to cynomolgus OX40 as well as human OX40 is beneficial as it permits testing of the specific binding member in cynomolgus monkeys for efficacy and toxicity prior to administration to humans. Specific binding members from the FS20-11 lineage showed binding to dimeric cynomolgus OX40 but with lower affinity, suggesting that they would be less suitable for preclinical testing in cynomolgus monkeys.

In a preferred embodiment, the specific binding member may bind to dimeric cynomolgus OX40 with an affinity ($K_D$) of 150 nM, 140 nM, 120 nM, 100 nM, 90 nM, 80 nM, 70 nM, 60 nM, 50 nM, 40 nM, 30 nM, 20 nM, 10 nM, 5 nM, 4 nM, 3 nM, or 2 nM or a higher affinity. Preferably, the specific binding member binds to cynomolgus OX40, with an affinity ($K_D$) of 2 nM, or a higher affinity.

As described in the present Examples, it is thought that the similarity in binding to human and cynomolgus antigens may be advantageous as it would be hoped that the behaviour of the $mAb^2$ in cynomolgus monkey studies could be extrapolated to humans. This is thought to be beneficial for carrying out efficacy and toxicity studies with the specific binding member in cynomolgus monkeys, which may be predictive of the efficacy and toxicity of the specific binding member in humans.

Thus, in a preferred embodiment, the specific binding member binds to dimeric cynomolgus OX40 with an affinity which is no more than 10-fold, preferably no more than 5-fold lower or higher than the affinity with which the specific binding member binds dimeric human OX40.

The binding affinity of a specific binding member to a cognate antigen, such as human or cynomolgus OX40 can be determined by surface plasmon resonance (SPR), such as Biacore, for example.

The specific binding member may be capable of blocking the interaction between OX40 and its ligand, OX40L, preferably human OX40 and human OX40L. The ability of the specific binding member to block the binding of OX40L to OX40 may be determined using an enzyme-linked immunosorbent assay (ELISA).

The term "specific binding member" describes an immunoglobulin, or fragment thereof, comprising a constant domain comprising an OX40 antigen-binding site. The term "specific binding member", as used herein, thus includes antigen-binding fragments, provided said antigen-binding fragments comprise an OX40 antigen-binding site located in a constant domain of the specific binding member. The constant domain may be a CL, CH1, CH2, CH3, or CH4 domain, preferably the constant domain is a CH1, CH2, or CH3 domain, more preferably a CH2 or CH3 domain, most preferably a CH3 domain. The specific binding member may be partly, or wholly, synthetically produced.

Preferably, the specific binding member comprises a CH2 and CH3 domain, wherein the CH2 or CH3 domain, preferably the CH3 domain, comprises an OX40 antigen-binding site.

The specific binding member is preferably a dimer of two (identical) polypeptide chains, each comprising a CH2 and a CH3 domain. In a preferred embodiment, the specific binding member further comprises an immunoglobulin hinge region, or part thereof, at the N-terminus of the CH2 domains. Such a molecule is also referred to herein as an antigen-binding Fc fragment, or Fcab™. The hinge region may consist of or comprise the sequence set forth in SEQ ID NO: 170 or a fragment thereof. Preferably, the fragment is a C-terminal fragment of the sequence set forth in SEQ ID NO: 170. The fragment may be up to 20, up to 10, up to 8 or up to 6 amino acids in length. The fragment may be at least 3, at least 4, at least 5, or at least 6 amino acids in length. In a preferred embodiment, the hinge region has the sequence set forth in SEQ ID NO: 171.

In a preferred embodiment, the specific binding member is an antibody molecule, preferably a monoclonal antibody, or a fragment thereof. The antibody molecule is preferably human or humanised. The antibody molecule may be an immunoglobulin G molecule, such as an IgG1, IgG2, IgG3 or IgG4 molecule, preferably an IgG1, IgG2 or IgG4 molecule, more preferably an IgG1 molecule, or a fragment thereof.

As antibodies can be modified in a number of ways, the term "antibody molecule" should be construed as covering antibody fragments, derivatives, functional equivalents and homologues of antibodies, whether natural or wholly or partially synthetic. An example of an antibody fragment comprising a CH3 domain is an Fc domain of an antibody. An example of an antibody fragment comprising both CDR sequences and a CH3 domain is a minibody, which comprises an scFv joined to a CH3 domain (Hu et al., 1996).

The specific binding member comprises an OX40 antigen-binding site. The OX40 antigen-binding site is located in a constant domain of the specific binding member, preferably a CH3 domain. The OX40 antigen-binding site comprises one or more modified structural loops in a constant domain of the specific binding member. Engineering of antibody constant domain structural loops to create antigen-binding sites for target antigens is known in the art and is described, for example, in Wozniak-Knopp G et al., 2010 and patent publication nos. WO2006/072620 and WO2009/132876.

Preferably, the OX40 antigen-binding site comprises a modified AB, CD, and/or EF structural loop. The present inventors have recognized that in some cases the AB and EF loop sequences play a greater role in antigen-binding than the CD loop sequence. This is evident from the fact that Fcabs FS20-22 and FS20-11 bound OX40 but did not comprise any modifications in their CD loop sequences (see FIG. 1). Thus, in a preferred embodiment, the OX40 antigen-binding site comprises a modified AB and EF structural loop. In an alternative preferred embodiment, the OX40 antigen-binding site comprises a modified AB, CD and EF structural loop.

In a preferred embodiment, the residues at positions 95 and 96 of the CH3 domain of the specific binding member are wild-type, i.e. are preferably arginine (R) and tryptophan (W), respectively. Both of these residues are located in the EF structural loop. Amino acid residue positions are numbered herein according to the ImMunoGeneTics (IMGT) numbering scheme, unless otherwise indicated. The IMGT numbering scheme is described in Lefranc et al., 2005.

Thus, the OX40 antigen-binding site of the specific binding member may comprise a first, second, and/or third sequence, preferably a first and third sequence, or a first, second, and third sequence, wherein the first, second and third sequence are located in the AB, the CD, and the EF structural loop of the constant domain, preferably the CH3 domain, of the specific binding member, respectively.

The first, second and third sequence may be a first, second and third sequence of the CH3 domain of: specific binding member FS20-22-49, FS20-22-41, FS20-22-47, FS20-22-85, or FS20-22-38, more preferably specific binding member FS20-22-49, FS20-22-41, FS20-22-47, or FS20-22-85, yet more preferably specific binding member FS20-22-49, FS20-22-41, or FS20-22-47, most preferably specific binding member FS20-22-49.

Alternatively, the first, second and third sequence may be a first, second and third sequence of the CH3 domain of: specific binding member FS20-31-115, FS20-31-108, FS20-31-58, FS20-31-94, FS20-31-102, or FS20-31-66, more preferably specific binding member FS20-31-115, FS20-31-108, FS20-31-58, FS20-31-94, or FS20-31-102, yet more preferably specific binding member FS20-31-115, or FS20-31-108, even more preferably specific binding member FS20-31-115.

As a further alternative, the first, second and third sequence may be a first, second and third sequence of the CH3 domain of: specific binding member FS20-11-131, FS20-11-127, or FS20-11-134, more preferably specific binding member FS20-11-131.

The CH3 domain sequence of specific binding member FS20-22-38, FS20-22-41, FS20-22-47, FS20-22-49, FS20-22-85, FS20-31-58, FS20-31-66, FS20-31-94, FS20-31-102, FS20-31-108, FS20-31-115, FS20-11-127, FS20-11-131, and FS20-11-134 is shown in SEQ ID NOs 46, 55, 63, 72, 81, 94, 103, 114, 124, 134, 143, 15, 24 and 33, respectively.

The first, second and third sequence of specific binding member FS20-22-49, FS20-22-41, FS20-22-47, FS20-22-85, and FS20-22-38 may be the sequence at positions:

(i) 14 to 18, 45.1 to 77 and 97 to 101; or (ii) 14 to 18, 45.1 to 77 and 93 to 101;

of the CH3 domain of FS20-22-49, FS20-22-41, FS20-22-47, FS20-22-85, and FS20-22-38, respectively.

All of the 76 specific binding members identified following affinity maturation of the FS20-31 lineage which bound OX40 comprised an aspartic acid (D) residue at position 77 of the CH3 domain, suggesting that this residue is likely to be important for OX40 binding in these molecules. Similarly, all of the specific binding members in the FS20-31 retained a wild-type glutamic acid (E) residue at position 45.3 of the CH3 domain, suggesting that this residue may also be important for OX40 binding in these molecules. Thus, the specific binding member may comprise the first sequence and third sequence of specific binding member FS20-31-115, FS20-31-108, FS20-31-58, FS20-31-94, FS20-31-102, or FS20-31-66, wherein the first sequence is the sequence located at position 14 to 18, and the second sequence is the sequence is the sequence located at position 92 to 101, or 97 to 101, of the CH3 domain of specific binding member FS20-31-115, FS20-31-108, FS20-31-58, FS20-31-94, FS20-31-102, or FS20-31-66, and wherein the specific binding member further comprises an aspartic acid (D) residue at position 77 of the CH3 domain, and optionally a glutamic acid (E) residue at position 45.3 of the CH3 domain. The specific binding member may optionally further comprise an amino acid substitution at position 45.1, 45.2 and/or 45.4 of the CH3 domain.

Alternatively, the first, second and third sequence of specific binding member FS20-31-115, FS20-31-108, FS20-31-58, FS20-31-94, FS20-31-102, and FS20-31-66 may be the sequence at positions:

(i) 14 to 18, 45.1 to 77, and 97 to 101; or (ii) 14 to 18, 45.1 to 77, and 92 to 101;

of the CH3 domain of FS20-31-115, FS20-31-108, FS20-31-58, FS20-31-94, FS20-31-102, and FS20-31-66, respectively.

The first, second and third sequence of specific binding member FS20-11-127, FS20-11-131, and FS20-11-134 may be the sequence between positions:

(i) 13 and 19, 45.2 and 78, and 96 and 102;

(ii) 11 and 19, 45.2 and 78, and 96 and 102;

(iii) 13 and 19, 45 and 78, and 96 and 102; or (iv) 11 and 19, 45 and 78, and 96 and 102;

of the CH3 domain of FS20-11-127, FS20-11-131, and FS20-11-134, respectively.

The first, second and third sequence may be the complete AB, CD, and EF structural loop sequences, of specific binding member FS20-22-49, FS20-22-41, FS20-22-47, FS20-22-85, FS20-22-38, FS20-31-115, FS20-31-108, FS20-31-58, FS20-31-94, FS20-31-102, FS20-31-66, FS20-11-131, FS20-11-127, or FS20-11-134, respectively. Determination of the location of the AB, CD, and EF structural loops in a CH3 domain sequence, for example in accordance with the IMGT, IMGT exon, EU, or Kabat numbering systems, is within the capabilities of the skilled person and is described in Hasenhindl et al. (2013). In a preferred embodiment, the AB, CD and EF structural loops according to the IMGT numbering system are located between positions 10 and 19, 42 and 79, and 91 and 102 of the CH3 domain of the specific binding member, respectively. In a preferred embodiment, the first, second and third sequence are therefore the sequence between positions 10 and 19, 42 and 79, and 91 and 102 of the CH3 domain of specific binding member FS20-22-49, FS20-22-41, FS20-22-47, FS20-22-85, FS20-22-38, FS20-31-115, FS20-31-108, FS20-31-58, FS20-31-94, FS20-31-102, FS20-31-66, FS20-11-131, FS20-11-127, or FS20-11-134, respectively In a preferred embodiment, the OX40 antigen-binding site of the specific binding member comprises the first, second, and third sequence of specific binding member:

(i) FS20-22-49 set forth in SEQ ID NOs 43, 54 and 71, respectively;

(ii) FS20-22-41 set forth in SEQ ID NOs 43, 54 and 45, respectively;

(iii) FS20-22-47 set forth in SEQ ID NOs 43, 54 and 62, respectively;

(iv) FS20-22-85 set forth in SEQ ID NOs 43, 54 and 80, respectively; or (v) FS20-22-38 set forth in SEQ ID NOs 43, 44 and 45, respectively;

wherein the first, second and third sequence are preferably located at positions 14 to 18, 45.1 to 77, and 93 to 101 of the CH3 domain of the specific binding member, respectively.

In a more preferred embodiment, the OX40 antigen-binding site of the specific binding member comprises the first, second, and third sequence of specific binding member:

(i) FS20-22-49 set forth in SEQ ID NOs 43, 54 and 71, respectively;

(ii) FS20-22-41 set forth in SEQ ID NOs 43, 54 and 45, respectively;

(iii) FS20-22-47 set forth in SEQ ID NOs 43, 54 and 62, respectively; or (iv) FS20-22-85 set forth in SEQ ID NOs 43, 54 and 80, respectively.

In an even more preferred embodiment, the OX40 antigen-binding site of the specific binding member comprises the first, second, and third sequence of specific binding member:

(i) FS20-22-49 set forth in SEQ ID NOs 43, 54 and 71, respectively;
(ii) FS20-22-41 set forth in SEQ ID NOs 43, 54 and 45, respectively; or
(iii) FS20-22-47 set forth in SEQ ID NOs 43, 54 and 62, respectively.

In a yet more preferred embodiment, the OX40 antigen-binding site of the specific binding member comprises the first, second, and third sequence of specific binding member FS20-22-49 set forth in SEQ ID NOs 43, 54 and 71, respectively.

The specific binding member may further comprise a leucine (L) at position 91 of the CH3 domain of the specific binding. In particular, a specific binding member comprising an OX40 antigen-binding site comprising the first, second, and third sequence of specific binding member FS20-22-85 may comprise a leucine at position 91 of the CH3 domain of the specific binding member.

In an alternative preferred embodiment, the OX40 antigen-binding site of the specific binding member comprises the first, second, and third sequence of specific binding member:
(i) FS20-31-115 set forth in SEQ ID NOs 122, 142 and 133, respectively;
(ii) FS20-31-108 set forth in SEQ ID NOs 122, 132 and 133, respectively;
(iii) FS20-31-58 set forth in SEQ ID NOs 91, 92 and 93, respectively;
(iv) FS20-31-94 set forth in SEQ ID NOs 111, 112 and 113, respectively;
(v) FS20-31-102 set forth in SEQ ID NOs 122, 123 and 102, respectively; or
(vi) FS20-31-66 set forth in SEQ ID NOs 91, 92 and 102, respectively;
wherein the first, second and third sequence are preferably located at positions 14 to 18, 45.1 to 77, and 92 to 101 of the CH3 domain of the specific binding member, respectively.

In a more preferred embodiment, the OX40 antigen-binding site of the specific binding member comprises the first, second, and third sequence of specific binding member:
(i) FS20-31-115 set forth in SEQ ID NOs 122, 142 and 133, respectively;
(ii) FS20-31-108 set forth in SEQ ID NOs 122, 132 and 133, respectively;
(iii) FS20-31-58 set forth in SEQ ID NOs 91, 92 and 93, respectively;
(iv) FS20-31-94 set forth in SEQ ID NOs 111, 112 and 113, respectively; or
(v) FS20-31-102 set forth in SEQ ID NOs 122, 123 and 102, respectively.

In an even more preferred embodiment, the OX40 antigen-binding site of the specific binding member comprises the first, second, and third sequence of specific binding member:
(i) FS20-31-115 set forth in SEQ ID NOs 122, 142 and 133, respectively; or
(ii) FS20-31-108 set forth in SEQ ID NOs 122, 132 and 133, respectively.

In a yet more preferred embodiment, the OX40 antigen-binding site of the specific binding member comprises the first, second, and third sequence of specific binding member FS20-31-115 set forth in SEQ ID NOs 122, 142 and 133, respectively.

In a further alternative preferred embodiment, the OX40 antigen-binding site of the specific binding member comprises the first, second, and third sequence of specific binding member:
(i) FS20-11-131 set forth in SEQ ID NOs 12, 13 and 23, respectively;
(ii) FS20-11-127 set forth in SEQ ID NOs 12, 13 and 14, respectively; or
(iii) FS20-11-134 set forth in SEQ ID NOs 12, 13 and 32, respectively;
wherein the first, second and third sequence are preferably located between positions 13 and 19, 45 and 78, and 96 and 102 of the CH3 domain of the specific binding member.

In a more preferred embodiment, the OX40 antigen-binding site of the specific binding member comprises the first, second, and third sequence of specific binding member FS20-11-131 set forth in SEQ ID NOs 12, 13 and 23, respectively.

The specific binding member may further comprise a glutamic acid (E) at position 12, an asparagine (N) at position 94, and/or a leucine (L) at position 103 of the CH3 domain of the specific binding member. In particular, a specific binding member comprising an OX40 antigen-binding site comprising the first, second, and third sequence of specific binding member FS20-11-131, FS20-11-127, or FS20-11-134 may further comprise a glutamic acid at position 12, and a leucine at position 103 of the CH3 domain of the specific binding member. In addition, a specific binding member comprising an OX40 antigen-binding site comprising the first, second, and third sequence of specific binding member FS20-11-131 may comprise an asparagine at position 94 of the CH3 domain of the specific binding member.

A specific binding member comprising an OX40 antigen-binding site comprising the AB, CD and EF structural loop sequences of specific binding member FS20-11-131, FS20-11-127, or FS20-11-134 may further comprise a leucine at position 103 of the CH3 domain of the specific binding member.

Where the OX40 antigen-binding site of the specific binding member comprises the first, second, and third sequence, or AB, CD and EF structural loop sequences of specific binding member FS20-11-131, FS20-11-127, or FS20-11-134, the specific binding member may comprise an amino acid deletion between position 13 and 19, for example at position 14, 15, 16, 17, or 18 of the CH3 domain of the specific binding member. The deletion present in these specific binding members is thought to have occurred as a result of a primer error and the precise position of the deletion is therefore not known. In FIG. 1A the deletion is shown at position 18 but may equally be located at position 14, 15, 16, or 17 of the CH3 domain.

As an alternative to IMGT numbering, amino acid residue positions, including the position of amino acid sequences, substitutions, deletions and insertions as described herein, may be numbered according to IMGT exon numbering (also referred to as consecutive numbering), EU numbering, or Kabat numbering. The concordance between IMGT numbering, IMGT exon numbering, EU numbering, and Kabat numbering of the residue positions of the CH3 domain are shown in FIG. 1. Thus, for example, where the present application refers to the first, second and third sequence being located at positions 14 to 18, 45.1 to 77, and 93 to 101 of the CH3 domain of the specific binding member, respectively, where the residue positions are numbered in accordance with the IMGT numbering scheme, the first, second and third sequence are located at positions 18 to 22, 46 to 50, and 74 to 82 of the CH3 domain, where the residue positions are numbered in accordance with the IMGT exon numbering scheme, as shown in FIG. 1. Alternatively, the position of amino acid residues in the CH3 domain, including the position of amino acid sequences, substitutions, deletions and insertions in the CH3 domain, as described herein, may be defined by reference to their position in the wild-type CH3 domain sequence set forth in SEQ ID NO: 4. The concordance between IMGT numbering and the wild-type CH3 domain sequence is also shown in FIG. 1.

In a preferred embodiment, the specific binding member comprises a CH3 domain which comprises, has, or consists of the CH3 domain sequence of specific binding member FS20-22-49, FS20-22-41, FS20-22-47, FS20-22-85, or FS20-22-38, preferably the CH3 domain sequence of specific binding member FS20-22-49, FS20-22-41, FS20-22-47, or FS20-22-85, more preferably the CH3 domain sequence of specific binding member FS20-22-49, FS20-22-41, or FS20-22-47, most preferably the CH3 domain sequence of specific binding member FS20-22-49, wherein the CH3 domain sequence of specific binding member FS20-22-38, FS20-22-41, FS20-22-47, FS20-22-49, and FS20-22-85 is set forth in SEQ ID NOs 46, 55, 63, 72, and 81, respectively.

In an alternative preferred embodiment, the specific binding member comprises a CH3 domain which comprises, has, or consists of the CH3 domain sequence of specific binding member FS20-31-115, FS20-31-108, FS20-31-58, FS20-31-94, FS20-31-102, or FS20-31-66, preferably the CH3 domain sequence of specific binding member FS20-31-115, FS20-31-108, FS20-31-58, FS20-31-94, or FS20-31-102, more preferably the CH3 domain sequence of specific binding member FS20-31-115, or FS20-31-108, most preferably the CH3 domain sequence of specific binding member FS20-31-115, wherein the CH3 domain sequence of specific binding member FS20-31-58, FS20-31-66, FS20-31-94, FS20-31-102, FS20-31-108, and FS20-31-115 is set forth in SEQ ID NOs 94, 103, 114, 124, 134, and 143, respectively.

In a further alternative preferred embodiment, the specific binding member comprises a CH3 domain which comprises, has, or consists of the CH3 domain sequence of specific binding member FS20-11-131, FS20-11-127, or FS20-11-134, more preferably the CH3 domain sequence of specific binding member FS20-11-131, wherein the CH3 domain sequence of specific binding member FS20-11-127, FS20-11-131, and FS20-11-134 is set forth in SEQ ID NOs 15, 24 and 33, respectively.

The CH3 domain of the specific binding member may optionally comprise an additional lysine residue (K) at the immediate C-terminus of the CH3 domain sequence.

It is possible to take monoclonal and other antibodies and use techniques of recombinant DNA technology to produce other antibodies or chimeric molecules which retain the specificity of the original antibody. Such techniques may involve introducing the CDRs, or variable regions, into a different immunoglobulin. Introduction of the CDRs of one immunoglobulin into another immunoglobulin is described, for example, in EP-A-184187, GB 2188638A and EP-A-239400. Similar techniques could be employed to introduce the constant domain sequences making up the OX40 antigen-binding site of a specific binding member according to the invention into a constant domain, e.g. a CH3 domain, of another specific binding member, thereby resulting in a specific binding member comprising an OX40 antigen-binding site in its constant domain. Alternatively, an entire constant domain sequence of a specific binding member could be replaced with the constant domain sequence of a specific binding member according to the invention to prepare a specific binding member comprising an OX40 antigen-binding site in its constant domain. Similarly, a fragment of the constant domain sequence of a specific binding member could be replaced with a corresponding fragment of a constant domain sequence of a specific binding member according to the invention comprising the OX40 antigen-binding site.

In addition, the specific binding member may comprise a CH2 domain of an immunoglobulin G molecule, such as a CH2 domain of an IgG1, IgG2, IgG3, or IgG4 molecule. Preferably the specific binding member comprises a CH2 domain of an IgG1 molecule. The CH2 domain may have the sequence set forth in SEQ ID NO: 5. The CH2 domain is known to bind to Fcγ receptors and complement. Binding of the CH2 domain to Fcγ receptors is required for antibody-dependent cell-mediated cytotoxicity (ADCC), while binding to complement is required for complement-dependent cytotoxicity (CDC). In some embodiments, the specific binding member elicits ADCC and/or CDC. This is preferred in the context where the specific binding member comprises a second antigen-binding site for a tumour antigen. Without wishing to be bound by theory, it is thought that binding of the specific binding member to a tumour cell would elicit ADCC or CDC-mediated killing of the tumour cell when the specific binding member is not bound to OX40. This effect would be in addition T cell-mediated killing of the tumour cells where the specific binding member is bound to both a tumour antigen and OX40, resulting in activation of the T cell.

The CH2 domain of the specific binding member may comprise one or more mutations that reduce or abrogate binding of the CH2 domain to one or more Fcγ receptors, such as FcγRI, FcγRIIa, FcγRIIb, FcγRIII, and/or to complement. The inventors postulate that reducing or abrogating binding to Fcγ receptors will decrease or eliminate ADCC mediated by the specific binding member. Similarly, reducing or abrogating binding to complement is expected to reduce or eliminate CDC mediated by the specific binding member. Mutations to decrease or abrogate binding of the CH2 domain to one or more Fcγ receptors and/or complement are known in the art (Wang et al., 2018). These mutations include the "LALA mutation" described in Bruhns et al., 2009 and Hezareh et al., 2001, which involves substitution of the leucine residues at IMGT positions 1.3 and 1.2 of the CH2 domain with alanine (L1.3A and L1.2A). Alternatively, the generation of a-glycosyl antibodies through mutation of the conserved N-linked glycosylation site by mutating the aparagine (N) at IMGT position 84.4 of the CH2 domain to alanine, glycine or glutamine (N84.4A, N84.4G or N84.4Q) is also known to decrease IgG1 effector function (Wang et al., 2018). As a further alternative, complement activation (C1q binding) and ADCC are known to be reduced through mutation of the proline at IMGT position 114 of the CH2 domain to alanine or glycine (P114A or P114G) (Idusogie et al., 2000; Klein et al., 2016). These mutations may also be combined in order to generate specific binding members with further reduced or no ADCC or CDC activity.

Thus, the specific binding member may comprise a CH2 domain, wherein the CH2 domain comprises:

(i) alanine residues at positions 1.3 and 1.2; and/or (ii) an alanine or glycine at position 114; and/or (iii) an alanine, glutamine or glycine at position 84.4;

wherein the amino acid residue numbering is according to the IMGT numbering scheme.

In a preferred embodiment, the specific binding member comprises a CH2 domain, wherein the CH2 domain preferably comprises:

(i) alanine residues at positions 1.3 and 1.2; and/or (ii) an alanine or glycine at position 114;

wherein the amino acid residue numbering is according to the IMGT numbering scheme.

In a preferred embodiment, the specific binding member comprises a CH2 domain, wherein the CH2 domain comprises:

(i) an alanine residue at position 1.3; and (ii) an alanine residue at position 1.2;

wherein the amino acid residue numbering is according to the IMGT numbering scheme.

For example, the CH2 domain may have the sequence set forth in SEQ ID NO: 6.

In an alternative preferred embodiment, the specific binding member comprises a CH2 domain, wherein the CH2 domain comprises:

(i) an alanine residue at position 1.3;

(ii) an alanine residue at position 1.2; and (iii) an alanine at position 114;

wherein the amino acid residue numbering is according to the IMGT numbering scheme.

For example, the CH2 domain may have the sequence set forth in SEQ ID NO: 7.

In a preferred embodiment, the specific binding member comprises, has, or consists of the CH2 and CH3 domain sequence of specific binding member FS20-22-49, FS20-22-41, FS20-22-47, FS20-22-85, or FS20-22-38, preferably the CH2 and CH3 domain sequence of specific binding member FS20-22-49, FS20-22-41, FS20-22-47, or FS20-22-85, more preferably the CH2 and CH3 domain sequence of specific binding member FS20-22-49, FS20-22-41, or FS20-22-47, most preferably the CH2 and CH3 domain sequence of specific binding member FS20-22-49, wherein the CH2 and CH3 domain sequence of specific binding member FS20-22-38, FS20-22-41, FS20-22-47, FS20-22-49, and FS20-22-85 is shown in SEQ ID NOs 48, 57, 65, 74, and 83, respectively, starting at amino acid 7 onwards.

In an alternative preferred embodiment, the specific binding member comprises, has, or consists of the CH2 and CH3 domain sequence of specific binding member FS20-22-49, FS20-22-41, FS20-22-47, FS20-22-85, or FS20-22-38, preferably the CH2 and CH3 domain sequence of specific binding member FS20-22-49, FS20-22-41, FS20-22-47, or FS20-22-85, more preferably the CH2 and CH3 domain sequence of specific binding member FS20-22-49, FS20-22-41, or FS20-22-47, most preferably the CH2 and CH3 domain sequence of specific binding member FS20-22-49, wherein the CH2 and CH3 domain sequence of specific binding member FS20-22-38, FS20-22-41, FS20-22-47, FS20-22-49, and FS20-22-85 is shown in SEQ ID NOs 50, 59, 67, 76, and 85, respectively, starting at amino acid 7 onwards.

In a further alternative preferred embodiment, the specific binding member comprises, has, or consists of the CH2 and CH3 domain sequence of specific binding member FS20-31-115, FS20-31-108, FS20-31-58, FS20-31-94, FS20-31-102, or FS20-31-66, preferably the CH2 and CH3 domain sequence of specific binding member FS20-31-115, FS20-31-108, FS20-31-58, FS20-31-94, or FS20-31-102, more preferably the CH2 and CH3 domain sequence of specific binding member FS20-31-115, or FS20-31-108, most preferably the CH2 and CH3 domain sequence of specific binding member FS20-31-115, wherein the CH2 and CH3 domain sequence of specific binding member FS20-31-58, FS20-31-66, FS20-31-94, FS20-31-102, FS20-31-108, and FS20-31-115 is shown in SEQ ID NOs 96, 105, 116, 126, 136, and 145, respectively, starting at amino acid 7 onwards.

In a further alternative preferred embodiment, the specific binding member comprises, has, or consists of the CH2 and CH3 domain sequence of specific binding member FS20-31-115, FS20-31-108, FS20-31-58, FS20-31-94, FS20-31-102, or FS20-31-66, preferably the CH2 and CH3 domain sequence of specific binding member FS20-31-115, FS20-31-108, FS20-31-58, FS20-31-94, or FS20-31-102, more preferably the CH2 and CH3 domain sequence of specific binding member FS20-31-115, or FS20-31-108, most preferably the CH2 and CH3 domain sequence of specific binding member FS20-31-115, wherein the CH2 and CH3 domain sequence of specific binding member FS20-31-58, FS20-31-66, FS20-31-94, FS20-31-102, FS20-31-108, and FS20-31-115 is shown in SEQ ID NOs 98, 107, 118, 128, 138, and 147, respectively, starting at amino acid 7 onwards.

In a still further alternative preferred embodiment, the specific binding member comprises, has, or consists of the CH2 and CH3 domain sequence of specific binding member FS20-11-131, FS20-11-127, or FS20-11-134, more preferably the CH2 and CH3 domain sequence of specific binding member FS20-11-131, wherein the CH2 and CH3 domain sequence of specific binding member FS20-11-127, FS20-11-131, or FS20-11-134 is shown in SEQ ID NOs 17, 26 and 35, respectively, starting at amino acid 7 onwards.

In a still further alternative preferred embodiment, the specific binding member comprises, has, or consists of the CH2 and CH3 domain sequence of specific binding member FS20-11-131, FS20-11-127, or FS20-11-134, more preferably the CH2 and CH3 domain sequence of specific binding member FS20-11-131, wherein the CH2 and CH3 domain sequence of specific binding member FS20-11-127, FS20-11-131, or FS20-11-134 is shown in SEQ ID NOs 19, 28 and 37, respectively, starting at amino acid 7 onwards.

In a preferred embodiment, the specific binding member comprises, has, or consists of the sequence of specific binding member FS20-22-49, FS20-22-41, FS20-22-47, FS20-22-85, or FS20-22-38, preferably the sequence of specific binding member FS20-22-49, FS20-22-41, FS20-22-47, or FS20-22-85, more preferably the sequence of specific binding member FS20-22-49, FS20-22-41, or FS20-22-47, most preferably the sequence of specific binding member FS20-22-49, wherein the sequence of specific binding member FS20-22-38, FS20-22-41, FS20-22-47, FS20-22-49, and FS20-22-85 is set forth in SEQ ID NOs 48, 57, 65, 74, and 83, respectively.

In an alternative preferred embodiment, the specific binding member comprises, has, or consists of the sequence of specific binding member FS20-22-49, FS20-22-41, FS20-22-47, FS20-22-85, or FS20-22-38, preferably the sequence of specific binding member FS20-22-49, FS20-22-41, FS20-22-47, or FS20-22-85, more preferably the sequence of specific binding member FS20-22-49, FS20-22-41, or FS20-22-47, most preferably the sequence of specific binding member FS20-22-49, wherein the sequence of specific binding member FS20-22-38, FS20-22-41, FS20-22-47, FS20-22-49, and FS20-22-85 is set forth in SEQ ID NOs 50, 59, 67, 76, and 85, respectively.

In a further alternative preferred embodiment, the specific binding member comprises, has, or consists of the sequence of specific binding member FS20-31-115, FS20-31-108, FS20-31-58, FS20-31-94, FS20-31-102, or FS20-31-66, preferably the sequence of specific binding member FS20-31-115, FS20-31-108, FS20-31-58, FS20-31-94, or FS20-31-102, more preferably the sequence of specific binding member FS20-31-115, or FS20-31-108, most preferably the sequence of specific binding member FS20-31-115, wherein the sequence of specific binding member FS20-31-58, FS20-31-66, FS20-31-94, FS20-31-102, FS20-31-108, and FS20-31-115 is set forth in SEQ ID NOs 96, 105, 116, 126, 136, and 145, respectively.

In a further alternative preferred embodiment, the specific binding member comprises, has, or consists of the sequence of specific binding member FS20-31-115, FS20-31-108, FS20-31-58, FS20-31-94, FS20-31-102, or FS20-31-66, preferably the sequence of specific binding member FS20-31-115, FS20-31-108, FS20-31-58, FS20-31-94, or FS20-31-102, more preferably the sequence of specific binding member FS20-31-115, or FS20-31-108, most preferably the sequence of specific binding member FS20-31-115, wherein the sequence of specific binding member FS20-31-58, FS20-31-66, FS20-31-94, FS20-31-102, FS20-31-108, and FS20-31-115 is set forth in SEQ ID NOs 98, 107, 118, 128, 138, and 147, respectively.

In a still further alternative preferred embodiment, the specific binding member comprises, has, or consists of the sequence of specific binding member FS20-11-131, FS20-11-127, or FS20-11-134, more preferably the sequence of specific binding member FS20-11-131, wherein the sequence of specific binding member FS20-11-127, FS20-11-131, and FS20-11-134 is set forth in SEQ ID NOs 17, 26, and 35, respectively.

In a still further alternative preferred embodiment, the specific binding member comprises, has, or consists of the sequence of specific binding member FS20-11-131, FS20-11-127, or FS20-11-134, more preferably the sequence of specific binding member FS20-11-131, wherein the sequence of specific binding member FS20-11-127, FS20-11-131, and FS20-11-134 is set forth in SEQ ID NOs 19, 28 and 37, respectively.

In a preferred embodiment, the specific binding member comprises one or more further antigen-binding sites that bind one or more further antigens, in addition to the OX40 antigen-binding site located in the constant domain of the specific binding member. The one or more further antigen-binding sites preferably bind their cognate antigens specifically.

The one or more further antigen-binding sites may bind OX40 or another antigen. The specific binding member may thus be a multispecific, for example a bispecific, trispecific, or tetraspecific molecule, preferably a bispecific molecule. In a preferred embodiment, the specific binding member is capable of simultaneously binding to OX40 and the one or more further antigens.

Antibody molecules are known to have a modular architecture comprising discrete domains, which can be combined in a multitude of different ways to create multispecific, e.g. bispecific, trispecific, or tetraspecific antibody formats. Exemplary multispecific antibody formats are described in Spiess et al. (2015) and Kontermann (2012), for example. The specific binding members of the present invention may be employed in such multispecific antibody formats.

This has the additional advantage of introducing a further antigen-binding site into such multispecific antibody format through the presence of the antigen-binding site the constant domain, e.g. the CH3 domain, of the specific binding member.

For example, the specific binding member of the invention may be a heterodimeric antibody molecule, such as a heterodimeric complete immunoglobulin molecule, or a fragment thereof. In this case, one part of the antibody molecule will have a sequence or sequences as described herein. For example, where the specific binding member of the invention is a bispecific heterodimeric antibody molecule, the specific binding member may comprise a heavy chain comprising a CH3 domain as described herein paired with a heavy chain which binds an antigen other than OX40. Techniques for preparing heterodimeric antibodies are known in the art and include knobs-into-holes (KIHs) technology, which involves engineering the CH3 domains of an antibody molecule to create either a “knob” or a “hole” to promote chain heterodimerization. Alternatively, heterodimeric antibodies can be prepared through the introduction of charge pairs into the antibody molecule to avoid homodimerization of CH3 domains by electrostatic repulsion and to direct heterodimerization by electrostatic attraction. Examples of heterodimeric antibody formats include CrossMab, mAb-Fv, SEED-body, and KIH IgG.

Alternatively, a multispecific specific binding member of the invention may comprise a complete immunoglobulin molecule or a fragment thereof and an additional antigen-binding moiety or moieties. The antigen-binding moiety may for example be an Fv, scFv or single domain antibody, and may be fused to the complete immunoglobulin molecule or a fragment thereof. Examples of multispecific antibody molecules comprising additional antigen-binding moieties fused to a complete immunoglobulin molecule include DVD-IgG, DVI-IgG, scFv4-IgG, IgG-scFv, and scFv-IgG molecules (Spiess et al., 2015; FIG. 1). Examples of multispecific antibody molecules comprising additional antigen-binding moieties fused to an immunoglobulin fragment comprising a CH3 domain include scDiabody-CH3, Diabody-CH3, and scFv-CH3 KIH, for example (Spiess et al., 2015; FIG. 1).

Other suitable multispecific formats would be readily apparent to the skilled person.

In a preferred embodiment, the specific binding member comprises a second antigen-binding site that binds a second antigen, wherein the second antigen-binding site preferably is a CDR-based antigen-binding site. A CDR-based antigen-binding site is an antigen-binding site in an antibody variable region. A CDR-based antigen-binding site is formed by six CDRs; three light chain variable domain (VL) CDRs and three heavy chain variable domain (VH) CDRs.

The preparation of antibody molecules against a given antigen and determination of the CDR sequences of such antibody molecules, is well established and many suitable techniques are known in the art. The CDR sequences may, for example, be determined according to Kabat et al., 1991 or the international ImMunoGeneTics information system (IMGT) (Lefranc et al., 2015).

For example, the specific binding member may be a $mAb^2$ (™) bispecific antibody. A $mAb^2$ bispecific antibody, as referred to herein, is an IgG immunoglobulin which includes a CDR-based antigen-binding site in each of its variable regions and at least one antigen binding site in a constant domain. Where the specific binding member of the invention is in a $mAb^2$ format, the specific binding member thus comprises a CDR-based antigen-binding site in each of its variable regions, in addition to an OX40 antigen-binding site in a constant domain of the specific binding member.

The three VH domain CDRs of the antigen-binding site may be located within an immunoglobulin VH domain and the three VL domain CDRs may be located within an immunoglobulin VL domain. For example, the CDR-based antigen-binding site may be located in an antibody variable region.

The specific binding member may have one or preferably more than one, for example two, CDR-based antigen binding sites for the second antigen. The specific binding member thus may comprise one VH and one VL domain but preferably comprises two VH and two VL domains, i.e. two VH/VL domain pairs, as is the case in naturally-occurring IgG molecules.

In some preferred embodiments, the specific binding member may be an immunoglobulin comprising two variable regions, each variable region comprising a CDR-based antigen binding site for the second antigen.

In a preferred embodiment, the antibody is thus an antibody that binds OX40 and a second antigen, the antibody molecule comprising:

(i) two antigen-binding sites for OX40 located in the two CH3 domains of the antibody molecule; and
(ii) two CDR-based antigen-binding sites for the second antigen, each formed by an immunoglobulin VH domain and an immunoglobulin VL domain.

In a more preferred embodiment, the antibody is a complete immunoglobulin molecule, e.g. a complete IgG1 molecule that binds OX40 and a second antigen, the antibody molecule comprising:

(i) two antigen-binding sites for OX40 located in the two CH3 domains of the antibody molecule; and
(ii) two CDR-based antigen-binding sites for the second antigen, each formed by an immunoglobulin VH domain and an immunoglobulin VL domain; and wherein the immunoglobulin molecule further comprises CH1, CH2 and CL domains.

Activation of OX40 requires clustering of OX40 on the T cell surface, which in turn stimulates intracellular signalling pathways and T cell activation. Binding of specific binding members to OX40 on the T cell surface in the absence of crosslinking of the specific binding members may not cause OX40 to form clusters, or may only induce limited clustering of OX40, and consequently may not result in T cell activation, or may result in only limited T cell activation.

The present inventors have shown that specific binding members FS20-11-131, FS20-11-127, and FS20-11-134 do not T cell activation in the absence of crosslinking of the specific binding member. In contrast, FS20-22-49, FS20-22-41, FS20-22-47, FS20-22-85, FS20-22-38, FS20-31-115, FS20-31-108, FS20-31-58, FS20-31-94, FS20-31-102, and FS20-31-66 induce limited T cell activation in the absence of crosslinking. OX40 agonism of these specific binding members is induced or increase on crosslinking of the specific binding member (see Example 5).

As explained above, crosslinking of antibody molecules through binding to Fcγ receptors is both inefficient and cannot be targeted to a particular location e.g. the site of a disease, as Fcγ receptor expressing cells are present throughout the human body. The second antigen bound by the second antigen-binding site is therefore preferably not an Fcγ receptor.

In a preferred embodiment, the specific binding members of the invention therefore comprise a second antigen binding site that binds a second antigen, wherein the second antigen is capable of binding to and crosslinking multiple specific binding members.

For example, the present inventors have shown that where the second antigen is a surface antigen, such as a cell-surface antigen, which can be monomeric or multimeric and is present in high concentrations and/or clustered at a surface, e.g. at a cell surface, binding of the specific binding member to the second antigen results in, or enhances, T cell activation.

Without wishing to be bound by theory, it is thought that binding of the specific binding member to an abundant cell-surface antigen, for example, results in a high concentration of specific binding members bound to the cell surface which places the specific binding members in sufficiently close proximity to be able to drive clustering of OX40 and T cell activation. In a preferred embodiment, the second antigen is therefore a surface antigen which is expressed at a high concentration on a surface, e.g. a cell surface.

The present inventors have also shown that where the second antigen is a multimeric soluble molecule, e.g. a multimeric soluble factor, binding of the specific binding member to the second antigen results in, or enhances, T cell activation. In a preferred embodiment, the second antigen when a soluble molecule is therefore a multimeric antigen, such as a dimer, trimer or higher-order multimer, and thus able to crosslink several specific binding members.

A specific binding member comprising a second antigen-binding site that binds a second antigen, as described herein, and which activates T cells only on binding to the second antigen, or whose T cell activation activity is enhanced on binding to the second antigen, is also referred to as a conditional agonist. This T cell activation activity on binding to the second antigen is independent of binding of the specific binding member to Fcγ receptors and/or external crosslinking agents, such as protein A or G or secondary antibodies, and therefore allows the conditional agonist activity of the specific binding member to be targeted to sites where the second antigen is present. For example, where the second antigen is a disease antigen, the specific binding member may activate the T cell selectively at the site of disease and not elsewhere in an individual, or may enhance activation of the T cell selectively at the site of disease and not elsewhere in an individual.

In addition, a specific binding member which activates T cells only on binding to a second antigen, or whose T cell activation activity is enhanced on binding to a second antigen, preferably has increased T cell activation activity compared with specific binding members that rely on crosslinking by other mechanisms, such as external crosslinking agents, or crosslinking via Fcγ receptor interaction. Because the activation of OX40 is more efficient, T cell activation may be achieved at lower concentrations of specific binding members described herein relative to other specific binding members.

Thus, the specific binding of the invention preferably induces increased T cell activation when the specific binding member is crosslinked, e.g. through binding to a second antigen, than when the specific binding member is not crosslinked.

The ability of an antibody molecule or specific binding member to activate T cells may be measured using a T cell activation assay. T cells release IL-2 on activation. A T cell activation assay may therefore measure IL-2 release to determine the level of T cell activation induced by the antibody molecule or specific binding member.

For example, the ability of the antibody molecule or specific binding member to activate T cells may be determined by measuring the concentration of the antibody molecule or specific binding member required to achieve half-maximal release of IL-2 by the T cells in a T cells activation assay when the specific binding member or antibody molecule is crosslinked. This is referred to as the $EC_{50}$ of the antibody molecule or specific binding member below. A lower $EC_{50}$ indicates that a lower concentration of the antibody molecule or specific binding member is needed to achieve half-maximal release of IL-2 by the T cells in the T cells activation assay, and thus that the antibody molecule or specific binding member has a higher T cell activation activity. The specific binding member or antibody molecule may be crosslinked using and anti-CH2 antibody, for example.

In a preferred embodiment, the antibody molecule or specific binding member has an $EC_{50}$ in a T cell activation assay which is within 50-fold, 40-fold, 30-fold, 20-fold, 10-fold, or 5-fold of the $EC_{50}$ of FS20-22-49/4420 (comprising the LALA mutation) in the same assay, wherein FS20-22-49/4420 (LALA) consists of or comprises the heavy chain set forth in SEQ ID NO: 78 and the light chain set forth in SEQ ID NO: 156.

In a preferred embodiment, the $EC_{50}$ of the antibody molecule or specific binding member in a T cell activation assay in the presence of crosslinking of the antibody molecule or specific binding member is 10-fold, 20-fold, 30-fold, or 40-fold lower than in the absence of crosslinking.

For example, the antibody molecule or specific binding member may have an $EC_{50}$ in a T cell activation assay of 5 nM or less, 4 nM or less, 3 nM or less, 2 nM or less, 1 nM or less, 0.5 nM or less, 0.3 nM or less, 0.2 nM or less, or 0.1 nM or less, preferably 0.1 nM or less.

In addition, or alternatively, the ability of an antibody molecule or specific binding member to activate T cells may be determined by measuring the maximum concentration of IL-2 released by the T cells in a T cell activation assay in the presence of the antibody molecule or specific binding member, wherein the antibody molecule or specific binding member is crosslinked.

In a preferred embodiment, the maximum concentration of IL-2 released by the T cells in a T cell activation assay in the presence of the antibody molecule or specific binding member in the presence of crosslinking is within 20%, or 10% of the maximum concentration of IL-2 released by the T cells in the presence of FS20-22-49/4420 (comprising the LALA mutation) in the same assay, wherein FS20-22-49/4420 (LALA) consists of or comprises the heavy chain set forth in SEQ ID NO: 78 and the light chain set forth in SEQ ID NO: 156. The T cell activation assay may be a T cell assay as described herein, such as a pan-T cell assay, as described in the present Examples.

For example, a T cell activation assay may be an IL-2 release assay based on T cells isolated from human Peripheral Blood Mononuclear Cells (PBMCs). For example, the T cell activation assay may comprise isolating human PBMCs from leucocyte depletion cones. Methods for isolating PBMCs are known in the art and described in the present examples. The T cells may then be isolated from the PBMCs. Methods for isolating T cells from PBMCs are known in the art and described in the present examples.

The T cell activation assay may comprise preparing the required number of T cells for example in a suitable medium, such as a T cell medium. The required number of T cells may be prepared at a concentration of $1.0\times10^6$ cells/ml. T cells may then be stimulated using a suitable T cell activation reagent that provides the signals required for T cell activation. For example, the T cell activation reagent may be a reagent comprising CD3 and CD28, such as beads comprising CD3 and CD28. Isolated T cells may be incubated overnight with the T cell activation reagent to activate the T cells. Following this, the activated T cells may be washed to separate the T cells from the T cell activation reagent and resuspended in T cell medium at a suitable concentration, such as $2.0\times10^6$ cells/ml. Activated T cells may then be added to plates coated with an anti-human CD3 antibody.

A suitable dilution of each test antibody molecule or specific binding member may be prepared and added to the wells. The T cells may then be incubated at 37° C., 5% $CO_2$ for 24 hours with the test antibody. Supernatants may be collected and assayed to determine the concentration of IL-2 in the supernatant. Methods for determining the concentration of IL-2 in a solution are known in the art and described in the present examples. The concentration of human IL-2 may be plotted versus the log concentration of the antibody molecule or specific binding member. The resulting curves may be fitted using the log (agonist) versus response equation.

The second antigen bound by the second antigen-binding site of the specific binding member may be an immune cell antigen, or a disease antigen. Disease antigens include pathogenic antigens and tumour antigens.

In a preferred embodiment, the second antigen-binding site of the specific binding member binds an immune cell antigen.

The immune cell antigen bound by the specific binding member may be present on the same immune cell or on a different immune cell to OX40.

The immune cell antigen may be a member of the tumour necrosis factor receptor superfamily (TNFRSF) other than OX40. TNFRSF receptors are membrane-bound cytokine receptors that comprise an extracellular cysteine rich domain which binds one or more ligands of the tumour necrosis factor superfamily (TNFSF).

The TNFRSF receptor may be located on the surface of an immune cell. Upon binding of a TNFRSF ligand, TNFRSF receptors form clusters on the immune cell surface which activates the immune cell. For example, ligand bound TNFRSF receptors may form multimers, such as trimers, or clusters of multimers. The presence of clusters of ligand-bound TNFRSF receptors stimulates intracellular signalling pathways which activate the immune cell.

Without wishing to be bound by theory it is thought that by engaging both OX40 and a second TNFRSF receptor on an immune cell surface, the specific binding members will cause both OX40 and the second TNFRSF receptor to cluster and activate the immune cell(s). In other words, the specific binding member will act as a TNFRSF receptor agonist when both targets are bound.

TNFRSF receptors include CD27, CD40, EDA2R, EDAR, FAS, LTBR, RELT, TNFRSF1A, TNFRSF1 B, TNFRSF6B, TNFRSF8, TNFRSF9, TNFRSF1 OA-10D, TNFRSF11A, TNFRSF11B, TNFRSF12A, TNFRSF13B, TNFRSF13C, TNFRSF14, TNFRSF17, TNFRSF18, TNFRSF19, TNFRSF21 and TNFRSF25.

In a preferred embodiment, the TNFRSF receptor is TNFRSF9 (CD137; 4-1 BB).

CD27 (TNFRSF7: Gene ID 939) has the reference amino acid sequence of NP_001233.1 and may be encoded by the reference nucleotide sequence of NM_001242.4. CD40 (TNFRSF5: Gene ID 958) has the reference amino acid sequence of NP_001241.1 and may be encoded by the reference nucleotide sequence of NM_001250.5. EDA2R (TNFRSF27: Gene ID 60401) has the reference amino acid sequence of NP_001186616.1 and may be encoded by the reference nucleotide sequence of NM_001199687.2. EDAR (Gene ID 10913) has the reference amino acid sequence of NP_071731.1 and may be encoded by the reference nucleotide sequence of NM_022336, 3. FAS (TNFRSF6: Gene ID 355) has the reference amino acid sequence of NP_000034.1 and may be encoded by the reference nucleotide sequence of NM_000043.5. LTBR (TNFRSF3: Gene ID 4055) has the reference amino acid sequence of NP_001257916.1 and may be encoded by the reference nucleotide sequence of NM_001270987.1. RELT (TNFRSF19L: Gene ID 84957)

has the reference amino acid sequence of NP_116260.2 and may be encoded by the reference nucleotide sequence of NM_032871.3. TNFRSF1A (Gene ID 7132) has the reference amino acid sequence of NP_001056.1 and may be encoded by the reference nucleotide sequence of NM_001065.3. TNFRSF1 B (Gene ID 7133) has the reference amino acid sequence of NP_001057.1 and may be encoded by the reference nucleotide sequence of NM_001066.2. TNFRSF6B (Gene ID 8771) has the reference amino acid sequence of NP_003814.1 and may be encoded by the reference nucleotide sequence of NM_003823.3. TNFRSF8 (Gene ID 943) has the reference amino acid sequence of NP_001234.3 and may be encoded by the reference nucleotide sequence of NM_001243.4. TNFRSF9 (Gene ID 3604) has the reference amino acid sequence of NP_001552 and may be encoded by the reference nucleotide sequence of NM001561). TNFRSF1OA (Gene ID 8797) has the reference amino acid sequence of NP_003835.3 and may be encoded by the reference nucleotide sequence of NM_003844.3. TNFRSF10B (Gene ID 8795) has the reference amino acid sequence of NP_003833.4 and may be encoded by the reference nucleotide sequence of NM_003842.4. TNFRSF10C (Gene ID 8794) has the reference amino acid sequence of NP_003832.2 and may be encoded by the reference nucleotide sequence of NM_003841.4. TNFRSF1 OD (Gene ID 8793) has the reference amino acid sequence of NP_003831.2 and may be encoded by the reference nucleotide sequence of NM_003840.4. TNFRSF11 A (Gene ID 8792) has the reference amino acid sequence of XP_011524547.1 and may be encoded by the reference nucleotide sequence of XM_11526245.2. TNFRSF11 B (Gene ID 4982) has the reference amino acid sequence of NP_002537.3 and may be encoded by the reference nucleotide sequence of NM_002546.3. TNFRSF12A (Gene ID 51330) has the reference amino acid sequence of NP_057723.1 and may be encoded by the reference nucleotide sequence of NM_016639.2. TNFRSF13B (Gene ID 23495) has the reference amino acid sequence of NP_0036584.1 and may be encoded by the reference nucleotide sequence of NM_012452.2. TNFRSF13C (Gene ID 115650) has the reference amino acid sequence of NP_443177.1 and may be encoded by the reference nucleotide sequence of NM_052945.3. TNFRSF14 (Gene ID 8764) has the reference amino acid sequence of NP_001284534.1 and may be encoded by the reference nucleotide sequence of NM_001297605.1. TNFRSF17 (Gene ID 608) has the reference amino acid sequence of NP_001183.2 and may be encoded by the reference nucleotide sequence of NM_001192.2. TNFRSF18 (Gene ID 8784) has the reference amino acid sequence of NP_004195.2 and may be encoded by the reference nucleotide sequence of NM_004186.1. TNFRSF19 (Gene ID 55504) has the reference amino acid sequence of NP_001191387.1 and may be encoded by the reference nucleotide sequence of NM_001204458.1. NFRSF21 (Gene ID 27242) has the reference amino acid sequence of NP_055267.1 and may be encoded by the reference nucleotide sequence of NM_014452.4. TNFRSF25 (DR3: Gene ID 8718) binds to ligand TNFSF15 (TL1A) has the reference amino acid sequence of NP_001034753.1 and may be encoded by the reference nucleotide sequence of NM_001039664.1.

Alternatively, the immune cell antigen bound by the second antigen-binding site may be a molecule which has a regulatory function in the immune system other than a TNFRSF member, e.g. an immune costimulatory molecule or an inhibitory checkpoint molecule. Examples of such immune regulatory molecules include ICOS (CD278), LAG3, PD1, PD-L1, PD-L2, B7H3, B7H4, CTLA4, TIGIT, BTLA, HVEM, T cell immunoglobulin, mucin-domain containing-3 (TIM-3), CD47, CD73, A2aR, CD200, CD200R, Colony stimulating factor 1 receptor (CSF-1R), VISTA CD28, CD80, LLT1, galectin-9, NKG2A, NKG2D, and KIR.

The immune cell on which the immune cell antigen is present may belong to any immune cell subset and can be a T cell, a tumour-infiltrating leukocyte (TIL), a myeloid lineage cell such as an antigen presenting cell (APC), an NK cell and/or a B cell. When the immune cell antigen is a TNFRSF receptor, the immune cell on which the TNFRSF receptor is present is preferably a T cell.

Alternatively, the second antigen-binding site may bind to a disease antigen as mentioned above. Without wishing to be bound by theory, it is thought that binding of the specific binding member to OX40 and a disease antigen will result in the activation of T cells in the vicinity of the disease. The activated T cells may then initiate, promote or take part in an immune response, for example an immune response against a pathogen or a cancer cell. An overview of the role the immune system plays in recognizing and eradicating cancer cells is provided by Chen and Mellman, 2013.

The second antigen-binding site of the specific binding member may bind a tumour antigen. A tumour antigen is an antigen that is predominantly present in the environment of a tumour, and is not ubiquitously present elsewhere in an individual. For example, the tumour antigen may be present on the surface of tumour cells or may be present on other stromal cells of the tumour microenvironment or in biological fluids in the vicinity of a tumour. The tumour antigen is therefore a marker of the location of tumour cells in an individual.

In some embodiments, the tumour antigen may be an antigen that is located on the surface of a cancer cell. The tumour antigen may be upregulated or overexpressed on tumour cells, whereas it may not be abundantly expressed by the corresponding normal somatic cells from the same tissue in the absence of a tumour.

In some embodiments, the tumour antigen is upregulated or overexpressed on stromal cells of the tumour microenvironment, compared with stromal cells of the corresponding normal tissue in the absence of a tumour.

The tumour antigen may exist on the cell surface and may not be rapidly internalised.

Tumour antigens that are suitable for targeting by the specific binding members may be identified using methods that are known in the art. For example, a specific binding member targeting OX40 receptor and a tumour antigen can be used in an assay where a OX40 expressing cell is co-cultured with a tumour antigen expressing cell and activation of the OX40 expressing cell is measured, for example by a T cell activation assay, a proliferation assay or cytotoxicity assay.

A cell surface tumour antigen may be a tumour-associated antigen (TAA) or a tumour-specific antigen (TSA).

Tumour antigens expressed by cancer cells may include, for example, cancer-testis (CT) antigens encoded by cancer-germ line genes, such as MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-I, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), MAGE-C1/CT7, MAGE-C2, NY-ESO-1, LAGE-1, SSX-I, SSX-2(HOM-MEL-40), SSX-3, SSX-4, SSX-5, SCP-I and XAGE and immunogenic fragments or variants thereof (Simpson et al., 2005; Gure et al., 2005; Velazquez et al., 2007; Andrade et al., 2008; Tinguely et al., 2008; Napoletano et al., 2008).

Other cell surface tumour antigens include, for example, AFP, $\alpha_v\beta_3$ (vitronectin receptor), $\alpha_v\beta_6$, B-cell maturation agent (BCMA), CA125 (MUC16), CD4, CD20, CD22, CD33, CD52, CD56, CD66e, CD80, CD140b, CD227 (MUC1), EGFR (HER1), EpCAM, GD3 ganglioside, HER2, prostate-specific membrane antigen (PSMA), prostate specific antigen (PSA), CD5, CD19, CD21, CD25, CD37, CD30, CD33, CD45, HLA-DR, anti-idiotype, carcinoembyronic antigen (CEA), e.g. carcinoembryonic antigen-related cell adhesion molecule 5 (CEACAM5), TAG-72, Folate-binding protein, A33, G250, ferritin, glycolipids such as gangliosides, carbohydrates such as CA-125, IL-2 receptor, fibroblast activation protein (FAP), IGF1R, B7H3, B7H4, PDL1, CD200, EphA2, and mesothelin or variants thereof. These and other cell surface tumour antigens are described in Carter et al., 2004; Scott and Renner, 2001; Cheever et al., 2009; Tai and Anderson, 2015; and Podojil and Miller, 2017.

Other tumour antigens include out-of-frame peptide-MHC complexes generated by the non-AUG translation initiation mechanisms employed by “stressed” cancer cells (Malarkannan et al., 1999).

Other tumour antigens include peptide-MHC complexes on the surface of tumour cells or of cells of the tumour microenvironment, where the peptide-MHC complexes comprise a tumour-specific neoantigen peptide fragment of a mutated intracellular tumour antigen, and where the peptide neoantigen harbours one or more tumour-specific mutations (Gubin et al., 2015). Other tumour antigens are well-known in the art (see for example WO00/20581; Cancer Vaccines and Immunotherapy (2000) Eds Stern, Beverley and Carroll, Cambridge University Press, Cambridge). The sequences of these tumour antigens are readily available from public databases but are also found in WO1992/020356 A1, WO1994/005304 A1, WO1994/023031 A1, WO1995/020974 A1, WO1995/023874 A1 and WO1996/026214 A1.

Exemplary tumour antigens include HER2, FAP, EpCAM, CEACAM5, CD20, CD73, PSMA, mesothelin, EphA2, IGF1R, CD200, $\alpha_v\beta_6$, BCMA, PD-L1, B7H3, B7H4 and EGFR.

For example, the tumour antigen may be mesothelin (MSLN).

HER2 (ERBB2; Gene ID 2064) may have the reference amino acid sequence of NP_001005862.1 and may be encoded by the reference nucleotide sequence of NM_001005862.2. FAP (Gene ID 2191) may have the reference amino acid sequence of NP_001278736.1 and may be encoded by the reference nucleotide sequence of NM_001291807.1. EpCAM (Gene ID 4072) may have the reference amino acid sequence of NP_002345.2 and may be encoded by the reference nucleotide sequence of NM_002354.2. CEACAM5 (Gene ID 1048) may have the reference amino acid sequence of NP_001278413.1and may be encoded by the reference nucleotide sequence of NM_001291484.2. CD20 (MS4A1; Gene ID 931) may have the reference amino acid sequence of NP_068769.2 and may be encoded by the reference nucleotide sequence of NM_021950.3. CD73 (NT5E; Gene ID 4907) may have the reference amino acid sequence of NP_001191742.1 and may be encoded by the reference nucleotide sequence of NM_001204813.1. PSMA (FOLH1; Gene ID 2346) may have the reference amino acid sequence of NP_001014986.1 and may be encoded by the reference nucleotide sequence of NM_001014986.1. Mesothelin (MSLN; Gene ID 10232) may have the reference amino acid sequence of NP_001170826.1 and may be encoded by the reference nucleotide sequence of NM_001177355.2. EphA2 (Gene ID 1969) may have the reference amino acid sequence of NP_001316019.1 and may be encoded by the reference nucleotide sequence of NM_001329090.1. IGF1R (Gene ID 3480) may have the reference amino acid sequence of NP_000866.1 and may be encoded by the reference nucleotide sequence of NM_000875.4. CD200 (Gene ID 4345) may have the reference amino acid sequence of NP_001004196.2 and may be encoded by the reference nucleotide sequence of NM_001004196.3. $\alpha_v\beta_6$ is a heterodimer composed of the integrin subunit alpha V and integrin subunit beta 6. Integrin subunit alpha V (ITGAV; Gene ID 3685) may have the reference amino acid sequence of NP_001138471.1 and may be encoded by the reference nucleotide sequence of NM_001144999.2. Integrin subunit beta 6 (ITGB6; Gene ID 3694) may have the reference amino acid sequence of NP_000879.2 and may be encoded by the reference nucleotide sequence of NM_000888.4. BCMA (TNFRSF17; Gene ID 608) may have the reference amino acid sequence of NP_001183.2 and may be encoded by the reference nucleotide sequence of NM_001192.2. PD-L1 (CD274; Gene ID 29126) may have the reference amino acid sequence of NP_001254635.1 and may be encoded by the reference nucleotide sequence of NM_001267706.1. B7H3 (CD276; Gene ID 80381) may have the reference amino acid sequence of NP_001019907.1 and may be encoded by the reference nucleotide sequence of NM_001024736.1. B7H4 (VTCN1; Gene ID 79679) may have the reference amino acid sequence of NP_001240778.1 and may be encoded by the reference nucleotide sequence of NM_001253849.1. EGFR (Gene ID 1956) may have the reference amino acid sequence of NP_001333826.1 and may be encoded by the reference nucleotide sequence of NM_001346897.1.

In other embodiments, the tumour antigen may be a soluble tumour antigen, for example a growth factor that is produced by or in response to cancer cells. A soluble factor may be upregulated or overexpressed in biological fluids in the vicinity of a tumour. A soluble tumour antigen may be multimeric, for example a dimer or a trimer. A soluble tumour antigen may be present in higher concentrations at the tumour site or in the tumour microenvironment than elsewhere in the body of an individual. The tumour microenvironment and associated soluble tumour antigens are described in more detail in Bhome et al. (2015).

Suitable soluble tumour antigens include VEGF, HGF, SDF1 and TGF-beta, e.g. TGF-beta-1, TGF-beta-2, TGF-beta-3 and TGF-beta-4.

VEGF (VEGFA; gene ID 7422) has the reference amino acid sequence of NP_001020537.2 and may be encoded by the reference nucleotide sequence of NM_001025366.2. HGF (gene ID 3082) has the reference amino acid sequence of NP_000592.3 and may be encoded by the reference nucleotide sequence of NM_000601.5. SDF1 (CXCL12; gene ID 6387) has the reference amino acid sequence of NP_000600.1 and may be encoded by the reference nucleotide sequence of NM_000609.6. TGF-beta-1 (TGFB1; gene ID 7040) may have the reference amino acid sequence of NP_000651.3 and may be encoded by the reference nucleotide sequence of NM_000660.6. TGF-beta-2 (TGFB2; gene ID 7042) may have the reference amino acid sequence of NP_001129071.1 and may be encoded by the reference nucleotide sequence of NM_001135599.3. TGF-beta-3 (TGFB3; gene ID 7043) may have the reference amino acid sequence of NP_001316867.1 and may be encoded by the reference nucleotide sequence of NM_001329938.1. TGF-beta-4 (LEFTY2; gene ID 7044) may have the reference amino acid sequence of NP_001165896.1 and may be encoded by the reference nucleotide sequence of NM_001172425.2.

In an alternative preferred embodiment, the disease antigen is a pathogenic antigen.

Activation of T cells by the specific binding member in the vicinity of a site of an infectious disease is expected to be useful in the treatment of the infectious disease. The infectious disease may be an acute or persistent infectious diseases but preferably is a persistent infectious diseases.

The pathogenic antigen is preferably an antigen expressed by a human pathogen, such as a viral, bacterial, fungal or parasitic antigen (e.g. a protozoal antigen), preferably a viral or bacterial antigen. A pathogenic antigen is an antigen that is predominantly present on a pathogen, or in the vicinity of a site of an infectious disease, and is not ubiquitously present elsewhere in an individual.

For example, the pathogenic antigen may be an antigen present on the surface of a virus, bacterium, fungus or parasite, or a soluble antigen expressed by a virus, bacterium, fungus or parasite. The virus, bacterium, fungus, or parasite may be a virus, bacterium, fungus, or parasite as referred to elsewhere herein.

Where the pathogenic antigen is a soluble antigen, the antigen may be upregulated or overexpressed in biological fluids in the vicinity of the site of the infectious disease. For example, a soluble pathogenic antigen may be present in higher concentrations at, or in the vicinity of, the site of the infectious disease than elsewhere in the body of an individual. The soluble pathogenic antigen may be multimeric, for example a dimer or a trimer.

Pathogenic antigens that are suitable for targeting by the specific binding member may be identified using methods that are known in the art. For example, a specific binding member targeting OX40 receptor and a pathogenic antigen can be used in an assay where an OX40 expressing cell is co-cultured with a pathogen or pathogenic antigen and activation of the OX40 expressing cell is measured, for example by T cell activation assay, a proliferation assay or cytotoxicity assay.

Many pathogenic antigens suitable for targeting by the specific binding member are further more known in the art and can be selected by the skilled person according to the infectious disease to be treated. Examples of viral antigens include proteins p24, gp120, and gp41 expressed by human immunodeficiency virus (HIV), hepatitis B surface antigen (HBsAg) expressed by hepatitis B virus (HBV), and haemagglutinin and neuraminidase expressed by influenza virus. Examples of bacterial antigens include Rv1733, Rv2389 and Rv2435n expressed by *Mycobacterium tuberculosis.*

The specific binding member may also comprise a variant of a first, second or third sequence, AB, CD or EF structural loop sequence, CH3 domain, CH2 domain, CH2 and CH3 domain, Fcab, CDR, VH domain, VL domain, light chain and/or heavy chain sequence as disclosed herein. Suitable variants can be obtained by means of methods of sequence alteration, or mutation, and screening. In a preferred embodiment, a specific binding member comprising one or more variant sequences retains one or more of the functional characteristics of the parent specific binding member, such as binding specificity and/or binding affinity for OX40. For example, a specific binding member comprising one or more variant sequences preferably binds to OX40 with the same affinity as, or a higher affinity than, the (parent) specific binding member. The parent specific binding member is a specific binding member which does not comprise the amino acid substitution(s), deletion(s), and/or insertion(s) which has (have) been incorporated into the variant specific binding member.

For example, a specific binding member may comprise a first, second or third sequence, AB, CD or EF structural loop sequence, CH3 domain, CH2 domain, CH2 and CH3 domain, Fcab, CDR, VH domain, VL domain, light chain and/or heavy chain sequence which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a first, second or third sequence, AB, CD or EF structural loop sequence, CH3 domain, CH2 domain, CH2 and CH3 domain, Fcab, CDR, VH domain, VL domain, light chain or heavy chain sequence disclosed herein.

The CH3 domain sequence of specific binding member FS20-22-49 has at least 95% sequence identity to the CH3 domains of specific binding members FS20-22-38, FS20-22-41, FS20-22-47, and FS20-22-85. The CH3 domain sequence of specific binding member FS20-31-115 has at least 92% sequence identity to the CH3 domains of specific binding members FS20-31-58, FS20-31-66, FS20-31-94, FS20-31-102, and FS20-31-108. The CH3 domain sequence of specific binding member FS20-11-131 has at least has at least 97% sequence identity to the CH3 domains of specific binding members FS20-11-127 and FS20-11-134.

Thus, in a preferred embodiment, the specific binding member has or comprises a CH3 domain sequence which has at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity, preferably at least 99%, at least 99.1%, at least 99.2%, at least 99.3%, at least 99.4%, at least 99.5%, at least 99.6%, at least 99.7%, at least 99.8%, or at least 99.9% sequence identity, to the CH3 domain sequence set forth in SEQ ID NO: 15, 24, 33, 46, 55, 63, 72, 81, 94, 103, 114, 124, 134, or 143.

In a further preferred embodiment, the specific binding member has or comprises a CH2 domain sequence, which has at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH2 domain sequence set forth in SEQ ID NO: 5, 6 or 7.

In another preferred embodiment, the specific binding member has, comprises, or consists of, a sequence, which has at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the Fcab sequence set forth in SEQ ID NO: 17, 19, 26, 28, 35, 37, 48, 50, 57, 59, 65, 67, 74, 76, 83, 85, 96, 98, 105, 107, 116, 118, 126, 128, 136, 138, 145, or 147.

Sequence identity is commonly defined with reference to the algorithm GAP (Wisconsin GCG package, Accelerys Inc, San Diego USA). GAP uses the Needleman and Wunsch algorithm to align two complete sequences, maximising the number of matches and minimising the number of gaps. Generally, default parameters are used, with a gap creation penalty equaling 12 and a gap extension penalty equaling 4. Use of GAP may be preferred but other algorithms may be used, e.g. BLAST (which uses the method of Altschul et al., 1990), FASTA (which uses the method of Pearson and Lipman, 1988), or the Smith-Waterman algorithm (Smith and Waterman, 1981), or the TBLASTN program, of Altschul et al., 1990 supra, generally employing default parameters. In particular, the psi-Blast algorithm (Altschul et al., 1997) may be used.

A specific binding member may comprise a first, second or third sequence, AB, CD or EF structural loop sequence, CH3 domain, CH2 domain, CH2 and CH3 domain, Fcab, CDR, VH domain, VL domain, light chain or heavy chain sequence which has one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with a first, second or third sequence, AB, CD or EF structural loop sequence, CH3 domain, CH2 domain, CH2 and CH3 domain, Fcab, CDR, VH domain, VL domain, light chain or heavy chain sequence disclosed herein.

In a preferred embodiment, the specific binding member may comprise a CH3 domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH3 domain sequence set forth in SEQ ID NO: 15, 24, 33, 46, 55, 63, 72, 81, 94, 103, 114, 124, 134, or 143.

In a further preferred embodiment, the specific binding member comprises a CH2 domain sequence, with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH2 domain sequence set forth in SEQ ID NO: 5, 6, or 7.

In a further preferred embodiment, the specific binding member comprises or consists of a sequence, with one or more amino acid sequence alterations (addition, deletion, substitution and/or insertion of an amino acid residue), preferably 40 alterations or fewer, 30 alterations or fewer, 20 alterations or fewer, 15 alterations or fewer, 10 alterations or fewer, 5 alterations or fewer, 4 alterations or fewer, 3 alterations or fewer, 2 alterations or fewer, or 1 alteration compared with the Fcab sequence set forth in SEQ ID NO: 17, 19, 26, 28, 35, 37, 48, 50, 57, 59, 65, 67, 74, 76, 83, 85, 96, 98, 105, 107, 116, 118, 126, 128, 136, 138, 145, or 147.

Where the specific binding member comprises a variant of CH3 domain, CH2 and CH3 domain, Fcab, light chain or heavy chain sequence disclosed herein, the variant preferably does not comprise any amino acid alterations in the first, second and third sequence located in the AB, CD and EF structural loops of the CH3 domain of the specific binding member. For example, the variant may not comprise any amino acid alterations in the AB, CD and EF structural loops of the CH3 domain of the specific binding member.

In preferred embodiments in which one or more amino acids are substituted with another amino acid, the substitutions may conservative substitutions, for example according to the following Table. In some embodiments, amino acids in the same category in the middle column are substituted for one another, i.e. a non-polar amino acid is substituted with another non-polar amino acid, for example. In some embodiments, amino acids in the same line in the rightmost column are substituted for one another.

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g. binding affinity) of the specific binding member comprising the substitution as compared to the equivalent unsubstituted specific binding member.

Also contemplated is a specific binding member which comprises an OX40 antigen-binding site located in a constant domain, preferably a CH3 domain, of the specific binding member and which competes with a specific binding member of the invention for binding to OX40, or that binds to the same epitope on OX40 as a specific binding member of the invention.

Methods for determining competition for an antigen by two specific binding members are known in the art. For example, competition of binding to an antigen by two specific binding members can be determined using surface plasmon resonance, such as Biacore. Methods for mapping In some embodiments, the specific binding member may not comprise a CDR-based antigen-binding site.

In particular, the specific binding member may not comprise a CDR-based antigen-binding site that binds CD137.

In addition, or alternatively, the specific binding member may not comprise a CDR-based antigen-binding site that binds mesothelin (MSLN).

For example, the specific binding member may not comprise a CDR-based antigen-binding site that binds CD137 or MSLN, wherein the specific binding member comprises the first, second and third sequence located in the AB, CD and EF structural loops of the CH3 domain of specific binding member FS20-22-49, the AB, CD and EF structural loop sequences of the CH3 domain of specific binding member FS20-22-49, and/or the CH3 domain sequence of specific binding member FS20-22-49.

For example, the specific binding member may not comprise the CDRs, and/or VH and/or VL domain of anti-CD137 mAb FS30-10-16 set forth below.

```
Heavy chain CDRs of FS30-10-16 mAb
CDR1 (IMGT)
GFTFSSYD (SEQ ID NO: 177)

CDR1 (Kabat)
SYDMS (SEQ ID NO: 178)

CDR2 (IMGT)
IDPTGSKT (SEQ ID NO: 179)

CDR2 Kabat)
DIDPTGSKTDYADSVKG (SEQ ID NO: 180)

CDR3 (IMGT)
ARDLLVYGFDY (SEQ ID NO: 181)

CDR3 (Kabat)
DLLVYGFDY (SEQ ID NO: 182)
```

-continued

VH domain domain of FS30-10-16 mAb (SEQ ID NO: 183)
EVQLLESGGGLVQPGGSLRLSCAASGFTFSSYDMSWVRQAPGKGLEWVS

DIDPTGSKTDYADSVKGRFTISRDNSKNTLYLQMNSLRAEDTAVYYCAR

DLLVYGFDYWGQGTLVTVSS

Light chain CDRs of FS30-10-16 mAb
CDR1 (IMGT)
QSVSSSY (SEQ ID NO: 184)

CDR1 (Kabat)
RASQSVSSSYLA (SEQ ID NO: 185)

CDR2 (IMGT)
GAS (SEQ ID NO: 186)

CDR2 (Kabat)
GASSRAT (SEQ ID NO: 187)

CDR3 (IMGT)
QQSYSYPVT (SEQ ID NO: 188)

CDR3 (Kabat)
QQSYSYPVT (SEQ ID NO: 193)

VL domain of FS30-10-16 mAb (SEQ ID NO: 189)
EIVLTQSPGTLSLSPGERATLSCRASQSVSSSYLAWYQQKPGQAPRLLI

YGASSRATGIPDRFSGSGSGTDFTLTISRLEPEDFAVYYCQQSYSYPVT

FGQGTKVEIK

In particular, the specific binding member may not comprise or consist of the heavy chain and light chain sequence of FS20-22-49-AA/FS30-10-16 set forth in SEQ ID NOs 172 and 173, respectively.

The specific binding member may be conjugated to a bioactive molecule or a detectable label. In this case, the specific binding member may be referred to as a conjugate. Such conjugates find application in the treatment of diseases as described herein.

For example, the bioactive molecule may be an immune system modulator, such as a cytokine, preferably a human cytokine. For example, the cytokine may be a cytokine which stimulates T cell activation and/or proliferation. Examples of cytokines for conjugation to the specific binding member include IL-2, IL-10, IL-12, IL-15, IL-21, GM-CSF and IFN-gamma.

Alternatively, the bioactive molecule may be a ligand trap, such as a ligand trap of a cytokine, e.g. of TGF-beta or IL-6.

Suitable detectable labels which may be conjugated to specific binding members are known in the art and include radioisotopes such as iodine-125, iodine-131, yttrium-90, indium-111 and technetium-99; fluorochromes, such as fluorescein, rhodamine, phycoerythrin, Texas Red and cyanine dye derivatives for example, Cy7 and Alexa750; chromogenic dyes, such as diaminobenzidine; latex beads; enzyme labels such as horseradish peroxidase; phosphor or laser dyes with spectrally isolated absorption or emission characteristics; and chemical moieties, such as biotin, which may be detected via binding to a specific cognate detectable moiety, e.g. labelled avidin.

The specific binding member may be conjugated to the bioactive molecule or detectable label by means of any suitable covalent or non-covalent linkage, such as a disulphide or peptide bond. Where the bioactive molecule is a cytokine, the cytokine may be joined to the specific binding member by means of a peptide linker. Suitable peptide linkers are known in the art and may be 5 to 25, 5 to 20, 5 to 15, 10 to 25, 10 to 20, or 10 to 15 amino acids in length.

In some embodiments, the bioactive molecule may be conjugated to the specific binding member by a cleavable linker. The linker may allow release of the bioactive molecule from the specific binding member at a site of therapy. Linkers may include amide bonds (e.g. peptidic linkers), disulphide bonds or hydrazones. Peptide linkers for example may be cleaved by site specific proteases, disulphide bonds may be cleaved by the reducing environment of the cytosol and hydrazones may be cleaved by acid-mediated hydrolysis.

The conjugate may be a fusion protein comprising the specific binding member and the bioactive molecule. In this case the bioactive molecule may be conjugated to the specific binding member by means of a peptide linker or peptide bond. Where the specific binding member is a multichain molecule, such as where the specific binding member is or comprises an Fcab or is a $mAb^2$, the bioactive molecule may be conjugated to one or more chains of the specific binding member. For example, the bioactive molecule may be conjugated to one or both of the heavy chains of the $mAb^2$ molecule. Fusion proteins have the advantage of being easier to produce and purify, facilitating the production of clinical-grade material.

The invention also provides an isolated nucleic acid molecule or molecules encoding a specific binding member of the invention. The skilled person would have no difficulty in preparing such nucleic acid molecules using methods well-known in the art.

In a preferred embodiment, the nucleic acid molecule encodes the CH3 domain of specific binding member: FS20-22-49, FS20-22-41, FS20-22-47, FS20-22-85, or FS20-22-38, preferably FS20-22-49, FS20-22-41, FS20-22-47, or FS20-22-85, more preferably FS20-22-49, FS20-22-41, or FS20-22-47, most preferably FS20-22-49.

In an alternative preferred embodiment, the nucleic acid molecule encodes the CH3 domain of specific binding member: FS20-31-115, FS20-31-108, FS20-31-58, FS20-31-94, FS20-31-102, or FS20-31-66, preferably FS20-31-115, FS20-31-108, FS20-31-58, FS20-31-94, or FS20-31-102, more preferably FS20-31-115, or FS20-31-108, most preferably FS20-31-115.

In a further alternative preferred embodiment, the nucleic acid molecule encodes the CH3 domain of specific binding member: FS20-11-131, FS20-11-127, or FS20-11-134, most preferably FS20-11-131.

The CH3 domain sequences of these specific binding members are described herein.

For example, a nucleic acid molecule which encodes the CH3 domain of specific binding member:

(i) FS20-22-38, FS20-22-41, FS20-22-47, FS20-22-49, or FS20-22-85 is set forth in SEQ ID NO: 47, 56, 64, 73, and 82, respectively;
(ii) FS20-31-58, FS20-31-66, FS20-31-94, FS20-31-102, FS20-31-108, or FS20-31-115 is set forth in SEQ ID NO: 95, 104, 115, 125, 135, and 144, respectively; or
(iii) FS20-11-127, FS20-11-131, or FS20-11-134 is set forth in SEQ ID NO: 16, 25, and 34, respectively.

In a preferred embodiment, the nucleic acid molecule encodes specific binding member: FS20-22-49, FS20-22-41, FS20-22-47, FS20-22-85, or FS20-22-38, preferably FS20-22-49, FS20-22-41, FS20-22-47, or FS20-22-85, more preferably FS20-22-49, FS20-22-41, or FS20-22-47, most preferably FS20-22-49.

In an alternative preferred embodiment, the nucleic acid molecule encodes specific binding member: FS20-31-115, FS20-31-108, FS20-31-58, FS20-31-94, FS20-31-102, or FS20-31-66, preferably FS20-31-115, FS20-31-108, FS20-

31-58, FS20-31-94, or FS20-31-102, more preferably FS20-31-115, or FS20-31-108, most preferably FS20-31-115.

In a further alternative preferred embodiment, the nucleic acid molecule encodes specific binding member: FS20-11-131, FS20-11-127, or FS20-11-134, most preferably FS20-11-131.

For example, a nucleic acid molecule which encodes the sequence of specific binding member:

(i) FS20-22-38, FS20-22-41, FS20-22-47, FS20-22-49, and FS20-22-85 is set forth in SEQ ID NO: 49, 58, 66, 75, and 84, respectively; and (ii) FS20-22-38, FS20-22-41, FS20-22-47, FS20-22-49, and FS20-22-85 is set forth in SEQ ID NO: 51, 60, 68, 77, and 86, respectively.

A nucleic acid molecule which encodes the sequence of specific binding memberof specific binding member:

(i) FS20-31-58, FS20-31-66, FS20-31-94, FS20-31-102, FS20-31-108, and FS20-31-115 is set forth in SEQ ID NO: 97, 106, 117, 127, 137, and 146, respectively; and (ii) FS20-31-58, FS20-31-66, FS20-31-94, FS20-31-102, FS20-31-108, and FS20-31-115 is set forth in SEQ ID NO: 99, 108, 119, 129, 139, and 148, respectively.

A nucleic acid molecule which encodes the sequence of specific binding member:

(i) FS20-11-127, FS20-11-131, or FS20-11-134 is set forth in SEQ ID NO: 18, 27, and 36, respectively; and (ii) FS20-11-127, FS20-11-131, or FS20-11-134 is set forth in SEQ ID NO: 20, 29, and 38, respectively.

An isolated nucleic acid molecule may be used to express a specific binding member of the invention. The nucleic acid will generally be provided in the form of a recombinant vector for expression. Another aspect of the invention thus provides a vector comprising a nucleic acid as described above. Suitable vectors can be chosen or constructed, containing appropriate regulatory sequences, including promoter sequences, terminator fragments, polyadenylation sequences, enhancer sequences, marker genes and other sequences as appropriate.

Preferably, the vector contains appropriate regulatory sequences to drive the expression of the nucleic acid in a host cell. Vectors may be plasmids, viral e.g. phage, or phagemid, as appropriate.

A nucleic acid molecule or vector as described herein may be introduced into a host cell. Techniques for the introduction of nucleic acid or vectors into host cells are well established in the art and any suitable technique may be employed. A range of host cells suitable for the production of recombinant specific binding members are known in the art, and include bacterial, yeast, insect or mammalian host cells. A preferred host cell is a mammalian cell, such as a CHO, NSO, or HEK cell, for example a HEK293 cell. A most preferred host cell is a CHO cell.

Another aspect of the invention provides a method of producing a specific binding member of the invention comprising expressing a nucleic acid encoding the specific binding member in a host cell and optionally isolating and/or purifying the specific binding member thus produced. Methods for culturing host cells are well-known in the art. The method may further comprise isolating and/or purifying the specific binding member. Techniques for the purification of recombinant specific binding members are well-known in the art and include, for example HPLC, FPLC or affinity chromatography, e.g. using Protein A or Protein L. In some embodiments, purification may be performed using an affinity tag on specific binding member. The method may also comprise formulating the specific binding member into a pharmaceutical composition, optionally with a pharmaceutically acceptable excipient or other substance as described below.

As explained above, OX40 is expressed on cells of the immune system, including activated T cells, in particular CD4+ T cells, CD8+ T cells, type 1 T helper (Th1) cells, type 2 T helper (Th2) cells and regulatory T (Treg) cells, and tumour-infiltrating T cells, as well as activated natural killer (NK) cells. OX40 activation has been shown to play a role in enhancing T cell activation, T cell clonal expansion, T cell differentiation and survival, and the generation of memory T cells. In light of the immune response enhancing activity of OX40, OX40 agonist molecules have been investigated in the context of cancer treatment.

The specific binding members as described herein may thus be useful for therapeutic applications, in particular in the treatment of cancer. In addition, the specific binding members are expected to be useful in the treatment of infectious diseases, such as persistent infectious diseases.

A specific binding member as described herein may be used in a method of treatment of the human or animal body. Related aspects of the invention provide;

(i) a specific binding member described herein for use as a medicament, (ii) a specific binding member described herein for use in a method of treatment of a disease or disorder, (iii) the use of a specific binding member described herein in the manufacture of a medicament for use in the treatment of a disease or disorder; and, (iv) a method of treating a disease or disorder in an individual, wherein the method comprises administering to the individual a therapeutically effective amount of a specific binding member as described herein.

The individual may be a patient, preferably a human patient.

Treatment may be any treatment or therapy in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, ameliorating, delaying, abating or arresting one or more symptoms and/or signs of the condition or prolonging survival of an individual or patient beyond that expected in the absence of treatment.

Treatment as a prophylactic measure (i.e. prophylaxis) is also included. For example, an individual susceptible to or at risk of the occurrence or re-occurrence of a disease such as cancer may be treated as described herein. Such treatment may prevent or delay the occurrence or re-occurrence of the disease in the individual.

A method of treatment as described may be comprise administering at least one further treatment to the individual in addition to the specific binding member. The specific binding member described herein may thus be administered to an individual alone or in combination with one or more other treatments. Where the specific binding member is administered to the individual in combination with another treatment, the additional treatment may be administered to the individual concurrently with, sequentially to, or separately from the administration of the specific binding member. Where the additional treatment is administered concurrently with the specific binding member, the specific binding member and additional treatment may be administered to the individual as a combined preparation. For example, the additional therapy may be a known therapy or therapeutic agent for the disease to be treated.

Whilst a specific binding member may be administered alone, specific binding members will usually be administered in the form of a pharmaceutical composition, which may comprise at least one component in addition to the specific binding member. Another aspect of the invention therefore provides a pharmaceutical composition comprising a specific binding member as described herein. A method comprising formulating a specific binding member into a pharmaceutical composition is also provided.

Pharmaceutical compositions may comprise, in addition to the specific binding member, a pharmaceutically acceptable excipient, carrier, buffer, stabilizer or other materials well known to those skilled in the art. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be by infusion, injection or any other suitable route, as discussed below.

For parenteral, for example subcutaneous or intravenous administration, e.g. by injection, the pharmaceutical composition comprising the specific binding member may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

In some embodiments, specific binding members may be provided in a lyophilised form for reconstitution prior to administration. For example, lyophilised specific binding members may be re-constituted in sterile water and mixed with saline prior to administration to an individual.

Administration may be in a "therapeutically effective amount", this being sufficient to show benefit to an individual. The actual amount administered, and rate and time-course of administration, will depend on the nature and severity of what is being treated, the particular individual being treated, the clinical condition of the individual, the cause of the disorder, the site of delivery of the composition, the type of specific binding member, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of immunoglobulins are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for an antibody molecule being administered, may be used. As for antibody molecules, a therapeutically effective amount or suitable dose of a specific binding member can be determined by comparing in vitro activity and in vivo activity in an animal model. Methods for extrapolation of effective dosages in mice and other test animals to humans are known. The precise dose will depend upon a number of factors, including whether the size and location of the area to be treated, and the precise nature of the specific binding member.

A typical immunoglobulin dose is in the range 100 μg to 1 g for systemic applications, and 1 μg to 1 mg for topical applications. An initial higher loading dose, followed by one or more lower doses, may be administered. This is a dose for a single treatment of an adult individual, which may be proportionally adjusted for children and infants, and also adjusted for other specific binding member formats in proportion to molecular weight.

Treatments may be repeated at daily, twice-weekly, weekly or monthly intervals, at the discretion of the physician. The treatment schedule for an individual may be dependent on the pharmocokinetic and pharmacodynamic properties of the specific binding member composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Suitable formulations and routes of administration are described above.

In a preferred embodiment, a specific binding member as described herein may be for use in a method of treating cancer.

Cancer may be characterised by the abnormal proliferation of malignant cancer cells. Where a particular type of cancer, such as breast cancer, is referred to, this refers to an abnormal proliferation of malignant cells of the relevant tissue, such as breast tissue. A secondary cancer which is located in the breast but is the result of abnormal proliferation of malignant cells of another tissue, such as ovarian tissue, is not a breast cancer as referred to herein but an ovarian cancer.

The cancer may be a primary or a secondary cancer. Thus, a specific binding member as described herein may be for use in a method of treating cancer in an individual, wherein the cancer is a primary tumour and/or a tumour metastasis.

A tumour of a cancer to be treated using a specific binding member as described herein may comprise tumour-infiltrating T cells that express OX40, e.g. on their cell surface. In one embodiment, the tumour may have been determined to comprise tumour-infiltrating T cells that express OX40. Methods for determining the expression of an antigen on a cell surface are known in the art and include, for example, flow cytometry.

For example, the cancer to be treated using a specific binding member as described herein may be selected from the group consisting of leukaemias, such as acute myeloid leukaemia (AML), chronic myeloid leukaemia (CML), acute lymphoblastic leukaemia (ALL) and chronic lymphocytic leukaemia (CLL); lymphomas, such as Hodgkin's lymphoma, non-Hodgkin's lymphoma and multiple myeloma; and solid cancers, such as sarcomas (e.g. soft tissue sarcomas), skin cancer (e.g. Merkel cell carcinoma), melanoma, bladder cancer (e.g. urothelial carcinoma), brain cancer (e.g. glioblastoma multiforme), breast cancer, uterus/endometrial cancer, ovarian cancer (e.g. ovarian serous cystadenoma), prostate cancer, lung cancer (e.g. non-small cell lung carcinoma (NSCLC) and small cell lung cancer (SCLC), colorectal cancer (e.g. colorectal adenocarcinoma), cervical cancer (e.g. cervical squamous cell cancer and cervical adenocarcinoma), liver cancer (e.g. hepatocellular carcinoma), head and neck cancer (e.g. head and neck squamous-cell carcinoma), oesophageal cancer, pancreatic cancer, renal cancer (e.g. renal cell cancer), adrenal cancer, stomach cancer, testicular cancer, cancer of the gall bladder and biliary tracts (e.g. cholangiocarcinoma), thyroid cancer, thymus cancer, bone cancer, and cerebral cancer.

In a preferred embodiment, the cancer to be treated using a specific binding member as described herein is a solid cancer. More preferably, the cancer to be treated using a specific binding member as described herein is a solid cancer selected from the group consisting of: sarcoma, melanoma, bladder cancer, brain cancer, breast cancer, uterine/endometrial cancer, ovarian cancer, prostate cancer, lung cancer, colorectal cancer, cervical cancer, liver cancer, head and neck cancer, pancreatic cancer, renal cancer and stomach cancer.

In the context of cancer, treatment may include inhibiting cancer growth, including complete cancer remission, and/or inhibiting cancer metastasis, as well as inhibiting cancer recurrence. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of anti-cancer immune cells or other anti-cancer immune responses, and a decrease in levels of tumour-specific antigens. Activating or enhancing immune responses to cancerous tumours in an individual may improve the capacity of the individual to resist cancer growth, in particular growth of a cancer already present in the subject and/or decrease the propensity for cancer growth in the individual.

In the context of cancer treatment, a specific binding member as described herein may be administered to an individual in combination with another anti-cancer therapy or therapeutic agent, such as an anti-cancer therapy or therapeutic agent which has been shown to be suitable, or is expected to be suitable, for the treatment of the cancer in question. For example, the specific binding member may be administered to the individual in combination with a chemotherapeutic agent, radiotherapy, an immunotherapeutic agent, an anti-tumour vaccine, an oncolytic virus, an adoptive cell transfer (ACT) therapy (such as adoptive NK cell therapy or therapy with chimeric antigen receptor (CAR) T-cells, autologous tumour infiltrating lymphocytes (TILs), or gamma/delta T cells, or an agent for hormone therapy.

Without wishing to be bound by theory, it is thought that the specific binding member described herein may act as an adjuvant in anti-cancer therapy. Specifically, it is thought that administration of the specific binding member to an in individual in combination with chemotherapy and/or radiotherapy, or in combination with an anti-tumour vaccine, for example, will trigger a greater immune response against the cancer than is achieved with chemotherapy and/or radiotherapy, or with an anti-tumour vaccine, alone.

One or more chemotherapeutic agents for administration in combination with a specific binding member as described herein may be selected from the group consisting of: taxanes, cytotoxic antibiotics, tyrosine kinase inhibitors, PARP inhibitors, B-Raf enzyme inhibitors, MEK inhibitors, c-MET inhibitors, VEGFR inhibitors, PDGFR inhibitors, alkylating agents, platinum analogues, nucleoside analogues, antifolates, thalidomide derivatives, antineoplastic chemotherapeutic agents and others. Taxanes include docetaxel, paclitaxel and nab-paclitaxel; cytotoxic antibiotics include actinomycin, bleomycin, and anthracyclines such as doxorubicin, mitoxantrone and valrubicin; tyrosine kinase inhibitors include erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide and temozolomide; platinum analogues include carboplatin, cisplatin and oxaliplatin; nucleoside analogues include azacitidine, capecitabine, fludarabine, fluorouracil and gemcitabine; antifolates include methotrexate and pemetrexed. Other chemotherapeutic agents suitable for use in the present invention include defactinib, entinostat, eribulin, irinotecan and vinblastine.

Preferred therapeutic agents for administration with an antibody molecule as described herein are doxorubicin, mitoxantrone, cyclophosphamide, cisplatin, and oxaliplatin.

A radiotherapy for administration in combination with a specific binding member as described herein may be external beam radiotherapy or brachytherapy.

An immunotherapeutic agent for administration in combination with a specific binding member as described herein may be a therapeutic antibody molecule, nucleic acid cytokine, or cytokine-based therapy. For example, the therapeutic antibody molecule may bind to an immune regulatory molecule, e.g. an inhibitory checkpoint molecule or an immune costimulatory molecule, or a tumour antigen, e.g. a cell surface tumour antigen or a soluble tumour antigen. Examples of immune regulatory molecules to which the therapeutic specific binding member may bind include CTLA-4, LAG-3, TIGIT, TIM-3, VISTA, PD-L1, PD-1, CD47, CD73, CSF-1R, KIR, CD40, HVEM, IL-10 and CSF-1. Examples of receptors of the innate immune system to which the therapeutic antibody molecule may bind include TLR1, TLR2, TLR4, TLR5, TLR7, TLR9, RIG-1-like receptors (e.g. RIG-1 and MDA-5), and STING. Examples of tumour antigens to which the therapeutic antibody molecule may bind include HER2, EGFR, CD20 and TGF-beta.

The nucleic acid for administration in combination with a specific binding member as described herein may be an siRNA.

The cytokines or cytokine-based therapy may be selected from the group consisting of: IL-2, prodrug of conjugated IL-2, GM-CSF, IL-7, IL-12, IL-9, IL-15, IL-18, IL-21, and type I interferon.

Anti-tumour vaccines for the treatment of cancer have both been implemented in the clinic and discussed in detail within scientific literature (such as Rosenberg, 2000). This mainly involves strategies to prompt the immune system to respond to various cellular markers expressed by autologous or allogenic cancer cells by using those cells as a vaccination method, both with or without granulocyte-macrophage colony-stimulating factor (GM-CSF). GM-CSF provokes a strong response in antigen presentation and works particularly well when employed with said strategies.

The chemotherapeutic agent, radiotherapy, immunotherapeutic agent, anti-tumour vaccine, oncolytic virus, ACT therapy, or agent for hormone therapy is preferably a chemotherapeutic agent, radiotherapy, immunotherapeutic agent, anti-tumour vaccine, oncolytic virus, ACT therapy, or agent for hormone therapy for the cancer in question, i.e. a chemotherapeutic agent, radiotherapy, immunotherapeutic agent, anti-tumour vaccine, oncolytic virus, ACT therapy, or agent for hormone therapy which has been shown to be effective in the treatment of the cancer in question. The selection of a suitable chemotherapeutic agent, radiotherapy, immunotherapeutic agent, anti-tumour vaccine, oncolytic virus, ACT therapy, or agent for hormone therapy which has been shown to be effective for the cancer in question is well within the capabilities of the skilled practitioner.

In light of the immune response enhancing activity of OX40, OX40 agonist molecules are expected to find application in the treatment of infectious diseases. Thus, in another preferred embodiment, the specific binding member as described herein may be for use in a method of treating an infectious disease, such as an acute or a persistent infectious disease.

Without wishing to be bound by theory, it is thought that the specific binding members of the invention will enhance the immune response against an acute infectious disease caused by a pathogen by inducing rapid infiltration and activation of innate immune cells, such as neutrophils and monocytes, thereby facilitating the clearance of the pathogen responsible for the acute infectious disease. Therefore, in a further embodiment, the specific binding member as described herein may be for use in a method of treating an acute infectious disease, such as an acute bacterial disease. In a preferred embodiment, the acute infectious disease is an acute bacterial disease caused by a gram positive bacterium, such as a bacterium of the genus *Listeria, Streptococcus pneumoniae*, or *Staphylococcus aureus.*

Infectious diseases are normally cleared by the immune system but some infections persist for long periods of time, such as months or years, and are ineffectively combatted by the immune system. Such infections are also referred to as persistent or chronic infections.

Preferably, the specific binding member as described herein is used to treat a persistent infectious disease, such as a persistent viral, bacterial, fungal or parasitic infection, preferably a persistent viral or bacterial infection.

In a preferred embodiment, the persistent viral infection to be treated using a specific binding member as described herein is a persistent infection of: human immunodeficiency virus (HIV), Epstein-Barr virus, Cytomegalovirus, Hepatitis B virus, Hepatitis C virus, or Varicella Zoster virus.

In a preferred embodiment, the persistent bacterial infection to be treated using a specific binding member as described herein is a persistent infection of: *Staphylococcus aureus, Hemophilus influenza, Mycobacterium tuberculosis, Mycobacterium leprae, Escherichia coli, Salmonella typhi, Helicobacter pylori, Pseudomonas aeruginosa, Treponema pallidum, Enterococcus faecalis*, or *Streptococcus pneumoniae.*

In a preferred embodiment, the persistent fungal infection to be treated using a specific binding member as described herein is a persistent infection of: *Candida* (e.g. *Candida albicans*), *Cryptococcus* (e.g. *Cryptococcus gattii* or *Cryptococcus neoformans*), *Talaromyces* (*Penicillium*) (e.g. *Talaromyces marneffe*), *Microsporum* (e.g. *Microsporum audouinii*), or *Trichophyton tonsurans.*

In a preferred embodiment, the persistent parasitic infection to be treated using a specific binding member as described herein is a persistent infection of: *Plasmodium*, such as *Plasmodium falciparum*, or *Leishmania*, such as *Leishmania donovani.*

In the context of the treatment of a persistent infectious disease, treatment may include eliminating the infection, reducing the pathogenic load of the individual, preventing recurrence of the infection. For example, the treatment may comprise preventing, ameliorating, delaying, abating or arresting one or more symptoms and/or signs of the persistent infection. Alternatively, the treatment may include preventing an infectious disease.

In the context of the treatment of infectious diseases, the specific binding member as described herein may be administered to an individual in combination with another therapeutic agent for the treatment of the infectious disease, such as a therapeutic agent which has been shown to be suitable, or is expected to be suitable, for the treatment of the infectious disease in question. For example, the specific binding member may be administered to the individual in combination with an immunotherapeutic agent. An immunotherapeutic agent for administration in combination with an antibody molecule as described herein may be a therapeutic antibody molecule. For example, the therapeutic antibody molecule may bind to a receptor of the innate immune system. Examples of receptors of the innate immune system to which the therapeutic antibody molecule may bind include TLR1, TLR2, TLR4, TLR5, TLR7, TLR9, RIG-1-like receptors (e.g. RIG-1 and MDA-5), and STING.

Where the specific binding member is used to prevent an infectious disease, the specific binding member may be administered in combination with a vaccine for the pathogen in question. Without wishing to be bound by theory, it is thought that the specific binding member described herein may act as an adjuvant in vaccination. Specifically, it is thought that administration of the specific binding member to an in individual in combination with vaccine, will trigger a greater immune response against the pathogen than is achieved with the vaccine alone.

Further aspects and embodiments of the invention will be apparent to those skilled in the art given the present disclosure including the following experimental exemplification.

All documents mentioned in this specification are incorporated herein by reference in their entirety. "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Other aspects and embodiments of the invention provide the aspects and embodiments described above with the term "comprising" replaced by the term "consisting of" or "consisting essentially of", unless the context dictates otherwise.

Certain aspects and embodiments of the invention will now be illustrated by way of example and with reference to the figures described above.

EXAMPLES

Example 1—Antigen selection and characterisation

OX40 antigens used for the selection of Fcabs specific for human and mouse OX40 and for testing cross-reactivity of selected Fcabs with cynomolgus OX40 were either prepared in-house or obtained from commercial sources as described below.

1.1 Antigens Prepared In-House

Recombinant, soluble, dimeric OX40 antigens, as well as cell lines expressing OX40 were prepared in-house.

1.1.1 Preparation of Recombinant, Soluble Human, Cynomolgus and Mouse OX40 Antigens To prepare recombinant, soluble, dimeric OX40 antigens, the extracellular domain of OX40 was fused to mouse Fc, which improved the solubility and stability of the antigen. Specifically, the extracellular domain of the relevant OX40 (human, cynomolgus or mouse) was cloned into the pFUSE-mlgG2aFc2 vector (Invivogen cat no pfuse-mg2afc2) using EcoRI-HF and Bglll restriction enzymes to produce antigens with a mouse IgG2a Fc domain at the C-terminus. The recombinant OX40 antigens were then produced by transient expression in HEK293-6E cells (National Research Council of Canada) and purified using mAb Select SuRe protein A columns (GE Healthcare, 11003494), followed by size-exclusion chromatography (SEC) to ensure that the resulting antigen was a single species and did not contain aggregates.

To prepare biotinylated versions of the recombinant OX40 antigens, the antigens were biotinylated using EZ-LINK™ SULFO-NHS-SS-BIOTIN biotinylation reagent (Thermo Fisher Scientific, cat no 21331) following the manufacturer's protocol. Biotinylated OX40 antigen was used for the selection experiments described below but not for binding affinity measurements. Purification of the biotinylated OX40 antigens was performed in two steps, using a PD10 desalting column GE Healthcare, 17-0851-01) followed by an Amicon 30k spin column Millipore, UFC903024) according to manufacturer's instructions. Biophysical properties of the recombinant antigens were characterized by SE-HPLC analysis to ensure that no aggregates were present and by PAGE to verify the size of the molecules. Size determination by PAGE indicated that the soluble antigens were dimeric, as their estimated molecular weight was double that of the predicted molecular weight of a monomer. The recombinant antigens were also analysed by gel-shift analysis which showed that the extent of biotinylation was above 90%. ELISA and surface plasmon resonance (SPR) were used to confirm that the biotinylated, recombinant human (hOX40-mFc), mouse (mOX40-mFc) and cynomolgus (cOX40-mFc) OX40 antigens could be bound by OX40-specific antibodies (antibody 11 D4 [European Patent No. 2242771] for human and cynomolgus OX40; polyclonal sheep anti-human OX40 antibody for cynomolgus OX40 [R&D Systems cat no AF3388]; antibody ACT35 for human OX40 [Biolegend cat no 35002] and antibody OX86 for mouse OX40 [Biolegend cat no 119408]). These antigens are listed in Table 2 below.

1.1.2 Preparation of Cell Lines Expressing Human, Cynomolgus and Mouse OX40

Human, cynomolgus and mouse OX40 (see Table 1 for sequences) were cloned into vector pLVX-EF1a-IRES-puro (Clontech, Cat. No 631253) using Spel-HF and Notl-HF restriction enzymes. The vectors were then transformed into the Lenti-X 293T cell line (Clontech, Cat. No 632180) together with a Lenti-X HTX packaging mix (Clontech cat no. 631249) to generate lentivirus. The lentivirus were then used to transduce DO11.10 cells (National Jewish Health). Cells overexpressing OX40 were selected by incubation of the cells with 5 μg/ml puromycin (Life Technologies cat no A11113803) for approximately 2 weeks, followed by cell line cloning by serial dilution. Expression of OX40 by the cell lines was tested by flow cytometry using fluorescently-labelled OX40-specific antibodies (OX86; ACT35; and polyclonal sheep anti-human OX40, as described in Example 1.1.1 and Table 2)). Cell lines expressing human (DO11.10-hOX40), mouse (DO11.10-mOX40) or cynomolgus (DO11.10-cOX40) OX40, in which all cells showed at least 10-fold higher fluorescence values than non-transduced cells in the flow cytometry analysis, were selected.

These cell lines are listed in Table 2 below.

TABLE 1

| OX40 sequences | | | | | |
|---|---|---|---|---|---|
| Gene of interest | Species | Source | Clone ID (catalogue no) | Genbank accession number | SEQ ID NO |
| OX40 | Human | Thermo Fisher Scientific | MHS6278-202858046 | BC105070 | 164 |
| OX40 | Cynomolgus | Gene synthesis | N/A | XP_005545179 | 166 |
| OX40 | Mouse | Gene synthesis | N/A | NM_011659.2 | 165 |

1.2 Commercially Available OX40 Antigens

Several commercially available OX40 antigens were tested.

Recombinant His-tagged human OX40 extracellular domain was obtained from SinoBiologicals (Cat #10481-H08H-50). However, SE-HPLC analysis of this antigen showed that less than 50% of the antigen was in a monomeric, non-aggregated form. This antigen was therefore not used in subsequent analysis.

Recombinant human OX40/human Fc (hOX40-hFc) and recombinant mouse OX40/human Fc (mOX40-hFc), which comprised the human IgG1 Fc domain at the C-terminus, were obtained from R&D Systems (hOX40-hFc: Cat #3388-OX-050; mOX40-hFc: Cat #1256-OX-050) and biotinylated in-house. The biophysical properties of these soluble antigens were characterised by SE-HPLC analysis to ensure that no aggregates were present and by PAGE to verify the size of the molecules. Size determination by PAGE indicated that the soluble antigens were dimeric, as their estimated molecular weight was twice that expected for the monomeric antigen. The soluble antigens were also analysed by gel-shift analysis which showed that the extent of biotinylation was above 90%. ELISA and SPR were used to confirm that the biotinylated, recombinant human (hOX40-hFc) and mouse (mOX40-hFc) OX40 antigens could be bound by OX40-specific antibodies (11 D4; ACT35; and OX86 as described in Example 1.1.1 and Table 2 below.

TABLE 2

| OX40 antigens | | | | | | |
|---|---|---|---|---|---|---|
| Antigen name | Source (commercial/ prepared in-house) | Biotinylated version prepared? | Species | Soluble/ cell-expressed antigen | Antigen format | SEQ ID NO/ Source of antigen |
| hOX40-mFc | in-house | yes | human | soluble | dimeric | 158 |
| mOX40-mFc | in-house | yes | mouse | soluble | dimeric | 159 |
| cOX40-mFc | in-house | yes | cynomolgus | soluble | dimeric | 160 |
| DO11.10-hOX40 | in-house | no | human | cell-expressed | natural conformation | 164 |
| DO11.10-mOX40- | in-house | no | mouse | cell-expressed | natural conformation | 165 |
| DO11.10-cOX40 | in-house | no | cynomolgus | cell-expressed | natural conformation | 166 |
| hOX40-hFc | commercial | yes | human | soluble | dimeric | Cat no 3388-OX-050 (R&D Systems) |
| mOX40-hFc | commercial | yes | mouse | soluble | dimeric | Cat no 1256-OX-050 (R&D Systems) |

Example 2—Selection and Characterisation of Anti-Human OX40 Fcabs 2.1 Naive Selection of Anti-Human OX40 Fcabs In order to select Fcabs specific for human OX40 from naive phage libraries both recombinant biotinylated soluble, dimeric human OX40 (hOX40-mFc; see Table 2) and cell-expressed human OX40 (DO11.10-hOX40) were used as antigens. Cells expressing human OX40 were used in addition to recombinant biotinylated soluble, dimeric human OX40 in some of the selection protocols to ensure that the selected Fcabs were capable of binding to OX40 in its natural conformation on the cell surface.

Six naive phage libraries displaying the CH3 domain (IMGT numbering 1.4-130) comprising partially randomised AB loops (residues 14 to 18 according to the IMGT numbering scheme) and EF loops (residues 92 to 101 according to the IMGT numbering scheme) in the CH3 domain. One of the six libraries additionally comprised clones with an insertion of either two or four amino acids (encoded by two or four NNK codons) at position 101 in the EF loop of the CH3 domain (inserted residues are numbered 101.1 to 101.4 according to the IMGT numbering scheme).

All six libraries were subjected to three rounds of selection using recombinant biotinylated soluble, dimeric human OX40 (hOX40-mFc; see Table 2). Specifically, the libraries were subjected to three rounds using (in rounds 1 and 3) hOX40-mFc captured on streptavidin-coated (Thermo Fisher Scientific, 11206D) or (in round 2) neutravidin-coated (Thermo Fisher Scientific, 14203 and A2666) Dynabeads.

All six libraries were also subjected to a further selection campaign using hOX40-mFc in a first round of selection followed by cell-expressed human OX40 (DO11.10-hOX40 in two further selection rounds; see Table 2).

Two of the libraries were subjected to three rounds of selection using DO11.10-hOX40 antigen-expressing cells.

2133 clones identified following the third round of selection from the six libraries were screened by ELISA for binding to human OX40. This resulted in 32 unique positive binders being identified, which were sub-cloned and expressed as soluble Fcabs (consisting of a truncated hinge [SEQ ID NO: 171], CH2 and CH3 domain) in HEK Expi293 cells (Fcabs cloned into pTT5 vector [National Research Council of Canada]transfected using ExpiFectamine 293 Transfection kit [Life Technologies, A14524] into Expi293F cells [Life technologies, A14527]).

The 32 unique Fcabs were tested for their ability to bind cell-expressed human OX40 (DO11.10-hOX40). 15 of the 32 Fcabs screened showed cell binding to DO11.10-hOX40 and the $EC_{50}$ for these interactions ranged from 0.1 to 62 nM. The 15 Fcabs that showed binding to DO11.10-hOX40 were tested in a human NF-κB reporter assay (described in Example 4.4 below). Six of the 15 Fcabs showed an increase in activity when crosslinked with an anti-human Fc antibody in the human NF-κB reporter assay. The three Fcabs, FS20-11, FS20-22 and FS20-31, which showed the highest levels of activity in this assay, and whose activity increased when the Fcab was crosslinked with an anti-human CH2 mAb (clone MK1A6 (Jefferis et al., 1985 and Jefferis et al., 1992), produced in-house), were selected for affinity maturation.

2.2 Affinity Maturation of Anti-Human OX40 Fcabs

Nine phage displayed affinity maturation libraries, three for each Fcab, were constructed based on the three Fcabs selected in Example 2.1 (FS20-11, FS20-22 and FS20-31) by randomizing five residues in the AB loop (residues 14 to 18) or five residues in the CD loop (residues 45.1 to 77) of the CH3 domain using randomized primers from ELLA Biotech using an equimolar distribution of amino acids excluding cysteines, or by randomizing portions of the EF loop (residues 92 to 94 and 97 to 101 in the case of FS20-22 and FS20-31, and residues 97 to 100 and 101.1 to 101.4 [see Example 2.1 above] in the case of FS20-11) of the CH3 domain (all residue numbering according to the IMGT numbering scheme). Affinity maturation of a fourth Fcab clone, FS20-10, was also attempted but resulted in progeny with inferior binding properties and functional activity compared to the other three Fcab lineages and so this lineage was not progressed further.

Three selection rounds were performed on the affinity maturation libraries using recombinant human biotinylated hOX40-mFc alternatingly captured on (in rounds 1 and 3) streptavidin-coated (Thermo Fisher Scientific, 11206D) and (in round 2) neutravidin-coated (Thermo Fisher Scientific, 14203 and A2666) Dynabeads. Decreasing antigen concentrations from 50 nM (round 1), to 10 nM (round 2), to 1 nM (round 3) (for the FS20-11 and FS20-22 lineages), or from 100 nM (round 1), to 50 nM (round 2), to 10 nM or 1 nM (round 3) (for the FS20-31 lineage) were used to identify high affinity binders. A fourth round of selection using a 1 nM concentration of the same antigen and streptavidin-coated Dynabeads was performed on two of the round three outputs only, namely those from the FS20-11 library with residues 14 to 18 randomised in the AB loop and the FS20-22 library with residues 45.1 to 77 randomised in the CD loop. 1410 Fcabs from the outputs of the third and fourth rounds of selection were screened by ELISA for binding to human OX40 and 204 unique positive binders were identified, sub-cloned and expressed as soluble Fcabs in HEK Expi293 cells as described in Example 2.1 above.

The off-rates of the soluble Fcabs when bound to hOX40-mFc were measured using a Biacore 3000 (GE Healthcare) in the absence and presence of anti-CH2 crosslinking using anti-human CH2 mAb clone MK1A6 (see Example 2.1). Fcabs with improved off-rates as compared to the relevant parental Fcab were further screened for binding to cell-expressed human OX40 and for activity in a human T cell activation assay (see Example 5.1 below). All of the Fcabs bound cell-expressed human OX40. The 20 Fcabs from the FS20-11 lineage, 10 Fcabs from the FS20-22 lineage and 18 Fcabs from the FS20-31 lineage with the highest activity in the human T cell activation assay were selected for loop shuffling as described below.

For the FS20-11 lineage, two loop-shuffled libraries were generated, one by shuffling nine AB loops with ten EF loops and the WT CD loop, and with the other by shuffling the AB and EF loops with an affinity matured CD loop. For the FS20-22 lineage, two loop-shuffled libraries were generated by shuffling three CD loops, six EF loops and either the parental AB loop or an affinity matured AB loop. For the FS20-31 lineage, one loop-shuffled library was generated containing four AB loops, seven CD loops and seven EF loops.

Shuffled sequences were expressed as soluble Fcabs in HEK Expi293 cells as described in Example 2.1 above and screened for binding to biotinylated hOX40-mFc antigen using Dip and Read™ Streptavidin Biosensors (Pall ForteBio, 18-5050) on an Octet QK$^e$ System (Pall ForteBio). Fcabs with an improved off-rate when bound to hOX40-mFc as compared to the parental Fcab were sequenced, resulting in 66 unique Fcab sequences from the FS20-11 lineage, 35 from the FS20-22 lineage and 62 from the FS20-31 lineage. The unique Fcabs identified were tested for binding to hOX40-mFc antigen in the presence and absence of CH2 crosslinking using anti-human CH2 mAb clone MK1A6 using a Biacore 3000 instrument (GE Healthcare).

For the FS20-11 lineage, the 18 Fcabs with the strongest binding to hOX40-mFc (as determined by giving the highest response on the Biacore instrument for a fixed concentration) were selected for expression in mock (4420 LALA) mAb$^2$ format and further characterisation as described below. For the FS20-22 lineage, 18 Fcabs were chosen for expression in mock (4420 LALA) mAb$^2$ format and further characterisation on the basis of the slowest off-rate with CH2 crosslinking when bound to hOX40-mFc, the greatest difference in the off-rate between non-crosslinked and CH2 crosslinked off-rates when bound to hOX40-mFc and the strength of binding to hOX40-mFc as above. For the FS20-31 lineage, the nine Fcabs with the slowest off-rate when bound to hOX40-mFc with CH2 crosslinking and the nine Fcabs with the slowest off-rate when bound to hOX40-mFc without CH2 crosslinking were chosen for expression and further characterisation in mock (4420 LALA) mAb$^2$ format. As a number of Fcabs were common to both these groups of nine Fcabs, additional Fcabs which showed slow off-rates when bound to hOX40-mFc in the absence of CH2 cross-linking were chosen from the FS20-31 lineage to bring the total number of Fcabs from this lineage for expression and further characterisation in mock mAb$^2$ format to 18. Using the data from the T cell activation assay, a further six Fcabs from the FS20-22 lineage and eight Fcabs from the FS20-31 lineage were identified which showed high activity in this assay and which were therefore also expressed in mock (4420 LALA) mAb$^2$ format and further characterised.

Example 3—Selection and Characterisation of Anti-Mouse OX40 Fcabs

3.1. Naive Selection of Anti-Mouse OX40 Fcabs

A naive yeast library displaying CH1 to CH3 domains of human IgG1, which contained randomisations in the AB loop (residues 11-18 according to the IMGT numbering scheme) and the EF loop (residues 92-101 according to the IMGT numbering scheme) of the CH3 domain and included a five-residue randomised insertion between residues 16 and 17 (according to the IMGT numbering scheme) of the AB loop, was used for selections. The yeast were incubated with biotinylated recombinant murine OX40 fused to a human IgG Fc domain (mOX40-hFc; Table 2) and sorted by MACS using streptavidin coated beads. Three rounds of FACS selections were then performed using decreasing concentrations of biotinylated mOX40-hFc in the presence of a five-fold molar excess of hFc. The cells were stained with streptavidin-allophycocyanin (APC) (BD Bioscience, 349024) or anti-Biotin-APC (Miltenyi Biotec, 130-090-856) and sorted using a FACSAria (BD Bioscience) cell sorter. 182 individual Fcabs from enriched populations were screened for antigen binding and two unique positive binders were subcloned and expressed as soluble Fcabs as previously described in Example 2.1. Fcabs were characterised for binding to mOX40-hFc by ELISA and for activity in the mouse NF-κB reporter assay 1 (see Example 4.5 below). Only one Fcab, FS20m-232, was active in the NF-κB reporter assay 1 and showed binding to cells expressing mouse OX40 so this Fcab was selected for affinity maturation.

3.2 Affinity Maturation of mOX40 Fcab

Three phage display affinity maturation libraries were constructed by randomising seven residues in the AB loop (residues 15-16.5 according to the IMGT numbering scheme) (Library 1), six residues in the CD loop (residues 45.1-78 according to the IMGT numbering scheme) (Library 2) or five residues in the EF loop (residues 92-94 and 97-98 according to the IMGT numbering scheme) (Library 3) of the FS20m-232 Fcab using randomized primers from ELLA Biotech using an equimolar distribution of amino acids excluding cysteine.

Three selection rounds were performed on the affinity maturation libraries using recombinant biotinylated mOX40-mFc alternatingly captured on streptavidin-coated (ThermoFisher Scientific, 11205D) and neutravidin-coated (ThermoFisher Scientific, 14203 and A2666) Dynabeads. Decreasing antigen concentrations from 50 nM (Round 1) to 10 nM (Round 2), to 1 nM (Round 3) were used to identify high affinity binders. 1655 individual phage from the third selection round were screened by phage ELISA for binding to mOX40-mFc and 98 unique positive binders were identified, subcloned and expressed as soluble Fcabs in HEK Expi293 cells as described in Example 2.1. The Fcabs were further screened for cell binding and activity in the mouse NF-κB reporter assay 2 (see Example 4.6 below for details). The most active Fcabs were selected for loop shuffling.

A loop-shuffled library was generated containing 27 CD loops (all 26 unique sequences identified from the affinity maturation and the WT sequence) shuffled with 37 EF loops (those with the best binding to mouse OX40 in phage ELISA and WT sequence), with all shuffled clones containing the AB loop of the FS20m-232 Fcab. 750 shuffled sequences were expressed as soluble Fcabs (containing a truncated hinge) in HEK Expi293 cells as described above. HEK supernatants containing the Fcabs were screened for improved off-rates by measuring binding of the Fcabs to biotinylated mOX40-mFc (Table 2) using Dip and Read™ Streptavidin Biosensors (Pall ForteBio, 18-5050) on an Octet QK° System (Pall ForteBio). The 11 unique AB loop randomized Fcabs and 60 unique EF loop randomized Fcabs were subcloned and expressed as soluble Fcabs in HEK Expi293 cells as described above. These Fcabs were further screened alongside the 43 shuffled Fcabs with the slowest off-rates for cell binding and activity in the mouse T cell activation assay (see Example 5.2 below). The FS20m-232-91 Fcab had the slowest off-rate when bound to biotinylated mOX40-mFc and the highest activity in the mouse T cell activation assay when crosslinked by anti-human CH2 mAb clone MK1A6 and was therefore selected as the mouse (surrogate) Fcab for use in subsequent experiments.

Example 4—Construction, Expression and Characterization of Mock mAb$^2$

4.1 Construction and Expression of Mock mAb$^2$

"Mock" mAb$^2$ comprising the anti-human OX40 and anti-mouse OX40 Fcabs identified above were prepared in order to allow the characterization of these Fcabs in mAb$^2$ format. These mock mAb$^2$ were prepared from the anti-OX40 Fcabs and the variable regions of anti-FITC antibody 4420 (Bedzyk et al., 1989 and Bedzyk et al., 1990) in a human IgG1 backbone (see SEQ ID NO: 167, SEQ ID NO: 168, and SEQ ID NO: 156 for details) or the variable regions of anti-hen egg white lysozyme (HEL) antibody D1.3 (Braden et al., 1996) in a human IgG1 backbone (see SEQ ID NO: 169 and 157 for details) by replacing the CH3 domains of the anti-FITC and anti-HEL antibodies with the CH3 domains of the anti-OX40 Fcabs within XhoI and BamHI sites present in the sequence of the unmodified CH3 domain of human IgG1.

The mock mAb$^2$ comprised the light chain of the anti-FITC mAb 4420 (SEQ ID NO: 156) or of the anti-HEL mAb D1.3 (SEQ ID NO: 157), respectively, and also contained the LALA mutation (Hezareh et al., 2001 and Bruhns et al., 2009) in the CH2 domain of the heavy chain to reduce Fc-gamma receptor interaction and potential Fc-gamma receptor-induced crosslinking. The presence of the LALA mutation in mock mAb$^2$ and mAb$^2$ referred to in these examples is denoted by the suffix 'AA' at the end of the Fcab part of their clone names.

The mock mAb$^2$ were produced by transient expression in HEK293-6E cells and purified using mAb Select SuRe protein A columns.

4.2 Binding Affinity of Anti-Human OX40 Fcabs in Mock mAb$^2$ Format to Cell-Expressed Human and Cynomolgus OX40

The affinity of the anti-human OX40 Fcabs in mock (4420 LALA) mAb$^2$ format to cell-expressed human or cynomolgus OX40 (DO11.10 cells expressing either human [DO11.10-hOX40] or cynomolgus OX40 [DO11.10-cOX40]; see Table 2) was measured using flow cytometry. Non-specific binding was also assessed by testing for binding to HEK cells not expressing OX40 by flow cytometry.

Mock (4420 LALA) mAb$^2$ and control mAb dilutions (2× final concentration) were prepared in triplicate in 1× DPBS (Gibco, 14190-094). DO11.10-hOX40 or DO11.10-cOX40 or HEK cell suspensions were prepared in PBS+2% BSA (Sigma, A7906) and seeded at $4\times10^6$ cell/ml with 50 μl/well in V-bottomed 96-well plates (Costar, 3897). 50p1 of the mock (4420 LALA) mAb$^2$ or control mAb (anti-human OX40 mAb, 11 D4) dilutions were added to the wells containing cells (final volume 100 μl) and incubated at 4° C. for 1 hour. The plates were washed and 100 μl/well of secondary antibody (anti-human Fc-488 antibody, Jackson ImmunoResearch, 109-546-098) diluted 1:1000 in PBS plus 2% BSA was then added and incubated for 30 mins at 4° C. in the dark. The plates were washed and resuspended in 100 μl of PBS containing DAPI (Biotium, cat no 40043) at 1 μg/ml. The plates were read using a Canto II flow cytometer (BD Bioscience). Dead cells were excluded and the fluorescence in the FITC channel (488 nm/530/30) was measured. The data was fit using log (agonist) vs response in GraphPad Prism Software.

The Fcabs (all tested in mock [4420 LALA] mAb$^2$ format) and the positive-control anti-human OX40 mAb, 11 D4, in a human IgG1 backbone and containing the LALA mutation in the CH2 domain of the heavy chain, bound to human OX40 with a range of affinities. Of the clones selected for further characterisation in mock mAb$^2$ format described in Example 2.2, 14 Fcabs (three from the FS20-11 lineage, five from the FS20-22 lineage, and six from the FS20-31 lineage) showed significantly higher affinities for human OX40 as compared to the other Fcabs. The binding affinities of these 14 Fcab clones for cell-expressed human and cynomolgus OX40 are set out in Table 3.

Fcabs from the FS20-22 and FS20-31 lineages bound cynomolgus OX40 with comparable affinity to human OX40. This is potentially advantageous, as subject to showing suitable activation of cynomolgus OX40 in vitro, these Fcabs may be able to be used in toxicology studies in cynomolgus monkeys, the results of which can be predictive of toxicology effects in humans. Fcabs from the FS20-11 lineage also bound to cynomolgus OX40 but with lower affinity, making them less suitable for testing in cynomolgus monkeys. The Fcabs tested and positive-control mAb did not show any non-specific binding to HEK cells.

TABLE 3

Binding affinity of anti-OX40 Fcabs in mock (4420 LALA) mAb$^2$ format to cell-expressed human or cynomolgus OX40

| mock (4420 LALA) mAb$^2$/mAb | Binding to DO11.10-hOX40 $EC_{50}$ (nM) | Binding to DO11.10-cOX40 $EC_{50}$ (nM) |
|---|---|---|
| FS20-11-127AA/4420 | 3.927 | 292.3 |
| FS20-11-131AA/4420 | 4.014 | 284 |
| FS20-11-134AA/4420 | 3.425 | 265.8 |
| FS20-22-38AA/4420 | 0.8315 | 0.5925 |
| FS20-22-41AA/4420 | 0.2991 | 0.1821 |
| FS20-22-47AA/4420 | 0.7655 | 0.5809 |
| FS20-22-49AA/4420 | 0.7412 | 0.3197 |
| FS20-22-85AA/4420 | 0.4486 | 1.058 |
| FS20-31-58AA/4420 | 0.7466 | 1.454 |
| FS20-31-66AA/4420 | 0.2677 | 2.038 |
| FS20-31-94AA/4420 | 0.6132 | 3.52 |
| FS20-31-102AA/4420 | 0.5366 | 0.3948 |
| FS20-31-108AA/4420 | 0.6516 | 0.3716 |
| FS20-31-115AA/4420 | 0.7853 | 1.235 |
| G1AA/11D4 | 0.8143 | 0.2126 |

4.3 Binding Affinity of the Anti-Mouse OX40 Fcab in Mock mAb$^2$ Format to Cell-Expressed Mouse OX40

The affinity of the anti-mouse OX40 Fcab in mock mAb$^2$ format (4420 LALA) to cell-expressed mouse OX40 (DO11.10-mOX40; see Table 2) was measured using flow cytometry. Non-specific binding was also assessed by testing for binding to HEK cells not expressing OX40 by flow cytometry.

Mock (4420 LALA) $mAb^2$ and control mAb dilutions (2× final concentration) were prepared in 1× DPBS (Gibco, 14190-094). DO11.10 mOX40 or HEK cell suspensions were prepared in PBS+2% BSA (Sigma, A7906) and seeded at $4\times10^6$ cell/ml with 50 μl/well in V-bottomed 96-well plates (Costar, 3897). 50 μl of the mock (4420 LALA) $mAb^2$ or control mAb (anti-mouse OX40 mAb, OX86 dilutions were added to the wells containing cells (final volume 100 μl) and incubated at 4° C. for 1 hour. The plates were washed and 100p1/well of secondary antibody (anti-human Fc-488 antibody, Jackson ImmunoResearch, 109-546-098) diluted 1:1000 in PBS+2% BSA was then added and incubated for 30 mins at 4° C. in the dark. The plates were washed and resuspended in 100 μl of PBS containing DAPI (Biotium, 40043) at 1 μg/ml. The plates were read using Canto II flow cytometer (BD Bioscience). Dead cells were excluded and the fluorescence in the FITC channel (488 nm/530/30) was measured. The data was fit using log (agonist) vs response in GraphPad Prism Software.

The Fcab tested in mock (4420 LALA) $mAb^2$ format and the positive-control anti-mouse OX40 mAb, OX86, in a human IgG1 backbone with the LALA mutation (SEQ ID NOs 175 and 176), bound specifically to mouse OX40 with the affinities set out in Table 4. The affinity of the anti-mouse OX40 Fcab to cell-expressed mouse OX40 was comparable to that of the anti-mouse OX40 positive-control mAb. The tested Fcab and the positive-control mAb did not show any non-specific binding to HEK cells.

TABLE 4

Binding affinity of the anti-mouse OX40 Fcab in mock (4420 LALA) $mAb^2$ format to cell-expressed mouse OX40

| mock (4420 LALA) $mAb^2$/mAb | Binding to DO11.10-mOX40 $EC_{50}$ (nM) |
|---|---|
| mFS20-232-91AA/4420 | 1.006 |
| G1AA/OX86 | 3.099 |

4.4 Human NF-κB Reporter Assay

An assay was needed to test Fcabs isolated during naive selections simply and quickly for OX40 agonist activity so that a rapid decision could be made on which Fcabs to continue to pursue. The development of such an assay was technically challenging as described below.

Binding of OX40 to its ligand results in OX40 clustering and activation of the NF-κB signalling pathway (Arch and Thompson, 1998). Anti-OX40 Fcabs with agonist activity mimic the OX40 ligand by inducing OX40 clustering and signalling. An assay which can detect activation of the NF-κB signalling pathway after OX40 clustering was therefore devised to test the activity of the anti-OX40 Fcabs.

The Flp-In T-REx 293 HEK cell line (Life Technologies, R780-07) was transduced with the Qiagen Cignal Lenti NFkB Reporter (luc) (Qiagen cat no 336851) lentivirus which contains a NF-κB-sensitive promoter controlling the expression of luciferase. These cells were then selected by culturing of the cells in the presence of 5 μg/ml puromycin (Life technologies cat no A11113803) for approximately 2 weeks, followed by cell line cloning through serial dilution. The presence of the luciferase reporter construct was tested by incubating the cells with 10 ng/ml TNFa (R&D Systems cat no 210-TA-005) for 24 hours in culture and measuring the luminescence 15 minutes after treatment with the Promega Bio-Glo luciferase assay system (Promega cat no G7941) according to manufacturer's instructions. Luminescence was measured (0.5 seconds integration time) in a plate reader with the Gen5 Software, BioTek.

Human OX40 was subcloned into vector pcDNA5FRT (Life Technologies cat no V6010-20) using EcoRI-HF and Notl-HF restriction enzymes. The vector was then transformed into the Flp-In T-REx 293 HEK cell line (Life Technologies, R780-07) using Lipofectamine 2000 (Life Technologies, 11668-019). Transformed Flp-In T-REx 293 cells (referred to as the HEK.FRT.luc cell line) were grown in DMEM (Life Technologies, 61965-026) containing 10% FBS (Life Technologies, 10270-1-6), 100 μg/ml Hygromycin B (Melford Laboratories Ltd, Z2475), 15 μg/ml Blasticidin (Melford Laboratories Ltd, B1105) for 3-4 weeks until colonies of stably transformed cells were apparent. These colonies were amplified in the presence of 1 μg/ml Doxycyclin (Sigma, D9891) and tested for human OX40 expression by flow cytometry using anti-OX40 mAb ACT35 (Thermo Fisher Scientific, cat no 17-1347-42).

Expression of human OX40 in the newly created HEK.FRT.luc cell line unexpectedly resulted in constitutive activation of the NF-κB signalling pathway and high levels of expression of luciferase. Therefore, it was not possible to detect differential activation of this signalling pathway by OX40 agonist antibodies. In order to reduce the constitutive activation of the NF-κB signalling pathway, reduction of the expression levels of OX40 was attempted by substituting the high expression CMV promoter with other promoters (from the Invivogen PromTest plasmids). However, contrary to expectations, OX40 expression levels were not altered with this strategy and the NF-κB signalling pathway remained constitutively active.

Another attempt to reduce the constitutive activation of the NF-κB signalling pathway was made by fusing the human OX40 extracellular domain with the intracellular domain of one of the other TNFR-family members (CD40, GITR, TNFRII, CD27, CD30, CD137, and HVEM) (Song et al., 2014) and expressing the resulting chimeric proteins in the HEK.FRT.luc cell line as detailed above. OX40 surface expression was determined by flow cytometry using OX40-specific antibodies. Surprisingly, the chimeric hOX40-hCD137 receptor expressing HEK.FRT.luc cells showed reduced background activation of the NF-κB signaling pathway and a concentration-dependent response to OX40 agonist antibodies. None of the other chimeric receptors tested resulted in decreased constitutive activation of the NF-κB signalling pathway. Only the hOX40-hCD137 chimera expressing cell line (HEK.FRT.luc.hOX40hCD137) could therefore be used to test and rank the anti-human OX40 Fcabs identified following naive selection in terms of their agonistic activity and was used to this effect.

Anti-OX40 Fcabs were expressed as soluble proteins as described in Example 2.1 and tested for OX40 agonist activity as follows. HEK.FRT.luc.hOX40hCD137 cells were plated overnight at a concentration of $1\times10^1$ cells/well in a 96-well white clear flat-bottomed plate at 37° C., 5% $CO_2$. The following day a 2 μM dilution of each Fcab or control mAb (11 D4 in human IgG1 format) to be tested was prepared in DPBS (Gibco) and further diluted 1:10 in reporter cell medium (DMEM (Gibco cat no 61965-026); 10% FCS (Gibco cat no 10270-106); 1× PennStrep (Gibco cat no 15140-122); Hygromycin B 100 μg/ml (Melford Laboratories Ltd. Z2475); Blasticidin 15 μg/ml (Melford Laboratories Ltd. B1105); Puromycin 5 μg/ml (Life technologies cat no A11113803); and Doxyciclin 1 μg/ml (Sigma cat no D9891)) (30 μl+270 μl) to obtain a 200 nM dilution.

The crosslinking agent (anti-human CH2 mAb clone MK1A6) was added to the wells in a 1:1 molar ratio with the test Fcab or control mAb where required. In a 96 well plate, serial dilutions of the Fcab or control mAb in the presence or absence of crosslinking agent were prepared and 100 μl of the dilutions were added to the cells on the plate.

Cells were incubated at 37° C., 5% $CO_2$ for 24 hours and luminescence was measured 15 minutes after treatment with the Promega Bio-Glo luciferase assay system (Promega cat no G7941) according to manufacturer's instructions. Luminescence was measured (0.5 seconds integration time) in a plate reader with the Gen5 Software, BioTek as a measure of the luciferase produced in response to activation of the NF-κB signalling pathway through clustering of human OX40 induced by binding of crosslinked agonistic Fcabs or positive control mAbs to OX40. The luminescence values were plotted vs the log concentration of Fcab/mAb and the resulting curves were fitted using the log (agonist) vs response equation in GraphPad Prism.

4.5 Mouse NF-κB reporter assay 1

To allow the anti-mouse OX40 Fcabs isolated to also be tested quickly and simply for OX40 agonist activity, a mouse NF-κB reporter assay was developed.

A similar approach was initially followed as described in Example 4.4 for generation of a human NF-κB reporter assay, using the mouse OX40 sequence. However, similar issues were encountered resulting in constitutive activation of the NF-κB signalling pathway.

To reduce the constitutive activation of the NF-κB signalling pathway the mouse OX40 extracellular domain was fused with the intracellular domain of the human CD40 receptor (Song et al., 2014) and expressed in the HEK.FRT-.luc cell line as detailed above. OX40 surface expression determination by flow cytometry using OX40-specific antibodies was used to test the presence of the chimeric receptor. The chimeric mOX40-hCD40 receptor expressing HEK-.FRT.luc cells (HEK.FRT.luc.mOX40hCD40 cells) showed reduced background activation of the NF-κB signaling pathway as compared to the cells expressing the full-length mouse OX40 and showed a concentration-dependent response to OX40 agonistic antibodies. This cell line was therefore selected for testing the OX40 agonist activity of the anti-mouse OX40 Fcabs identified following naive selection. The assay protocol was essentially as described in Example 4.4 but testing the mouse OX40 binding Fcabs with these HEK.FRT.luc.mOX40hCD40 cells and using OX86 in human IgG1 format as a positive control.

4.6 Mouse NF-κB Reporter Assay 2

In order to develop an improved mouse OX40 NF-κB reporter assay the strategy used for the human OX40 NF-κB reporter assay was employed. The mouse OX40 extracellular domain was fused to the intracellular domain of the human CD137 receptor and expressed in the HEK.FRT.luc cell line as described in Example 4.4. OX40 surface expression was determined by flow cytometry using OX40-specific antibodies to detect the presence of the chimeric receptor. The chimeric mOX40-hCD137 receptor expressing HEK-.FRT.luc cells (HEK.FRT.luc.mOX40hCD137 cells) showed reduced background activation of the NF-κB signaling pathway compared with the background activation observed in the mouse NF-κB reporter assay 1 and showed a concentration dependent response to anti-mouse OX40 agonistic antibodies. This cell line therefore allowed improved testing and ranking of anti-mouse OX40 Fcabs and was used to test and rank the anti-mouse OX40 Fcabs identified following affinity maturation for their mouse OX40 agonist activity. The assay protocol using these cells was essentially as described in Example 4.5.

4.7 Binding Affinity of Anti-Human OX40 Fcabs for Human and Cynomolgus OX40

The affinity of the anti-human OX40 Fcabs (in OX40/EGFR $mAb^2$ format) for human and cynomolgus OX40 was measured by SPR. As the orientation of mAb or $mAb^2$ molecules can influence the binding kinetics when antigen is passed over the flow cells, it was sought to mitigate this by positioning the Fcab part of the $mAb^2$ away from the binding surface of the Biacore chip when measuring the affinity of an Fcab, and by positioning the Fab part of the $mAb^2$ away from the binding surface of the Biacore chip when measuring the affinity of a Fab. To achieve this, a target capture method was used to orientate the $mAb^2$ molecules as required. EGFR was used as the antigen to capture the OX40/EGFR $mAb^2$ (see Table 5), which were constructed using the anti-human OX40 Fcabs and the variable regions of the anti-EGFR antibody cetuximab (U.S. Pat. No. 6,217,866; indicated by 'Cx' in Table 5) in the same way as the mock $mAb^2$ described in Example 4.1. In order to compare the affinity of the anti-OX40 Fcabs to that of an anti-OX40 mAb, an EGFR-binding Fcab (Patent Publication No. WO 2018/015448 A1) was paired with the Fab of the anti-OX40 mAb 11 D4 (EP 2 242 771 B1) and EGFR was used as the antigen to capture the resulting EGFR/OX40 $mAb^2$. This allowed both the Fcabs and the positive-control mAb to be oriented away from the Biacore chip surface and towards the OX40 antigens that were flowed over the Biacore chip.

EGFR (R&D Systems cat no 344-ER) was immobilized on a Series S CM5 chip (GE Healthcare, BR-1005-30) by amine coupling (GE Healthcare, BR-1000-50) to a surface density of 5000 RU by following the manufacturer's instructions for the BIAcore T200 instrument. The $mAb^2$ samples were captured to approximately 150 RU by injecting a 1 μg/ml solution of $mAb^2$ diluted in HBS-EP+ buffer (GE cat no BR100669) for 40 seconds at 10 μl/min. Then different concentrations of OX40 antigen (unbiotinylated hOX40-mFc or unbiotinylated cOX40-mFc produced in-house; see Table 2) in HBS-EP+ buffer (GE cat no BR100669) were flowed over the chip for 3 min at 70 μl/min and then allowed to dissociate for 6 min. After each antigen concentration the chip was regenerated by injecting 30 mM sodium hydroxide (NaOH) at a flow rate of 30 μl/min for 10 seconds. Buffer HBS-EP+ was injected before the highest concentration of antigen and after the lowest concentration of antigen for reference subtraction.

The binding kinetics were fit with a 1:1 Langmuir model to generate equilibrium binding constants ($K_D$) for each sample. Data analysis was performed with BiaEvaluation software version 3.2. The results are shown in Table 5.

TABLE 5

Binding affinity for human and cynomolgus OX40 as determined by SPR

| Clone name | Human OX40 $K_D$ (nM) | Cynomolgus OX40 $K_D$ (nM) |
|---|---|---|
| FS20-11-127AA/Cx | 10 | Below detection threshold |
| FS20-11-131AA/Cx | 11 | Below detection threshold |
| FS20-11-134AA/Cx | 5.5 | Below detection threshold |
| FS20-22-41AA/Cx | 0.4 | 3.5 |
| FS20-22-47AA/Cx | 0.5 | 3.5 |
| FS20-22-49AA/Cx | 0.5 | 1.8 |
| FS20-22-85AA/Cx | 0.9 | 40 |
| FS20-31-58AA/Cx | 58 | 138 |

TABLE 5-continued

| Binding affinity for human and cynomolgus OX40 as determined by SPR | | |
|---|---|---|
| Clone name | Human OX40 $K_D$ (nM) | Cynomolgus OX40 $K_D$ (nM) |
| FS20-31-66AA/Cx | 60 | 116 |
| FS20-31-94AA/Cx | 30 | 81 |
| FS20-31-102AA/Cx | 9.5 | 21 |
| FS20-31-108AA/Cx | 7.5 | 16 |
| FS20-31-115AA/Cx | 19 | 46 |
| FS1-65AA/11D4 LALA | 0.09 | 3.3 |

The OX40 Fcabs were observed to have a range of affinities for human OX40 (see Table 5). Binding of the Fcabs from the FS20-11 lineage to cynomolgus OX40 was below the threshold for detection, indicating that these Fcabs have low affinity for cynomolgus OX40 as was also observed in the cell binding experiments described in Example 4.2 above. The anti-human OX40 Fcabs from the FS20-22 and FS20-31 lineages bound to cynomolgus OX40 with comparable affinity to human OX40.

4.8 Binding Affinity of the Anti-Mouse OX40 Fcab for Mouse OX40

The affinity for mouse OX40 of the FS20m-232-91 anti-mouse OX40 Fcab was measured by SPR using the same target capture and EGFR immobilisation methodology as described in Example 4.7, but with the difference that the $mAb^2$ samples were captured to approximately 200 RU by injecting a 5 nM solution of $mAb^2$ diluted in HBS-EP+ buffer (GE cat no BR100669) for 1 min at 10 µl/min. The OX40/EGFR $mAb^2$ was constructed using the FS20m-232-91 anti-mouse OX40 Fcab (with the LALA mutation) and the variable regions of the anti-EGFR antibody cetuximab (U.S. Pat. No. 6,217,866 B1; indicated by Cx in Table 6 below). Different concentrations of OX40 antigen (mOX40-mFc produced in house; see Table 2 for details) in HBS-EP+ buffer (GE cat no BR100669) were then flowed over the chip for 5 min at 70 µl/min and then allowed to dissociate for 10 min. After each antigen concentration the chip was regenerated by injecting 30 mM sodium hydroxide (NaOH) at a flow rate of 30 µl/min for 10 seconds. Buffer HBS-EP+ was injected before the highest concentration of antigen and after the lowest concentration of antigen for reference subtraction.

The binding kinetics were fit with a 1:1 Langmuir model to generate equilibrium binding constants ($K_D$) for the sample. Data analysis was performed with BiaEvaluation software version 3.2. Table 6 shows that the affinity of the anti-mouse OX40 Fcab FS20m-232-91 is approximately 0.7 nM.

TABLE 6

| Binding affinity of $mAb^2$ to mouse OX40 as determined by SPR | |
|---|---|
| $mAb^2$ | $K_D$ (nM) |
| FS20m-232-91AA/Cx | 0.681 |

4.9 Specificity of Anti-Human OX40 Fcabs

Specificity of the anti-human OX40 Fcabs for human OX40 was tested in mock $mAb^2$ format and measured by SPR in a Biacore T200 by testing for binding of the Fcabs to other human TNFR family receptors (CD40, TNFRI, TNFRII, NGFR and CD137). Amine coupling (amine coupling kit, GE Healthcare, BR-1000-50) was used to coat human CD40, TNFRI, TNFRII, NGFR, CD137 receptors (all obtained from R&D Systems) to approximately 1000 RU in Biacore CM5 chips (GE Healthcare, cat no 29149603). Dilutions of anti-human OX40 Fcabs in mock $mAb^2$ format (see Table 7) starting at 1 µM were prepared in HBS-EP+ buffer (BR100669) and injected for 3 min at 30 µl/min and then allowed to dissociate in buffer for 4 min. The chip was regenerated by injection of 10 mM glycine pH 2.5 for 12 s at 30 µl/min. Antibodies specific to the different TNFR family members were used as positive controls to verify Biacore chip coating. Data was double reference subtracted and analyzed using BIAevaluation 3.2 software. The Fcabs listed in Table 7 did not bind to any of the TNFR family receptors tested, demonstrating their specificity for human OX40.

TABLE 7

| Anti-human OX40 Fcabs in mock $mAb^2$ format tested for specificity by SPR. |
|---|
| Mock $mAb^2$ tested |
| FS20-11-127AA/4420 |
| FS20-11-131AA/4420 |
| FS20-11-134AA/4420 |
| FS20-22-38AA/4420 |
| FS20-22-41AA/4420 |
| FS20-22-47AA/4420 |
| FS20-22-49AA/4420 |
| FS20-22-85AA/4420 |
| FS20-31-58AA/4420 |
| FS20-31-66AA/4420 |
| FS20-31-94AA/4420 |
| FS20-31-102AA/4420 |
| FS20-31-108AA/4420 |
| FS20-31-115AA/4420 |

4.10 Specificity of Anti-Mouse OX40 Fcab

Specificity of the anti-mouse OX40 Fcab (FS20m-232-91) in mock (HEL D1.3 LALA) $mAb^2$ format was measured by SPR in a Biacore T200 instrument by testing for binding to other mouse TNFR family receptors (mouse CD40, TNFRI, TNFRII, NGFR and CD137 receptors). Amine coupling (amine coupling kit, GE Healthcare, BR-1000-50) was used to coat mouse CD40, TNFRI, TNFRII, NGFR, CD137 receptors (all obtained from R&D Systems) to approximately 1000 RU in Biacore CM5 chips (GE Healthcare, cat no 29149603). Dilutions of the mock $mAb^2$ (FS20m-232-91AA/HEL D1.3) starting at 1 µM were prepared in HBS-EP+ buffer (BR100669) and injected for 3 min at 30 µl/min and then allowed to dissociate in buffer for 6 min. The chip was regenerated by injection of 10 mM glycine pH 2.5 for 20 s at 30 µl/min. Antibodies specific to the different TNFR family members were used as positive controls to verify Biacore chip coating.

Data was double reference subtracted and analysed using BIAevaluation 3.2 software. The anti-mouse OX40 Fcab FS20m-232-91 in mock (HEL D1.3 LALA) $mAb^2$ format did not bind to any of the related TNFR family members tested, demonstrating the specificity of this Fcab for mouse OX40.

Examples 5 to 8 —Functional Activity of Fcabs to Induce OX40 Activity by Different Crosslinkinq Means In Vitro and Vivo In the previous examples, Fcabs were identified which can bind to human OX40 or mouse OX40. These Fcabs in mock (4420 LALA) $mAb^2$ format were subsequently tested for their ability to activate OX40 clustering and signalling in NF-κB assays. The following examples demonstrate the ability of the Fcabs in mock $mAb^2$ and $mAb^2$ formats to activate OX40 in vitro and in vivo, when crosslinked by their Fc regions or by Fab binding to another target. Since the Fcabs are able to result in clustering and activation of OX40 in $mAb^2$ format containing a variety of Fabs, they are expected to have utility in treating a number of different diseases.

Example 5—Activation of OX40 In Vitro and In Vivo by Anti-OX40 Fcabs in Mock $mAb^2$ Format Activated T cells express OX40 on their cell surface. Binding of the trimeric OX40 ligand to OX40 results in trimerisation of the receptor. As the OX40 ligand is expressed as clusters on the cell surface of antigen-presenting cells, the interaction between the OX40 ligand and OX40 results in the clustering of OX40, which is known to be essential for OX40 signalling and further T cell activation. Antibodies that agonise OX40 must mimic this clustering activity of the OX40 ligand. In the case of monospecific anti-OX40 antibodies, Fc gamma receptors bind to the Fc domains of the antibodies and crosslink them, resulting in OX40 clustering.

The anti-human OX40 and anti-mouse OX40 Fcabs in mock (4420) LALA format described in Example 4 were tested in T cell activation assays for their ability to activate OX40 expressed on T cells upon crosslinking of the Fcabs in the presence of a crosslinking agent. The FS20m-232-91 anti-mouse OX40 Fcab was also tested, in mock (HEL D1.3) $mAb^2$ format (see Example 4.1), for its ability to inhibit tumour growth in vivo in a CT26 syngeneic mouse tumour growth model via activation of OX40-expressing tumour infiltrating lymphocytes.

5.1 Human T Cell Activation Assay Using Anti-Human OX40 Fcabs in Mock $mAb^2$ Format Activated human T cells express human OX40 on their cell surface. Clustering of OX40 is known to be essential to induce receptor signalling and further T cell activation. A T cell activation assay was used to assess clustering and signalling of OX40 in the presence of the mock (4420 LALA) $mAb^2$ and mAb molecules detailed in Table 8 below. T cell activation was detected by measuring the release of IL-2.

5.1.1 Isolating and Activating Human T Cells

To isolate T cells, peripheral blood mononuclear cells (PBMCs) were isolated from leucocyte depletion cones (NHS Blood and Transplant service), a by-product of platelet donations. Briefly, leucocyte cone contents were flushed with PBS and overlaid on a Ficoll gradient (GE Lifesciences cat no 17144002). PBMCs were isolated by centrifugation and recovery of cells that did not cross the Ficoll gradient. PBMCs were further washed with PBS and remaining red blood cells were lysed through the addition of 10 ml red blood cell lysis buffer (eBioscience) according to the manufacturer's instructions. T cells were isolated from the PBMCs present in the eluant using the pan T cell isolation kit II (Miltenyi Biotec Ltd) according to the manufacturer's instructions.

Human T-Activator CD3/CD28 Dynabeads (Life Technologies 11452D) were resuspended by vortexing. Beads were washed twice with T cell medium (RPMI medium (Life Technologies) with 10% FBS (Life Technologies), 1× Penicillin Streptomycin (Life Technologies), Sodium Pyruvate (Gibco), 10 mM Hepes (Gibco), 2 mM L-Glutamine (Gibco) and 50 μM 2-mercaptoethanol (Gibco)).

The required amount of T cells at a concentration of $1.0\times10^6$ cells/ml in T cell medium were stimulated with the washed human T-Activator CD3/CD28 Dynabeads at a 2:1 cell to bead ratio in a T-25 flask (Sigma) and incubated overnight at 37° C., 5% $CO_2$ to activate the T cells. Activated T cells were washed from the Dynabeads and resuspended in T cell medium at a concentration of $2.0\times10^6$ cells/ml. 96-well flat-bottomed plates were coated with anti-human CD3 antibody through incubation with 2.5 μg/ml anti-human CD3 antibody (R&D Systems clone UHCT1) diluted in PBS for 2 hours at 37° C., 5% $CO_2$ and then washed twice with PBS. Activated T cells were added to the plates at $2\times10^1$ cell/well. 2 μM dilutions of the mock (4420 LALA) $mAb^2$ molecules, the positive-control 11 D4 mAb (in a human IgG1 backbone and comprising the LALA mutation) and the negative control 4420 mAb (in a human IgG1 backbone and comprising the LALA mutation) were prepared in DPBS (Gibco) and further diluted 1:10 in T cell medium (30 μl+270 μl) to obtain 200 nM dilutions. Anti-human CH2 mAb clone MK1A6, used for crosslinking of the positive-control mAb via the Fc, or FITC-dextran (Sigma), used for crosslinking of the Fcabs in mock (4420 LALA) $mAb^2$ format (see Table 8) via Fab binding, were added to the wells in a 1:1 molar ratio with the mock $mAb^2$ or the positive-control mAb. In a 96 well plate, serial dilutions of (1) the positive control or mock $mAb^2$ or (2) the positive control or mock $mAb^2$ each with the relevant crosslinking agent were prepared. 100 μl of the diluted mock $mAb^2$/positive control mAb, or the diluted mock $mAb^2$ or positive control mAb and the crosslinking agent, were added to the activated T cells on the plate.

T cells were incubated at 37° C., 5% $CO_2$ for 72 hours. Supernatants were collected and IL-2 release measured using a human IL-2 ELISA kit (eBioscience or R&D systems) following the manufacturer's instructions. Plates were read at 450 nm using the plate reader with the Gen5 Software, BioTek. Absorbance values of 630 nm were subtracted from those of 450 nm (Correction). The standard curve for calculation of cytokine concentration was based on a four parameter logistic curve fit (Gen5 Software, BioTek). The concentration of human IL-2 (hlL-2) was plotted vs the log concentration of the mock $mAb^2$ positive control mAb and the resulting curves were fitted using the log (agonist) vs response equation in GraphPad Prism. Table 8 shows the $EC_{50}$ values and maximum response of the IL-2 release observed in the T cell activation assay in the presence of the mock $mAb^2$ and positive-control mAb tested with and without crosslinking. FIG. 2 shows representative plots of IL-2 release for the T cell activation assay for a representative clone from each of the lineages (lineages FS20-11, FS20-22 and FS20-31).

TABLE 8

T cell activation using anti-human OX40 Fcabs in mock (4420 LALA) $mAb^2$ format

| Clone Name | Crosslinked EC$_{50}$ (nM) | Crosslinked Max response (hIL-2 pg/ml) | Not crosslinked EC$_{50}$ (nM) | Not crosslinked Max response (hIL-2 pg/ml) | Activity increase with crosslinking EC$_{50}$ Not crosslinked/ EC$_{50}$ crosslinked |
|---|---|---|---|---|---|
| FS20-11-127AA/4420 | 2.253 | 27380 | n/a* | n/a* | n/a* |
| FS20-11-131AA/4420 | 1.208 | 23687 | n/a* | n/a* | n/a* |
| FS20-11-134AA/4420 | 1.243 | 22725 | n/a* | n/a* | n/a* |
| FS20-22-38AA/4420 | 0.3861 | 26994 | 3.138 | 20796 | 8.127428 |
| FS20-22-41AA/4420 | 0.1501 | 27722 | 4.019 | 17940 | 26.77548 |
| FS20-22-47AA/4420 | 0.1256 | 27414 | 3.269 | 17065 | 26.02707 |
| FS20-22-49AA/4420 | 0.05636 | 26613 | 2.494 | 15254 | 44.25124 |
| FS20-22-85AA/4420 | 0.13 | 26360 | 4.281 | 12664 | 32.93077 |
| FS20-31-58AA/4420 | 0.2192 | 24256 | 10.72 | 16261 | 48.90511 |
| FS20-31-66AA/4420 | 0.1214 | 23531 | 9.424 | 17857 | 77.62768 |
| FS20-31-94AA/4420 | 0.2904 | 27229 | 8.818 | 24408 | 30.36501 |
| FS20-31-102AA/4420 | 0.08859 | 31687 | 1.173 | 21903 | 13.24077 |
| FS20-31-108AA/4420 | 0.01208 | 29006 | 0.8837 | 20510 | 73.15397 |
| FS20-31-115AA/4420 | 0.1706 | 29717 | 1.77 | 13745 | 10.37515 |
| G1AA/11D4 | 0.04931 | 26708 | n/a* | n/a* | n/a* |

*These mock $mAb^2$/control mAb did not show any activity in the T cell activation assay in the absence of cross-linking.

As shown in Table 8, the anti-human OX40 Fcabs in mock (4420 LALA) $mAb^2$ format when crosslinked by the Fab target (FITC-dextran) showed a range of activities in the T cell activation assay. All of the Fcabs had the ability to co-stimulate T cells in the presence of an anti-CD3 antibody and induce the production of human IL2.

The FS20-11 lineage Fcabs were only able to co-stimulate T cells when crosslinked and had no activity in the absence of crosslinking. This activity only when crosslinked means that these Fcabs are expected to only activate T cells in the presence of the Fab target or other crosslinking means when administered to a patient. FS20-11-131 has a lower $EC_5$o compared with the other clones in this lineage. However, since there is low cross-reactivity of the clones of the FS20-11 lineage to cynomolgus OX40, further improvements in affinity to cynomolgus OX40 would be needed for toxicology studies in this species.

The Fcabs from the FS20-22 and FS20-31 lineages showed an activity both with and without crosslinking. Specifically, the Fcabs from these lineages had activity in the absence of a crosslinking agent which was increased upon crosslinking. Since these Fcabs have high cross-reactivity to cynomolgus OX40 (comparable to binding human OX40), toxicology studies would be possible in this species. Of the clones in the FS20-22 lineage, clones FS20-22-41, FS20-22-47, FS20-22-49 and FS20-22-85 had the lowest $EC_{50}$ values for their agonistic activity when crosslinked and are therefore the preferred clones from this lineage.

Of these, clone FS20-22-49 showed the highest increase in agonist activity upon crosslinking and also had the lowest $EC_5$ for its agonist activity in the presence of crosslinking and is therefore the preferred clone. Of the clones in the FS20-31 lineage, clones FS20-31-108, FS20-31-108 and FS20-31-115 showed the greatest maximum response whilst also showing low $EC_{50}$ values and therefore good potency.

The fact that the clones in the FS20-22 and FS20-31 lineages showed some limited T cell activation in the absence of crosslinking is not expected to present a safety risk, as OX40-targeting molecules have shown no adverse effects in the clinic. Rather, it is thought that the limited T cell activation activity of these clones in the absence of crosslinking may be beneficial, as these clones may be able to activate OX40-expressing memory T cells in the absence of crosslinking, thereby inducing them to proliferate and thus creating a larger T cell population which can then be further activated through OX40 clustering driven by binding of cross-linked anti-OX40 Fcabs.

5.2 Mouse T Cell Activation Assay Using Anti-Mouse OX40 Fcab in Mock $mAb^2$ Format In order to assess the activity of the mouse OX40-binding Fcab, a T cell activation assay was used to assess clustering and signalling of mouse OX40 in the presence of the mock (4420 LALA) $mAb^2$ and mAb molecules detailed in Table 9 below. As in the human assay, T cell activation was detected by measuring the release of IL-2.

5.2.1 Isolating and Activating Mouse T Cells

To isolate T cells, spleens were collected from 4-8 week old female Balb/C mice (Charles River). Mice were humanely euthanised and spleens were isolated by dissection. Splenocytes were isolated by pushing the spleens through a 70 μm cell strainer (Corning) using the inside of a 5 ml plastic syringe. The cell strainer was washed 10 times with 1 ml Dulbecco's phosphate-buffered saline (DPBS) (Gibco) and the eluant collected in a 50 ml tube. Red blood cells present in the eluant were lysed through the addition of 10 ml red blood cell lysis buffer (eBioscience) according to the manufacturer's instructions. T cells were isolated from the splenocytes present in the eluant using the pan T cell isolation kit II (Miltenyi Biotec Ltd) according to the manufacturer's instructions.

Mouse T-Activator CD3/CD28 Dynabeads (Life technologies, 11452D) were resuspended by vortexing. Beads were washed twice with T cell medium (RPMI medium (Life Technologies) with 10% FBS (Life Technologies), 1× Penicillin Streptomycin (Life Technologies), Sodium Pyruvate (Gibco), 10 mM Hepes (Gibco), 2 mM L-Glutamine (Gibco) and 50 μM 2-mercaptoethanol (Gibco)).

The required amount of T cells at a concentration of $1.0\times10^6$ cells/ml in T cell medium were stimulated with the washed Mouse T-Activator CD3/CD28 Dynabeads at a 2:1 cell to bead ratio in a T-25 flask (Sigma) and incubated overnight at 37° C., 5% $CO_2$ to activate the T cells.

After overnight incubation, the activated T cells were washed from the Dynabeads and resuspended in T cell medium at a concentration of $2.0\times10^6$ cells/ml. 96-well flat-bottomed plates were coated with anti-mouse CD3 antibody through incubation with 2.5 μg/ml anti-mouse CD3 antibody (Biolegend clone 145-2C11) diluted in PBS for 2 hours at 37° C., 5% $CO_2$ and then washed twice with PBS. Activated T cells were added to the plates at $2\times10^5$ cell/well. 2 μM dilutions of the mock (4420 LALA) $mAb^2$ and the positive-control anti-mouse OX40 OX86 mAb (in a human IgG1 backbone with the LALA mutation; SEQ ID NOs 175 and 176) (see Table 9 for details) were prepared in DPBS (Gibco) and further diluted 1:10 in T cell medium (30 μl+270 μl) to obtain 200 nM dilutions. Anti-human CH2 mAb clone MK1A6, used for crosslinking via the Fc of the OX86 positive-control mAb, and FITC-dextran (Sigma), used for crosslinking via Fab-binding of the Fcab in mock (4420 LALA) $mAb^2$ format, were added to the wells in a 1:1 molar ratio with the mock $mAb^2$ or the positive-control mAb. In a 96 well plate, serial dilutions of (1) the positive control or mock $mAb^2$ or (2) the positive control or the mock $mAb^2$ each with the relevant crosslinking agent were prepared. 100 μl of the diluted mock (4420 LALA) $mAb^2$/control mAb or the mixture of the mock (4420 LALA) $mAb^2$ or positive control mAb and the crosslinking antibody was added to the activated T cells on the plate.

T cells were incubated at 37° C., 5% $CO_2$ for 72 hours. Supernatants were collected and IL-2 release measured using a mouse IL-2 ELISA kit (eBioscience or R&D systems) following the manufacturer's instructions. Plates were read at 450 nm using the plate reader with the Gen5 Software, BioTek. Absorbance values of 630 nm were subtracted from those of 450 nm (Correction). The standard curve for calculation of cytokine concentration was based on a four parameter logistic curve fit (Gen5 Software, BioTek). The concentration of mouse IL-2 (mIL-2) was plotted vs the log concentration of the mock $mAb^2$ or positive control mAb and the resulting curves were fitted using the log (agonist) vs response equation in GraphPad Prism. Table 9 shows the $EC_{50}$ values and maximum response of the IL-2 release observed in the T cell activation assay in the presence of the mock $mAb^2$ and the positive-control mAb tested.

TABLE 9

T cell activation using anti-mouse OX40 Fcab in mock (4420 LALA) $mAb^2$ format

| | Crosslinked | | Not crosslinked | |
|---|---|---|---|---|
| mock (4420 LALA) $mAb^2$/mAb | $EC_{50}$ (nM) | Max response (mIL-2 pg/ml) | $EC_{50}$ (nM) | Max response (mIL-2 pg/ml) |
| FS20m-232-91AA/4420 | 0.6699 | 25645 | n/a* | n/a* |
| G1AA/OX86 | 1.753 | 25570 | n/a* | n/a* |

*The mock $mAb^2$/control mAb did not show any activity in the T cell activation assay in the absence of cross-linking.

As shown in Table 9, the activity of the anti-mouse OX40 Fcab in mock (4420 LALA) $mAb^2$ format when crosslinked by the Fab target (FITC-dextran) in the T cell activation assay was comparable to the activity of the positive control anti-mouse OX40 mAb OX86 when in a human IgG1 backbone and crosslinked by anti-human CH2 mAb clone MK1A6. No T cell activation was observed in the absence of crosslinking for either the anti-mouse OX40 Fcab in mock (4420 LALA) $mAb^2$ format or the anti-mouse OX40 mAb positive-control antibody.

These results show that the anti-mouse OX40 Fcab had similar agonistic activity as the positive-control anti-mouse OX40 mAb and demonstrate that the Fcab format, when crosslinked, can mediate clustering and activation of the OX40. The activity of the anti-mouse OX40 Fcab was similar to that of the FS20-11 lineage of anti-human OX40 Fcabs, which were also observed to have activity only when crosslinked. The FS20-22 and FS20-31 lineages of Fcabs were shown to have agonist activity in the absence of crosslinking which was further enhanced in the presence of crosslinking. As explained above, the background agonist activity of these Fcabs in the absence of crosslinking is expected to make these Fcabs more potent in the clinic than Fcabs which do not show such background agonist activity. The clinical activity of the anti-human OX40 Fcabs from the FS20-22 and FS20-31 lineages may therefore be greater than the in vivo activity observed with the anti-mouse OX40 Fcab.

5.3 In Vivo Anti-Tumour Efficacy of Anti-Mouse OX40 Fcab in Mock $mAb^2$ Format

The CT26 syngeneic tumour model was used to test the anti-tumour activity of the anti-mouse OX40 Fcab FS20m-232-91 in mock $mAb^2$ format in vivo. The CT26 syngeneic tumour model has previously been shown to be sensitive to OX40 agonist antibodies (Sadun et al., 2008) and tumour infiltrating lymphocytes (TILs) isolated from CT26 tumours are expected to express OX40.

The anti-mouse OX40 Fcab FS20m-232-91 and the anti-human OX40 Fcabs are potent agonists of T cell activation as shown using T cell activation assays. No T cell activation was observed without crosslinking for the anti-mouse OX40 Fcab in mock (4420 LALA) $mAb^2$ format (see Example 5.2). Since the FS20-11 lineage only has T cell activity when crosslinked, like the FS20m-232-91 anti-mouse OX40 Fcab, the results from in vivo studies performed with the FS20m-232-91 anti-mouse OX40 Fcab are expected to be predictive of the clinical efficacy of the anti-human OX40 Fcabs from this FS20-11 lineage in human patients (see Example 5.1). The anti-human OX40 Fcabs from the FS20-22 and FS20-31 lineages showed OX40 agonist activity in the absence of crosslinking (see Example 5.1). As explained in Example 5.2.1, it is expected that Fcabs from the FS20-22 and FS20-31 lineages will show a higher clinical efficacy than Fcabs which do not have OX40 agonist activity in the absence of crosslinking. The clinical efficacy of the anti-human OX40 Fcabs from the FS20-22 and FS20-31 lineages may therefore be greater than the in vivo results observed with the FS20m-232-91 anti-mouse OX40 Fcab.

The ability of the FS20m-232-91 anti-mouse OX40 Fcab in mock (HEL D1.3) $mAb^2$ format, with and without the LALA mutation, to inhibit tumour growth was compared to a positive control anti-mouse OX40 mAb (OX86 in a human IgG1 backbone) and a negative control anti-FITC antibody (4420 in a human IgG1 backbone).

BALB/c female mice (Charles River) aged 8-10 weeks and weighing approximately 20 g each were rested for one week prior to the study start. All animals were micro-chipped and given a unique identifier. Each cohort had 12 mice. The CT26 colon carcinoma cell line (ATCC, CRL-2638) was initially expanded, stored, and then pre-screened by IDEXX Bioresearch for pathogens using the IMPACT I protocol and shown to be pathogen free. CT26 cells (approximately $3\text{-}5\times10^6$) were thawed from −150° C. storage and added to 20 ml DMEM (Gibco, 61965-026) with 10% FCS (Gibco, 10270-106) in a T175 tissue culture flask. Mice were anaesthetised using isoflurane (Abbott Laboratories) and each animal received $1 \times 10^6$ cells injected subcutaneously in the left flank. On day 10 following tumour cell inoculation, mice were monitored for health and tumour growth and were sorted and randomised into study cohorts. Any mice which did not have tumours at this point were removed from the study.

The mock (HEL D1.3) $mAb^2$ molecules and the control mAbs were analysed by SEC-HPLC profiling and checked for impurities within 24 hours prior to injection. The mock (HEL D1.3) $mAb^2$ and mAbs were prepared to a final concentration of 0.1 mg/ml in PBS, and a volume of 200 μl/mouse was administered by intraperitoneal (IP) injection, giving a final dose of 1 mg/kg for a 20 g mouse, on days 10, 12 and 14 following tumour inoculation. Animals were health screened under anaesthesia three times a week in a blinded fashion, during which time accurate measurements of tumours were taken. Tumour volume measurements were taken with callipers to determine the longest axis and the shortest axis of the tumour. The following formula was used to calculate the tumour volume:

$$L \times (S^2)/2$$

(Where $L$=longest axis; $S$=shortest axis)

Figure 3:
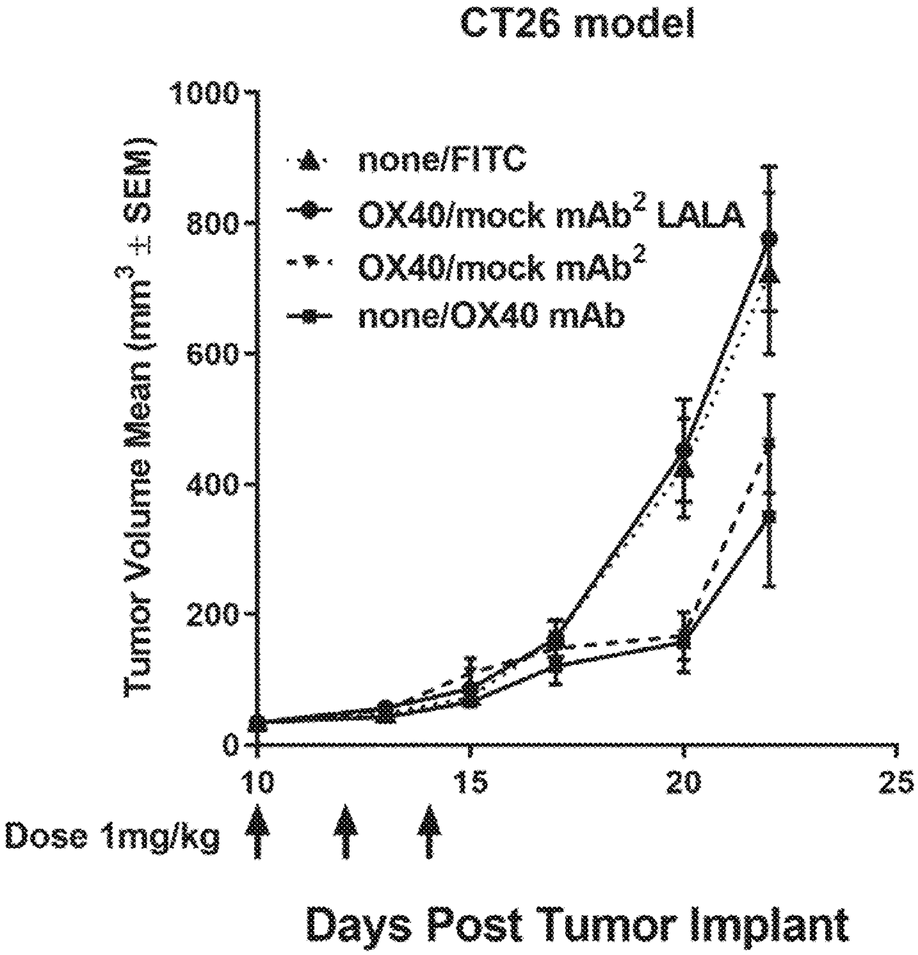
FIG. 3 shows the in vivo anti-tumour activity of the anti-mouse OX40 Fcab in mock (HEL D1.3 LALA) $mAb^2$ format in a CT26 tumour model. A tumour growth curve of the CT26 syngeneic model in Balb/c mice cohorts is shown. The in vivo anti-tumour activity of the anti-mouse OX40 Fcab in mock (HEL D1.3) $mAb^2$ format with (OX40/mock $mAb^2$ LALA) and without (OX40/mock $mAb^2$) the LALA mutation was compared to a positive control anti-mouse OX40 mAb (OX86 in a human IgG1 backbone; none/OX40mAb) and a negative control antibody (4420 antibody in a human IgG1 backbone; none/FITC). The different molecules were dosed at 1 mg/kg on days 10, 12 and 14 after tumour inoculation. The mean tumour volume plus or minus the standard error mean is plotted.

The trial was halted at day 22 when the tumour burden was considered close to restrictions and all mice were humanely sacrificed. The results are shown in FIG. 3. Statistical analysis of the end tumour volumes was performed using a two tailed Student's t-test within the GraphPad Prism software package.

There was a demonstrated statistically significant difference between positive control anti-mouse OX40 mAb (G1/OX86) and negative control anti-FITC control antibody (normal growth) in suppressing tumour growth. There was also a demonstrated statistically significant difference between mock (HEL D1.3) $mAb^2$ and the mock (HEL D1.3) $mAb^2$ with the LALA mutation in suppressing tumour growth.

The CT26 tumour model is an aggressive, fast growing tumour model, one that is inherently prone to mice developing intestinal metastasis, and as a result has a very limited therapeutic window. The clustering and activation of OX40 expressed on tumour-infiltrating T cells in this tumour model, resulting in the suppression of tumour growth, is driven by FcγR-mediated crosslinking of the FS20m-232-91 Fcab in mock $mAb^2$ format and the G1/OX86 positive control, both of which do not contain the LALA mutation. However, as seen with the LALA mutation-containing FS20m-232-91AA Fcab in mock $mAb^2$ format, when there is little or no FcγR-mediated crosslinking of the Fcab and therefore no clustering and activation of OX40, no suppression of tumour growth is observed. It can therefore be concluded from this that the anti-mouse OX40 Fcab has activity resulting in tumour growth reduction only when crosslinked.

Based on these results, it is expected that the anti-human OX40 Fcabs when crosslinked will similarly be able to inhibit the growth of tumours comprising tumour-infiltrating T cells expressing OX40 in human patients.

Example 6—$mAb^2$ Crosslinking Through Cell Surface Receptor Binding

Activated T cells express OX40 on their cell surface. Binding of the trimeric OX40 ligand to OX40 results in trimerization of the receptor. As the OX40 ligand is expressed as clusters on the cell surface of antigen-presenting cells, the interaction between the OX40 ligand and OX40 results in the clustering of OX40, which is known to be essential for OX40 signalling and further T cell activation. Antibodies that agonise OX40 must mimic this clustering activity of the OX40 ligand. In the case of monospecific anti-OX40 antibodies, Fc gamma receptors bind to the Fc domains of the antibodies and crosslink them, resulting in OX40 clustering. Bispecific antibodies can bind to a second cell-surface-expressed receptor via their second antigen-binding site resulting in crosslinking of the antibodies and OX40 clustering. The second cell surface expressed receptor bound by the bispecific antibody may be a tumour-associated antigen (TAA). This has the advantage that the bispecific antibody is crosslinked at the site of the tumour, resulting in OX40 clustering and T cell activation at the tumour site. The use of bispecific antibodies thus has the potential to result in tumour-localized activation of the immune system and consequent elimination or control of the tumour.

Tumour cells that express TAAs at their surface were thus used in T cell activation assays as described below to assess whether TAA binding by $mAb^2$ comprising the anti-OX40 Fcabs of the invention and a TAA antigen-binding site in the variable region could result in $mAb^2$ crosslinking and consequently induce clustering and signalling of OX40.

6.1 Human T Cell Activation Assays Using $mAb^2$ Comprising an Anti-Human OX40 Fcab Paired with an Anti-EGFR, Anti-EphA2, Anti-CEACAM5 or Anti-EpCAM Fab The antibody molecules set out in Tables 10 and 11 below were prepared with the LALA mutation, as described in Example 4.1, for testing in T cell activation assays. Antibody molecules were constructed using the variable regions of the anti-FITC antibody 4420 (SEQ ID NOs 167, 168 and 156), anti-EGFR antibody cetuximab (U.S. Pat. No. 6,217,866; indicated by 'Cx'), EphA2 antibody E2A (WO 2004/014292 A2), EpCAM antibody MOC31 (U.S. Pat. No. 8,637,017), OX40 antibody 11 D4 (EP 2 242 771 B1), or anti-CEACAM5 antibody CEA (U.S. Pat. No. 8,771,690 B2, clone hMN15) in the same way as the mock $mAb^2$ described in Example 4.1. In these assays, the tumour cells served as crosslinkers for the $mAb^2$, which comprised an anti-human OX40 Fcab and a variable region specific for a TAA (EGFR, EphA2, CEACAM5 or EpCAM in the case of the anti-human OX40 Fcab FS20-22-49AA in Table 10, and EphA2 or CEACAM5 in the case of the anti-human OX40 Fcab FS20-11-131AA in Table 11), via binding of the variable region binding site to the TAA. T cell activation was determined by the release of IL-2.

TABLE 10 mAbs and $mAb^2$ tested

| $mAb/mAb^2$ | Fab binding to | Fcab binding to | Isotype | LALA mutation | Crosslinker |
|---|---|---|---|---|---|
| G1/4420 | FITC | n/a | hIgG1 | no | FITC-dextran |
| G1/11D4 | OX40 | n/a | hIgG1 | no | anti-hCH2 |

TABLE 10-continued

| mAbs and mAb$^2$ tested | | | | | |
|---|---|---|---|---|---|
| mAb/mAb$^2$ | Fab binding to | Fcab binding to | Isotype | LALA mutation | Crosslinker |
| FS20-22-49AA/4420 | FITC | OX40 | hIgG1 | yes | FITC-dextran |
| FS20-22-49AA/Cx | EGFR | OX40 | hIgG1 | yes | HPAC cells |
| FS20-22-49AA/E2A | EphA2 | OX40 | hIgG1 | yes | HPAC cells |
| FS20-22-49AA/CEA | CEACAM5 | OX40 | hIgG1 | yes | HPAC cells |
| FS20-22-49AA/MOC31 | EpCAM | OX40 | hIgG1 | yes | HPAC cells |

TABLE 11

| mAbs and mAb$^2$ tested | | | | | |
|---|---|---|---|---|---|
| mAb/mAb$^2$ | Fab binding to | Fcab binding to | Isotype | LALA mutation | Crosslinker |
| G1AA/4420 | FITC | n/a | hIgG1 | no | FITC-dextran |
| G1/11D4 | OX40 | n/a | hIgG1 | no | anti-hCH2 |
| FS20-11-131AA/4420 | FITC | OX40 | hIgG1 | yes | none |
| FS20-11-131AA/4420 | FITC | OX40 | hIgG1 | yes | FITC-dextran |
| FS20-11-131AA/E2A | EphA2 | OX40 | hIgG1 | yes | HPAC cells |
| FS20-11-131AA/CEA | CEACAM5 | OX40 | hIgG1 | yes | HPAC cells |

T cells were isolated and activated as described in Example 5.1.1 above.

HPAC cells (ATCC, CRL-2119), which express EGFR, EpCAM, EphrinA2 and CEACAM5 on their cell surface, were maintained in DMEM medium (Life Technologies) with 10% FBS (Life Technologies). HPAC cells were washed once in T cell medium and added to the plates at $2.5 \times 10^4$ cells/well where required.

2 μM dilutions of each test mAb/mAb$^2$ (see Tables 10 and 11 for details) were prepared in DPBS (Gibco) and further diluted 1:10 in T cell medium (30 μl+270 μl) to obtain 200 nM dilutions.

The crosslinking agents (anti-human CH2 mAb clone MK1A6 or FITC-dextran (Sigma); see Tables 10 and 11) were added to the wells in a 1:1 molar ratio with the test mAb/mAb$^2$ where required. In a 96-well plate, serial dilutions of the test mAb/mAb$^2$ were prepared and 100 μl of the diluted mAb/mAb$^2$ mixture was added to the activated T cells and HPAC cells on the plate.

T cells were incubated and supernatants collected as described in Example 5.1.1. Plates were read, the concentration of human IL-2 (hIL-2) plotted vs the log concentration of the test mAb/mAb$^2$, and the resulting curves fitted using the log (agonist) vs response equation as described in Example 5.1.1.

Table 12 shows T cell activation ($EC_{50}$ values and maximum IL-2 release) by the mAbs/mAb$^2$ set out in Table 10 in the presence or absence of crosslinking by either crosslinking agents or HPAC cells. FIG. 4 shows plots of IL-2 release for the T cell activation assay.

TABLE 12

| T cell activation in the presence of HPAC tumour cells | | | | |
|---|---|---|---|---|
| mAbs/mAb$^2$ (in the presence of HPAC cells) | $EC_{50}$ (nM) | $EC_{50}$ (95% Conf. Int.) | Max response (mIL-2 pg/ml) | Max response 95% Conf. Int. |
| G1AA/4420 Xlink | n/a* | n/a* | n/a* | n/a* |
| G1/11D4 Xlink | 0.2283 | 0.04341 to 1.2 | 14827 | 11049 to 18606 |
| FS20-22-49AA/4420 | 8.033 | 2.42 to 26.67 | 13186 | 9401 to 16970 |
| FS20-22-49AA/4420 Xlink | 0.3658 | 0.1036 to 1.291 | 16546 | 13190 to 19903 |
| FS20-22-49AA/Cx | 0.1303 | 0.05061 to 0.3355 | 14860 | 12909 to 16812 |
| FS20-22-49AA/E2A | 0.4657 | 0.2338 to 0.9276 | 11304 | 10042 to 12566 |
| FS20-22-49AA/MOC31 | 0.04922 | 0.0008316 to 2.913 | 6716 | 2706 to 10727 |
| FS20-22-49AA/CEA | 0.04859 | 0.002753 to 0.8579 | 13635 | 8248 to 19023 |

*This control mAb did not show any activity in the T cell activation assay in the absence of cross-linking.

FIG. 4 shows that there is an increase in T cell activation when OX40 is bound by crosslinked anti-OX40 mAb/mAb$^2$. No T cell activation was observed with the crosslinked anti-FITC antibody G1AA/4420, as expected, which served as a negative control. The OX40-targeting mAb G1/11 D4 when crosslinked by the anti-human CH2 antibody induced T cell activation in the presence of HPAC cells. The OX40-targeting Fcab in mock mAb$^2$ (4420 LALA) format, FS20-22-49AA/4420, had agonistic activity in the absence of crosslinking, as seen before, and this activity was enhanced in the presence of the crosslinker FITC-dextran which binds to the Fab arms of the mock mAb$^2$. When the OX40-targeting Fcab was paired with anti-TAA Fabs (cetuximab for EGFR, E2A for EphrinA2, MOC31 for EpCAM and CEA for CEACAM5), the agonistic activity of the resulting $mAb^2$ was increased compared with the Fcab in mock $mAb^2$ format, indicating binding of the TAA Fabs to cell surface-expressed TAAs on HPAC cells resulted in crosslinking of the $mAb^2$ and consequently OX40 clustering and activation.

Table 13 shows T cell activation ($EC_{50}$ values and maximum IL-2 release) using the mAbs/$mAb^2$ set out in Table 11 in the presence or absence of crosslinking by either crosslinking agents or HPAC cells. FIG. 5 shows plots of IL-2 release for the T cell activation assay.

TABLE 13

T cell activation assay in the presence of HPAC tumour cells

| mAbs/$mAb^2$ (in the presence of HPAC cells) | $EC_{50}$ (nM) | $EC_{50}$ 95% Conf. Int. | Max reponse (mIL-2 pg/ml) | Max response 95% Conf. Int. |
|---|---|---|---|---|
| G1AA/4420 Xlink | n/a* | n/a* | n/a* | n/a* |
| G1/11D4 Xlink | 0.2283 | 0.04341 to 1.2 | 14827 | 11049 to 18606 |
| FS20-11-131AA/4420 | 0.1647 | 4.429e−010 to 61235362 | −621.9 | −805.5 to −438.3 |
| FS20-11-131AA/4420 Xlink | 3.918 | 1.052 to 14.59 | 7904 | 5582 to 10227 |
| FS20-11-131AA/E2A | 0.02072 | 0.0009138 to 0.4699 | 2952 | 1639 to 4266 |
| FS20-11-131AA/CEA | 0.949 | 0.08275 to 10.88 | 4210 | 1969 to 6451 |

*This control mAb did not show any activity in the T cell activation assay in the absence of cross-linking.

The data plotted in FIG. 5 shows that there is an increase in T cell activation when OX40 is bound by crosslinked anti-OX40 mAb/$mAb^2$. No T cell activation was observed with the crosslinked anti-FITC antibody G1/4420, as expected, which served as a negative control. The OX40-targeting mAb antibody G1/11 D4 when crosslinked by the anti-human CH2 antibody induced T cell activation in the presence of HPAC cells. The OX40-targeting Fcab in mock $mAb^2$ (4420 LALA) format, FS20-11-131AA/4420, did not have agonistic activity in the absence of crosslinking, as seen before, and only displayed agonistic activity in the presence of the crosslinker FITC-dextran which binds to the Fab arms of the mock $mAb^2$.

When the OX40-targeting Fcab was paired with anti-TAA Fabs (E2A for EphrinA2, or CEA for CEACAM5), the agonistic activity of the resulting $mAb^2$ was increased compared with the Fcab in mock $mAb^2$ format in the presence of the TAA-expressing HPAC cells, indicating that binding of the TAA Fabs to cell surface-expressed TAAs on HPAC cells resulted in crosslinking of the $mAb^2$ and consequently OX40 clustering and activation.

The T cell activation observed with the anti-OX40/anti-EGFR, anti-OX40/anti-CEACAM5, anti-OX40/anti-EphA2 or anti-OX40/anti-EpCAM $mAb^2$ antibodies demonstrates that more than one type of cell surface receptor can be paired with the anti-OX40 Fcabs.

6.2 Mouse T Cell Activation Assays Using $mAb^2$ Comprising the Anti-Mouse OX40 Fcab Paired with an Anti-EphA2 Fab This T cell activation assay was used to assess clustering and signalling of OX40 in the presence of the test mAb/$mAb^2$ set out in Table 14 below. The $mAb^2$ were prepared with the LALA mutation as described in Example 4.1. The tumour cells used in the assay served as crosslinkers for the positive control mAb and $mAb^2$that target the TAA EphA2, via Fab binding to the EphA2.

TABLE 14 mAbs and $mAb^2$ tested

| mAb/$mAb^2$ | Molecule type | Fab target | Fab clone | Fcab target |
|---|---|---|---|---|
| G1/4420 | mAb | FITC | 4420 | n/a |
| FS20m-232-91AA/4420 | $mAb^2$ | FITC | 4420 | mOX40 |
| G1/E2A | mAb | EphA2 | E2A | n/a |
| FS20m-232-91AA/E2A | $mAb^2$ | EphA2 | E2A | mOX40 |
| G1/OX86 | mAb | mOX40 | OX86 | n/a |

Mouse T cells were isolated and activated as described in Example 5.2.1 and were used in a protocol essentially the same as the human T cell activation assay described in Example 6.1 using HPAC cells but with different crosslinking agents and control antibodies as described above and below, and IL-2 production was assessed.

Crosslinking agents (anti-human Fc (a-hFc), Jackson Immunoresearch; or FITC-dextran, Sigma) were added to the wells in a 1:1 molar ratio with the test mAbs/$mAb^2$where required. In a 96-well plate, six five-fold serial dilutions of the mAb/$mAb^2$ or mAb/$mAb^2$ and crosslinking antibody mixture were prepared (60 μl+240 μl T cell medium). 100 μl of the diluted mAb/$mAb^2$ or mAb/$mAb^2$ and crosslinking antibody mixture was added to the activated T cells on the plate.

Figure 6:
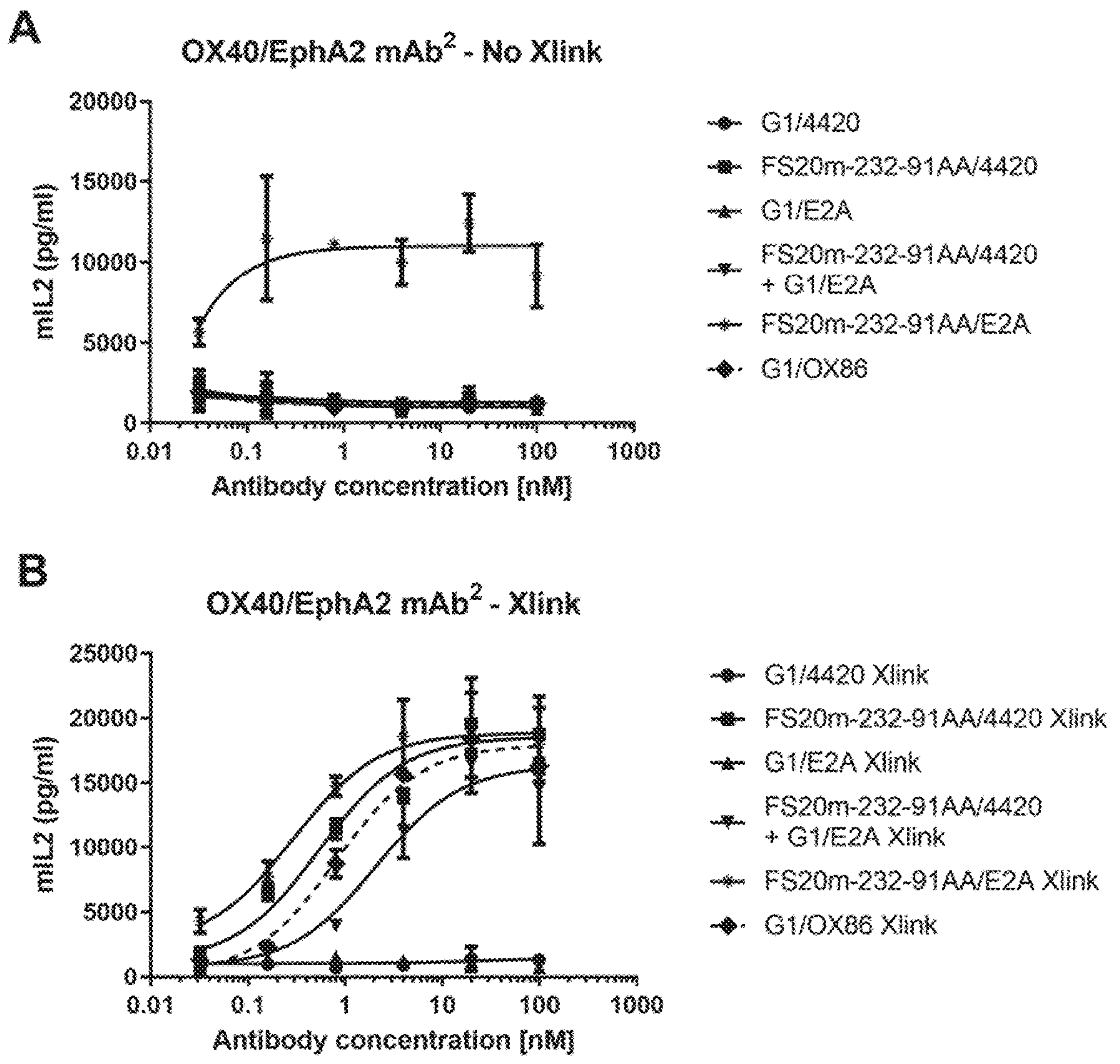
FIG. 6A shows that there was an increase in T cell activation in the presence of EphA2-expressing cells (HPAC) when a $mAb^2$ targeting OX40and EphA2 was present but not when other antibodies targeting OX40 were present but not crosslinked. This indicates that the $mAb^2$ is crosslinked by binding to the two targets, OX40 and EphA2.
FIG. 6B shows that antibodies targeting OX40 activated T cells in the presence of non-physiological crosslinking agents (anti-Fc antibody or FITC-dextran). The anti-EphA2 and anti-FITC antibodies did not induce T cell activation in the presence of crosslinking agents, as expected. The anti-mouse OX40 antibody (G1/OX86) induced some T cell activation when crosslinked by an anti-Fc antibody. The anti-mouse OX40 Fcab when paired with an anti-FITC Fab in a mock $mAb^2$ (FS20m-232-91AA/4420) activated T cells when crosslinked by FITC-dextran with a lower $EC_{50}$ and higher maximum response than the anti-OX40 antibody G1/OX86. The same anti-OX40 Fcab when paired with an anti-EphA2 Fab in a $mAb^2$ (FS20m-232-91AA/E2A) activated T cells in the presence of HPAC cells with a lower $EC_{50}$ and comparable maximum response as compared to the anti-OX40/anti-FITC $mAb^2$.

Table 15 shows T cell activation ($EC_{50}$ values and maximum IL-2 release) by the mAb/$mAb^2$ set out in Table 14 in the presence or absence of crosslinking by either crosslinking agents or HPAC cells. FIG. 6 shows representative plots of IL-2 release for the T cell activation assay.

TABLE 15

T cell activation in the presence of HPAC tumour cells

| Antibody molecule + crosslinking agent (in the presence of HPAC cells) | $EC_{50}$ (nM) | $EC_{50}$ 95% Conf. Int. | Max response (mIL-2 pg/ml) | Max response 95% Conf. Int. |
|---|---|---|---|---|
| No Crosslinking agent | | | | |
| G1/4420 | n/a* | n/a* | n/a* | n/a* |
| FS20m-232-91AA/4420 | n/a* | n/a* | n/a* | n/a* |
| G1/E2A | n/a* | n/a* | n/a* | n/a* |
| FS20m-232-91AA/4420 + G1/E2A | n/a* | n/a* | n/a* | n/a* |
| FS20m-232-91AA/E2A | ~1.845e−005 | n/a* | 11030 | 9159 to 12901 |
| G1/OX86 | n/a* | n/a* | n/a* | n/a* |
| Crosslinking agent | | | | |
| G1/4420 + FITCdex | n/a* | n/a* | n/a* | n/a* |
| FS20m-232-91AA/4420 + FITCdex | 0.5484 | 0.2053 to 1.465 | 18520 | 16257 to 20782 |
| G1/E2A + a-hFc | n/a* | n/a* | n/a* | n/a* |
| FS20m-232-91AA/4420 + G1/E2A + a-hFc + FITCdex | 2.092 | 0.7427 to 5.895 | 16368 | 13537 to 19199 |
| FS20m-232-91AA/E2A + a-hFc | 0.289 | 0.08632 to 0.9675 | 18835 | 16616 to 21054 |
| G1/OX86 + a-hFc | 0.8106 | 0.4725 to 1.39 | 17911 | 16515 to 19308 |

*These mAb/mAb$^2$ did not show any activity in the T cell activation assay.

FIG. 6 shows representative plots of IL-2 release for T cell activation assays containing EphA2-expressing HPAC cells in the presence of various mAbs/mAb$^2$. Six different mAb/mAb$^2$or combinations thereof were tested at increasing concentrations in this assay, labelled according to their human IgG isotype/Fab clone or Fcab/Fab clone name as appropriate (G 1/4420, G 1/E2A, G 1/OX86, FS20m-232-91 AA/4420, FS20m-232-91 AA/4420 +G1/E2A, and FS20m-232-91AA/E2A). The results shown in FIG. 6A demonstrate that there was an increase in the activation of T cells by the FS20m-232-91AA/E2A mAb$^2$ antibody in the presence of the EphA2-expressing HPAC cells. This demonstrates that crosslinking is required for OX40-targeting antibodies to increase T cell activation and that the FS20m-232-91AA/E2A mAb$^2$ antibody is the only molecule that can be crosslinked just by the presence of HPAC (EphA2+) cells and does not require any additional non-physiological cross-linking agents. FIG. 6B shows that there was an increase in the activation of T cells when OX40 was targeted and the anti-OX40 mAbs/mAb$^2$ were crosslinked. These results demonstrate that crosslinking is required for OX40-targeting mAbs/mAb$^2$ to increase T cell activation.

T cell activation observed with the anti-mouse OX40/anti-EphA2 mAb$^2$ (FS20m-232-91AA/E2A) in the presence of HPAC cells expressing EphA2 demonstrates that this receptor can also mediate crosslinking of OX40 when targeted by a mAb$^2$ with binding sites for both EphA2 and OX40.

6.3 Anti-mOX40/Anti-EphA2 mAb$^2$ Suppresses Tumour Growth In Vivo

The CT26 syngeneic tumour model was used in this experiment as CT26 cells express EphA2 and TILs isolated from CT26 tumours include T cells expressing OX40. The anti-mOX40/anti-EphA2 mAb$^2$ antibody (FS20m-232-91AA/E2A) described in Example 6.2 was tested for in vivo activity in a CT26 syngeneic mouse tumour growth model.

The ability of the anti-mOX40/anti-EphA2 mAb$^2$ to inhibit tumour growth was compared to that of the anti-OX40 Fcab in mock mAb$^2$ format (FS20m-232-91AA/4420), the combination of the anti-OX40 Fcab in mock mAb$^2$ format (FS20m-232-91AA/4420) and the anti-EphA2 mAb (G1/E2A), and the anti-FITC mAb (G1/4420) as controls.

BALB/c female mice were injected with CT26 cells, monitored for health and tumour growth, sorted and randomised into study cohorts as described in Example 5. Any mice which did not have tumours at this point were removed from the study.

Figure 7:
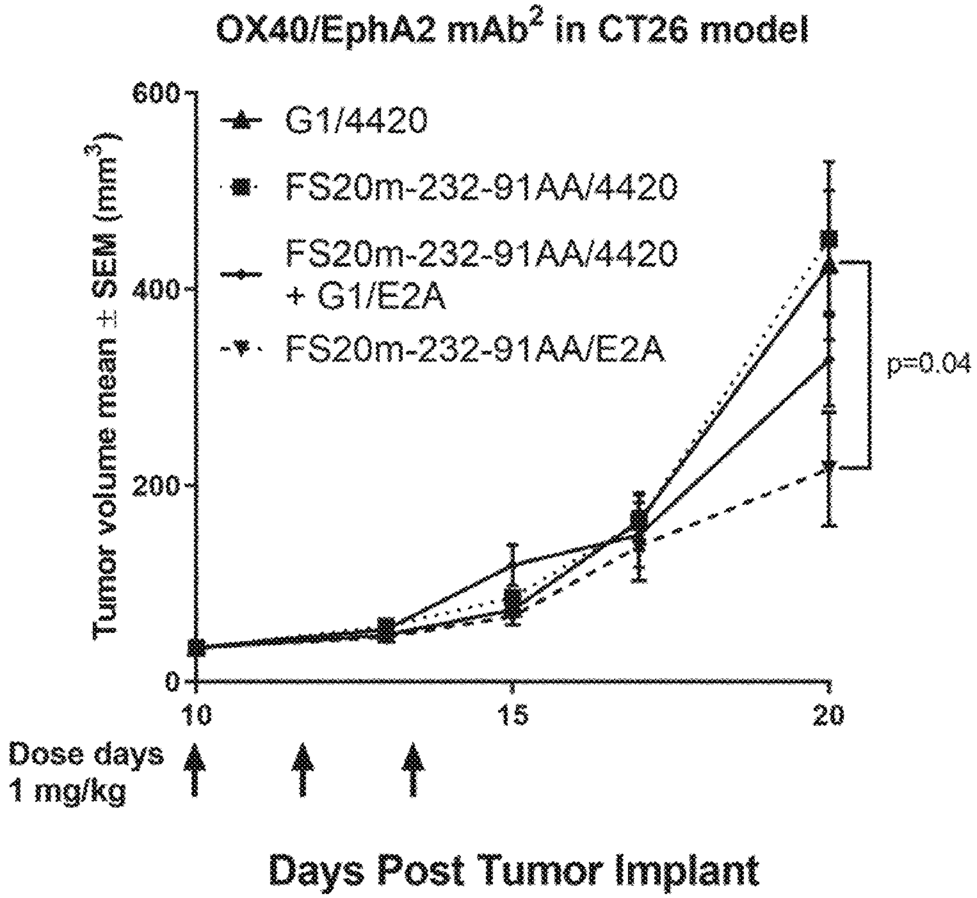
FIG. 7 shows a tumour growth curve of the CT26 syngeneic model in Balb/c mice cohorts treated with G1/4420, FS20m-232-91AA/4420, FS20m-232-91AA/4420+G1/E2A, and FS20m-232-91AA/E2A. The mean tumour volume plus or minus the standard error mean is plotted. The tumour volume on the final day was compared across the different groups using a two-tailed t-test. The group treated with the anti-mOX40/anti-EphA2 $mAb^2$ (FS20m-232-91AA/E2A) showed a statistically significant tumour volume reduction as compared to the group treated with the control antibody (G1/4420).

The mAb$^2$/mAbs were profiled, checked for impurities, prepared, and administered to the mice as described in Example 5. Animals were health screened, tumour measurements were taken and the tumour volumes calculated as described in Example 5. The trial was halted at day 20 when the tumour burden was considered close to restrictions and all mice were humanely sacrificed. The results are shown in FIG. 7. Statistical analysis of the end tumour volumes was performed using a two tailed Student's t-test within the GraphPad Prism software package.

There was a demonstrated statistically significant difference between anti-OX40/anti-EphA2 mAb$^2$ (FS20m-232-91AA/E2A) and anti-FITC mAb (G1/4420) control (normal growth) in suppressing tumour growth. Such a statistically significant difference was not observed with either the combination of FS20m-232-91AA/4420 and G1/E2A or FS20m-232-91AA/4420 and G1/4420 control groups.

Surprisingly, the combination of antibodies targeting OX40 and EphA2 did not significantly suppress tumour growth compared to the IgG1 control (G1/4420) cohort. However, the cohort treated with the anti-mOX40/anti-EphA2 mAb$^2$ (FS20m-232-91AA/E2A) did reveal a significant suppression of growth compared to the IgG1 control. This trial shows that, similar to the observed in vitro results, the crosslinking of OX40 by a mAb$^2$ targeting the EphA2 expressed on the tumour cells and the OX40 expressed on tumour-infiltrating T cells resulted in T cell activation and subsequent tumour growth control above what was observed with the controls.

FIG. 7 shows a tumour growth curve of the CT26 syngeneic model in Balb/c mice cohorts treated with G1/4420, FS20m-232-91AA/4420, FS20m-232-91AA/4420+G1/E2A, and FS20m-232-91AA/E2A. The mean tumour volume plus or minus the standard error mean is plotted and the tumour volume on the final day was compared across the different groups using a two-tailed t-test. The group treated with the anti-mOX40/anti-EphA2 mAb$^2$ antibody (FS20m-232-91AA/E2A) showed a statistically significant tumour volume reduction as compared to the group treated with the control antibody (G1/4420). This result demonstrates that the anti-mOX40/anti-EphA2 $mAb^2$ antibody has a better anti-tumour efficacy in vivo against an EphA2-expressing tumour than the combination of the FS20m-232-91AA/4420 and G1/E2A antibodies, indicating that the in vivo cross-linking of OX40 by the bispecific engagement of OX40 and EphA2 mediated by the anti-mOX40/anti-EphA2 $mAb^2$ is effective in controlling tumour growth.

Example 7 —$mAb^2$ crosslinking through binding to soluble factors Vascular Endothelial Growth Factor (VEGF) is a soluble homodimeric molecule that is expressed in response to hypoxia and binds to receptors on endothelial cells resulting in the formation of new blood vessels, a process termed angiogenesis. The Tumour Micro Environment (TME) is hypoxic and has increased levels of VEGF such that tumour cells are supplied with enough nutrients for their growth. Targeting VEGF using monoclonal antibodies is an established form of anti-tumour therapy. As cell surface expressed TAAs were capable of mediating the crosslinking of OX40-targeting $mAb^2$, crosslinking of OX40 and VEGF targeting $mAb^2$ using soluble VEGF was also tested.

7.1 Human T cell activation assay using $mAb^2$ comprising an anti-human OX40 Fcab and an anti-VEGF Fab A T cell activation assay in the presence or absence of additional VEGF was used to assess clustering and signalling of OX40 in the presence of the antibodies listed in the Table 16 below. The OX40/VEGF $mAb^2$ and OX40/FITC mock $mAb^2$ were prepared with the LALA mutation as described in Example 4.1. In this assay, VEGF acted as a crosslinker for the OX40/VEGF $mAb^2$, which was constructed using the OX40-targeting Fcab FS20-22-49AA and the variable regions of the anti-VEGF antibody bevacizumab (EP1325932B9 clone A4.6.1; indicated by 'Bev' in Tables 16 and 17).

TABLE 16 mAb and $mAb^2$ tested

| $mAb/mAb^2$ | Fab binding to | Fcab binding to | Isotype | LALA mutation | Crosslinker |
|---|---|---|---|---|---|
| G1/4420 | FITC | none | hIgG1 | no | FITC-dextran |
| G1/11D4 | OX40 | none | hIgG1 | no | anti-hCH2 |
| FS20-22-49AA/4420 | FITC | OX40 | hIgG1 | yes | FITC-dextran |
| FS20-22-49AA/Bev | VEGF | OX40 | hIgG1 | yes | none |
| FS20-22-49AA/Bev | VEGF | OX40 | hIgG1 | yes | VEGF |

T cells were isolated and activated as described in Example 5.1.1 above and were used in a protocol essentially the same as the human T cell activation assay described in Example 6.1 using the positive control antibodies and $mAb^2$ described above and crosslinking agents (e.g. soluble VEGF instead of HPAC cells) below. hIL-2 production was determined as previously described. The crosslinking agents (anti-human CH2 mAb clone MK1A6, FITCdex (Sigma) or VEGF (Peprotech, catalogue no. 100-20); see Table 16) were added to the wells in a 1:1 molar ratio with the test mAbs/$mAb^2$ where required.

Figure 8:
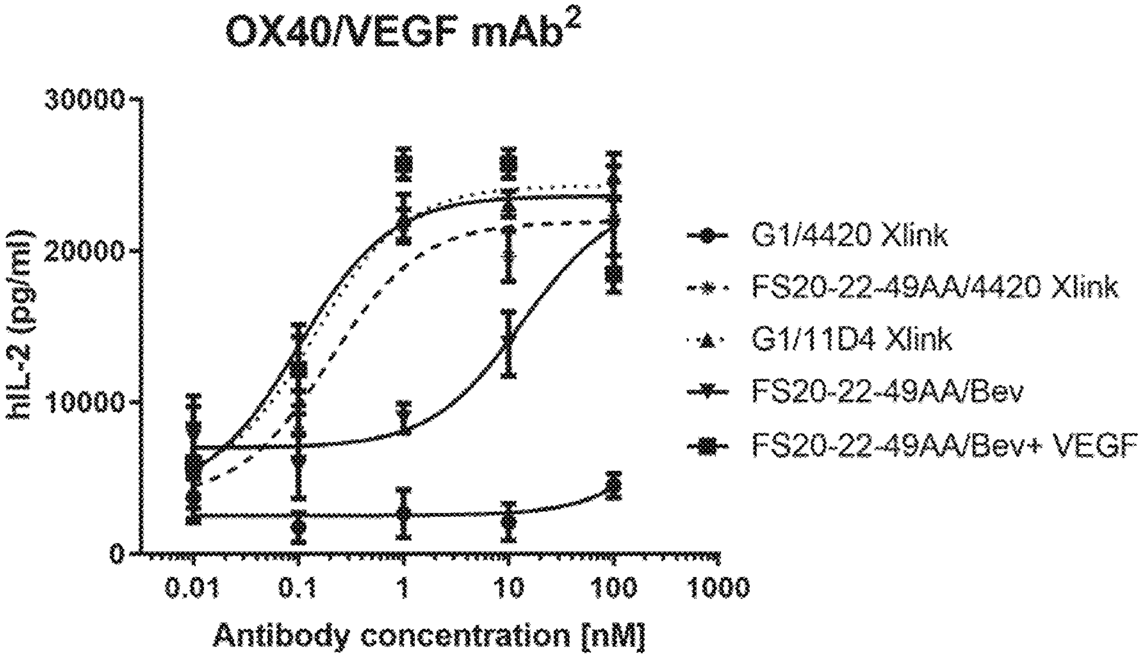
FIG. 8 shows a representative plot of IL-2 release for a T cell activation assay in the presence of soluble VEGF. mAb/$mAb^2$ were tested at increasing concentrations in this assay, labelled according to their Fcab/Fab clone name. The results show that there is a concentration dependent increase in the activation of T cells by OX40-targeting mAb/$mAb^2$ when crosslinked by their crosslinking agents (anti-hCH2, FITC-dextran or VEGF).

Table 17 shows T cell activation ($EC_{50}$ values and maximum IL-2 release) by the mAb/$mAb^2$ set out in Table 16 in the presence or absence of crosslinking with crosslinking agents. FIG. 8 shows plots of IL-2 release for the T cell activation assay.

TABLE 17

T cell activation in the presence of VEGF

| mAbs/$mAb^2$ | $EC_{50}$ (nM) | $EC_{50}$ 95% Conf. Int. | Max reponse (mIL-2 pg/ml) | Max response 95% Conf. Int. |
|---|---|---|---|---|
| G1/4420 Xlink | n/a* | n/a* | n/a* | n/a* |
| G1/11D4 Xlink | 0.199 | 0.05607 to 0.7086 | 21948 | 18767 to 25285 |
| FS20-22-49AA/4420 Xlink | 0.1411 | 0.06534 to 0.3228 | 24306 | 22497 to 26178 |
| FS20-22-49AA/Bev | 13.5 | 3.555 to 67.68 | 23557 | 19000 to 32457 |
| FS20-22-49AA/Bev + VEGF | 0.1008 | 0.00377 to 0.5848 | 23638 | 19259 to 28181 |

*This control mAb did not show any activity in the T cell activation assay in the absence of cross-linking.

FIG. 8 shows that there is an increase in the activation of T cells when OX40 is targeted and the anti-OX40 mAb/$mAb^2$ are crosslinked. No T cell activation was observed with the crosslinked anti-FITC antibody G1/4420, as expected. The OX40-targeting mAb G1/11 D4 when crosslinked by the anti-human CH2 antibody induced T cell activation. The OX40-targeting Fcab in the mock $mAb^2$ (4420 LALA) format, FS20-22-49AA/4420, had agonistic activity in the presence of the crosslinker FITC-dextran which binds to the Fab arms of the mock $mAb^2$. When the OX40-targeting Fcab was paired with the anti-VEGF Fab bevacizumab, the $mAb^2$ antibody had some agonistic activity in the absence of crosslinking that is likely to be the product of the agonist activity in the absence of crosslinking observed with the anti-OX40 Fcab FS20-22-49. When VEGF was added to the OX40/bevacizumab $mAb^2$ antibody, the agonist activity increased as demonstrated by an approximately 100-fold reduction in the $EC_5o$, indicating that the anti-VEGF Fab is capable of crosslinking the $mAb^2$ in the presence of VEGF.

The T cell activation observed with the anti-hOX40/anti-VEGF $mAb^2$ demonstrates that soluble factors can be used as crosslinking agents.

7.2 Mouse T Cell Activation Assay Using $mAb^2$ Comprising an Anti-Mouse OX40 Fcab and Anti-VEGF Fab A T cell activation assay was used to assess clustering and signalling of OX40 in the presence of the mAbs/$mAb^2$ listed in Table 18 below. The anti-mouse OX40 Fcab FS20m-232-

91 was paired with the Fab region of the anti-VEGF mAb R84 (Patent Publication No. US 2009/0175791 A1) and all $mAb^2$ were prepared with the LALA mutation as described in Example 4.1. In this assay, VEGF acted as a crosslinker for the $mAb^2$ that binds to mouse OX40 and VEGF.

TABLE 18 mAb and $mAb^2$ tested

| $mAb/mAb^2$ | Fab binding to | Fcab binding to | Isotype | LALA mutation | Crosslinker |
|---|---|---|---|---|---|
| G1/4420 Xlink | FITC | none | hIgG1 | no | FITC-dextran |
| G1/R84 Xlink | VEGF | none | hIgG1 | no | VEGF |
| G1/OX86 Xlink | OX40 | none | hIgG1 | no | anti-hFC |
| FS20m-232-91AA/4420 | FITC | OX40 | hIgG1 | yes | none |
| FS20m-232-91AA/4420 Xlink | FITC | OX40 | hIgG1 | yes | FITC-dextran |
| FS20m-232-91AA/R84 | VEGF | OX40 | hIgG1 | yes | none |
| FS20m-232-91AA/R84 | VEGF | OX40 | hIgG1 | yes | VEGF |

Mouse T cells were isolated and activated as described in Example 5.2.1 and were used in a protocol essentially the same as in Example 7.1 but using the positive control antibodies and mAb2 described above and crosslinking agents as described below. mIL-2 production was determined as previously described.

The crosslinking agents (anti-human CH2 mAb clone MK1A6, FITCdex, (Sigma) or VEGF (Peprotech, catalogue no. 100-20); see Table 18) were added to the wells in a 1:1 molar ratio with the test antibodies where required.

Figure 9:
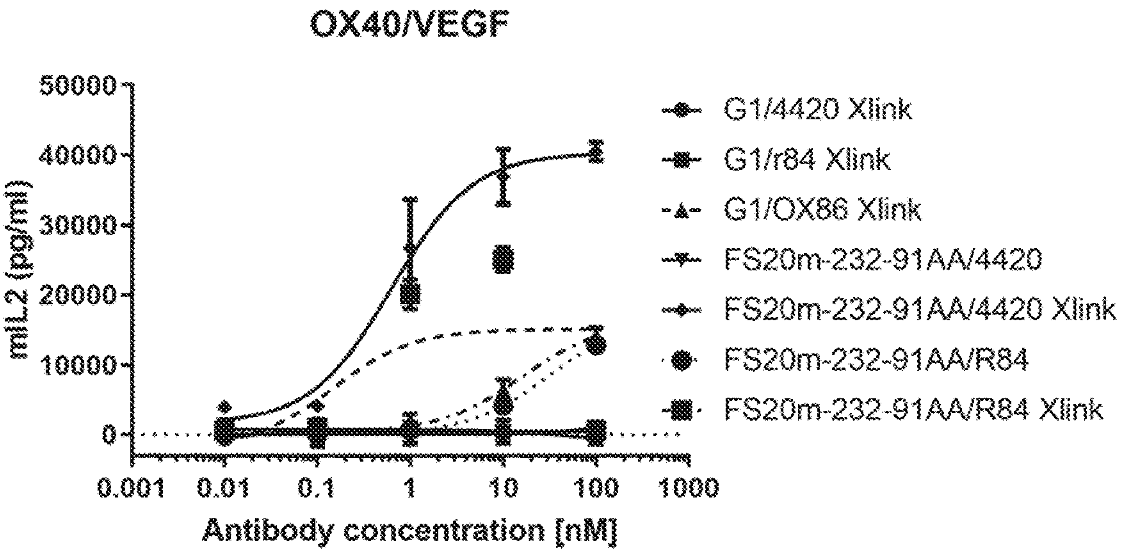
FIG. 9 shows representative plots of IL-2 release for T cell activation assays in the presence of various mAb/$mAb^2$. Five different mAb/$mAb^2$were tested at increasing concentrations in this assay, labelled according to their Fcab/Fab clone name (G1/4420, G1/R84, G1/OX86, FS20m-232-91AA/4420, and FS20m-232-91AA/R84). The results show that there is an increase in the activation of T cells by the anti-mouse OX40/anti-VEGF $mAb^2$ (FS20m-232-91AA/R84) in the presence of VEGF. This result demonstrates that crosslinking is required for OX40-targeting antibodies to increase the activation of T cells and that the anti-OX40/anti-VEGF $mAb^2$ can be crosslinked by the Fab target VEGF.

Table 19 shows the $EC_{50}$ values and maximum response of the IL-2 release observed in the T cell activation assay in the presence of the $mAb^2$ and mAbs tested. FIG. 9 shows a representative plot of IL2 release for the T cell activation assay.

TABLE 19

T cell activation in the presence of VEGF.

| $mAbs/mAb^2$ + crosslinking agent | $EC_{50}$ (nM) | $EC_{50}$ 95% Conf. Int. | Max response (mIL-2 pg/ml) | Max response 95% Conf. Int. |
|---|---|---|---|---|
| G1/4420 Xlink | n/a* | n/a* | n/a* | n/a* |
| G1/R84 Xlink | n/a* | n/a* | n/a* | n/a* |
| G1/OX86 Xlink | 15.6 | 8.841 to 29.38 | 16168 | 13952 to 18978 |
| FS20m-232-91AA/4420 | n/a* | n/a* | n/a* | n/a* |
| FS20m-232-91AA/4420 Xlink | 0.629 | 0.2852 to 1.364 | 40278 | 35633 to 45137 |
| FS20m-232-91AA/R84 | 29.94 | 17.47 to 62.67 | 16707 | 14234 to 21305 |
| FS20m-232-91AA/R84 Xlink | 0.1437 | n/a* | 15148 | 4739 to 26770 |

*This control mAb did not show any activity in the T cell activation assay in the absence of cross-linking.

FIG. 9 shows that there is an increase in the activation of T cells in the presence of VEGF when a $mAb^2$ targeting OX40 and the VEGF soluble factor is present but not when other $mAb^2$ targeting OX40 are present but not crosslinked. This indicates that the $mAb^2$ is crosslinked by binding to OX40 and VEGF. FIG. 9 shows that $mAb/mAb^2$ targeting OX40 activate T cells in the presence of non-physiological crosslinking agents (anti-Fc antibody or FITC-dextran). The anti-VEGF and anti-FITC control antibodies did not induce T cell activation in the presence of crosslinking agents, as expected. The anti-mouse OX40 antibody induced some T cell activation when crosslinked by an anti-Fc antibody (G1/OX86 Xlink) (see Table 19). The anti-OX40 Fcab when paired with an anti-FITC Fab in a $mAb^2$ activated T cells when crosslinked by FITC-dextran (FS20m-232-91AA/4420 Xlink) with a lower $EC_{50}$ and higher maximum response than the OX40 antibody G1/OX86. The same anti-OX40 Fcab when paired with an anti-VEGF Fab in a $mAb^2$ (FS20m-232-91AA/R84) activated T cells in the absence of additional crosslinking agents, likely due to the production of VEGF by activated T cells. The addition of VEGF increased T cell activation by the anti-OX40/anti-VEGF $mAb^2$ (FS20m-232-91AA/R84) as observed by a lower $EC_{50}$ and comparable maximum response as compared with the anti-OX40/anti-VEGF $mAb^2$ antibody in the absence of additional VEGF.

T cell activation observed with the anti-mOX40/anti-VEGF $mAb^2$ in the presence of VEGF demonstrates that soluble factors can also mediate crosslinking of OX40, such as when targeted by a $mAb^2$ which binds to VEGF and OX40.

7.3 Anti-mOX40/anti-VEGF $mAb^2$ suppresses tumour growth in vivo

The anti-mOX40/anti-VEGF $mAb^2$ antibody (FS20m-232-91AA/R84) described in Example 7.2 was tested for in vivo activity in a CT26 syngeneic mouse tumour growth model.

The CT26 syngeneic tumour model was used in this experiment, as CT26 tumours have been described to have an increased concentration of VEGF (Voron et al., 2015) and TILs isolated from CT26 tumours include T cells expressing OX40.

The ability of the anti-mOX40/anti-VEGF $mAb^2$ to inhibit tumour growth was compared to that of mAb G1/4420, the combination of FS20m-232-91AA/4420 and mAb G1/R84, and mAb G1/R84 as controls.

BALB/c female mice were injected with CT26 cells, monitored for health and tumour growth, sorted and randomised into study cohorts as described in Example 5. Any mice which did not have tumours at this point were removed from the study.

Figure 10:
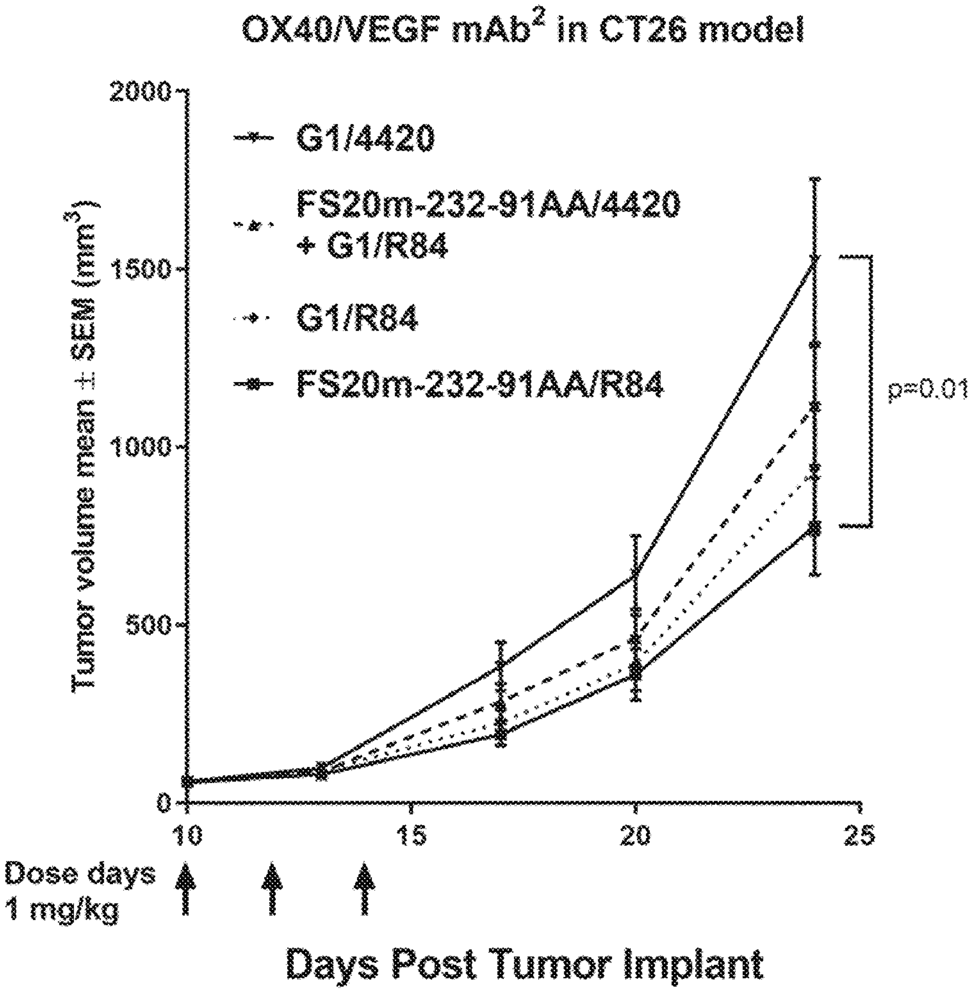
FIG. 10 shows a tumour growth curve of the CT26 syngeneic model in Balb/c mice cohorts treated with G1/4420, G1/R84, FS20m-232-91AA/4420+G1/R84, and FS20m-232-91AA/R84. The mean tumour volume plus or minus the standard error mean is plotted and the tumour volume on the final day was compared across the different groups using a two-tailed t-test. The anti-mOX40/anti-VEGF $mAb^2$ antibody treated group showed a statistically significant tumour volume reduction as compared to the control antibody none/FITC treated group. This result demonstrates that the anti-mOX40/anti-VEGF $mAb^2$ antibody has a better anti-tumour efficacy in vivo against tumours described to have an increased VEGF concentration in its microenvironment than the combination of the OX40 Fcab in mock $mAb^2$-format and VEGF antibodies, indicating that the in vivo crosslinking of OX40 by the bispecific engagement of OX40 and VEGF mediated by the anti-mOX40/anti-VEGF $mAb^2$ is effective in controlling tumour growth.

The $mAb^2$/mAb were profiled, checked for impurities, prepared, and administered to the mice as described in Example 5. Animals were health screened, tumour measurements were taken and the tumour volumes calculated as described in Example 5. The trial was halted at day 24 when the tumour burden was considered close to restrictions and all mice were humanely sacrificed. The results are shown in FIG. 10. Statistical analysis of the end tumour volumes was performed using a two tailed Student's t-test within the GraphPad Prism software package.

There was a demonstrated statistically significant difference between anti-mOX40/anti-VEGF mAb$^2$ (FS20m-232-91AA/R84) and anti-FITC mAb G1/4420 control (normal growth) in suppressing tumour growth. Such a statistically significant difference was not observed with either the combination of FS20m-232-91AA/4420 and no FS20m-232-91AA/R84 control or anti-VEGF mAb G1/R84 control versus the G1/4420 control.

The CT26 tumour model is an aggressive, fast growing tumour model. Surprisingly, the combination of antibodies targeting OX40 and VEGF did not significantly suppress tumour growth compared to the IgG1 control (G1/4420) cohort. However, the cohort treated with the anti-mOX40/VEGF mAb$^2$ (FS20m-232-91AA/R84) did reveal a significant suppression of growth compared to the IgG1 control. This trial shows that, similar to the observed in vitro results, the crosslinking of OX40 by a mAb$^2$ targeting the VEGF overexpressed by tumour cells or within or at the tumour microenvironment and the OX40 expressed on tumour-infiltrating T cells resulted in T cell activation and subsequent tumour growth control above what was observed with controls.

Example 8 —mAb$^2$ Crosslinking Through Binding to Co-Expressed Receptors

OX40 expression on tumour-infiltrating T cells is likely to be accompanied by expression of other receptors, both co-stimulatory receptors and immune checkpoint receptors. Using these co-expressed receptors as the Fab targets in OX40-Fcab containing mAb$^2$ may also serve to crosslink the mAb2 resulting in clustering of OX40, as well as the Fab target, causing activation of both receptors. In order to test this concept, the following T cell activation assays were performed.

8.1 Human T Cell Activation Assay Using mAb$^2$ Comprising an Anti-Human OX40 Fcab Paired with Anti-ICOS, Anti-CD27 or Anti-GITR Fabs In this assay, co-expression of human OX40 and the co-stimulatory molecules ICOS, CD27 and GITR was utilised to determine crosslinking of the mAbs/mAb$^2$ set out in Table 20 below. The mAb$^2$ were prepared with the LALA mutation using the variable regions of the anti-FITC antibody 4420 (SEQ ID NOs 167, 168 and 156), anti-OX40 antibody 11 D4 (EP 2 242 771 B1), anti-ICOS antibody ICOSj (US 2016/0304610 A1), anti-CD27 antibody 695 (US 2013/0243795 A1) or anti-GITR antibody 6C8 (U.S. Pat. No. 7,812,135 B2) in the same way as described in Example 4.1.

TABLE 20 mAbs and mAb$^2$ tested

| mAb/mAb$^2$ | Fab binding to | Fcab binding to | Isotype | LALA mutation | Crosslinker |
|---|---|---|---|---|---|
| G1/4420 | FITC | none | hIgG1 | no | FITC-dextran |
| G1/11D4 | OX40 | none | hIgG1 | yes | anti-hCH2 |
| G1AA/ICOSj | ICOS | none | hIgG1 | no | anti-hCH2 |
| G1AA/695 | CD27 | none | hIgG1 | yes | anti-hCH2 |
| G1AA/6C8 | GITR | none | hIgG1 | yes | anti-hCH2 |
| FS20-22-49AA/4420 | FITC | OX40 | hIgG1 | yes | none |
| FS20-22-49AA/4420 Xlink | FITC | OX40 | hIgG1 | yes | FITC-dextran |
| FS20-22-49AA/ICOSj | ICOS | OX40 | hIgG1 | yes | none |
| FS20-22-49AA/695 | CD27 | OX40 | hIgG1 | yes | none |
| FS20-22-49AA/6C8 | GITR | OX40 | hIgG1 | yes | none |

T cells were isolated and activated as described in Example 5.1.1 above and were used in a protocol essentially the same as the human T cell activation assay described in Example 6.1 using the positive control antibodies and mAb2 described above and crosslinking agents below. Human IL-2 production was determined as previously described.

The crosslinking agents (anti-human CH2 mAb clone MK1A6 or FITC-dextran (Sigma); see Table 20) were added to the wells in a 1:1 molar ratio with the test mAbs/mAb$^2$ where required.

Figure 11:
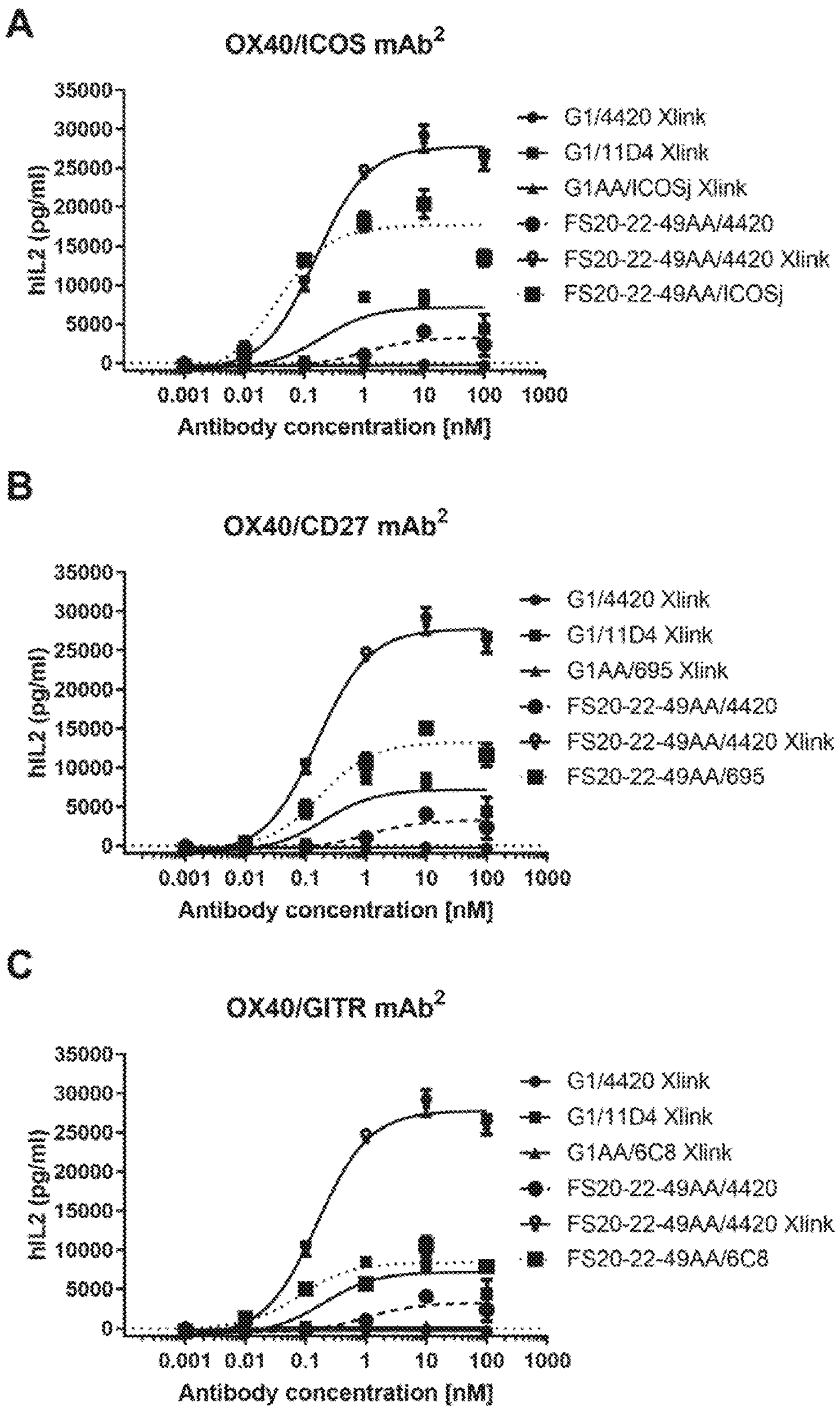
FIG. 11A to C show representative plots of IL-2 release for a T cell activation assay. Antibodies were used at increasing concentrations in this assay, labelled according to their Fcab/Fab clone name. The results show that there is a concentration dependent increase in the activation of T cells by OX40-targeting antibodies when crosslinked by their crosslinking agents (anti-hCH2; FITC-dextran) and that the anti-OX40/anti-ICOS $mAb^2$ (FS20-22-49AA/ICOSj), anti-OX40/anti-CD27 $mAb^2$ (FS20-22-49AA/695) and anti-OX40/anti-GITR $mAb^2$ (FS20-22-49AA/6C8) all have agonistic activity in the absence of additional crosslinking agents which is superior to that of the non-crosslinked anti-OX40 Fcab in mock $mAb^2$ format (FS20-22-49AA/4420).

Table 21 shows the $EC_{50}$ values and maximum response of the IL-2 release observed in the T cell activation assay in the presence or absence of crosslinking with crosslinking agents. FIG. 11 shows plots of IL-2 release for the T cell activation assay.

TABLE 21

T cell activation in the presence of co-expressed receptors

| mAbs/mAb$^2$ | $EC_{50}$ (nM) | $EC_{50}$ 95% Conf. Int. | Max reponse (mIL-2 pg/ml) | Max response 95% Conf. Int. |
|---|---|---|---|---|
| G1/4420 Xlink | n/a* | n/a* | n/a* | n/a* |
| G1/11D4 Xlink | 0.1964 | 0.03569 to 0.8802 | 7203 | 5010 to 9491 |
| G1AA/ICOSj Xlink | n/a* | n/a* | n/a* | n/a* |

TABLE 21-continued

T cell activation in the presence of co-expressed receptors

| mAbs/mAb$^2$ | $EC_{50}$ (nM) | $EC_{50}$ 95% Conf. Int. | Max reponse (mIL-2 pg/ml) | Max response 95% Conf. Int. |
|---|---|---|---|---|
| G1AA/695 Xlink | n/a* | n/a* | n/a* | n/a* |
| G1AA/6C8 Xlink | n/a* | n/a* | n/a* | n/a* |
| FS20-22-49AA/4420 | 1.043 | 0.1675 to 4.52 | 3282 | 2193 to 4454 |
| FS20-22-49AA/4420 Xlink | 0.1548 | 0.1084 to 0.2238 | 27771 | 26319 to 29246 |
| FS20-22-49AA/ICOSj | 0.03581 | 0.01229 to 0.1019 | 17662 | 15176 to 20226 |
| FS20-22-49AA/695 | 0.1759 | 0.07543 to 0.4395 | 13249 | 11680 to 14898 |
| FS20-22-49AA/6C8 | 0.07958 | 0.0119 to 0.9973 | 8416 | 6787 to 10374 |

*These control mAb did not show any activity in the T cell activation assay in the absence of cross-linking FIG. 11 shows that there is an increase in the activation of T cells when OX40 is targeted and the anti-OX40 antibodies are crosslinked. No T cell activation was observed with the crosslinked anti-FITC antibody G1/4420 or with the cross-linked anti-ICOS, anti-CD27 or anti-GITR antibodies (G1AA/ICOSj, G1AA/695 or G1AA/6C8, respectively), as expected. The OX40-targeting mAb G1/11 D4 when cross-linked by an anti-human CH2 antibody induced T cell activation, as seen before. The OX40-targeting Fcab in the mock mAb$^2$ (4420 LALA) format, FS20-22-49AA/4420, had agonistic activity in the absence of crosslinking, as seen before, and this activity was enhanced with the addition of the crosslinker FITC-dextran which binds to the Fab arms. When the OX40-targeting Fcab was paired with anti-ICOS, anti-CD27 or anti-GITR Fabs (ICOSj, 695 or 6C8, respectively), the agonistic activity of the Fcab was increased, indicating that the mAb$^2$ was being crosslinked by binding to the co-expressed receptors on the T cell surface.

T cell activation observed with the anti-OX40/anti-ICOS, anti-OX40/anti-CD27 and anti-OX40/anti-GITR mAb$^2$ antibodies demonstrates that receptors that are co-expressed with human OX40 on the T cell surface can be used as crosslinking agents.

8.2 Human T Cell Activation Assay Using mAb$^2$ Comprising an Anti-Human OX40 Fcab and Anti-PD1 Fab In this assay, co-expression of human OX40 and PD1 was utilised to determine crosslinking of the mAbs/mAb$^2$ set out in Table 22 below. The mAb$^2$ were prepared with the LALA mutation using the variable regions of the anti-FITC antibody 4420 (SEQ ID NOs 167 and 156), anti-PD1 antibody 5C4 (U.S. Pat. No. 8,008,449 B2) or anti-OX40 antibody 11 D4 (EP 2 242 7711B1) in the same way as described in Example 4.1.

TABLE 22 mAbs and mAb$^2$ tested

| mAb/mAb$^2$ | Fab binding to | Fcab binding to | Isotype | LALA mutation | Crosslinker |
|---|---|---|---|---|---|
| G1/4420 | FITC | none | hIgG1 | No | FITC-dextran |
| G1AA/5C4 | PD1 | none | hIgG1 | Yes | anti-hCH2 |
| G1/11D4 | OX40 | none | hIgG1 | No | anti-hCH2 |
| FS20-22-49AA/4420 | FITC | OX40 | hIgG1 | Yes | None |
| FS20-22-49AA/4420 | FITC | OX40 | hIgG1 | Yes | FITC-dextran |
| FS20-22-49AA/5C4 | PD1 | OX40 | hIgG1 | Yes | None |

T cells were isolated and activated as described in Example 5.1.1 above and were used in a protocol essentially the same as in Example 8.1 but using the positive control antibodies and mAb2 described above and crosslinking agents as described below. hIL-2 production was determined as previously described.

The crosslinking agents (anti-human CH2 mAb clone MK1A6 or FITCdex (Sigma); see Table 22) were added to the wells in a 1:1 molar ratio with the test mAbs/mAb$^2$ where required.

Figure 12:
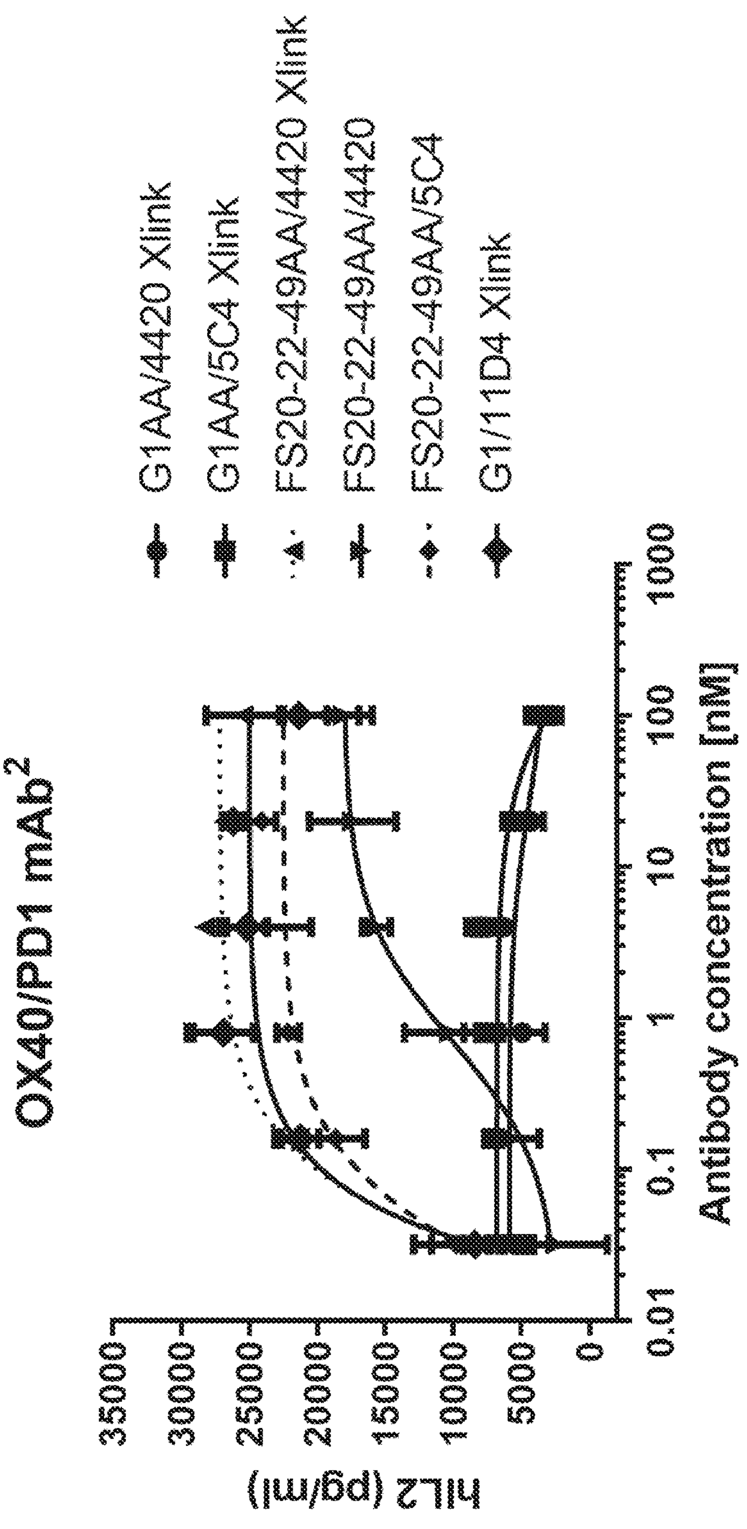
FIG. 12 shows a representative plot of IL-2 release for a T cell activation assay. Antibodies were used at increasing concentrations in this assay, labelled according to their Fcab/Fab clone name. The results show that there is a concentration dependent increase in the activation of T cells by OX40-targeting antibodies when crosslinked by their crosslinking agents (anti-hCH2; FITC-dextran) and that the anti-OX40/anti-PD1 $mAb^2$ (FS20-22-49AA/5C4) without additional crosslinking agents has agonistic activity that is comparable to that of the crosslinked anti-OX40 Fcab (FS20-22-49AA/4420 Xlink).

Table 23 shows the $EC_{50}$ values and maximum response of the IL-2 release observed in the T cell activation assay in the presence or absence of crosslinking with crosslinking agents. FIG. 12 shows plots of IL-2 release for the T cell activation assay.

TABLE 23

T cell activation assay with mAb$^2$ targeting co-expressed receptors

| mAbs/mAb$^2$ | $EC_{50}$ (nM) | $EC_{50}$ 95% Conf. Int. | Max reponse (mIL-2 pg/ml) | Max response 95% Conf. Int. |
|---|---|---|---|---|
| G1AA/4420 Xlink | n/a* | n/a* | n/a* | n/a* |
| G1AA/5C4 Xlink | n/a* | n/a* | n/a* | n/a* |
| G1/11D4 Xlink | ~0.0001527 | (Very wide) | 25002 | 22891 to 27113 |

TABLE 23-continued

| T cell activation assay with $mAb^2$ targeting co-expressed receptors | | | | |
|---|---|---|---|---|
| $mAbs/mAb^2$ | $EC_{50}$ (nM) | $EC_{50}$ 95% Conf. Int. | Max reponse (mIL-2 pg/ml) | Max response 95% Conf. Int. |
| FS20-22-49AA/4420 | 0.7115 | 0.2329 to 2.174 | 18067 | 15564 to 20571 |
| FS20-22-49AA/4420 Xlink | 0.0138 | 0.0005459 to 0.3489 | 27163 | 25553 to 28774 |
| FS20-22-49AA/PD1 | 0.01948 | 0.0001145 to 3.314 | 22516 | 20071 to 24962 |

*These control mAb did not show any activity in the T cell activation assay in the absence of cross-linking FIG. 12 shows that there is an increase in the activation of T cells when OX40 is targeted and the anti-OX40 antibodies are crosslinked. No T cell activation was observed with the crosslinked anti-FITC antibody G1/4420 or with the crosslinked anti-PD1 antibody G1AA/5C4, as expected. The OX40-targeting mAb G1/11 D4 when crosslinked by an anti-human CH2 antibody induced T cell activation as seen before. The OX40-targeting Fcab in the mock $mAb^2$ (4420 LALA) format, FS20-22-49AA/4420, had agonistic activity in the absence of crosslinking, as seen before, and this activity was enhanced with the addition of the crosslinker FITC-dextran which binds to the Fab arms of the $mAb^2$. When the OX40-targeting Fcab was paired with an anti-PD1 Fab (5C4), the agonistic activity of the Fcab was increased, indicating that the $mAb^2$ was being crosslinked by binding to the co-expressed receptor PD1 on the T cell surface.

The T cell activation observed with the anti-OX40/anti-PD1 $mAb^2$ antibody demonstrates that Fab binding sites specific for receptors that are co-expressed with human OX40 on the T cell surface can be used as crosslinking agents.

8.3 Human T Cell Activation Assay Using $mAb^2$ Comprising an Anti-Human OX40 Fcab and an Anti-LAG3 Fab In this assay, co-expression of human OX40 and LAG-3 was utilised to determine crosslinking of the $mAb/mAb^2$ set out in Table 24 below. The $mAb^2$ were prepared with the LALA mutation as described in Example 4.1.

TABLE 24

| mAbs and $mAb^2$ tested | | | | | |
|---|---|---|---|---|---|
| $mAb/mAb^2$ | Fab binding to | Fcab binding to | Isotype | LALA mutation | Crosslinker |
| G1/4420 | FITC | none | hIgG1 | no | FITC-dextran |
| G1/25F7 | LAG3 | none | hIgG1 | yes | anti-hCH2 |
| G1/11D4 | OX40 | none | hIgG1 | no | anti-hCH2 |
| FS20-22-41AA/4420 | FITC | OX40 | hIgG1 | yes | none |
| FS20-22-41AA/4420 | FITC | OX40 | hIgG1 | yes | FITC-dextran |
| FS20-22-41AA/25F7 | LAG3 | OX40 | hIgG1 | yes | none |

T cells were isolated and activated as described in Example 5.1.1 above and were used in a protocol essentially the same as in Example 8.1 but using the positive control antibodies and mAb2 described above and crosslinking agents as described below. hIL-2 production was determined as previously described.

The crosslinking agents (anti-human CH2 mAb clone MK1A6 or FITC-dextran (Sigma); see Table 24) were added to the wells in a 1:1 molar ratio with the test $mAbs/mAb^2$ where required.

TABLE 25

| T cell activation in the presence of co-expressed receptor LAG3 | | | | |
|---|---|---|---|---|
| $mAbs/mAb^2$ | $EC_{50}$ (nM) | $EC_{50}$ 95% Conf. Int. | Max reponse (mIL-2 pg/ml) | Max response 95% Conf. Int. |
| G1AA/4420 Xlink | n/a* | n/a* | n/a* | n/a* |
| G1/25F7 Xlink | n/a* | n/a* | n/a* | n/a* |
| G1/11D4 Xlink | 0.1403 | 0.06368 to 0.309 | 24527 | 22115 to 26938 |
| FS20-22-41AA/4420 | 19.46 | 14.2 to 26.66 | 20329 | 18615 to 22042 |
| FS20-22-41AA/4420 Xlink | 0.4598 | 0.3249 to 0.6506 | 25551 | 24247 to 26856 |
| FS20-22-41AA/25F7 | 1.066 | 0.186 to 6.104 | 18751 | 14193 to 23310 |

Figure 13:
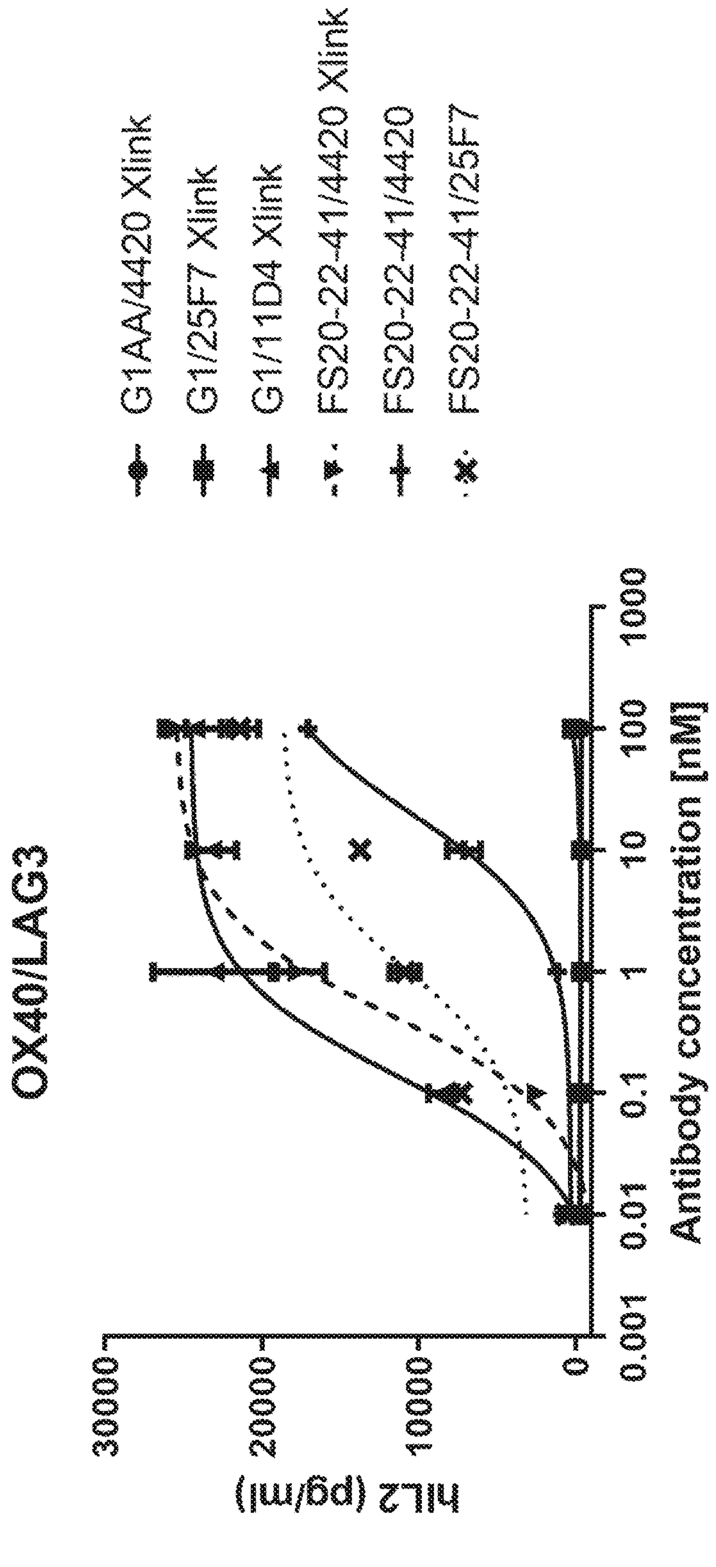
FIG. 13 shows a representative plot of IL-2 release for a T cell activation assay. Antibodies were used at increasing concentrations in this assay, labelled according to their Fcab/Fab clone name. The results show that there is a concentration dependent increase in the activation of T cells by OX40-targeting antibodies when crosslinked by their crosslinking agents (anti-hCH2; FITC-dextran) and that the anti-OX40/anti-LAG3 $mAb^2$ (FS20-22-41AA/25F7) without additional crosslinking agents has agonistic activity that is comparable to that of the crosslinked anti-OX40 Fcab (FS20-22-41AA/4420 Xlink).

*These control mAb did not show any activity in the T cell activation assay in the absence of cross-linking FIG. 13 shows that there is an increase in the activation of T cells when OX40 is targeted and the anti-OX40 antibodies are crosslinked. No T cell activation was observed with the crosslinked anti-FITC antibody G1/4420 or with the crosslinked anti-LAG3 antibody G1/25F7, as expected. The OX40-targeting mAb G1/11 D4 when cross-linked by an anti-human CH2 antibody induces T cell activation as seen before. The OX40-targeting Fcab in the mock $mAb^2$ (4420 LALA) format, FS20-22-41AA/4420, had agonistic activity in the absence of crosslinking, as seen before, and this activity is enhanced with the addition of the crosslinker FITC-dextran which binds to the Fab arms of the $mAb^2$. When the OX40-targeting Fcab was paired with an anti-LAG3 Fab (25F7) the agonistic activity of the Fcab was increased, indicating that the $mAb^2$ was being crosslinked by binding to the co-expressed receptors on the T cell surface.

T cell activation observed with the anti-OX40/anti-LAG3 $mAb^2$ antibody demonstrates that Fab binding sites specific for receptors that are co-expressed with human OX40 on the T cell surface can be used as crosslinking agents.

8.4 Mouse T Cell Activation Assay Using $mAb^2$ Comprising the Anti-Mouse OX40 Fcab and an Anti-LAG3 Fab In this assay, co-expression of mouse OX40 and LAG3 receptors was utilised to determine crosslinking of the bispecific antibodies set out in Table 26. The $mAb^2$ were prepared with the LALA mutation as described in Example 4.1.

TABLE 26

| mAb and $mAb^2$ tested | | | | | |
|---|---|---|---|---|---|
| $mAb/mAb^2$ | Fab binding to | Fcab binding to | Isotype | LALA mutation | Crosslinker |
| G1/4420 | FITC | none | hIgG1 | no | FITC-dextran |
| G1/C9B7W | LAG3 | none | hIgG1 | no | anti-hCH2 |
| G1/OX86 | OX40 | none | hIgG1 | no | anti-hCH2 |
| FS20m-232-91AA/4420 | FITC | OX40 | hIgG1 | yes | none |
| FS20m-232-91AA/4420 | FITC | OX40 | hIgG1 | yes | FITC-dextran |
| FS20m-232-91AA/C9B7W | LAG3 | OX40 | hIgG1 | yes | none |

Mouse T cells were isolated and activated as described in Example 5.2.1 and were used in a protocol essentially the same as in Example 8.3 but using the positive control antibodies and mAb2 described above and crosslinking agents as described below. mIL-2 production was determined as previously described.

The crosslinking agents (anti-human CH2 mAb clone MK1A6 or FITC-dextran (Sigma); see Table 26) were added to the wells in a 1:1 molar ratio with the test $mAb/mAb^2$ where needed.

Figure 14:
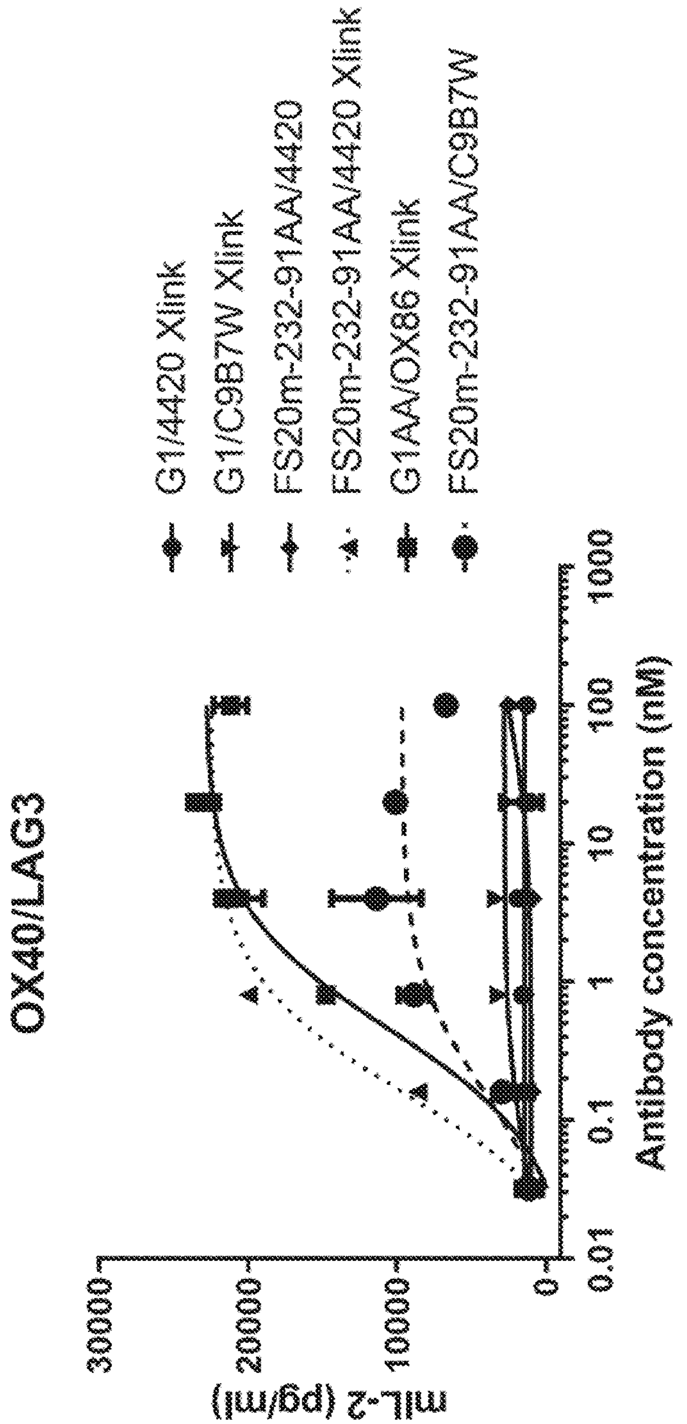
FIG. 14 shows a representative plot of IL-2 release for a T cell activation assay. Antibodies were used at increasing concentrations in this assay, labelled according to their Fcab/Fab clone name. The results show that there is a concentration dependent increase in the activation of T cells by OX40-targeting antibodies when crosslinked by their crosslinking agents (anti-hCH2; FITC-dextran) and that the anti-OX40/anti-LAG3 $mAb^2$ (FS20m-232-91AA/C9B7W) without additional crosslinking agents has agonistic activity that is higher than that of the non-crosslinked anti-OX40 Fcab (FS20m-232-91AA/4420). This indicates that the LAG3 binding Fab crosslinks the anti-OX40 Fcab and activates the T cells.

Table 27 shows the $EC_{50}$ values and maximum response of the IL-2 release observed in the T cell activation assay in the presence of the $mAb^2$ and mAbs tested. FIG. 14 shows a representative plot of IL2 release for the T cell activation assay.

TABLE 27

| T cell activation in the presence of LAG3 | | | | |
|---|---|---|---|---|
| $mAbs/mAb^2$ | $EC_{50}$ (nM) | $EC_{50}$ 95% Conf. Int. | Max reponse (mIL-2 pg/ml) | Max response 95% Conf. Int. |
| G1/4420 Xlink | n/a* | n/a* | n/a* | n/a* |
| G1AA/OX86 Xlink | 0.4634 | 0.2743 to 0.7827 | 22908 | 21274 to 24543 |
| FS20m-232-91AA/4420 | 76.41 | 0.6866 to 8504 | 3746 | −2372 to 9865 |
| FS20m-232-91AA/4420 Xlink | 0.1581 | 0.09226 to 0.2708 | 22528 | 21246 to 23811 |
| G1/C9B7W Xlink | n/a* | n/a* | n/a* | n/a* |
| FS20m-232-91AA/C9B7W | 0.1755 | 0.02122 to 1.452 | 9670 | 7536 to 11804 |

*This control mAb did not show any activity in the T cell activation assay in the absence of cross-linking FIG. 14 shows that there is an increase in the activation of T cells when OX40 is targeted and the anti-OX40 antibodies are crosslinked. No T cell activation was observed with the crosslinked anti-FITC antibody G1/4420 or with the crosslinked anti-LAG3 antibody G1/C9B7W as expected. The OX40-targeting mAb G1/OX86 when cross-linked by an anti-human CH2 antibody induced T cell activation as seen before. The OX40-targeting Fcab in the mock $mAb^2$ (4420 LALA) format, FS20m-232-91AA/4420, had no agonistic activity in the absence of crosslinking, and when crosslinked with the addition of the crosslinker FITC-dextran which binds to the Fab arms, it showed potent T cell activation. When the OX40-targeting Fcab was paired with an anti-LAG3 Fab (C9B7W) the resulting $mAb^2$ showed T cell activity in the absence of any additional crosslinking agents. This indicates that the $mAb^2$ was being crosslinked by binding to LAG3.

The T cell activation observed with the anti-OX40/anti-LAG3 $mAb^2$ antibodies demonstrates that receptors that are co-expressed with mouse OX40 on the T cell surface can be used as crosslinking agents.

8.5 Anti-mOX40/Anti-LAG3 $mAb^2$ Capable of OX40 Agonism In Vitro Suppress Tumour Growth In Vivo The CT26 syngeneic tumour model was used in this experiment as TILs isolated from CT26 tumours include T cells expressing OX40 and LAG3 receptors.

The anti-mOX40/anti-LAG3 $mAb^2$ antibody (FS20m-232-91AA/C9B7W) of Example 8.4 was tested for in vivo activity in a CT26 syngeneic mouse tumour growth model. The ability of the anti-mOX40/anti-LAG3 $mAb^2$ to inhibit tumour growth was compared to a PBS control.

BALB/c female mice were injected with CT26 cells, monitored for health and tumour growth, sorted and randomised into study cohorts as described in Example 5. Any mice which did not have tumours at this point were removed from the study.

The $mAb^2$/mAb were profiled, checked for impurities, prepared, and administered to the mice as describe in Example 5. Animals were health screened, tumour measurements were taken and the tumour volumes calculated as described in Example 5.

Figure 15:
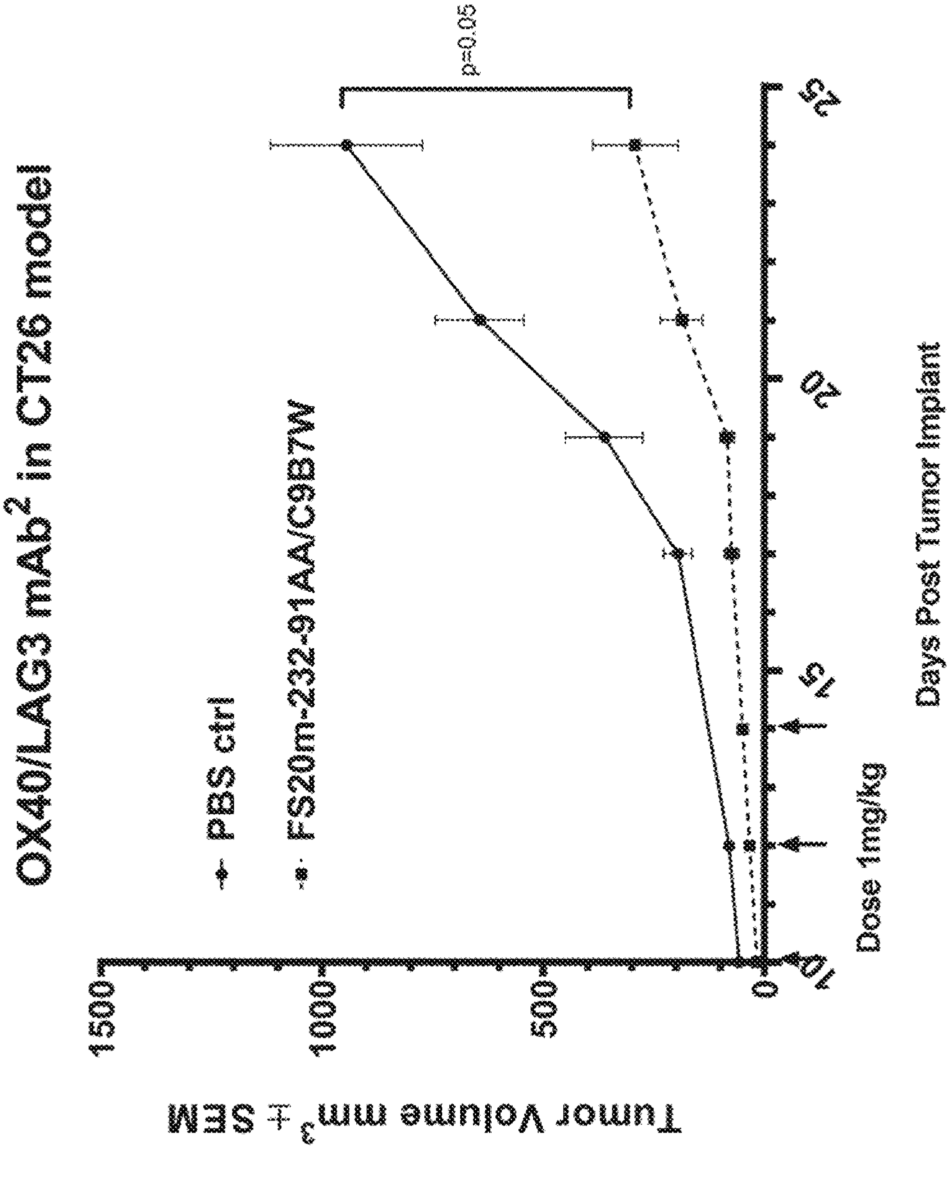
FIG. 15 shows a tumour growth curve of the CT26 syngeneic model in Balb/c mice cohorts treated with the anti-mOX40/anti-LAG3 $mAb^2$. The mean tumour volume plus or minus the standard error mean is plotted and the tumour volume on the final day was compared across the different groups using a two-tailed t-test. The group treated with the anti-OX40/anti-LAG3 $mAb^2$ showed a statistically significant tumour volume reduction as compared to the control group treated with PBS. This result demonstrates that the anti-OX40/anti-LAG3 $mAb^2$ antibody has anti-tumour efficacy in vivo against a tumour described to comprise tumour-infiltrating lymphocytes (TILs) which include OX40 and LAG3-expressing T cells, indicating that the in vivo clustering of OX40 by the bispecific engagement of OX40 and the LAG3 mediated by the anti-OX40/anti-LAG3 $mAb^2$ is effective in controlling tumour growth.

The trial was halted at day 24 when the tumour burden was considered close to restrictions and all mice were humanely sacrificed. The results are shown in FIG. 15. Statistical analysis of the end tumour volumes was performed using a two tailed Student's t-test within the GraphPad Prism software package.

There was a demonstrated statistically significant difference between anti-mOX40/anti-LAG3 $mAb^2$ and the PBS control (normal growth) in suppressing tumour growth.

Surprisingly, the cohort treated with anti-mOX40/anti-LAG3 $mAb^2$ revealed a significant suppression of growth compared to PBS control. This trial shows that, similar to the observed in vitro results, the crosslinking of OX40 by a $mAb^2$ targeting LAG3 co-expressed with OX40 expressed in tumour-infiltrating T cells results in T cell activation and subsequent tumour growth control.

SEQUENCE LISTING

```
Sequence listing
Amino acid sequences of WT Fcab CH3 domain structural loops
WT Fcab AB loop-
                                                            (SEQ ID NO: 1)
RDELTKNQ

WT Fcab CD loop-
                                                            (SEQ ID NO: 2)
SNGQPENNY

WT Fcab EF loop-
                                                            (SEQ ID NO: 3)
DKSRWQQGNV

Amino acid sequence of WT Fcab CH3 domain
AB, CD and EF loops underlined
                                                            (SEQ ID NO: 4)
GQPREPQVYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPG

Amino acid sequence of the Fcab CH2 domain
                                                            (SEQ ID NO: 5)
APELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAK

Amino acid sequence of the Fcab CH2 domain with LALA mutation
LALA mutation underlined
                                                            (SEQ ID NO: 6)
APEAAGGPSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAK

Amino acid sequence of the Fcab CH2 domain with LALA-PA mutation
LALA-PA mutation underlined
                                                            (SEQ ID NO: 7)
APEAAGGPSVFLFPPKPKDTLMISRTPEVTCVVVDVSHEDPEVKFNWYVDGVEVHNAKTKPREEQY

NSTYRVVSVLTVLHQDWLNGKEYKCKVSNKALAAPIEKTISKAK
```

-continued

Amino acid sequence of WT Fcab with LALA mutation
Hinge region (underlined), CH2 domain (bold), CH3 domain (italics),
LALA mutation (bold and underlined)

(SEQ ID NO: 8)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*ELTKNQVSLTCLVKGFYPSDIAVEWESNGQPENNYKTTPPVLDSDGSFFLYSKLTVDKSRWQQGNV*

*FSCSVMHEALHNHYTQKSLSLSPGK*

Amino acid sequence of WT Fcab without LALA mutation
Hinge region (underlined), CH2 domain (bold) and CH3 domain (italics)

(SEQ ID NO: 9)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*ELTKNQVSLTCLVKGFYPSDIAVEWESNGQPENNYKTTPPVLDSDGSFFLYSKLTVDKSRWQQGNV*

*FSCSVMHEALHNHYTQKSLSLSPG*

Amino acid sequence of Fcab FS20-11 with LALA mutation
Hinge region (underlined), CH2 domain (bold), CH3 domain (italics),
LALA mutation (bold and underlined)

(SEQ ID NO: 10)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*ETSEENVSLTCLVKGFYPSDIAVEWESNGQPENNYKTTPPVLDSDGSFFLYSKLTVDKSRWWKHYV*

*DEHPFLCSVMHEALHNHYTQESLSLSPG*

Amino acid sequence of Fcab FS20-11 without LALA mutation
Hinge region (underlined), CH2 domain (bold) and CH3 domain (italics)

(SEQ ID NO: 11)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*ETSEENVSLTCLVKGFYPSDIAVEWESNGQPENNYKTTPPVLDSDGSFFLYSKLTVDKSRWWKHYV*

*DEHPFLCSVMHEALHNHYTQESLSLSPG*

Amino acid sequences of Fcab FS20-11-127 CH3 domain structural loop sequences
FS20-11-127 first sequence- (SEQ ID NO: 12)

DDND

FS20-11-127 second sequence- (SEQ ID NO: 13)

IPIGP

FS20-11-127 third sequence- (SEQ ID NO: 14)

WRHYVEEHP

Amino acid sequence of Fcab FS20-11-127 CH3 domain
First, second and third sequences underlined (SEQ ID NO: 15)

GQPREPQVYTLPPSREEDDNDVSLTCLVKGFYPSDIAVEWESNGIPIGPYKTTPPVLDSDGSFFLYSK

LTVDKSRWWRHYVEEHPFLCSVMHEALHNHYTQKSLSLSPG

Nucleic acid sequence of Fcab FS20-11-127 CH3 domain (SEQ ID NO: 16)

GGACAGCCTCGAGAACCACAGGTGTACACCCTGCCCCCATCCCGGGAGGAAGATGATAACGAT

GTCAGCCTGACCTGCCTGGTCAAAGGCTTCTATCCCAGCGACATCGCCGTGGAGTGGGAGAGC

AATGGGATCCCAATCGGTCCATACAAGACCACGCCTCCCGTGCTGGACTCCGACGGCTCCTTCT

TCCTCTACAGCAAGCTCACCGTGGACAAGAGCAGATGGTGGAGGCATTATGTTGAGGAGCATCC

GTTCTTGTGCTCCGTGATGCATGAGGCTCTGCACAACCACTACACTCAGAAGAGCTTGTCCCTGT

CGCCCGGA

-continued

Amino acid sequence of Fcab FS20-11-127 with LALA mutation
Hinge region (underlined), CH2 domain (bold), CH3 domain (italics), LALA mutation (bold and underlined)

(SEQ ID NO: 17)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRE*

*EDDNDVSLTCLVKGFYPSDIAVEWESNGIPIGPYKTTPPVLDSDGSFFLYSKLTVDKSRWWRHYVEE*

*HPFLCSVMHEALHNHYTQKSLSLSPG*

Nucleic acid sequence of Fcab FS20-11-127 with LALA mutation (SEQ ID NO: 18)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGAGGAAGATGATAACGATGTCAGCCTGACCTGCCTGGTCAAAGGCTTCTATC

CCAGCGACATCGCCGTGGAGTGGGAGAGCAATGGGATCCCAATCGGTCCATACAAGACCACGC

CTCCCGTGCTGGACTCCGACGGCTCCTTCTTCCTCTACAGCAAGCTCACCGTGGACAAGAGCAG

ATGGTGGAGGCATTATGTTGAGGAGCATCCGTTCTTGTGCTCCGTGATGCATGAGGCTCTGCAC

AACCACTACACTCAGAAGAGCTTGTCCCTGTCGCCCGGA

Amino acid sequence of Fcab FS20-11-127 without LALA mutation
Hinge region (underlined), CH2 domain (bold) and CH3 domain (italics)

(SEQ ID NO: 19)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRE*

*EDDNDVSLTCLVKGFYPSDIAVEWESNGIPIGPYKTTPPVLDSDGSFFLYSKLTVDKSRWWRHYVEE*

HPFLCSVMHEALHNHYTQKSLSLSPG

Nucleic acid sequence of Fcab FS20-11-127 without LALA mutation (SEQ ID NO: 20)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGACAGCCTCGAGAACCACAGGTGTACACCCTGC

CCCCATCCCGGGAGGAAGATGATAACGATGTCAGCCTGACCTGCCTGGTCAAAGGCTTCTATCC

CAGCGACATCGCCGTGGAGTGGGAGAGCAATGGGATCCCAATCGGTCCATACAAGACCACGCC

TCCCGTGCTGGACTCCGACGGCTCCTTCTTCCTCTACAGCAAGCTCACCGTGGACAAGAGCAGA

TGGTGGAGGCATTATGTTGAGGAGCATCCGTTCTTGTGCTCCGTGATGCATGAGGCTCTGCACA

ACCACTACACTCAGAAGAGCTTGTCCCTGTCGCCCGGA

Amino acid sequence of the heavy chain of FS20-11-127/4420 mock $mAb^2$ with LALA mutation
VH domain (underlined)

(SEQ ID NO: 21)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

-continued

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSREEDDNDVSLTCLVKGFYPSDIAVEWESNGIPIGPYKTTPPVLDSD

GSFFLYSKLTVDKSRWWRHYVEEHPFLCSVMHEALHNHYTQKSLSLSPG

Amino acid sequence of the heavy chain of FS20-11-127/4420 mock mAb[2] without LALA mutation
VH domain (underlined)

(SEQ ID NO: 22)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSREEDDNDVSLTCLVKGFYPSDIAVEWESNGIPIGPYKTTPPVLDSD

GSFFLYSKLTVDKSRWWRHYVEEHPFLCSVMHEALHNHYTQKSLSLSPG

Amino acid sequences of Fcab FS20-11-131 CH3 domain structural loop sequences
FS20-11-131 first sequence- (SEQ ID NO: 12)

DDND

FS20-11-131 second sequence- (SEQ ID NO: 13)

IPIGP

FS20-11-131 third sequence- (SEQ ID NO: 23)

WKHYVDEHP

Amino acid sequence of Fcab FS20-11-131 CH3 domain
First, second and third sequences underlined (SEQ ID NO: 24)

GQPREPQVYTLPPSREEDDNDVSLTCLVKGFYPSDIAVEWESNGIPIGPYKTTPPVLDSDGSFFLYSK

LTVDKNRWWKHYVDEHPFLCSVMHEALHNHYTQKSLSLSPG

Nucleic acid sequence of Fcab FS20-11-131 CH3 domain (SEQ ID NO: 25)

GGACAGCCTCGAGAACCACAGGTGTACACCCTGCCCCCATCCCGGGAGGAAGATGATAACGAT

GTCAGCCTGACCTGCCTGGTCAAAGGCTTCTATCCCAGCGACATCGCCGTGGAGTGGGAGAGC

AATGGGATCCCAATCGGTCCATACAAGACCACGCCTCCCGTGCTGGACTCCGACGGCTCCTTCT

TCCTCTACAGCAAGCTCACCGTGGACAAGAACAGATGGTGGAAGCATTATGTTGATGAGCATCC

GTTCTTGTGCTCCGTGATGCATGAGGCTCTGCACAACCACTACACTCAGAAGAGCTTGTCCCTGT

CGCCCGGA

Amino acid sequence of Fcab FS20-11-131 with LALA mutation
Hinge region (underlined), CH2 domain (bold), CH3 domain (italics),
LALA mutation (bold and underlined)

(SEQ ID NO: 26)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRE*

*EDDNDVSLTCLVKGFYPSDIAVEWESNGIPIGPYKTTPPVLDSDGSFFLYSKLTVDKNRWWKHYVDE*

*HPFLCSVMHEALHNHYTQKSLSLSPG*

Nucleic acid sequence of Fcab FS20-11-131 with LALA mutation (SEQ ID NO: 27)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

-continued

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGAGGAAGATGATAACGATGTCAGCCTGACCTGCCTGGTCAAAGGCTTCTATC

CCAGCGACATCGCCGTGGAGTGGGAGAGCAATGGGATCCCAATCGGTCCATACAAGACCACGC

CTCCCGTGCTGGACTCCGACGGCTCCTTCTTCCTCTACAGCAAGCTCACCGTGGACAAGAACAG

ATGGTGGAAGCATTATGTTGATGAGCATCCGTTCTTGTGCTCCGTGATGCATGAGGCTCTGCACA

ACCACTACACTCAGAAGAGCTTGTCCCTGTCGCCCGGA

Amino acid sequence of Fcab FS20-11-131 without LALA mutation
Hinge region (underlined), CH2 domain (bold) and CH3 domain (italics)
(SEQ ID NO: 28)
TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRE*

*EDDNDVSLTCLVKGFYPSDIAVEWESNGIPIGPYKTTPPVLDSDGSFFLYSKLTVDKNRWWKHYVDE*

*HPFLCSVMHEALHNHYTQKSLSLSPG*

Nucleic acid sequence of Fcab FS20-11-131 without LALA mutation
(SEQ ID NO: 29)
ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGACAGCCTCGAGAACCACAGGTGTACACCCTGC

CCCCATCCCGGGAGGAAGATGATAACGATGTCAGCCTGACCTGCCTGGTCAAAGGCTTCTATCC

CAGCGACATCGCCGTGGAGTGGGAGAGCAATGGGATCCCAATCGGTCCATACAAGACCACGCC

TCCCGTGCTGGACTCCGACGGCTCCTTCTTCCTCTACAGCAAGCTCACCGTGGACAAGAACAGA

TGGTGGAAGCATTATGTTGATGAGCATCCGTTCTTGTGCTCCGTGATGCATGAGGCTCTGCACAA

CCACTACACTCAGAAGAGCTTGTCCCTGTCGCCCGGA

Amino acid sequence of the heavy chain of FS20-11-131/4420 mock mAb$^2$ with LALA mutation
VH domain (underlined)
(SEQ ID NO: 30)
EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSREEDDNDVSLTCLVKGFYPSDIAVEWESNGIPIGPYKTTPPVLDSD

GSFFLYSKLTVDKNRWWKHYVDEHPFLCSVMHEALHNHYTQKSLSLSPG

Amino acid sequence of the heavy chain of FS20-11-131/4420 mock mAb$^2$ without LALA mutation
VH domain (underlined)
(SEQ ID NO: 31)
EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

-continued

IEKTISKAKGQPREPQVYTLPPSREEDDNDVSLTCLVKGFYPSDIAVEWESNGIPIGPYKTTPPVLDSD

GSFFLYSKLTVDKNRWWKHYVDEHPFLCSVMHEALHNHYTQKSLSLSPG

Amino acid sequences of Fcab FS20-11-134 CH3 domain structural loop sequences

FS20-11-134 first sequence- (SEQ ID NO: 12)

DDND

FS20-11-134 second sequence- (SEQ ID NO: 13)

IPIGP

FS20-11-134 third sequence- (SEQ ID NO: 32)

WKHYVEEHP

Amino acid sequence of Fcab FS20-11-134 CH3 domain

First, second and third sequences underlined (SEQ ID NO: 33)

GQPREPQVYTLPPSREEDDNDVSLTCLVKGFYPSDIAVEWESNGIPIGPYKTTPPVLDSDGSFFLYSK

LTVDKSRWWKHYVEEHPFLCSVMHEALHNHYTQKSLSLSPG

Nucleic acid sequence of Fcab FS20-11-134 CH3 domain (SEQ ID NO: 34)

GGACAGCCTCGAGAACCACAGGTGTACACCCTGCCCCCATCCCGGGAGGAAGATGATAACGAT

GTCAGCCTGACCTGCCTGGTCAAAGGCTTCTATCCCAGCGACATCGCCGTGGAGTGGGAGAGC

AATGGGATCCCAATCGGTCCATACAAGACCACGCCTCCCGTGCTGGACTCCGACGGCTCCTTCT

TCCTCTACAGCAAGCTCACCGTGGACAAGAGCAGATGGTGGAAGCATTATGTTGAGGAGCATCC

GTTCTTGTGCTCCGTGATGCATGAGGCTCTGCACAACCACTACACTCAGAAGAGCTTGTCCCTGT

CGCCCGGA

Amino acid sequence of Fcab FS20-11-134 with LALA mutation

Hinge region (underlined), CH2 domain (bold), CH3 domain (italics),
LALA mutation (bold and underlined)

(SEQ ID NO: 35)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRE*

*EDDNDVSLTCLVKGFYPSDIAVEWESNGIPIGPYKTTPPVLDSDGSFFLYSKLTVDKSRWWKHYVEE*

*HPFLCSVMHEALHNHYTQKSLSLSPG*

Nucleic acid sequence of Fcab FS20-11-134 with LALA mutation (SEQ ID NO: 36)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGAGGAAGATGATAACGATGTCAGCCTGACCTGCCTGGTCAAAGGCTTCTATC

CCAGCGACATCGCCGTGGAGTGGGAGAGCAATGGGATCCCAATCGGTCCATACAAGACCACGC

CTCCCGTGCTGGACTCCGACGGCTCCTTCTTCCTCTACAGCAAGCTCACCGTGGACAAGAGCAG

ATGGTGGAAGCATTATGTTGAGGAGCATCCGTTCTTGTGCTCCGTGATGCATGAGGCTCTGCAC

AACCACTACACTCAGAAGAGCTTGTCCCTGTCGCCCGGA

Amino acid sequence of Fcab FS20-11-134 without LALA mutation

Hinge region (underlined), CH2 domain (bold) and CH3 domain (italics)

(SEQ ID NO: 37)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRE*

-continued

*EDDNDVSLTCLVKGFYPSDIAVEWESNGIPIGPYKTTPPVLDSDGSFFLYSKLTVDKSRWWKHYVEE*

*HPFLCSVMHEALHNHYTQKSLSLSPG*

Nucleic acid sequence of Fcab FS20-11-134 without LALA mutation (SEQ ID NO: 38)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGACAGCCTCGAGAACCACAGGTGTACACCCTGC

CCCCATCCCGGGAGGAAGATGATAACGATGTCAGCCTGACCTGCCTGGTCAAAGGCTTCTATCC

CAGCGACATCGCCGTGGAGTGGGAGAGCAATGGGATCCCAATCGGTCCATACAAGACCACGCC

TCCCGTGCTGGACTCCGACGGCTCCTTCTTCCTCTACAGCAAGCTCACCGTGGACAAGAGCAGA

TGGTGGAAGCATTATGTTGAGGAGCATCCGTTCTTGTGCTCCGTGATGCATGAGGCTCTGCACA

ACCACTACACTCAGAAGAGCTTGTCCCTGTCGCCCGGA

Amino acid sequence of the heavy chain of FS20-11-134/4420 mock $mAb^2$ with LALA mutation
VH domain (underlined)

(SEQ ID NO: 39)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSREEDDNDVSLTCLVKGFYPSDIAVEWESNGIPIGPYKTTPPVLDSD

GSFFLYSKLTVDKSRWWKHYVEEHPFLCSVMHEALHNHYTQKSLSLSPG

Amino acid sequence of the heavy chain of FS20-11-134/4420 mock $mAb^2$ without LALA mutation
VH domain (underlined)

(SEQ ID NO: 40)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSREEDDNDVSLTCLVKGFYPSDIAVEWESNGIPIGPYKTTPPVLDSD

GSFFLYSKLTVDKSRVWVKHYVEEHPFLCSVMHEALHNHYTQKSLSLSPG

Amino acid sequence of Fcab FS20-22 with LALA mutation
Hinge region (underlined), CH2 domain (bold), CH3 domain (italics), LALA mutation (bold and underlined)

(SEQ ID NO: 41)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGQPENNYKTTPPVLDSDGSFFLYSKLTVDQYRWNPGGY*

*FSCSVMHEALHNHYTQKSLSLSPG*

-continued

Amino acid sequence of Fcab FS20-22 without LALA mutation
Hinge region (underlined), CH2 domain (bold) and CH3 domain (italics)

(SEQ ID NO: 42)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGQPENNYKTTPPVLDSDGSFFLYSKLTVDQYRWNPGGY*

*FSCSVMHEALHNHYTQKSLSLSPG*

Amino acid sequences of Fcab FS20-22-38 CH3 domain structural loop sequences
FS20-22-38 first sequence- (SEQ ID NO: 43)

YWDQE

FS20-22-38 second sequence- (SEQ ID NO: 44)

AEKYQ

FS20-22-38 third sequence- (SEQ ID NO: 45)

QYRWNPGDY

Amino acid sequence of Fcab FS20-22-38 CH3 domain
First, second and third sequences underlined (SEQ ID NO: 46)

GQPREPQVYTLPPSRDEYWDQEVSLTCLVKGFYPSDIAVEWESNGAEKYQYKTTPPVLDSDGSFFL

YSKLTVDQYRWNPGDYFSCSVMHEALHNHYTQKSLSLSPG

Nucleic acid sequence of Fcab FS20-22-38 CH3 domain (SEQ ID NO: 47)

GGACAGCCTCGAGAACCACAGGTGTACACCCTGCCCCCATCCCGGGATGAGTACTGGGACCAG

GAAGTCAGCCTGACCTGCCTGGTCAAAGGCTTCTATCCCAGCGACATCGCCGTGGAGTGGGAG

AGCAATGGGGCAGAAAAATACCAGTACAAGACCACGCCTCCCGTGCTGGACTCCGACGGCTCCT

TCTTCCTCTACAGCAAGCTCACCGTGGATCAGTATAGGTGGAACCCAGGCGACTATTTCTCATGC

TCCGTGATGCATGAGGCTCTGCACAACCACTACACACAGAAGAGCCTCTCCCTGTCTCCGGGT

Amino acid sequence of Fcab FS20-22-38 with LALA mutation
Hinge region (underlined), CH2 domain (bold), CH3 domain (italics)
and LALA mutation (bold and italics)

(SEQ ID NO: 48)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGAEKYQYKTTPPVLDSDGSFFLYSKLTVDQYRWNPGDY*

*FSCSVMHEALHNHYTQKSLSLSPG*

Nucleic acid sequence of Fcab FS20-22-38 with LALA mutation (SEQ ID NO: 49)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGATGAGTACTGGGACCAGGAAGTCAGCCTGACCTGCCTGGTCAAAGGCTTC

TATCCCAGCGACATCGCCGTGGAGTGGGAGAGCAATGGGGCAGAAAAATACCAGTACAAGACC

ACGCCTCCCGTGCTGGACTCCGACGGCTCCTTCTTCCTCTACAGCAAGCTCACCGTGGATCAGT

ATAGGTGGAACCCAGGCGACTATTTCTCATGCTCCGTGATGCATGAGGCTCTGCACAACCACTA

CACACAGAAGAGCCTCTCCCTGTCTCCGGGT

-continued

Amino acid sequence of Fcab FS20-22-38 without LALA mutation
Hinge region (underlined), CH2 domain (bold) and CH3 domain (italics)

(SEQ ID NO: 50)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGAEKYQYKTTPPVLDSDGSFFLYSKLTVDQYRWNPGDY*

*FSCSVMHEALHNHYTQKSLSLSPG*

Nucleic acid sequence of Fcab FS20-22-38 without LALA mutation (SEQ ID NO: 51)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGACAGCCTCGAGAACCACAGGTGTACACCCTGC

CCCCATCCCGGGATGAGTACTGGGACCAGGAAGTCAGCCTGACCTGCCTGGTCAAAGGCTTCTA

TCCCAGCGACATCGCCGTGGAGTGGGAGAGCAATGGGGCAGAAAAATACCAGTACAAGACCAC

GCCTCCCGTGCTGGACTCCGACGGCTCCTTCTTCCTCTACAGCAAGCTCACCGTGGATCAGTAT

AGGTGGAACCCAGGCGACTATTTCTCATGCTCCGTGATGCATGAGGCTCTGCACAACCACTACA

CACAGAAGAGCCTCTCCCTGTCTCCGGGT

Amino acid sequence of the heavy chain of FS20-22-38/4420 mock mAb²
with LALA mutation
VH domain (underlined)

(SEQ ID NO: 52)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEYWDQEVSLTCLVKGFYPSDIAVEWESNGAEKYQYKTTPPVL

DSDGSFFLYSKLTVDQYRWNPGDYFSCSVMHEALHNHYTQKSLSLSPG

Amino acid sequence of the heavy chain of FS20-22-38/4420 mock mAb²
without LALA mutation
VH domain (underlined)

(SEQ ID NO: 53)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEYWDQEVSLTCLVKGFYPSDIAVEWESNGAEKYQYKTTPPVL

DSDGSFFLYSKLTVDQYRWNPGDYFSCSVMHEALHNHYTQKSLSLSPG

Amino acid sequences of Fcab FS20-22-41 CH3 domain structural loop sequences
FS20-22-41 first sequence- (SEQ ID NO: 43)

YWDQE

FS20-22-41 second sequence- (SEQ ID NO: 54)

DEQFA

-continued

FS20-22-41 third sequence- (SEQ ID NO: 45)

QYRWNPGDY

Amino acid sequence of Fcab FS20-22-41 CH3 domain
First, second and third sequences underlined (SEQ ID NO: 55)

GQPREPQVYTLPPSRDEYWDQEVSLTCLVKGFYPSDIAVEWESNGDEQFAYKTTPPVLDSDGSFFL

YSKLTVDQYRWNPGDYFSCSVMHEALHNHYTQKSLSLSPG

Nucleic acid sequence of Fcab FS20-22-41 CH3 domain (SEQ ID NO: 56)

GGACAGCCTCGAGAACCACAGGTGTACACCCTGCCCCCATCCCGGGATGAGTACTGGGACCAG

GAAGTCAGCCTGACCTGCCTGGTCAAAGGCTTCTATCCCAGCGACATCGCCGTGGAGTGGGAG

AGCAATGGGGATGAACAGTTCGCATACAAGACCACGCCTCCCGTGCTGGACTCCGACGGCTCCT

TCTTCCTCTACAGCAAGCTCACCGTGGATCAGTATAGGTGGAACCCAGGCGACTATTTCTCATGC

TCCGTGATGCATGAGGCTCTGCACAACCACTACACACAGAAGAGCCTCTCCCTGTCTCCGGGA

Amino acid sequence of Fcab FS20-22-41 with LALA mutation
Hinge region (underlined), CH2 domain (bold), CH3 domain (italics),
LALA mutation (bold and underlined)

(SEQ ID NO: 57)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGDEQFAYKTTPPVLDSDGSFFLYSKLTVDQYRWNPGDY*

*FSCSVMHEALHNHYTQKSLSLSPG*

Nucleic acid sequence of Fcab FS20-22-41 with LALA mutation (SEQ ID NO: 58)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGATGAGTACTGGGACCAGGAAGTCAGCCTGACCTGCCTGGTCAAAGGCTTC

TATCCCAGCGACATCGCCGTGGAGTGGGAGAGCAATGGGGATGAACAGTTCGCATACAAGACC

ACGCCTCCCGTGCTGGACTCCGACGGCTCCTTCTTCCTCTACAGCAAGCTCACCGTGGATCAGT

ATAGGTGGAACCCAGGCGACTATTTCTCATGCTCCGTGATGCATGAGGCTCTGCACAACCACTA

CACACAGAAGAGCCTCTCCCTGTCTCCGGGA

Amino acid sequence of Fcab FS20-22-41 without LALA mutation
Hinge region (underlined), CH2 domain (bold) and CH3 domain (italics)

(SEQ ID NO: 59)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGDEQFAYKTTPPVLDSDGSFFLYSKLTVDQYRWNPGDY*

*FSCSVMHEALHNHYTQKSLSLSPG*

Nucleic acid sequence of Fcab FS20-22-41 without LALA mutation (SEQ ID NO: 60)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

-continued

CCAATTGAGAAAACTATCTCGAAAGCCAAGGGACAGCCTCGAGAACCACAGGTGTACACCCTGC

CCCCATCCCGGGATGAGTACTGGGACCAGGAAGTCAGCCTGACCTGCCTGGTCAAAGGCTTCTA

TCCCAGCGACATCGCCGTGGAGTGGGAGAGCAATGGGGATGAACAGTTCGCATACAAGACCAC

GCCTCCCGTGCTGGACTCCGACGGCTCCTTCTTCCTCTACAGCAAGCTCACCGTGGATCAGTAT

AGGTGGAACCCAGGCGACTATTTCTCATGCTCCGTGATGCATGAGGCTCTGCACAACCACTACA

CACAGAAGAGCCTCTCCCTGTCTCCGGGA

Amino acid sequence of the heavy chain of FS20-22-41/4420 mock $mAb^2$ with LALA mutation
VH domain (underlined)

(SEQ ID NO: 61)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEYWDQEVSLTCLVKGFYPSDIAVEWESNGDEQFAYKTTPPVL

DSDGSFFLYSKLTVDQYRWNPGDYFSCSVMHEALHNHYTQKSLSLSPG

Amino acid sequence of the heavy chain of FS20-22-41/4420 mock $mAb^2$ without LALA mutation
VH domain (underlined)

(SEQ ID NO: 174)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEYWDQEVSLTCLVKGFYPSDIAVEWESNGDEQFAYKTTPPVL

DSDGSFFLYSKLTVDQYRWNPGDYFSCSVMHEALHNHYTQKSLSLSPG

Amino acid sequences of Fcab FS20-22-47 CH3 domain structural loop sequences

FS20-22-47 first sequence- (SEQ ID NO: 43)

YWDQE

FS20-22-47 second sequence- (SEQ ID NO: 54)

DEQFA

FS20-22-47 third sequence- (SEQ ID NO: 62)

QYRWSPGDY

Amino acid sequence of Fcab FS20-22-47 CH3 domain
First, second and third sequences underlined (SEQ ID NO: 63)

GQPREPQVYTLPPSRDEYWDQEVSLTCLVKGFYPSDIAVEWESNGDEQFAYKTTPPVLDSDGSFFL

YSKLTVDQYRWSPGDYFSCSVMHEALHNHYTQKSLSLSPG

Nucleic acid sequence of Fcab FS20-22-47 CH3 domain (SEQ ID NO: 64)

GGACAGCCTCGAGAACCACAGGTGTACACCCTGCCCCCATCCCGGGATGAGTACTGGGACCAG

GAAGTCAGCCTGACCTGCCTGGTCAAAGGCTTCTATCCCAGCGACATCGCCGTGGAGTGGGAG

AGCAATGGGGATGAACAGTTCGCATACAAGACCACGCCTCCCGTGCTGGACTCCGACGGCTCCT

TCTTCCTCTACAGCAAGCTCACCGTGGATCAGTATAGGTGGAGTCCGGGTGATTATTTCTCATGC

TCCGTGATGCATGAGGCTCTGCACAACCACTACACTCAGAAGAGCTTGTCCCTGTCGCCCGGA

-continued

Amino acid sequence of Fcab FS20-22-47 with LALA mutation
Hinge region (underlined), CH2 domain (bold), CH3 domain (italics),
LALA mutation (bold and underlined)

(SEQ ID NO: 65)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGDEQFAYKTTPPVLDSDGSFFLYSKLTVDQYRWSPGDY*

*FSCSVMHEALHNHYTQKSLSLSPG*

Nucleic acid sequence of Fcab FS20-22-47 with LALA mutation (SEQ ID NO: 66)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGATGAGTACTGGGACCAGGAAGTCAGCCTGACCTGCCTGGTCAAAGGCTTC

TATCCCAGCGACATCGCCGTGGAGTGGGAGAGCAATGGGGATGAACAGTTCGCATACAAGACC

ACGCCTCCCGTGCTGGACTCCGACGGCTCCTTCTTCCTCTACAGCAAGCTCACCGTGGATCAGT

ATAGGTGGAGTCCGGGTGATTATTTCTCATGCTCCGTGATGCATGAGGCTCTGCACAACCACTAC

ACTCAGAAGAGCTTGTCCCTGTCGCCCGGA

Amino acid sequence of Fcab FS20-22-47 without LALA mutation
Hinge region (underlined), CH2 domain (bold) and CH3 domain (italics)

(SEQ ID NO: 67)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGDEQFAYKTTPPVLDSDGSFFLYSKLTVDQYRWSPGDY*

*FSCSVMHEALHNHYTQKSLSLSPG*

Nucleic acid sequence of Fcab FS20-22-47 without LALA mutation (SEQ ID NO: 68)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGACAGCCTCGAGAACCACAGGTGTACACCCTGC

CCCCATCCCGGGATGAGTACTGGGACCAGGAAGTCAGCCTGACCTGCCTGGTCAAAGGCTTCTA

TCCCAGCGACATCGCCGTGGAGTGGGAGAGCAATGGGGATGAACAGTTCGCATACAAGACCAC

GCCTCCCGTGCTGGACTCCGACGGCTCCTTCTTCCTCTACAGCAAGCTCACCGTGGATCAGTAT

AGGTGGAGTCCGGGTGATTATTTCTCATGCTCCGTGATGCATGAGGCTCTGCACAACCACTACA

CTCAGAAGAGCTTGTCCCTGTCGCCCGGA

Amino acid sequence of the heavy chain of FS20-22-47/4420 mock $mAb^2$
with LALA mutation
VH domain (underlined)

(SEQ ID NO: 69)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

-continued

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEYWDQEVSLTCLVKGFYPSDIAVEWESNGDEQFAYKTTPPVL

DSDGSFFLYSKLTVDQYRWSPGDYFSCSVMHEALHNHYTQKSLSLSPG

Amino acid sequence of the heavy chain of FS20-22-47/4420 mock mAb[2] without LALA mutation
VH domain (underlined)

(SEQ ID NO: 70)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEYWDQEVSLTCLVKGFYPSDIAVEWESNGDEQFAYKTTPPVL

DSDGSFFLYSKLTVDQYRWSPGDYFSCSVMHEALHNHYTQKSLSLSPG

Amino acid sequences of Fcab FS20-22-49 CH3 domain structural loop sequences
FS20-22-49 first sequence- (SEQ ID NO: 43)

YWDQE

FS20-22-49 second sequence- (SEQ ID NO: 54)

DEQFA

FS20-22-49 third sequence- (SEQ ID NO: 71)

QYRWNPADY

Amino acid sequence of Fcab FS20-22-49 CH3 domain
First, second and third sequences underlined (SEQ ID NO: 72)

GQPREPQVYTLPPSRDEYWDQEVSLTCLVKGFYPSDIAVEWESNGDEQFAYKTTPPVLDSDGSFFL

YSKLTVDQYRWNPADYFSCSVMHEALHNHYTQKSLSLSPG

Nucleic acid sequence of Fcab FS20-22-49 CH3 domain (SEQ ID NO: 73)

GGACAGCCTCGAGAACCACAGGTGTACACCCTGCCCCCATCCCGGGATGAGTACTGGGACCAG

GAAGTCAGCCTGACCTGCCTGGTCAAAGGCTTCTATCCCAGCGACATCGCCGTGGAGTGGGAG

AGCAATGGGGATGAACAGTTCGCATACAAGACCACGCCTCCCGTGCTGGACTCCGACGGCTCCT

TCTTCCTCTACAGCAAGCTCACCGTGGATCAGTATAGGTGGAATCCTGCTGATTATTTCTCATGC

TCCGTGATGCATGAGGCTCTGCACAACCACTACACTCAGAAGAGCTTGTCCCTGTCGCCCGGA

Amino acid sequence of Fcab FS20-22-49 with LALA mutation
Hinge region (underlined), CH2 domain (bold), CH3 domain (italics),
LALA mutation (bold and underlined)

(SEQ ID NO: 74)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGDEQFAYKTTPPVLDSDGSFFLYSKLTVDQYRWNPADY*

*FSCSVMHEALHNHYTQKSLSLSPG*

Nucleic acid sequence of Fcab FS20-22-49 with LALA mutation (SEQ ID NO: 75)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

-continued

CCCAATTGAGAAAACTATCTCGAAAGCCAAGGGACAGCCTCGAGAACCACAGGTGTACACCCTG

CCCCCATCCCGGGATGAGTACTGGGACCAGGAAGTCAGCCTGACCTGCCTGGTCAAAGGCTTC

TATCCCAGCGACATCGCCGTGGAGTGGGAGAGCAATGGGGATGAACAGTTCGCATACAAGACC

ACGCCTCCCGTGCTGGACTCCGACGGCTCCTTCTTCCTCTACAGCAAGCTCACCGTGGATCAGT

ATAGGTGGAATCCTGCTGATTATTTCTCATGCTCCGTGATGCATGAGGCTCTGCACAACCACTAC

ACTCAGAAGAGCTTGTCCCTGTCGCCCGGA

Amino acid sequence of Fcab FS20-22-49 without LALA mutation
Hinge region (underlined), CH2 domain (bold) and CH3 domain (italics)

(SEQ ID NO: 76)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGDEQFAYKTTPPVLDSDGSFFLYSKLTVDQYRWNPADY*

*FSCSVMHEALHNHYTQKSLSLSPG*

Nucleic acid sequence of Fcab FS20-22-49 without LALA mutation (SEQ ID NO: 77)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGACAGCCTCGAGAACCACAGGTGTACACCCTGC

CCCCATCCCGGGATGAGTACTGGGACCAGGAAGTCAGCCTGACCTGCCTGGTCAAAGGCTTCTA

TCCCAGCGACATCGCCGTGGAGTGGGAGAGCAATGGGGATGAACAGTTCGCATACAAGACCAC

GCCTCCCGTGCTGGACTCCGACGGCTCCTTCTTCCTCTACAGCAAGCTCACCGTGGATCAGTAT

AGGTGGAATCCTGCTGATTATTTCTCATGCTCCGTGATGCATGAGGCTCTGCACAACCACTACAC

TCAGAAGAGCTTGTCCCTGTCGCCCGGA

Amino acid sequence of the heavy chain of FS20-22-49/4420 mock
$mAb^2$ with LALA mutation
VH domain (underlined)

(SEQ ID NO: 78)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEYWDQEVSLTCLVKGFYPSDIAVEWESNGDEQFAYKTTPPVL

DSDGSFFLYSKLTVDQYRWNPADYFSCSVMHEALHNHYTQKSLSLSPG

Amino acid sequence of the heavy chain of FS20-22-49/4420 mock
$mAb^2$ without LALA mutation
VH domain (underlined)

(SEQ ID NO: 79)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

-continued

IEKTISKAKGQPREPQVYTLPPSRDEYWDQEVSLTCLVKGFYPSDIAVEWESNGDEQFAYKTTPPVL

DSDGSFFLYSKLTVDQYRWNPADYFSCSVMHEALHNHYTQKSLSLSPG

Amino acid sequences of Fcab FS20-22-85 CH3 domain structural loop sequences

FS20-22-85 first sequence- (SEQ ID NO: 43)

YWDQE

FS20-22-85 second sequence- (SEQ ID NO: 54)

DEQFA

FS20-22-85 third sequence- (SEQ ID NO: 80)

QYRWNPFDD

Amino acid sequence of Fcab FS20-22-85 CH3 domain

First, second and third sequences underlined (SEQ ID NO: 81)

GQPREPQVYTLPPSRDEYWDQEVSLTCLVKGFYPSDIAVEWESNGDEQFAYKTTPPVLDSDGSFFL

YSKLTLDQYRWNPFDDFSCSVMHEALHNHYTQKSLSLSPG

Nucleic acid sequence of Fcab FS20-22-85 CH3 domain (SEQ ID NO: 82)

GGACAGCCTCGAGAACCACAGGTGTACACCCTGCCCCCATCCCGGGATGAGTACTGGGACCAG

GAAGTCAGCCTGACCTGCCTGGTCAAAGGCTTCTATCCCAGCGACATCGCCGTGGAGTGGGAG

AGCAATGGGGATGAACAGTTCGCATACAAGACCACGCCTCCCGTGCTGGACTCCGACGGCTCCT

TCTTCCTCTACAGCAAGCTCACCTTGGATCAGTATAGGTGGAATCCGTTTGATGATTTCTCATGCT

CCGTGATGCATGAGGCTCTGCACAACCACTACACTCAGAAGAGCTTGTCCCTGTCGCCCGGA

Amino acid sequence of Fcab FS20-22-85 with LALA mutation

Hinge region (underlined), CH2 domain (bold), CH3 domain (italics),
LALA mutation (bold and underlined)

(SEQ ID NO: 83)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYWDQEVSLTCLVKGFYPSDIAVEWESNGDEQFAYKTTPPVLDSDGSFFLYSKLTLDQYRWNPFDD*

*FSCSVMHEALHNHYTQKSLSLSPG*

Nucleic acid sequence of Fcab FS20-22-85 with LALA mutation (SEQ ID NO: 84)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGATGAGTACTGGGACCAGGAAGTCAGCCTGACCTGCCTGGTCAAAGGCTTC

TATCCCAGCGACATCGCCGTGGAGTGGGAGAGCAATGGGGATGAACAGTTCGCATACAAGACC

ACGCCTCCCGTGCTGGACTCCGACGGCTCCTTCTTCCTCTACAGCAAGCTCACCTTGGATCAGT

ATAGGTGGAATCCGTTTGATGATTTCTCATGCTCCGTGATGCATGAGGCTCTGCACAACCACTAC

ACTCAGAAGAGCTTGTCCCTGTCGCCCGGA

Amino acid sequence of Fcab FS20-22-85 without LALA mutation

Hinge region (underlined), CH2 domain (bold) and CH3 domain (italics)

(SEQ ID NO: 85)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

-continued

*EYWDQEVSLTCLVKGFYPSDIAVEWESNGDEQFAYKTTPPVLDSDGSFFLYSKLTLDQYRWNPFDD*

*FSCSVMHEALHNHYTQKSLSLSPG*

Nucleic acid sequence of Fcab FS20-22-85 without LALA mutation (SEQ ID NO: 86)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGATGAGTACTGGGACCAGGAAGTCAGCCTGACCTGCCTGGTCAAAGGCTTC

TATCCCAGCGACATCGCCGTGGAGTGGGAGAGCAATGGGGATGAACAGTTCGCATACAAGACC

ACGCCTCCCGTGCTGGACTCCGACGGCTCCTTCTTCCTCTACAGCAAGCTCACCTTGGATCAGT

ATAGGTGGAATCCGTTTGATGATTTCTCATGCTCCGTGATGCATGAGGCTCTGCACAACCACTAC

ACTCAGAAGAGCTTGTCCCTGTCGCCCGGA

Amino acid sequence of the heavy chain of FS20-22-85/4420 mock mAb$^2$ with LALA mutation
VH domain (underlined)

(SEQ ID NO: 87)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEYWDQEVSLTCLVKGFYPSDIAVEWESNGDEQFAYKTTPPVL

DSDGSFFLYSKLTLDQYRWNPFDDFSCSVMHEALHNHYTQKSLSLSPG

Amino acid sequence of the heavy chain of FS20-22-85/4420 mock mAb$^2$ without LALA mutation
VH domain (underlined)

(SEQ ID NO: 88)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEYWDQEVSLTCLVKGFYPSDIAVEWESNGDEQFAYKTTPPVL

DSDGSFFLYSKLTLDQYRWNPFDDFSCSVMHEALHNHYTQKSLSLSPG

Amino acid sequence of Fcab FS20-31 with LALA mutation
Hinge region (underlined), CH2 domain (bold), CH3 domain (italics),
LALA mutation (bold and underlined)

(SEQ ID NO: 89)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYYSGEVSLTCLVKGFYPSDIAVEWESNGQPENDYKTTPPVLDSDGSFFLYSKLTVPYWRWGGPGT*

*FSCSVMHEALHNHYTQKSLSLSPG*

-continued

Amino acid sequence of Fcab FS20-31 without LALA mutation
Hinge region (underlined), CH2 domain (bold) and CH3 domain (italics)

(SEQ ID NO: 90)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYYSGEVSLTCLVKGFYPSDIAVEWESNGQPENDYKTTPPVLDSDGSFFLYSKLTVPYWRWGGPGT*

*FSCSVMHEALHNHYTQKSLSLSPG*

Amino acid sequences of Fcab FS20-31-58 CH3 domain structural loop sequences
FS20-31-58 first sequence- (SEQ ID NO: 91)

YYSGE

FS20-31-58 second sequence- (SEQ ID NO: 92)

QPEND

FS20-31-58 third sequence- (SEQ ID NO: 93)

PYWRWGSPRT

Amino acid sequence of Fcab FS20-31-58 CH3 domain
First, second and third sequences underlined (SEQ ID NO: 94)

GQPREPQVYTLPPSRDEYYSGEVSLTCLVKGFYPSDIAVEWESNGQPENDYKTTPPVLDSDGSFFLY

SKLTVPYWRWGSPRTFSCSVMHEALHNHYTQKSLSLSPG

Nucleic acid sequence of Fcab FS20-31-58 CH3 domain (SEQ ID NO: 95)

GGACAGCCTCGAGAACCACAGGTGTACACCCTGCCCCCATCCCGGGATGAGTACTACTCTGGT

GAAGTCAGCCTGACCTGCCTGGTCAAAGGCTTCTATCCCAGCGACATCGCCGTGGAGTGGGAG

AGCAATGGGCAGCCGGAGAACGACTACAAGACCACGCCTCCCGTGCTGGACTCCGACGGCTCC

TTCTTCCTCTACAGCAAGCTCACCGTGCCTTATTGGAGGTGGGGTAGTCCGCGTACTTTCTCATG

CTCCGTGATGCATGAGGCTCTGCACAACCACTACACACAGAAGAGCCTCTCCCTGTCTCCGGGT

Amino acid sequence of Fcab FS20-31-58 with LALA mutation
Hinge region (underlined), CH2 domain (bold), CH3 domain (italics),
LALA mutation (bold and underlined)

(SEQ ID NO: 96)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*PREPQVYTLPPSRDEY*

*YSGEVSLTCLVKGFYPSDIAVEWESNGQPENDYKTTPPVLDSDGSFFLYSKLTVPYWRWGSPRTFS*

*CSVMHEALHNHYTQKSLSLSPG*

Nucleic acid sequence of Fcab FS20-31-58 with LALA mutation (SEQ ID NO: 97)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGATGAGTACTACTCTGGTGAAGTCAGCCTGACCTGCCTGGTCAAAGGCTTCT

ATCCCAGCGACATCGCCGTGGAGTGGGAGAGCAATGGGCAGCCGGAGAACGACTACAAGACCA

CGCCTCCCGTGCTGGACTCCGACGGCTCCTTCTTCCTCTACAGCAAGCTCACCGTGCCTTATTG

GAGGTGGGGTAGTCCGCGTACTTTCTCATGCTCCGTGATGCATGAGGCTCTGCACAACCACTAC

ACACAGAAGAGCCTCTCCCTGTCTCCGGGT

-continued

Amino acid sequence of Fcab FS20-31-58 without LALA mutation
Hinge region (underlined), CH2 domain (bold) and CH3 domain (italics)

(SEQ ID NO: 98)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYYSGEVSLTCLVKGFYPSDIAVEWESNGQPENDYKTTPPVLDSDGSFFLYSKLTVPYWRWGSPRT*

*FSCSVMHEALHNHYTQKSLSLSPG*

Nucleic acid sequence of Fcab FS20-31-58 without LALA mutation (SEQ ID NO: 99)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGACAGCCTCGAGAACCACAGGTGTACACCCTGC

CCCCATCCCGGGATGAGTACTACTCTGGTGAAGTCAGCCTGACCTGCCTGGTCAAAGGCTTCTA

TCCCAGCGACATCGCCGTGGAGTGGGAGAGCAATGGGCAGCCGGAGAACGACTACAAGACCAC

GCCTCCCGTGCTGGACTCCGACGGCTCCTTCTTCCTCTACAGCAAGCTCACCGTGCCTTATTGG

AGGTGGGGTAGTCCGCGTACTTTCTCATGCTCCGTGATGCATGAGGCTCTGCACAACCACTACA

CACAGAAGAGCCTCTCCCTGTCTCCGGGT

Amino acid sequence of the heavy chain of FS20-31-58/4420 mock mAb$^2$ with LALA mutation
VH domain (underlined)

(SEQ ID NO: 100)

QVQLQESGPGLVRPSQTLSLTCTVSGSTFSGYGVNWVRQPPGRGLEWIGMIWGDGNTDYNSALKS

RVTMLVDTSKNQFSLRLSSVTAADTAVYYCARERDYRLDYWGQGSLVTVSSASTKGPSVFPLAPSS

KSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDEYYSGEVSLTCLVKGFYPSDIAVEWESNGQPENDYKTTPPVLD

SDGSFFLYSKLTVPYWRWGSPRTFSCSVMHEALHNHYTQKSLSLSPG

Amino acid sequence of the heavy chain of FS20-31-58/4420 mock mAb$^2$ without LALA mutation
VH domain (underlined)

(SEQ ID NO: 101)

QVQLQESGPGLVRPSQTLSLTCTVSGSTFSGYGVNWVRQPPGRGLEWIGMIWGDGNTDYNSALKS

RVTMLVDTSKNQFSLRLSSVTAADTAVYYCARERDYRLDYWGQGSLVTVSSASTKGPSVFPLAPSS

KSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDEYYSGEVSLTCLVKGFYPSDIAVEWESNGQPENDYKTTPPVLD

SDGSFFLYSKLTVPYWRWGSPRTFSCSVMHEALHNHYTQKSLSLSPG

Amino acid sequences of Fcab FS20-31-66 CH3 domain structural loop sequences
FS20-31-66 first sequence- (SEQ ID NO: 91)

YYSGE

FS20-31-66 second sequence- (SEQ ID NO: 92)

QPEND

-continued

FS20-31-66 third sequence- (SEQ ID NO: 102)

PYWRWGVPRT

Amino acid sequence of Fcab FS20-31-66 CH3 domain
First, second and third sequences underlined (SEQ ID NO: 103)

GQPREPQVYTLPPSRDEYYSGEVSLTCLVKGFYPSDIAVEWESNGQPENDYKTTPPVLDSDGSFFLY

SKLTVPYWRWGVPRTFSCSVMHEALHNHYTQKSLSLSPG

Nucleic acid sequence of Fcab FS20-31-66 CH3 domain (SEQ ID NO: 104)

GGACAGCCTCGAGAACCACAGGTGTACACCCTGCCCCCATCCCGGGATGAGTACTACTCTGGT

GAAGTCAGCCTGACCTGCCTGGTCAAAGGCTTCTATCCCAGCGACATCGCCGTGGAGTGGGAG

AGCAATGGGCAGCCGGAGAACGACTACAAGACCACGCCTCCCGTGCTGGACTCCGACGGCTCC

TTCTTCCTCTACAGCAAGCTCACCGTGCCGTATTGGAGGTGGGGTGTTCCGCGTACTTTCTCATG

CTCCGTGATGCATGAGGCTCTGCACAACCACTACACACAGAAGAGCCTCTCCCTGTCTCCGGGT

Amino acid sequence of Fcab FS20-31-66 with LALA mutation
Hinge region (underlined), CH2 domain (bold), CH3 domain (italics),
LALA mutation (bold and underlined)

(SEQ ID NO: 105)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYYSGEVSLTCLVKGFYPSDIAVEWESNGQPENDYKTTPPVLDSDGSFFLYSKLTVPYWRWGVPRT*

*FSCSVMHEALHNHYTQKSLSLSPG*

Nucleic acid sequence of Fcab FS20-31-66 with LALA mutation (SEQ ID NO: 106)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGATGAGTACTACTCTGGTGAAGTCAGCCTGACCTGCCTGGTCAAAGGCTTCT

ATCCCAGCGACATCGCCGTGGAGTGGGAGAGCAATGGGCAGCCGGAGAACGACTACAAGACCA

CGCCTCCCGTGCTGGACTCCGACGGCTCCTTCTTCCTCTACAGCAAGCTCACCGTGCCGTATTG

GAGGTGGGGTGTTCCGCGTACTTTCTCATGCTCCGTGATGCATGAGGCTCTGCACAACCACTAC

ACACAGAAGAGCCTCTCCCTGTCTCCGGGT

Amino acid sequence of Fcab FS20-31-66 without LALA mutation
Hinge region (underlined), CH2 domain (bold) and CH3 domain (italics)

(SEQ ID NO: 107)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EYYSGEVSLTCLVKGFYPSDIAVEWESNGQPENDYKTTPPVLDSDGSFFLYSKLTVPYWRWGVPRT*

*FSCSVMHEALHNHYTQKSLSLSPG*

Nucleic acid sequence of Fcab FS20-31-66 without LALA mutation (SEQ ID NO: 108)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

-continued

CCAATTGAGAAAACTATCTCGAAAGCCAAGGGACAGCCTCGAGAACCACAGGTGTACACCCTGC

CCCCATCCCGGGATGAGTACTACTCTGGTGAAGTCAGCCTGACCTGCCTGGTCAAAGGCTTCTA

TCCCAGCGACATCGCCGTGGAGTGGGAGAGCAATGGGCAGCCGGAGAACGACTACAAGACCAC

GCCTCCCGTGCTGGACTCCGACGGCTCCTTCTTCCTCTACAGCAAGCTCACCGTGCCGTATTGG

AGGTGGGGTGTTCCGCGTACTTTCTCATGCTCCGTGATGCATGAGGCTCTGCACAACCACTACA

CACAGAAGAGCCTCTCCCTGTCTCCGGGT

Amino acid sequence of the heavy chain of FS20-31-66/4420 mock mAb[2] with LALA mutation
VH domain (underlined)

(SEQ ID NO: 109)

QVQLQESGPGLVRPSQTLSLTCTVSGSTFSGYGVNWVRQPPGRGLEWIGMIWGDGNTDYNSALKS

RVTMLVDTSKNQFSLRLSSVTAADTAVYYCARERDYRLDYWGQGSLVTVSSASTKGPSVFPLAPSS

KSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDEYYSGEVSLTCLVKGFYPSDIAVEWESNGQPENDYKTTPPVLD

SDGSFFLYSKLTVPYWRWGVPRTFSCSVMHEALHNHYTQKSLSLSPG

Amino acid sequence of the heavy chain of FS20-31-66/4420 mock mAb[2] without LALA mutation
VH domain (underlined)

(SEQ ID NO: 110)

QVQLQESGPGLVRPSQTLSLTCTVSGSTFSGYGVNWVRQPPGRGLEWIGMIWGDGNTDYNSALKS

RVTMLVDTSKNQFSLRLSSVTAADTAVYYCARERDYRLDYWGQGSLVTVSSASTKGPSVFPLAPSS

KSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDEYYSGEVSLTCLVKGFYPSDIAVEWESNGQPENDYKTTPPVLD

SDGSFFLYSKLTVPYWRWGVPRTFSCSVMHEALHNHYTQKSLSLSPG

Amino acid sequences of Fcab FS20-31-94 Fcab CH3 domain structural loop sequences
FS20-31-94 first sequence- (SEQ ID NO: 111)

WEHGE

FS20-31-94 second sequence- (SEQ ID NO: 112)

IREHD

FS20-31-94 third sequence- (SEQ ID NO: 113)

PYWRWGGPGT

Amino acid sequence of Fcab FS20-31-94 Fcab CH3 domain
First, second and third sequences underlined (SEQ ID NO: 114)

GQPREPQVYTLPPSRDEWEHGEVSLTCLVKGFYPSDIAVEWESNGIREHDYKTTPPVLDSDGSFFLY

SKLTVPYWRWGGPGTFSCSVMHEALHNHYTQKSLSLSPG

Nucleic acid sequence of Fcab FS20-31-94 Fcab CH3 domain (SEQ ID NO: 115)

GGACAGCCTCGAGAACCACAGGTGTACACCCTGCCCCCATCCCGGGATGAGTGGGAACATGGT

GAAGTCAGCCTGACCTGCCTGGTCAAAGGCTTCTATCCCAGCGACATCGCCGTGGAGTGGGAG

AGCAATGGGATCAGAGAACATGATTACAAGACCACGCCTCCCGTGCTGGACTCCGACGGCTCCT

TCTTCCTCTACAGCAAGCTCACCGTGCCATATTGGAGGTGGGGCGGCCCAGGCACCTTCTCATG

CTCCGTGATGCATGAGGCTCTGCACAACCACTACACTCAGAAGAGCTTGTCCCTGTCGCCCGGA

-continued

Amino acid sequence of Fcab FS20-31-94 Fcab with LALA mutation
Hinge region (underlined), CH2 domain (bold), CH3 domain (italics), LALA mutation (bold and underlined)

(SEQ ID NO: 116)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQVYTLPPSRD

EWEHGEVSLTCLVKGFYPSDIAVEWESNGIREHDYKTTPPVLDSDGSFFLYSKLTVPYWRWGGPGT

FSCSVMHEALHNHYTQKSLSLSPG

Nucleic acid sequence of Fcab FS20-31-94 Fcab with LALA mutation (SEQ ID NO: 117)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGATGAGTGGGAACATGGTGAAGTCAGCCTGACCTGCCTGGTCAAAGGCTTCT

ATCCCAGCGACATCGCCGTGGAGTGGGAGAGCAATGGGATCAGAGAACATGATTACAAGACCAC

GCCTCCCGTGCTGGACTCCGACGGCTCCTTCTTCCTCTACAGCAAGCTCACCGTGCCATATTGG

AGGTGGGGCGGCCCAGGCACCTTCTCATGCTCCGTGATGCATGAGGCTCTGCACAACCACTAC

ACTCAGAAGAGCTTGTCCCTGTCGCCCGGA

Amino acid sequence of Fcab FS20-31-94 Fcab without LALA mutation
Hinge region (underlined), CH2 domain (bold) and CH3 domain (italics)

(SEQ ID NO: 118)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EWEHGEVSLTCLVKGFYPSDIAVEWESNGIREHDYKTTPPVLDSDGSFFLYSKLTVPYWRWGGPGT*

*FSCSVMHEALHNHYTQKSLSLSPG*

Nucleic acid sequence of Fcab FS20-31-94 Fcab without LALA mutation (SEQ ID NO: 119)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGACAGCCTCGAGAACCACAGGTGTACACCCTGC

CCCCATCCCGGGATGAGTGGGAACATGGTGAAGTCAGCCTGACCTGCCTGGTCAAAGGCTTCTA

TCCCAGCGACATCGCCGTGGAGTGGGAGAGCAATGGGATCAGAGAACATGATTACAAGACCAC

GCCTCCCGTGCTGGACTCCGACGGCTCCTTCTTCCTCTACAGCAAGCTCACCGTGCCATATTGG

AGGTGGGGCGGCCCAGGCACCTTCTCATGCTCCGTGATGCATGAGGCTCTGCACAACCACTAC

ACTCAGAAGAGCTTGTCCCTGTCGCCCGGA

Amino acid sequence of the heavy chain of FS20-31-94/4420 mock $mAb^2$ with LALA mutation
VH domain (underlined)

(SEQ ID NO: 120)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

-continued

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

EKTISKAKGQPREPQVYTLPPSRDEWEHGEVSLTCLVKGFYPSDIAVEWESNGIREHDYKTTPPVLD

SDGSFFLYSKLTVPYWRWGGPGTFSCSVMHEALHNHYTQKSLSLSPG

Amino acid sequence of the heavy chain of FS20-31-94/4420 mock mAb[2] without LALA mutation
VH domain (underlined)

(SEQ ID NO: 121)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

EKTISKAKGQPREPQVYTLPPSRDEWEHGEVSLTCLVKGFYPSDIAVEWESNGIREHDYKTTPPVLD

SDGSFFLYSKLTVPYWRWGGPGTFSCSVMHEALHNHYTQKSLSLSPG

Amino acid sequences of Fcab FS20-31-102 CH3 domain structural loop sequences
FS20-31-102 first sequence- (SEQ ID NO: 122)

WASGE

FS20-31-102 second sequence- (SEQ ID NO: 123)

QPEVD

FS20-31-102 third sequence- (SEQ ID NO: 102)

PYWRWGVPRT

Amino acid sequence of Fcab FS20-31-102 CH3 domain
First, second and third sequences underlined (SEQ ID NO: 124)

GQPREPQVYTLPPSRDEWASGEVSLTCLVKGFYPSDIAVEWESNGQPEVDYKTTPPVLDSDGSFFL

YSKLTVPYWRWGVPRTFSCSVMHEALHNHYTQKSLSLSPG

Nucleic acid sequence of Fcab FS20-31-102 CH3 domain (SEQ ID NO: 125)

GGCCAGCCTCGAGAACCACAGGTGTACACCCTGCCCCCATCCCGGGATGAGTGGGCATCTGGT

GAAGTCAGCCTGACCTGCCTGGTCAAAGGCTTCTATCCCAGCGACATCGCCGTGGAGTGGGAG

AGCAATGGGCAGCCAGAAGTTGATTACAAGACCACGCCTCCCGTGCTGGACTCCGACGGCTCCT

TCTTCCTCTACAGCAAGCTCACCGTGCCGTATTGGAGGTGGGGTGTTCCGCGTACTTTCTCATG

CTCCGTGATGCATGAGGCTCTGCACAACCACTACACACAGAAGAGCCTCTCCCTGTCTCCGGGT

Amino acid sequence of Fcab FS20-31-102 with LALA mutation
Hinge region (underlined), CH2 domain (bold), CH3 domain (italics), LALA mutation (bold and underlined)

(SEQ ID NO: 126)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EWASGEVSLTCLVKGFYPSDIAVEWESNGQPEVDYKTTPPVLDSDGSFFLYSKLTVPYWRWGVPRT*

*FSCSVMHEALHNHYTQKSLSLSPG*

Nucleic acid sequence of Fcab FS20-31-102 with LALA mutation (SEQ ID NO: 127)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

-continued

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGCCAGCCTCGAGAACCACAGGTGTACACCCTG

CCCCCATCCCGGGATGAGTGGGCATCTGGTGAAGTCAGCCTGACCTGCCTGGTCAAAGGCTTCT

ATCCCAGCGACATCGCCGTGGAGTGGGAGAGCAATGGGCAGCCAGAAGTTGATTACAAGACCA

CGCCTCCCGTGCTGGACTCCGACGGCTCCTTCTTCCTCTACAGCAAGCTCACCGTGCCGTATTG

GAGGTGGGGTGTTCCGCGTACTTTCTCATGCTCCGTGATGCATGAGGCTCTGCACAACCACTAC

ACACAGAAGAGCCTCTCCCTGTCTCCGGGT

Amino acid sequence of Fcab FS20-31-102 without LALA mutation
Hinge region (underlined), CH2 domain (bold) and CH3 domain (italics)

(SEQ ID NO: 128)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EWASGEVSLTCLVKGFYPSDIAVEWESNGQPEVDYKTTPPVLDSDGSFFLYSKLTVPYWRWGVPRT*

*FSCSVMHEALHNHYTQKSLSLSPG*

Nucleic acid sequence of Fcab FS20-31-102 without LALA mutation (SEQ ID NO: 129)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGCCAGCCTCGAGAACCACAGGTGTACACCCTGC

CCCCATCCCGGGATGAGTGGGCATCTGGTGAAGTCAGCCTGACCTGCCTGGTCAAAGGCTTCTA

TCCCAGCGACATCGCCGTGGAGTGGGAGAGCAATGGGCAGCCAGAAGTTGATTACAAGACCAC

GCCTCCCGTGCTGGACTCCGACGGCTCCTTCTTCCTCTACAGCAAGCTCACCGTGCCGTATTGG

AGGTGGGGTGTTCCGCGTACTTTCTCATGCTCCGTGATGCATGAGGCTCTGCACAACCACTACA

CACAGAAGAGCCTCTCCCTGTCTCCGGGT

Amino acid sequence of the heavy chain of FS20-31-102/4420 mock mAb$^2$ with LALA mutation
VH domain (underlined)

(SEQ ID NO: 130)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEWASGEVSLTCLVKGFYPSDIAVEWESNGQPEVDYKTTPPVL

DSDGSFFLYSKLTVPYWRWGVPRTFSCSVMHEALHNHYTQKSLSLSPG

Amino acid sequence of the heavy chain of FS20-31-102/4420 mock mAb$^2$ without LALA mutation
VH domain (underlined)

(SEQ ID NO: 131)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

-continued

EKTISKAKGQPREPQVYTLPPSRDEWASGEVSLTCLVKGFYPSDIAVEWESNGQPEVDYKTTPPVL

DSDGSFFLYSKLTVPYWRWGVPRTFSCSVMHEALHNHYTQKSLSLSPG

Amino acid sequences of Fcab FS20-31-108 CH3 domain structural loop sequences

FS20-31-108 first sequence- (SEQ ID NO: 122)

WASGE

FS20-31-108 second sequence- (SEQ ID NO: 132)

EKEID

FS20-31-108 third sequence- (SEQ ID NO: 133)

PYWRWGAKRT

Amino acid sequence of Fcab FS20-31-108 CH3 domain

First, second and third sequences underlined (SEQ ID NO: 134)

GQPREPQVYTLPPSRDEWASGEVSLTCLVKGFYPSDIAVEWESNGEKEIDYKTTPPVLDSDGSFFLY

SKLTVPYWRWGAKRTFSCSVMHEALHNHYTQKSLSLSPG

Nucleic acid sequence of Fcab FS20-31-108 CH3 domain (SEQ ID NO: 135)

GGCCAGCCTCGAGAACCACAGGTGTACACCCTGCCCCCATCCCGGGATGAGTGGGCATCTGGT

GAAGTCAGCCTGACCTGCCTGGTCAAAGGCTTCTATCCCAGCGACATCGCCGTGGAGTGGGAG

AGCAATGGGGAAAAAGAAATCGATTACAAGACCACGCCTCCCGTGCTGGACTCCGACGGCTCCT

TCTTCCTCTACAGCAAGCTCACCGTGCCGTATTGGAGGTGGGGTGCTAAGCGTACTTTCTCATG

CTCCGTGATGCATGAGGCTCTGCACAACCACTACACACAGAAGAGCCTCTCCCTGTCTCCGGGT

Amino acid sequence of Fcab FS20-31-108 with LALA mutation

Hinge region (underlined), CH2 domain (bold), CH3 domain (italics), LALA mutation (bold and underlined)

(SEQ ID NO: 136)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EWASGEVSLTCLVKGFYPSDIAVEWESNGEKEIDYKTTPPVLDSDGSFFLYSKLTVPYWRWGAKRTF*

*SCSVMHEALHNHYTQKSLSLSPG*

Nucleic acid sequence of Fcab FS20-31-108 with LALA mutation (SEQ ID NO: 137)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGCCAGCCTCGAGAACCACAGGTGTACACCCTG

CCCCCATCCCGGGATGAGTGGGCATCTGGTGAAGTCAGCCTGACCTGCCTGGTCAAAGGCTTCT

ATCCCAGCGACATCGCCGTGGAGTGGGAGAGCAATGGGGAAAAAGAAATCGATTACAAGACCAC

GCCTCCCGTGCTGGACTCCGACGGCTCCTTCTTCCTCTACAGCAAGCTCACCGTGCCGTATTGG

AGGTGGGGTGCTAAGCGTACTTTCTCATGCTCCGTGATGCATGAGGCTCTGCACAACCACTACA

CACAGAAGAGCCTCTCCCTGTCTCCGGGT

Amino acid sequence of Fcab FS20-31-108 without LALA mutation

Hinge region (underlined), CH2 domain (bold) and CH3 domain (italics)

(SEQ ID NO: 138)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

-continued

*EWASGEVSLTCLVKGFYPSDIAVEWESNGEKEIDYKTTPPVLDSDGSFFLYSKLTVPYWRWGAKRTF*

*SCSVMHEALHNHYTQKSLSLSPG*

Nucleic acid sequence of Fcab FS20-31-108 without LALA mutation (SEQ ID NO: 139)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGCCAGCCTCGAGAACCACAGGTGTACACCCTGC

CCCCATCCCGGGATGAGTGGGCATCTGGTGAAGTCAGCCTGACCTGCCTGGTCAAAGGCTTCTA

TCCCAGCGACATCGCCGTGGAGTGGGAGAGCAATGGGGAAAAAGAAATCGATTACAAGACCAC

GCCTCCCGTGCTGGACTCCGACGGCTCCTTCTTCCTCTACAGCAAGCTCACCGTGCCGTATTGG

AGGTGGGGTGCTAAGCGTACTTTCTCATGCTCCGTGATGCATGAGGCTCTGCACAACCACTACA

CACAGAAGAGCCTCTCCCTGTCTCCGGGT

Amino acid sequence of the heavy chain of FS20-31-108/4420 mock $mAb^2$ with LALA mutation VH domain (underlined)

(SEQ ID NO: 140)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEWASGEVSLTCLVKGFYPSDIAVEWESNGEKEIDYKTTPPVLD

SDGSFFLYSKLTVPYWRWGAKRTFSCSVMHEALHNHYTQKSLSLSPG

Amino acid sequence of the heavy chain of FS20-31-108/4420 mock $mAb^2$ without LALA mutation VH domain (underlined)

(SEQ ID NO: 141)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEWASGEVSLTCLVKGFYPSDIAVEWESNGEKEIDYKTTPPVLD

SDGSFFLYSKLTVPYWRWGAKRTFSCSVMHEALHNHYTQKSLSLSPG

Amino acid sequences of Fcab FS20-31-115 CH3 domain structural loop sequences

FS20-31-115 first sequence- (SEQ ID NO: 122)

WASGE

FS20-31-115 second sequence- (SEQ ID NO: 142)

EQEFD

FS20-31-115 third sequence- (SEQ ID NO: 133)

PYWRWGAKRT

-continued

Amino acid sequence of Fcab FS20-31-115 CH3 domain
First, second and third sequences underlined (SEQ ID NO: 143)

GQPREPQVYTLPPSRDEWASGEVSLTCLVKGFYPSDIAVEWESNGEQEFDYKTTPPVLDSDGSFFL

YSKLTVPYWRWGAKRTFSCSVMHEALHNHYTQKSLSLSPG

Nucleic acid sequence of Fcab FS20-31-115 CH3 domain (SEQ ID NO: 144)

GGACAGCCTCGAGAACCACAGGTGTACACCCTGCCCCCATCCCGGGATGAGTGGGCATCTGGT

GAAGTCAGCCTGACCTGCCTGGTCAAAGGCTTCTATCCCAGCGACATCGCCGTGGAGTGGGAG

AGCAATGGGGAACAGGAATTCGATTACAAGACCACGCCTCCCGTGCTGGACTCCGACGGCTCCT

TCTTCCTCTACAGCAAGCTCACCGTGCCGTATTGGAGGTGGGGTGCTAAGCGTACTTTCTCATG

CTCCGTGATGCATGAGGCTCTGCACAACCACTACACTCAGAAGAGCTTGTCCCTGTCGCCCGGA

Amino acid sequence of Fcab FS20-31-115 with LALA mutation
Hinge region (underlined), CH2 domain (bold), CH3 domain (italics),
LALA mutation (bold and underlined)

(SEQ ID NO: 145)

TCPPCPAPEAAGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EWASGEVSLTCLVKGFYPSDIAVEWESNGEQEFDYKTTPPVLDSDGSFFLYSKLTVPYWRWGAKRT*

*FSCSVMHEALHNHYTQKSLSLSPG*

Nucleic acid sequence of Fcab FS20-31-115 with LALA mutation (SEQ ID NO: 146)

ACTTGCCCGCCTTGCCCAGCCCCGGAAGCTGCCGGTGGTCCTTCGGTGTTCCTCTTCCCGCCC

AAGCCGAAGGATACCCTGATGATCTCACGGACCCCCGAAGTGACCTGTGTGGTGGTGGACGTG

TCCCACGAGGACCCGGAAGTGAAATTCAATTGGTACGTGGATGGAGTGGAAGTGCACAACGCCA

AGACCAAGCCACGGGAAGAACAGTACAACTCTACCTACCGCGTGGTGTCCGTGCTCACTGTGCT

GCACCAAGACTGGCTGAACGGGAAGGAGTACAAGTGCAAAGTGTCCAACAAGGCGCTGCCTGC

CCCAATTGAGAAAACTATCTCGAAAGCCAAGGGACAGCCTCGAGAACCACAGGTGTACACCCTG

CCCCCATCCCGGGATGAGTGGGCATCTGGTGAAGTCAGCCTGACCTGCCTGGTCAAAGGCTTCT

ATCCCAGCGACATCGCCGTGGAGTGGGAGAGCAATGGGGAACAGGAATTCGATTACAAGACCA

CGCCTCCCGTGCTGGACTCCGACGGCTCCTTCTTCCTCTACAGCAAGCTCACCGTGCCGTATTG

GAGGTGGGGTGCTAAGCGTACTTTCTCATGCTCCGTGATGCATGAGGCTCTGCACAACCACTAC

ACTCAGAAGAGCTTGTCCCTGTCGCCCGGA

Amino acid sequence of Fcab FS20-31-115 without LALA mutation
Hinge region (underlined), CH2 domain (bold) and CH3 domain (italics)

(SEQ ID NO: 147)

TCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK*GQPREPQVYTLPPSRD*

*EWASGEVSLTCLVKGFYPSDIAVEWESNGEQEFDYKTTPPVLDSDGSFFLYSKLTVPYWRWGAKRT*

*FSCSVMHEALHNHYTQKSLSLSPG*

Nucleic acid sequence of Fcab FS20-31-115 without LALA mutation (SEQ ID NO: 148)

ACTTGCCCGCCTTGCCCAGCCCCGGAACTGCTGGGTGGTCCTTCGGTGTTCCTCTTCCCGCCCA

AGCCGAAGGATACCCTGATGATCTCACGGACCCCCGAAGTGACCTGTGTGGTGGTGGACGTGT

CCCACGAGGACCCGGAAGTGAAATTCAATTGGTACGTGGATGGAGTGGAAGTGCACAACGCCAA

GACCAAGCCACGGGAAGAACAGTACAACTCTACCTACCGCGTGGTGTCCGTGCTCACTGTGCTG

CACCAAGACTGGCTGAACGGGAAGGAGTACAAGTGCAAAGTGTCCAACAAGGCGCTGCCTGCC

CCAATTGAGAAAACTATCTCGAAAGCCAAGGGACAGCCTCGAGAACCACAGGTGTACACCCTGC

CCCCATCCCGGGATGAGTGGGCATCTGGTGAAGTCAGCCTGACCTGCCTGGTCAAAGGCTTCTA

-continued

TCCCAGCGACATCGCCGTGGAGTGGGAGAGCAATGGGGAACAGGAATTCGATTACAAGACCAC

GCCTCCCGTGCTGGACTCCGACGGCTCCTTCTTCCTCTACAGCAAGCTCACCGTGCCGTATTGG

AGGTGGGGTGCTAAGCGTACTTTCTCATGCTCCGTGATGCATGAGGCTCTGCACAACCACTACA

CTCAGAAGAGCTTGTCCCTGTCGCCCGGA

Amino acid sequence of the heavy chain of FS20-31-115/4420 mock mAb$^2$ with LALA mutation
VH domain (underlined)

(SEQ ID NO: 149)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEWASGEVSLTCLVKGFYPSDIAVEWESNGEQEFDYKTTPPVLD

SDGSFFLYSKLTVPYWRWGAKRTFSCSVMHEALHNHYTQKSLSLSPG

Amino acid sequence of the heavy chain of FS20-31-115/4420 mock mAb$^2$ without LALA mutation
VH domain (underlined)

(SEQ ID NO: 150)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDEWASGEVSLTCLVKGFYPSDIAVEWESNGEQEFDYKTTPPVLD

SDGSFFLYSKLTVPYWRWGAKRTFSCSVMHEALHNHYTQKSLSLSPG

Amino acid sequence of Fcab FS20m-232-91 CH3 domain
AB, CD and EF loops underlined (SEQ ID NO: 151)

GQPREPQVYTLPPSRDELFDPMYYYNQVSLTCLVKGFYPSDIAVEWESNGEPLWDYKTTPPVLDSD

GSFFLYSKLTVWRDRWEDGNVFSCSVMHEALHNHYTQKSLSLSPGK

Amino acid sequence of the heavy chain of FS20m-232-91/4420 mock mAb$^2$ with LALA mutation
VH domain (underlined)

(SEQ ID NO: 152)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDELFDPMYYYNQVSLTCLVKGFYPSDIAVEWESNGEPLWDYKTT

PPVLDSDGSFFLYSKLTVWRDRWEDGNVFSCSVMHEALHNHYTQKSLSLSPG

Amino acid sequence of the heavy chain of FS20m-232-91/4420 mock mAb$^2$ without LALA mutation
VH domain (underlined)

(SEQ ID NO: 153)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

-continued

VSHEDPEVKFNWYVDGVEVHNAKTKPREEQYNSTYRVVSVLTVLHQDWLNGKEYKCKVSNKALPAP

IEKTISKAKGQPREPQVYTLPPSRDELFDPMYYYNQVSLTCLVKGFYPSDIAVEWESNGEPLWDYKTT

PPVLDSDGSFFLYSKLTVWRDRWEDGNVFSCSVMHEALHNHYTQKSLSLSPG

Amino acid sequence of the heavy chain of FS20m-232-91/HelD1.3 mock mAb$^2$ with LALA mutation
VH domain (underlined)

(SEQ ID NO: 154)
QVQLQESGPGLVRPSQTLSLTCTVSGSTFSGYGVNWVRQPPGRGLEWIGMIWGDGNTDYNSALKS

RVTMLVDTSKNQFSLRLSSVTAADTAVYYCARERDYRLDYWGQGSLVTVSSASTKGPSVFPLAPSS

KSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELFDPMYYYNQVSLTCLVKGFYPSDIAVEWESNGEPLWDYKTT

PPVLDSDGSFFLYSKLTVWRDRWEDGNVFSCSVMHEALHNHYTQKSLSLSPG

Amino acid sequence of the heavy chain of FS20m-232-91/HelD1.3 mock mAb$^2$ without LALA mutation
VH domain (underlined)

(SEQ ID NO: 155)
QVQLQESGPGLVRPSQTLSLTCTVSGSTFSGYGVNWVRQPPGRGLEWIGMIWGDGNTDYNSALKS

RVTMLVDTSKNQFSLRLSSVTAADTAVYYCARERDYRLDYWGQGSLVTVSSASTKGPSVFPLAPSS

KSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELFDPMYYYNQVSLTCLVKGFYPSDIAVEWESNGEPLWDYKTT

PPVLDSDGSFFLYSKLTVWRDRWEDGNVFSCSVMHEALHNHYTQKSLSLSPG

Amino acid sequence of the light chain of 4420 mAb
VL domain (underlined)

(SEQ ID NO: 156)
DVVMTQTPLSLPVSLGDQASISCRSSQSLVHSNGNTYLRWYLQKPGQSPKVLIYKVSNRFSGVPDRF

SGSGSGTDFTLKISRVEAEDLGVYFCSQSTHVPWTFGGGTKLEIKRTVAAPSVFIFPPSDEQLKSGTA

SVVCLLNNFYPREAKVQWKVDNALQSGNSQESVTEQDSKDSTYSLSSTLTLSKADYEKHKVYACEV

THQGLSSPVTKSFNRGEC

Amino acid sequence of the light chain of HelD1.3 mock mAb$^2$
VL domain (underlined)

(SEQ ID NO: 157)
DIQMTQSPASLSASVGETVTITCRASGNIHNYLAWYQQKQGKSPQLLVYNAKTLADGVPSRFSGSGS

GTQYSLKINSLQPEDFGSYYCQHFWSTPRTFGGGTKLEIKRTVAAPSVFIFPPSDEQLKSGTASVVCL

LNNFYPREAKVQWKVDNALQSGNSQESVTEQDSKDSTYSLSSTLTLSKADYEKHKVYACEVTHQGL

SSPVTKSFNRGEC

Amino acid sequence of human OX40-mFc
IL-2 leader sequence (underlined), OX40 extracellular domain (italics),
Mouse IgG2a Fc domain (bold)

(SEQ ID NO: 158)
MYRMQLLSCIALSLALVTNS*LHCVGDTYPSNDRCCHECRPGNGMVSRCSRSQNTVCRPCGPGFYN*

*DVVSSKPCKPCTWCNLRSGSERKQLCTATQDTVCRCRAGTQPLDSYKPGVDCAPCPPGHFSPGDN*

*QACKPWTNCTLAGKHTLQPASNSSDAICEDRDPPATQPQETQGPPARPITVQPTEAWPRTSQGPST*

*RPVEVPGGRAVA*GSPRGPTIKPCPPCKCPAPNLLGGPSVFIFPPKIKDVLMISLSPIVTCVVVDVSED

DPDVQISWFVNNVEVHTAQTQTHREDYNSTLRVVSALPIQHQDWMSGKEFKCKVNNKDLPAPIERT

-continued

ISKPKGSVRAPQVYVLPPPEEEMTKKQVTLTCMVTDFMPEDIYVEWTNNGKTELNYKNTEPVLDSD

GSYFMYSKLRVEKKNWVERNSYSCSVVHEGLHNHHTTKSFSRTPGK

Amino acid sequence of mouse OX40-mFc
IL-2 leader sequence (underlined), OX40 extracellular domain (italics),
Mouse IgG2a Fc domain (bold)

(SEQ ID NO: 159)

MYRMQLLSCIALSLALVTNS*VTARRLNCVKHTYPSGHKCCRECQPGHGMVSRCDHTRDTLCHPCET*

*GFYNEAVNYDTCKQCTQCNHRSGSELKQNCTPTQDTVCRCRPGTQPRQDSGYKLGVDCVPCPPG*

*HFSPGNNQACKPWTNCTLSGKQTRHPASDSLDAVCEDRSLLATLLWETQRPTFRPTTVQSTTVWPR*

*TSELPSPPTLVTPEGPA*GSPRGPTIKPCPPCKCPAPNLLGGPSVFIFPPKIKDVLMISLSPIVTCVVVD

VSEDDPDVQISWFVNNVEVHTAQTQTHREDYNSTLRVVSALPIQHQDWMSGKEFKCKVNNKDLPA

PIERTISKPKGSVRAPQVYVLPPPEEEMTKKQVTLTCMVTDFMPEDIYVEWTNNGKTELNYKNTEPV

LDSDGSYFMYSKLRVEKKNWVERNSYSCSVVHEGLHNHHTTKSFSRTPGK

Amino acid sequence of cynomolgus monkey OX40-mFc
IL-2 leader sequence (underlined), OX40 extracellular domain (italics),
Mouse IgG2a Fc domain (bold)

(SEQ ID NO: 160)

MYRMQLLSCIALSLALVTNS*LHCVGDTYPSNDRCCQECRPGNGMVSRCNRSQNTVCRPCGPGFYN*

*DVVSAKPCKACTWCNLRSGSERKQPCTATQDTVCRCRAGTQPLDSYKPGVDCAPCPPGHFSPGDN*

QACKPWTNCTLAGKHTLQPASNSSDAICEDRDPPPTQPQETQGPPARPTTVQPTEAWPRTSQRPST

*RPVEVPRGPAVAAI*GSPRGPTIKPCPPCKCPAPNLLGGPSVFIFPPKIKDVLMISLSPIVTCVVVDVSE

DDPDVQISWFVNNVEVHTAQTQTHREDYNSTLRVVSALPIQHQDWMSGKEFKCKVNNKDLPAPIER

TISKPKGSVRAPQVYVLPPPEEEMTKKQVTLTCMVTDFMPEDIYVEWTNNGKTELNYKNTEPVLDS

DGSYFMYSKLRVEKKNWVERNSYSCSVVHEGLHNHHTTKSFSRTPGK

Amino acid sequence of human OX40 extracellular domain (SEQ ID NO: 161)

LHCVGDTYPSNDRCCHECRPGNGMVSRCSRSQNTVCRPCGPGFYNDVVSSKPCKPCTWCNLRSG

SERKQLCTATQDTVCRCRAGTQPLDSYKPGVDCAPCPPGHFSPGDNQACKPWTNCTLAGKHTLQP

ASNSSDAICEDRDPPATQPQETQGPPARPITVQPTEAWPRTSQGPSTRPVEVPGGRA

Amino acid sequence of cynomolgus monkey OX40 extracellular domain (SEQ ID NO: 162)

LHCVGDTYPSNDRCCQECRPGNGMVSRCNRSQNTVCRPCGPGFYNDVVSAKPCKACTWCNLRSG

SERKQPCTATQDTVCRCRAGTQPLDSYKPGVDCAPCPPGHFSPGDNQACKPWTNCTLAGKHTLQP

ASNSSDAICEDRDPPPTQPQETQGPPARPTTVQPTEAWPRTSQRPSTRPVEVPRGPA

Amino acid sequence of mouse OX40 extracellular domain (SEQ ID NO: 163)

VTARRLNCVKHTYPSGHKCCRECQPGHGMVSRCDHTRDTLCHPCETGFYNEAVNYDTCKQCTQCN

HRSGSELKQNCTPTQDTVCRCRPGTQPRQDSGYKLGVDCVPCPPGHFSPGNNQACKPWTNCTLS

GKQTRHPASDSLDAVCEDRSLLATLLWETQRPTFRPTTVQSTTVWPRTSELPSPPTLVTPEGP

Amino acid sequence of DO11.10-hOX40 and human OX40 receptor (SEQ ID NO: 164)

LHCVGDTYPSNDRCCHECRPGNGMVSRCSRSQNTVCRPCGPGFYNDVVSSKPCKPCTWCNLRSG

SERKQLCTATQDTVCRCRAGTQPLDSYKPGVDCAPCPPGHFSPGDNQACKPWTNCTLAGKHTLQP

ASNSSDAICEDRDPPATQPQETQGPPARPITVQPTEAWPRTSQGPSTRPVEVPGGRAVAAILGLGLV

LGLLGPLAILLALYLLRRDQRLPPDAHKPPGGGSFRTPIQEEQADAHSTLAKI

Amino acid sequence of DO11.10-mOX40 and mouse OX40 receptor (SEQ ID NO: 165)

VTARRLNCVKHTYPSGHKCCRECQPGHGMVSRCDHTRDTLCHPCETGFYNEAVNYDTCKQCTQCN

HRSGSELKQNCTPTQDTVCRCRPGTQPRQDSGYKLGVDCVPCPPGHFSPGNNQACKPWTNCTLS

-continued

GKQTRHPASDSLDAVCEDRSLLATLLWETQRPTFRPTTVQSTTVWPRTSELPSPPTLVTPEGPAFAV

LLGLGLGLLAPLTVLLALYLLRKAVVRLPNTPKPCWGNSFRTPIQEEHTDAHFTLAKI

Amino acid sequence of DO11.10-cOX40 and cynomolgus monkey OX40 receptor (SEQ ID NO: 166)

KLHCVGDTYPSNDRCCQECRPGNGMVSRCNRSQNTVCRPCGPGFYNDVVSAKPCKACTWCNLRS

GSERKQPCTATQDTVCRCRAGTQPLDSYKPGVDCAPCPPGHFSPGDNQACKPWTNCTLAGKHTLQ

PASNSSDAICEDRDPPPTQPQETQGPPARPTTVQPTEAWPRTSQRPSTRPVEVPRGPAVAAILGLGL

ALGLLGPLAMLLALLLLRRDQRLPPDAPKAPGGGSFRTPIQEEQADAHSALAKI

Amino acid sequence of the heavy chain of anti-FITC mAb G1AA/4420 comprising LALA mutation Position of the CDRs are underlined. Position of LALA mutation is in bold.

(SEQ ID NO: 167)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Amino acid sequence of the heavy chain of anti-FITC mAb G1/4420 without LALA mutation Position of the CDRs are underlined.

(SEQ ID NO: 168)

EVKLDETGGGLVQPGRPMKLSCVASGFTFSDYWMNWVRQSPEKGLEWVAQIRNKPYNYETYYSDS

VKGRFTISRDDSKSSVYLQMNNLRVEDMGIYYCTGSYYGMDYWGQGTSVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Amino acid sequence of the heavy chain of the G1/HelD1.3 antibody with LALA mutation (SEQ ID NO: 169)

QVQLQESGPGLVRPSQTLSLTCTVSGSTFSGYGVNWVRQPPGRGLEWIGMIWGDGNTDYNSALKS

RVTMLVDTSKNQFSLRLSSVTAADTAVYYCARERDYRLDYWGQGSLVTVSSASTKGPSVFPLAPSS

KSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

Amino acid of the full-length IgG1 hinge region (SEQ ID NO: 170)

EPKSCDKTHTCPPCP

Amino acid sequence of the truncated Fcab hinge region (SEQ ID NO: 171)

TCPPCP

Amino acid heavy chain sequence of FS20-22-49-AA/FS30-10-16

(SEQ ID NO: 172)

EVQLLESGGGLVQPGGSLRLSCAASGFTFSSYDMSWVRQAPGKGLEWVSDIDPTGSKTDYADSVK

GRFTISRDNSKNTLYLQMNSLRAEDTAVYYCARDLLVYGFDYWGQGTLVTVSSASTKGPSVFPLAPS

-continued

SKSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDEYWDQEVSLTCLVKGFYPSDIAVEWESNGDEQFAYKTTPPVLD

SDGSFFLYSKLTVDQYRWNPADYFSCSVMHEALHNHYTQKSLSLSPG

Amino acid light chain sequence of FS20-22-49-AA/FS30-10-16

(SEQ ID NO: 173)

EIVLTQSPGTLSLSPGERATLSCRASQSVSSSYLAWYQQKPGQAPRLLIYGASSRATGIPDRFSGSGS

GTDFTLTISRLEPEDFAVYYCQQSYSYPVTFGQGTKVEIKRTVAAPSVFIFPPSDEQLKSGTASVVCLL

NNFYPREAKVQWKVDNALQSGNSQESVTEQDSKDSTYSLSSTLTLSKADYEKHKVYACEVTHQGLS

SPVTKSFNRGEC

Amino acid sequence of heavy chain of G1/OX86 mAb comprising LALA mutation (G1AA/OX86)

(SEQ ID NO: 175)

QVQLKESGPGLVQPSQTLSLTCTVSGFSLTGYNLHWVRQPPGKGLEWMGRMRYDGDTYYNSVLKS

RLSISRDTSKNQVFLKMNSLQTDDTAIYYCTRDGRGDSFDYWGQGVMVTVSSASTKGPSVFPLAPS

SKSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Amino acid sequence of light chain of G1AA/OX86 mAb (SEQ ID NO: 176)

DIVMTQGALPNPVPSGESASITCRSSQSLVYKDGQTYLNWFLQRPGQSPQLLTYWMSTRASGVSDR

FSGSGSGTYFTLKISRVRAEDAGVYYCQQVREYPFTFGSGTKLEIKRTVAAPSVFIFPPSDEQLKSGT

ASVVCLLNNFYPREAKVQWKVDNALQSGNSQESVTEQDSKDSTYSLSSTLTLSKADYEKHKVYACE

VTHQGLSSPVTKSFNRGEC

REFERENCES

All documents mentioned in this specification are incorporated herein by reference in their entirety.

Ali S A, Ahmad M, Lynam J, McLean C S, Entwisle C, Loudon P, Choolun E, McArdle S E, Li G, Mian S, Rees R C. Anti-tumour therapeutic efficacy of OX40L in murine tumour model. Vaccine 22(27-28), 3585-94 (2004).

Altschul S F, Gish W, Miller W, Myers E W, Lipman D J. Basic local alignment search tool. J. Mol. Biol. 215(3), 403-10 (1990).

Altschul S F, Madden T L, SchAffer A A, Zhang J, Zhang Z, Miller W, Lipman D J. Gapped BLAST and PSI-BLAST: a new generation of protein database search programs. Nucleic Acids Res. 25(17), 3389-402 (1997).

Andrade V C, Vettore A L, Felix R S, Almeida M S, Carvalho F, Oliveira J S, Chauffaille M L, Andriolo A, Caballero O L, Zago M A, Colleoni G W. Prognostic impact of cancer/testis antigen expression in advanced stage multiple myeloma patients. Cancer Immun. 8, 2 (2008).

Arch R H, Thompson C B. 4-1 B B and 0x40 are members of a tumor necrosis factor (TNF)-nerve growth factor receptor subfamily that bind TNF-receptor-associated factors and activate nuclear factor K B. Mol. Cell. Biol. 18(1), 558-65 (1998).

Bagshawe $K_D$, Sharma S K, Springer C J, Antoniw P, Rogers G T, Burke P J, Melton R. Antibody-enzyme conjugates can generate cytotoxic drugs from inactive precursors at tumor sites. Antibody, Immunoconjugates and Radiopharmaceuticals 4, 915-922 (1991).

Bedzyk W D, Johnson L S, Riordan G S, Voss E W Jr. Comparison of variable region primary structures within an anti-fluorescein idiotype family. J. Biol. Chem. 264(3), 1565-69 (1989).

Bedzyk W D, Weidner K M, Denzin L K, Johnson L S, Hardman K D, Pantoliano M W, Asel E D, Voss E W Jr. Immunological and structural characterization of a high affinity anti-fluorescein single-chain antibody. J. Biol. Chem. 265(30), 18615-20 (1990).

Bhome R, Bullock M D, A1 Saihati H A, Goh R W, Primrose J N, Sayan A E, Mirnezami A H. A top-down view of the tumor microenvironment: structure, cells and signaling. Front. Cel. Dev. Biol. 3, 33 (2015).

Braden B C, Fields B A, Ysern X, Goldbaum F A, Dall'Acqua W, Schwarz F P, Poljak R J, Mariuzza R A. Crystal structure of the complex of the variable domain of antibody D1.3 and turkey egg white lysozyme: a novel conformational change in antibody CD3-L3 selects for antigen. J. Mol. Biol. 257(5), 889-94 (1996).

Bruhns P, lannascoli B, England P, Mancardi D A, Fernandez N, Jorieux S, Dasron M. Specificity and affinity of human Fcγ receptors and their polymorphic variants for human IgG subclasses. Blood 113(16), 3716-25 (2009).

Carter P, Smith L, Ryan M. Identification and validation of cell surface antigens for antibody targeting in oncology. Endocr. Relat. Cancer 11(4), 659-87 (2004).

Cheever M A, Allison J P, Ferris A S, Finn O J, Hastings B M, Hecht T T, Mellman I, Prindiville S A, Viner J L, Weiner L M, Matrisian L M. Clin. Cancer Res. 15(17), 5323-37 (2009).

Chen D S, Mellman I. Oncology meets immunology: the cancer-immunity cycle. Immunity 39(1), 1-10 (2013).

Chodorge M, Zuger S, Stirnimann C, Briand C, Jermutus L, Grutter M G, Minter R R. A series of Fas receptor agonist antibodies that demonstrate an inverse correlation between affinity and potency. Cell Death Differ. 2012, 19(7), 1187-95 (2012).

Croft M. Control of immunity by the TNFR-related molecule OX40 (CD134). Annu. Rev. Immunol. 28, 57-78 (2010).

Curti B D, Kovacsovics-Bankowski M, Morris N, Walker E, Chisholm L, Floyd K, Walker J, Gonzalez 1, Meeuwsen T, Fox B A, Moudgil T, Miller W, Haley D, Coffey T, Fisher B, Delanty-Miller L, Rymarchyk N, Kelly T, Crocenzi T, Bernstein E, Sanborn R, Urba W J, Weinberg A D. OX40 is a potent immune-stimulating target in late-stage cancer patients. Cancer Res. 73(24), 7189-7198 (2013).

El-Khoueiry A B, Hamid O, Thompson J A, Ros W, Eskens F, Doi T, Hu-Lieskovan S, Chou J, Liao K, Ganguly B J, Fleener C, Joh T, Diab A. The relationship of pharmacodynamics (P D) and pharmacokinetics (P K) to clinical outcomes in a phase I study of OX40 agonistic monoclonal antibody (mAb) PF-04518600 (PF-8600). J. Clin. Oncol. 35(15_suppl), 3027 (2017).

Glisson B S, Leidner R, Ferris R L, Powderly J, Rizvi N, Norton J D, Burton J, Lanasa M C, Patel S P. Phase 1 study of MED10562, a humanized OX40 agonist monoclonal antibody (mAb), in adult patients (pts) with advanced solid tumors. Ann. Oncol. 27(Supplement 6), 1052P D (2016).

Gubin M M, Artyomov M N, Mardis E R, Schreiber R D. Tumor neoantigens: building a framework for personalized cancer immunotherapy. J. Clin. Invest. 125(9), 3413-21 (2015).

Gure A O, Chua R, Williamson B, Gonen M, Ferrera C A, Gnjatic S, Ritter G, Simpson A J, Chen Y T, Old L J, Altorki N K. Cancer-testis genes are coordinately expressed and are markers of poor outcome in non-small cell lung cancer. Clin. Cancer Res. 11(22), 8055-62 (2005).

Hasenhindl C, Traxlmayr M W, Wozniak-Knopp G, Jones P C, Stadlmayr G, Ruker F, Obinger C. Stability assessment on a library scale: a rapid method for the evaluation of the commutability and insertion of residues in C-terminal loops of the CH3 domains of IgG1-Fc. Protein Eng. Des. Sel., 26(10), 675-82 (2013).

Guo Z, Wang X, Cheng D, Xia Z, Luan M, Zhang S. PD-1 blockade and OX40 triggering synergistically protects against tumor growth in a murine model of ovarian cancer. PLoS ONE 9(2), e89350 (2014).

Hezareh M, Hessell A J, Jensen R C, van de Winkel J G, Parren P W. Effector function activities of a panel of mutants of a broadly neutralizing antibody against human immunodeficiency virus type 1. J. Virol. 75(24), 12161-8 (2001).

Hu S, Shively L, Raubitschek A, Sherman M, Williams L E, Wong J Y, Shively J E, Wu A M. Minibody: A novel engineered anti-carcinoembryonic antigen antibody fragment (single-chain Fv-CH3) which exhibits rapid, high-level targeting of xenografts. Cancer Res. 56(13), 3055-61 (1996).

Idusogie E E, Presta L G, Gazzano-Santoro H, Totpal K, Wong P Y, Ultsch M, Meng Y G, Mulkerrin M G. Mapping of the C1q binding site on rituxan, a chimeric antibody with a human IgG1 Fc. J. Immunol. 164(8), 4178-84 (2000).

Jefferis R, Reimer C B, Skvaril F, de Lange G, Ling N R, Lowe J, Walker M R, Phillips D J, Aloisio C H, Wells T W. Evaluation of monoclonal antibodies having specificity for human IgG sub-classes: results of an IUIS/WHO collaborative study. Immunol. Lett. 1, 223-52 (1985).

Jefferis R, Reimer C B, Skvaril F, de Lange G G, Goodall D M, Bentley T L, Phillips D J, Vlug A, Harada S, Radl J. Evaluation of monoclonal antibodies having specificity for human IgG subclasses: results of the 2nd IUIS/WHO collaborative study. Immunol. Lett. 31(2). 143-68 (1992).

Kabat E A, Wu T T, Perry H M, Gottesman K S, Foeller C. Sequences of Proteins of Immunological Interest, 5th ed. NIH Publication No. 91-3242. Washington, D.C.: U.S. Department of Health and Human Services (1991).

Kjaergaard J, Tanaka J, Kim J A, Rothchild K, Weinberg A, Shu S. Therapeutic efficacy of OX-40 receptor antibody depends on tumor immunogenicity and anatomic site of tumor growth. Cancer Res. 60(19), 5514-21 (2000).

Klein C, Schaefer W, Regula J T. The use of CrossMAb technology for the generation of bi- and multispecific antibodies. MAbs 8(6), 1010-20 (2016).

Kontermann (2012). Dual targeting strategies with bispecific antibodies. MAbs 4(2):182-97.

Ledermann J A, Begent R H, Massof C, Kelly A M, Adam T, Bagshawe $K_D$. A phase-I study of repeated therapy with radiolabelled antibody to carcinoembryonic antigen using intermittent or continuous administration of cyclosporin A to supress the immune response. Int. J. Cancer 47(5), 659-64 (1991).

Lefranc M P, Pommié C, Kaas Q, Duprat E, Bosc N, Guiraudou D, Jean C, Ruiz M, Da Piedade I, Rouard M, Foulquier E, Thouvenin V, Lefranc G. IMGT unique numbering for immunoglobulin and T cell receptor constant domains and Ig superfamily C-like domains. Dev. Comp. Immunol. 29(3), 185-203 (2005).

Lefranc M P, Giudicelli V, Duroux P, Jabado-Michaloud J, Folch G, Aouinti S, Carillon E, Duvergey H, Houles A, Paysan-Lafosse T, Hadi-Saljoqi S, Sasorith S, Lefranc G, Kossida S. IMGT®, the international ImMunoGeneTics information system® 25 years on. Nucleic Acids Res. 43 (Database issue), D413-22 (2015).

Malarkannan S, Horng T, Shih P P, Schwab S, Shastri N. Presentation of out-of-frame peptide/MHC class I complexes by a novel translation initiation mechanism. Immunity 10(6), 681-90 (1999).

Morris A, Vetto J T, Ramstad T, Funatake C J, Choolun E, Entwisle C, Weinberg A D. Induction of anti-mammary cancer immunity by engaging the OX-40 receptor in vivo. Breast Cancer Res. Treat. 67(1), 71-80 (2001).

Napoletano C, Bellati F, Tarquini E, Tomao F, Taurino F, Spagnoli G, Rughetti A, Muzii L, Nuti M, Benedetti Panici P. MAGE-A and N Y-ESO-1 expression in cervical cancer: prognostic factors and effects of chemotherapy. Am. J. Obstet. Gynecol. 198(1), 99.e1-99.e7 (2008).

Pearson W R, Lipman D J. Improved tools for biological sequence comparison. Proc. Natl. Acad. Sci. U.S.A. 85(8), 2444-8 (1988).

Podojil J R, Miller S D. Potential targeting of B7-H4 for the treatment of cancer. Immunol. Rev. 276(1), 40-51 (2017).

Redmond W L, Gough M J, Weinberg A D. Ligation of the OX40 co-stimulatory receptor reverses self-Ag and tumor-induced CD8 T-cell anergy in vivo. Eur. J. Immunol. 39(8), 2184-94 (2009).

Redmond W L, Linch S N, Kasiewicz M J. Combined targeting of costimulatory (OX40) and coinhibitory (CTLA-4) pathways elicits potent effector T cells capable of driving robust antitumor immunity. Cancer Immunol. Res. 2(2), 142-53 (2014).

Rosenberg S. Development of Cancer Vaccines. ASCO Educational Book Spring: 60-62 (2000).

Sadun R E, Hsu W E, Zhang N, Nien Y C, Bergfeld S A, Sabzevari H, Lutsiak M E, Khawli L, Hu P, Epstein A L. Fc-mOX40L fusion protein produces complete remission and enhanced survival in 2 murine tumour models. J. Immunother. 31(3), 235-45 (2008).

Scott A M, Renner C. Tumour Antigens Recognized by Antibodies. eLS (2001).

Simpson A J, Cabellero O L, Jungbluth O L, Chen Y T, Old U. Cancer/testis antigens, gametogenesis and cancer. Nat. Rev. Cancer 5(8), 615-25 (2005).

Smith T F, Waterman M S. Identification of common molecular subsequences. J. Mol. Biol. 147(1), 195-7 (1981).

Song Y, Margolles-Clark E, Bayer A, Buchwald P. Small-molecule modulators of the OX40-OX40 ligand co-stimulatory protein-protein interaction. Br. J. Pharamcol. 171 (21), 4955-69 (2014).

Spiess, Zhai, Carter (2015). Alternative molecular formats and therapeutic applications for bispecific antibodies. Molecular Immunology. 67:95-106.

Tai Y T, Anderson K C. Targeting B-cell maturation antigen in multiple myeloma. Immunotherapy 7(11), 1187-99 (2015).

Tinguely M, Jenni B, Knights A, Lopes B, Korol D, Rousson V, Curioni Fontecedro A, Cogliatti Bittermann A G, Schmid U, Dommann-Scherrer C, Maurer R, Renner C, Probst-Hensch N M, Moch H, Knuth A, Zippelius A. MAGE-C1/CT-7 expression in plasma cell myeloma: sub-cellular localization impacts on clinical outcome. Cancer Sci. 99(4), 720-5 (2008).

Velazquez E F, Jungbluth A A, Yancovitz M, Gnjatic S, Adams S, O'Neill D, Zavilevich K, Albukh T, Christos P, Mazumdar M, Pavlick A, Polsky D, Shapiro R, Berman R, Spira J, Busam K, Osman I, Bhardwaj N. Expression of the cancer/testis antigen N Y-ESO-1 in primary and metastatic malignant melanoma (M M)—correlation with prognostic factors. Cancer Immun. 7, 11 (2007).

Voron T, Colussi O, Marcheteau E, Pernot S, Nizard M, Point et al., Latreche S, Bergaya S, Benhamouda N, Tanchot C, Stockmann C, Combe P, Berger A, Zinzindohoue F, Yagita H, Tartour E, Taieb J, Terme M. VEGF-A modulates expression of inhibitory checkpoints on CD8+ T cells in tumors. J. Exp. Med. 212(2), 139-48 (2015).

Wajant H. Principles of antibody-mediated TNF receptor activation. Cell Death Differ. 22(11), 1727-41 (2015).

Wang X, Mathieu M, Brezski R J. IgG Fc engineering to modulate antibody effector functions. Protein Cell 9(1), 63-73 (2018).

Weinberg A D, Rivera M M, Prell R, Morris A, Ramstad T, Vetto J T, Urba W J, Alvord G, Bunce C, Shields J. Engagement of the OX-40 receptor in vivo enhances antitumour immunity. J. Immunol. 164(4), 2160-9 (2000).

Wozniak-Knopp G, Bartl S, Bauer A, Mostageer M, Woisetschlager M, Antes B, Ettl K, Kainer M, Weberhofer G, Wiederkum S, Himmler G, Mudde G C, Ruker F. Introducing antigen-binding sites in structural loops of immunoglobulin constant domains: Fc fragments with engineered HER2/neu-binding sites and antibody properties. Protein Eng. Des. Sel. 23(4), 289-97 (2010).

The invention claimed is:

1. A specific binding member that binds OX40 and comprises an OX40 antigen-binding site located in a CH3 domain of the specific binding member, wherein the OX40 antigen-binding site comprises the first, second, and third sequence of specific binding member:

(i) FS20-22-49 set forth in SEQ ID NOs: 43, 54 and 71, respectively;

(ii) FS20-22-41 set forth in SEQ ID NOs: 43, 54 and 45, respectively;

(iii) FS20-22-47 set forth in SEQ ID NOs: 43, 54 and 62, respectively;

(iv) FS20-22-85 set forth in SEQ ID NOs: 43, 54 and 80, respectively; or (v) FS20-22-38 set forth in SEQ ID NOs: 43, 44 and 45, respectively; and wherein the first, second, and third sequence are located in the AB, CD and EF structural loops of the CH3 domain of the specific binding member, respectively.

2. The specific binding member according to claim 1, wherein the specific binding member comprises the CH3 domain sequence of specific binding member FS20-22-49, FS20-22-41, FS20-22-47, FS20-22-85, or FS20-22-38 set forth in SEQ ID NOs: 72, 55, 63, 81, and 46, respectively.

3. The specific binding member according to claim 1, wherein the specific binding member comprises the sequence of specific binding member:

(i) FS20-22-49, FS20-22-41, FS20-22-47, FS20-22-85, or FS20-22-38 set forth in SEQ ID NOs: 74, 57, 65, 83, and 48, respectively; or (ii) FS20-22-49, FS20-22-41, FS20-22-47, FS20-22-85, or FS20-22-38 set forth in SEQ ID NOs: 76, 59, 67, 85, and 50, respectively.

4. The specific binding member according to claim 1, wherein the specific binding member further comprises a CDR-based antigen-binding site, wherein said CDR-based antigen-binding site is formed by three light chain variable region CDRs and three heavy chain variable region CDRs.

5. The specific binding member according to claim 4, wherein the specific binding member is an antibody molecule.

6. The antibody molecule according to claim 5, wherein the CDR-based antigen-binding site binds a second antigen selected from the group consisting of: an immune cell antigen, a tumour antigen, and a pathogenic antigen.

7. The specific binding member according to claim 1, wherein the specific binding member does not bind to Fcγ receptors.

8. A nucleic acid encoding the specific binding member according to claim 1.

9. A recombinant host cell comprising the nucleic acid of claim 8.

10. A method of producing a specific binding member, comprising culturing the recombinant host cell of claim 9 under conditions for production of the specific binding member or antibody molecule.

11. A method of treating a colorectal cancer in a patient comprising administering to the patient a therapeutically effective amount of the antibody molecule according to claim 5, wherein the patient has colorectal cancer.

12. The antibody molecule according to claim 5, wherein the antibody molecule has been modified to reduce or abrogate binding of the CH2 domain of the antibody molecule to one or more Fcγ receptors.

13. A pharmaceutical composition comprising the antibody molecule according to claim 5 and a pharmaceutically acceptable excipient.

14. The specific binding member according to claim 2, wherein the CH3 domain of the specific binding member comprises a lysine residue (K) at the immediate C-terminus of the CH3 domain sequence set forth in SEQ ID NO: 72, 55, 63, 81, or 46.

15. The specific binding member according to claim 3, wherein the CH3 domain of the specific binding member comprises a lysine residue (K) at the immediate C-terminus of the sequence set forth in SEQ ID NO: 74, 57, 65, 83, 48, 76, 59, 67, 85, or 50.

* * * * *